(12) United States Patent
Jung et al.

(10) Patent No.: US 9,406,891 B2
(45) Date of Patent: Aug. 2, 2016

(54) COMPOUND FOR ORGANIC OPTOELECTRONIC DEVICE, ORGANIC LIGHT EMITTING DIODE INCLUDING THE SAME, AND DISPLAY INCLUDING THE ORGANIC LIGHT EMITTING DIODE

(71) Applicants: SAMSUNG ELECTRONICS CO., LTD., Suwon-si, Gyeonggi-do (KR); CHEIL INDUSTRIES INC., Gumi-si, Gyeongsanbuk-do (KR)

(72) Inventors: Yong Sik Jung, Seoul (KR); Ho Suk Kang, Suwon-si (KR); Hyeon Ho Choi, Seoul (KR); Sang Mo Kim, Hwaseong-si (KR); Jhun Mo Son, Yongin-si (KR); Kyu Young Hwang, Ansan-si (KR)

(73) Assignees: SAMSUNG ELECTRONICS CO., LTD. (KR); CHEIL INDUSTRIES INC. (KR)

( * ) Notice: Subject to any disclaimer, the term of this patent is extended or adjusted under 35 U.S.C. 154(b) by 401 days.

(21) Appl. No.: 13/939,811

(22) Filed: Jul. 11, 2013

(65) Prior Publication Data

US 2014/0158999 A1   Jun. 12, 2014

(30) Foreign Application Priority Data

Dec. 12, 2012   (KR) .......................... 10-2012-0144602

(51) Int. Cl.
*H01L 51/50* (2006.01)
*H01L 51/00* (2006.01)
(Continued)

(52) U.S. Cl.
CPC .......... *H01L 51/0067* (2013.01); *C07D 403/14* (2013.01); *C09K 11/06* (2013.01);
(Continued)

(58) Field of Classification Search
None
See application file for complete search history.

(56) References Cited

U.S. PATENT DOCUMENTS

2006/0082291 A1   4/2006   Hahm et al.
2006/0134460 A1   6/2006   Kondakova et al.
(Continued)

FOREIGN PATENT DOCUMENTS

CN   102597158 A    7/2012
DE   102010048497 A1   4/2012
(Continued)

OTHER PUBLICATIONS

The Extended European Search Report for European Patent Appl. 13193162.8 dated Jun. 23, 2014.
(Continued)

*Primary Examiner* — Gregory Clark
(74) *Attorney, Agent, or Firm* — Cantor Colburn LLP

(57) ABSTRACT

Disclosed are a compound for an organic optoelectronic device, an organic light emitting diode including the same, and a display device including the organic light emitting diode. A compound for an organic optoelectronic device represented by Chemical Formula 1 provides an organic optoelectronic device having an excellent life-span and improved luminous efficiency at a low driving voltage due to excellent electrochemical and thermal stability.

19 Claims, 4 Drawing Sheets

(51) Int. Cl.
    *C09K 11/06*         (2006.01)
    *C07D 403/14*       (2006.01)

(52) U.S. Cl.
    CPC ........ H01L51/0071 (2013.01); H01L 51/0072 (2013.01); *C09K 2211/104* (2013.01); *C09K 2211/1007* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *H01L 51/0042* (2013.01); *H01L 51/0085* (2013.01); *H01L 51/5016* (2013.01); *Y02E 10/549* (2013.01)

(56) References Cited

U.S. PATENT DOCUMENTS

| | | | |
|---|---|---|---|
| 2009/0153031 | A1 | 6/2009 | Kai et al. |
| 2009/0236973 | A1 | 9/2009 | Yabe et al. |
| 2010/0207105 | A1 | 8/2010 | Katakura et al. |
| 2012/0126221 | A1 | 5/2012 | Kitamura et al. |
| 2012/0126691 | A1 | 5/2012 | Ise et al. |
| 2012/0126692 | A1 | 5/2012 | Ise et al. |
| 2012/0205636 | A1 | 8/2012 | Kim et al. |
| 2012/0211736 | A1 | 8/2012 | Kim et al. |
| 2012/0256173 | A1 | 10/2012 | Kitamura et al. |
| 2013/0200357 | A1 | 8/2013 | Ludemann et al. |
| 2013/0240796 | A1 | 9/2013 | Perham et al. |
| 2013/0341613 | A1 | 12/2013 | Nagao et al. |
| 2014/0231779 | A1 | 8/2014 | Kim et al. |
| 2015/0069368 | A1 | 3/2015 | Kim et al. |

FOREIGN PATENT DOCUMENTS

| | | | | |
|---|---|---|---|---|
| JP | 4474493 | B1 | 3/2010 | |
| JP | 4523992 | B1 | 6/2010 | |
| JP | 4590020 | B1 | 9/2010 | |
| JP | 4729642 | B1 | 4/2011 | |
| JP | 4741028 | B1 | 5/2011 | |
| KR | 1020110014752 | A | 2/2011 | |
| KR | 1020110016044 | A | 2/2011 | |
| KR | 1020110041191 | * | 4/2011 | ............ H01L 51/50 |
| KR | 1020110066763 | A | 6/2011 | |
| KR | 1020110088427 | A | 8/2011 | |
| KR | 1020110105269 | A | 9/2011 | |
| KR | 1020110105272 | A | 9/2011 | |
| KR | 1020120018231 | A | 2/2012 | |
| KR | 1020120038056 | A | 4/2012 | |
| KR | 1020120070468 | A | 6/2012 | |
| KR | 10-2012-0122813 | A | 11/2012 | |
| WO | 2006038767 | A1 | 4/2006 | |
| WO | 2006062062 | A1 | 6/2006 | |
| WO | 2007015412 | A1 | 2/2007 | |
| WO | 2011021803 | A2 | 2/2011 | |
| WO | 2011049325 | A4 | 4/2011 | |
| WO | 2011086861 | A1 | 7/2011 | |
| WO | 2012005360 | A1 | 1/2012 | |
| WO | 2012069121 | A1 | 5/2012 | |
| WO | 2012087955 | A1 | 6/2012 | |
| WO | 2012124622 | A1 | 9/2012 | |

OTHER PUBLICATIONS

English Summary of Office Action dated May 23, 2016 in the corresponding Taiwanese Patent Application No. 102145754.

Office Action dated May 23, 2016 in the Corresponding Taiwanese Patent Application No. 102145754.

* cited by examiner

COMPOUND FOR ORGANIC OPTOELECTRONIC DEVICE, ORGANIC LIGHT EMITTING DIODE INCLUDING THE SAME, AND DISPLAY INCLUDING THE ORGANIC LIGHT EMITTING DIODE

CROSS-REFERENCE TO RELATED APPLICATION

This application claims priority to Korean Patent Application No. 10-2012-0144602, filed on Dec. 12, 2012, and all the benefits accruing therefrom under 35 U.S.C. §119, the content of which in its entirety is herein incorporated by reference.

BACKGROUND

1. Field

A compound for an organic optoelectronic device being capable of providing an organic optoelectronic device having excellent life-span, efficiency, electrochemical stability, and thermal stability, an organic light emitting diode including the compound, and a display device including the organic light emitting diode are disclosed.

2. Description of the Related Art

An organic optoelectronic device is, in a broad sense, a device for transforming photo-energy to electrical energy, or conversely, a device for transforming electrical energy to photo-energy.

An organic optoelectronic device may be classified in accordance with its driving principles. A first organic optoelectronic device is an electronic device driven as follows: excitons are generated in an organic material layer by photons from an external light source; the excitons are separated into electrons and holes; and the electrons and holes are transferred to different electrodes as a current source (voltage source).

A second organic optoelectronic device is an electronic device driven as follows: a voltage or a current is applied to at least two electrodes to inject holes and/or electrons into an organic semiconductor positioned at an interface of the electrodes, and the device is driven by the injected electrons and holes.

Examples of the organic optoelectronic device include an organic light emitting diode, an organic solar cell, an organic photoconductor drum, an organic transistor, and the like, which require a hole injecting or transport material, an electron injecting or transport material, or a light emitting material.

Particularly, an organic light emitting diode (OLED) has recently drawn attention due to an increasing demand for flat panel displays. In general, organic light emission refers to conversion of electrical energy into photo-energy.

An organic light emitting diode can convert electrical energy into light by applying current to an organic light emitting material. It has a structure in which a functional organic material layer is interposed between an anode and a cathode. The organic material layer includes a multi-layer including different materials, for example a hole injection layer (HIL), a hole transport layer (HTL), an emission layer, an electron transport layer (ETL), and an electron injection layer (EIL), in order to improve efficiency and stability of an organic light emitting diode.

In such an organic light emitting diode, when a voltage is applied between an anode and a cathode, holes from the anode and electrons from the cathode are injected to an organic material layer and recombined to generate excitons having high energy. The generated excitons generate light having certain wavelengths while shifting to a ground state.

Recently, it has become known that a phosphorescent light emitting material may be used as a light emitting material of an organic light emitting diode in addition to the fluorescent light emitting material. Such a phosphorescent material emits lights by first transporting the electrons from a ground state to an exited state, then transiting a singlet exciton to a triplet exciton through intersystem crossing, and finally transiting a triplet exciton to a ground state to emit light.

In an organic light emitting diode, an organic material layer includes a light emitting material and a charge transport material, for example a hole injection material, a hole transport material, an electron transport material, an electron injection material, and the like.

The light emitting material is classified as blue, green, and red light emitting materials according to emitted colors, and yellow and orange light emitting materials which emit colors approaching natural colors.

When a material is used as a light emitting material, its maximum light emitting wavelength can be shifted to a long wavelength or its color purity can decrease because of interactions between molecules. In addition, device efficiency can decrease because of a light emitting quenching effect. Therefore, a host/dopant system is included for a light emitting material in order to improve color purity and increase luminous efficiency and stability through energy transfer.

In order to achieve excellent performance of an organic light emitting diode, a material for an organic material layer, for example a hole injection material, a hole transport material, a light emitting material, an electron transport material, an electron injection material, and a light emitting material such as a host and/or a dopant, should be stable and have good efficiency. However, development of such a material has thus far been elusive and there is still a need for an improved material for an organic light emitting diode and other organic optoelectronic devices.

A low molecular organic light emitting diode is manufactured as a thin film in a vacuum deposition method, and can have good efficiency and life-span. A polymer organic light emitting diode manufactured in an Inkjet or spin coating method has an advantage of low initial cost and being large-sized.

Both low molecular organic light emitting and polymer organic light emitting diodes have an advantage of self-light emitting, high speed response, wide viewing angle, ultra-thinness, high image quality, durability, large driving temperature range, and the like. In particular, they have good visibility due to the self-light emitting characteristic. Compared with a liquid crystal display ("LCD"), an organic light emitting display ("OLED") can be up to about one third thinner and lighter, because they do not need a backlight.

In addition, since they have a response speed of a microsecond unit, which is 1000 times faster than an LCD, they can realize a motion picture without an after-image. Based on these advantages, they have been remarkably developed to be 80 times more efficient and to have a 100 times longer life-span since they first came out in the late 1980's. Recently, they have become rapidly larger such that a 40-inch organic light emitting diode panel is now possible.

In order for the organic light emitting diode panel to be larger, it is necessary that the organic light emitting diodes have improved luminous efficiency and improved life-span at the same time. Luminous efficiency requires smooth combination between holes and electrons in an emission layer. However, since an organic material in general has slower electron mobility than hole mobility, it has a drawback of inefficient combination between holes and electrons. Accordingly, increasing electron injection and mobility from a cathode and simultaneously preventing movement of holes is required.

In order to improve the life-span, it is required to prevent material crystallization caused by Joule heat generated during device operation. Accordingly, there has been a strong need for an organic compound having excellent electron injection and mobility, and high electrochemical stability.

SUMMARY

A compound for an organic optoelectronic device that may act as a light emitting or electron injection and/or transport material, and also act as a light emitting host along with an appropriate dopant, is provided.

An organic light emitting diode having excellent life-span, efficiency, driving voltage, electrochemical stability, and thermal stability and a display device including the same are provided.

In one embodiment, a compound for an organic optoelectronic device represented by Chemical Formula 1 is provided.

Chemical Formula 1

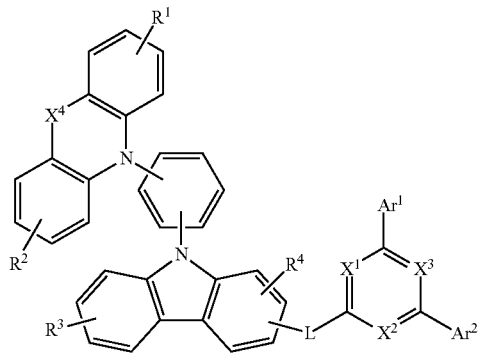

In Chemical Formula 1, $X^1$ to $X^3$ are independently —C(R')— or —N—, provided that at least one of $X^1$ to $X^3$ is —N—, $X^4$ is a single bond, —C(R')(R")—, —O—, —S—, —S(=O)—, —S(=O)$_2$—, —Si(R')(R")—, or —C(C=O)—, $R^1$ to $R^4$, R', and R" are independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, L is a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, and $Ar^1$ and $Ar^2$ are independently a substituted or unsubstituted C6 to C30 aryl group or a substituted or unsubstituted C2 to C30 heteroaryl group.

The $X^4$ may be a single bond.
The $X^4$ may be —C(R')(R")—.
The $X^4$ may be —O—.
The $X^4$ may be —S—.
The $X^4$ may be —S(=O)—.
The $X^4$ may be —S(=O)$_2$—.
The $X^4$ may be —Si(R')(R")—.
The $X^4$ may be —C(C=O)—. The compound for an organic optoelectronic device may be represented by Chemical Formula 2.

Chemical Formula 2

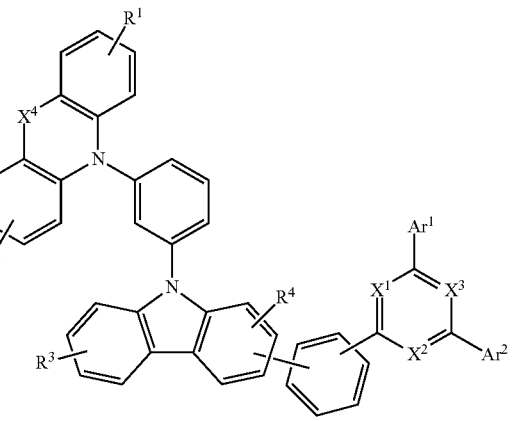

In Chemical Formula 2, $X^1$ to $X^3$ are independently —C(R')— or —N—, provided that at least one of $X^1$ to $X^3$ is N, $X^4$ is a single bond, —C(R')(R")—, —O—, —S—, —S(=O)—, —S(=O)$_2$—, —Si(R')(R")—, or —C(C=O)—, $R^1$ to $R^4$, R', and R" are independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and $Ar^1$ and $Ar^2$ are independently a substituted or unsubstituted C6 to C30 aryl group or a substituted or unsubstituted C2 to C30 heteroaryl group.

The compound for an organic optoelectronic device may be represented by Chemical Formula 3.

Chemical Formula 3

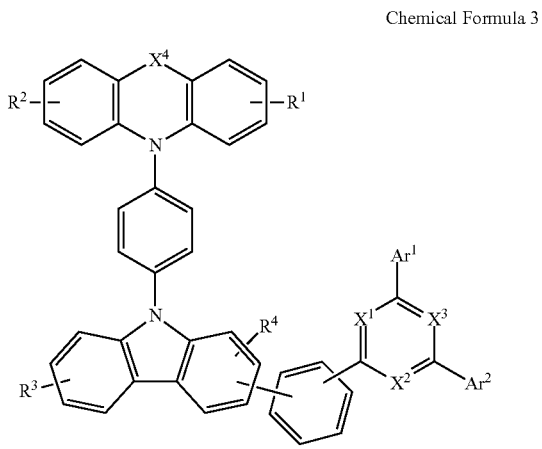

In Chemical Formula 3, $X^1$ to $X^3$ are independently —C(R')— or —N—, provided that at least one of $X^1$ to $X^3$ is —N—, $X^4$ is a single bond, —C(R')(R")—, —O—, —S—, —S(=O)—, —S(=O)$_2$—, —Si(R')(R")—, or —C(C=O)—, $R^1$ to $R^4$, R', and R" are independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and $Ar^1$ and $Ar^2$ are independently a substituted or unsubstituted C6 to C30 aryl group or a substituted or unsubstituted C2 to C30 heteroaryl group.

The compound for an organic optoelectronic device may be represented by Chemical Formula 4.

Chemical Formula 4

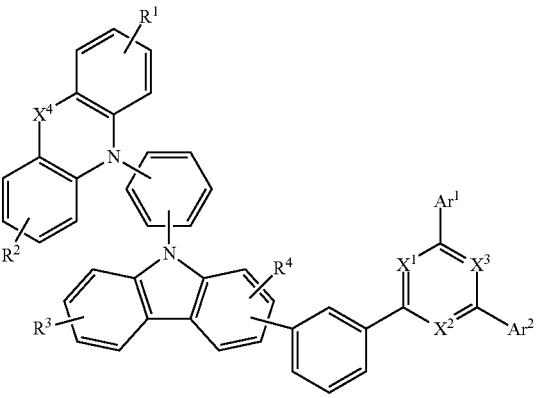

In Chemical Formula 4, $X^1$ to $X^3$ are independently —C(R')— or —N—, provided that at least one of $X^1$ to $X^3$ is —N—, $X^4$ is a single bond, —C(R')(R")—, —O—, —S—, —S(=O)—, —S(=O)$_2$—, —Si(R')(R")—, or —C(C=O)—, $R^1$ to $R^4$, R', and R" are independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and $Ar^1$ and $Ar^2$ are independently a substituted or unsubstituted C6 to C30 aryl group or a substituted or unsubstituted C2 to C30 heteroaryl group.

The compound for an organic optoelectronic device may be represented by Chemical Formula 5.

Chemical Formula 5

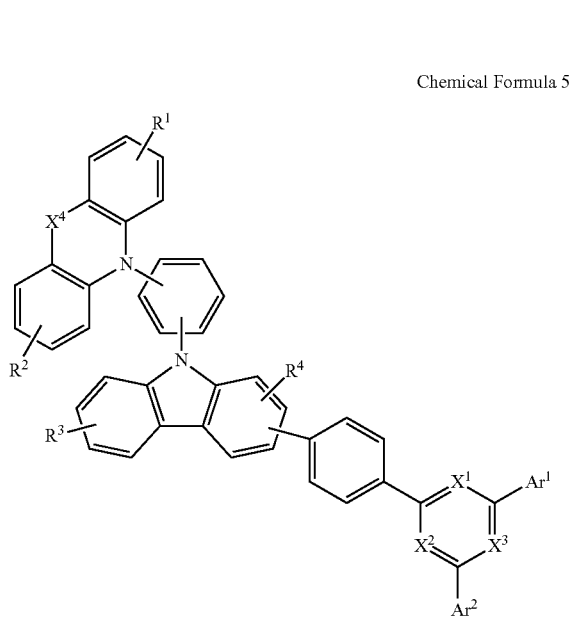

In Chemical Formula 5, $X^1$ to $X^3$ are independently —C(R')— or —N—, provided that at least one of $X^1$ to $X^3$ is —N—, $X^4$ is a single bond, —C(R')(R'')—, —O—, —S—, —S(=O)—, —S(=O)$_2$—, —Si(R')(R'')—, or —C(C=O)—, $R^1$ to $R^4$, R', and R'' are independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and $Ar^1$ and $Ar^2$ are independently a substituted or unsubstituted C6 to C30 aryl group or a substituted or unsubstituted C2 to C30 heteroaryl group.

The compound for an organic optoelectronic device may be represented by the Chemical Formula 6.

Chemical Formula 6

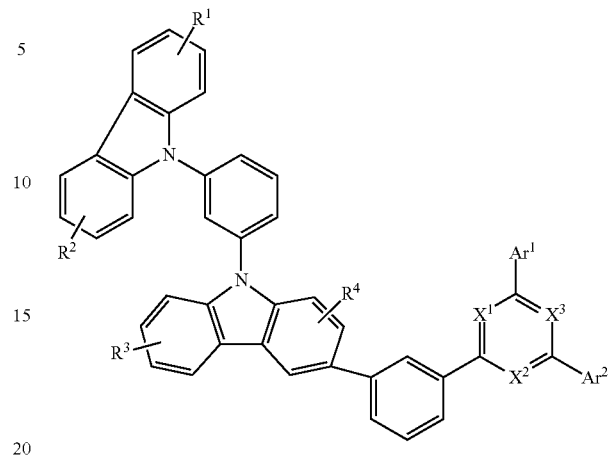

In Chemical Formula 6, $X^1$ to $X^3$ are independently —C(R')— or —N—, provided that at least one of $X^1$ to $X^3$ is —N—, $R^1$ to $R^4$ and R' are independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and $Ar^1$ and $Ar^2$ are independently a substituted or unsubstituted C6 to C30 aryl group or a substituted or unsubstituted C2 to C30 heteroaryl group.

The $Ar^1$ and $Ar^2$ may be independently a substituted or unsubstituted C6 to C30 aryl group.

The $X^1$ to $X^3$ may be independently CR' or N, and at least two of the $X^1$ to $X^3$ are N.

The compound for an organic optoelectronic device may be represented by one of Chemical Formulae A-1 to A-140.

A-1
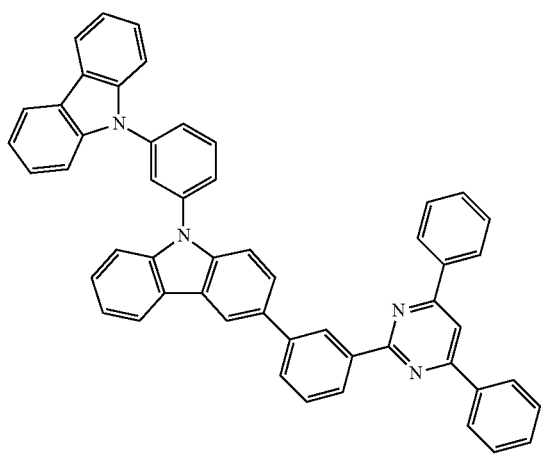
A-2
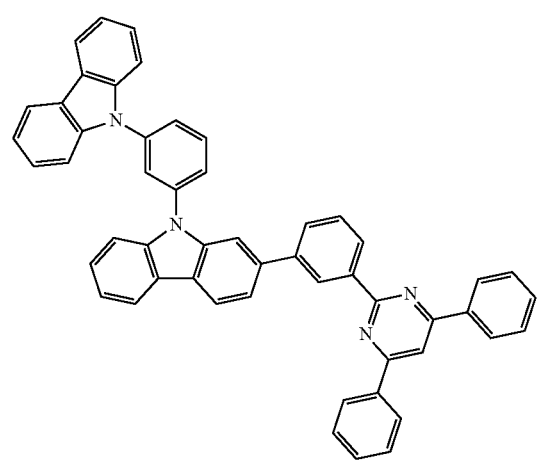
A-3
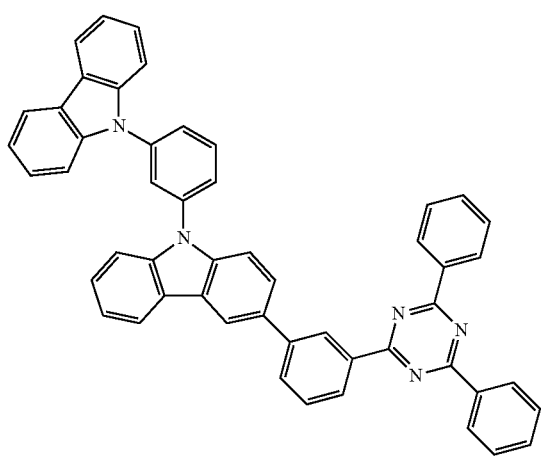
A-4
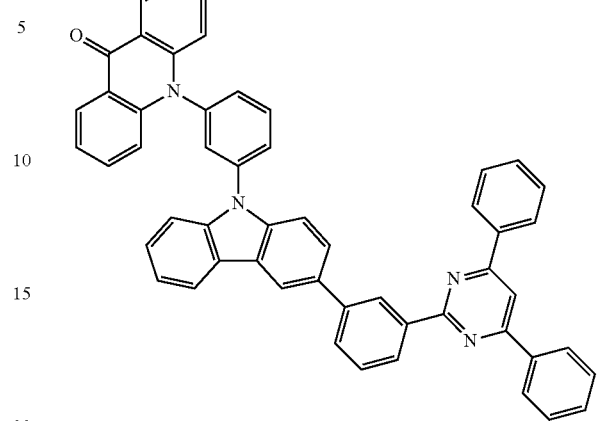
A-5
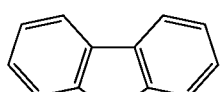
A-6
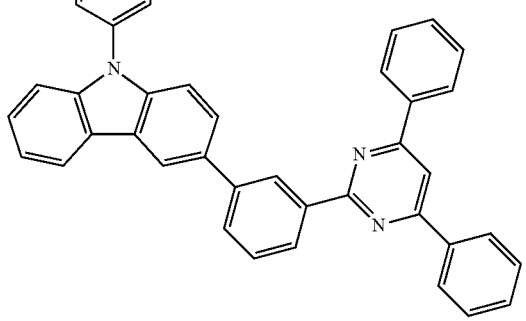

A-7
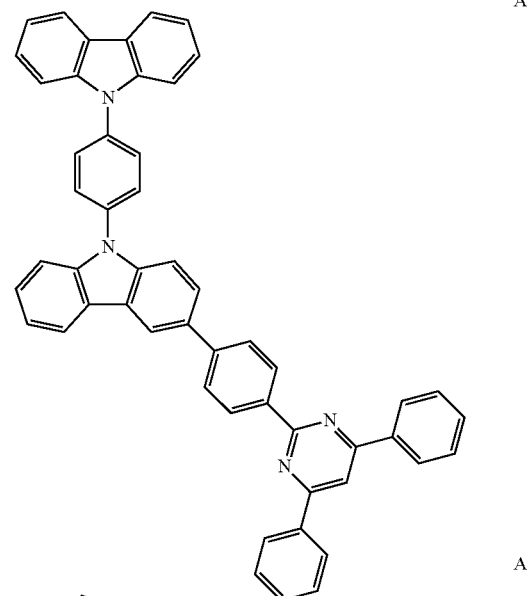
A-8
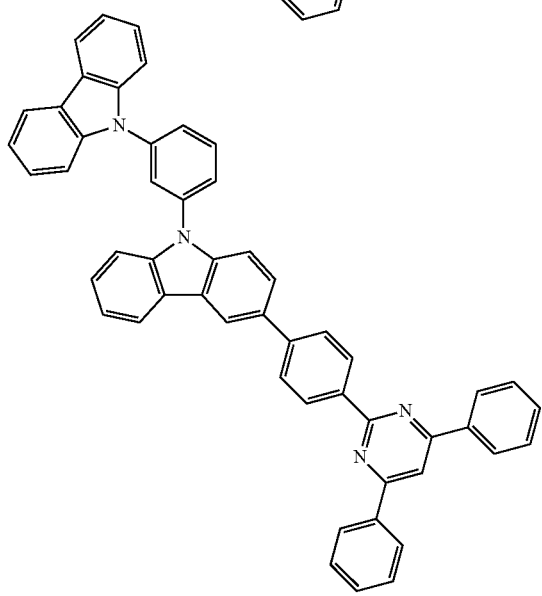
A-9
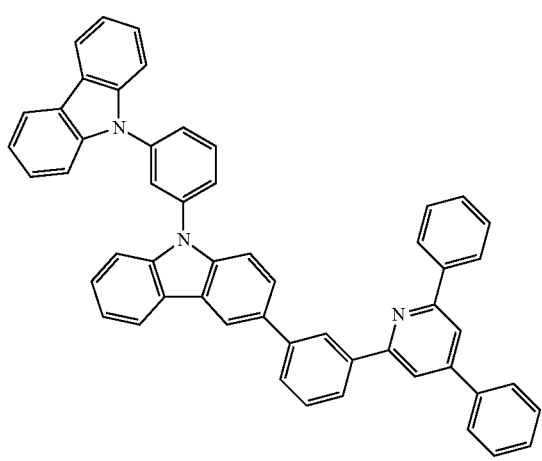
A-10
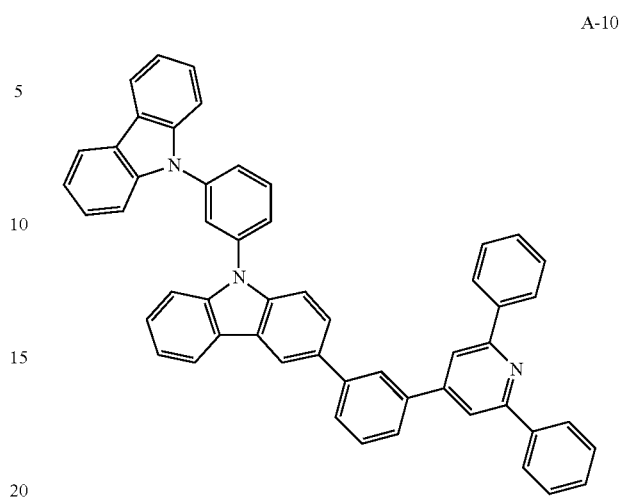
A-11
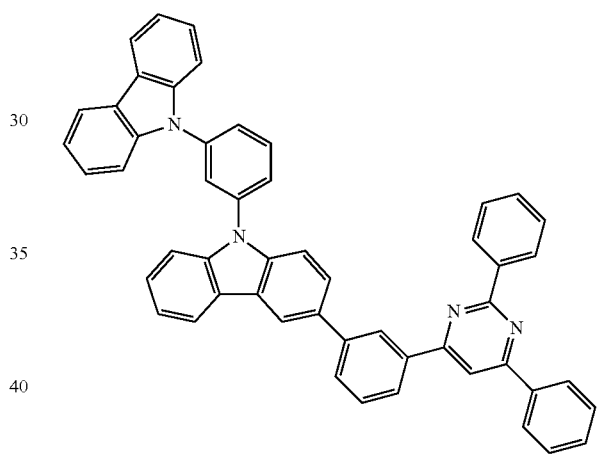
A-12
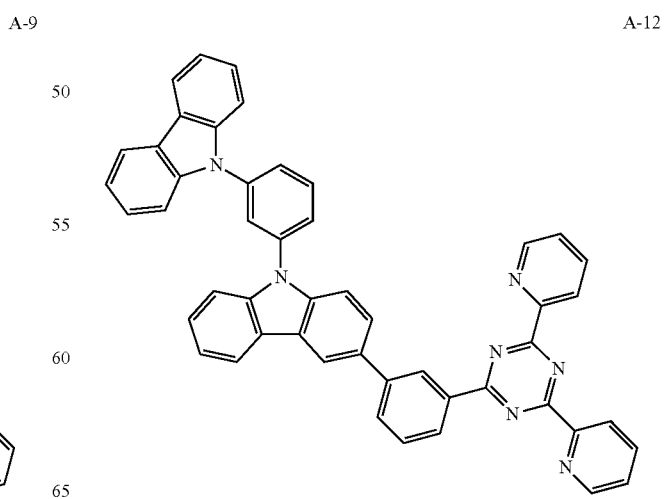

A-13
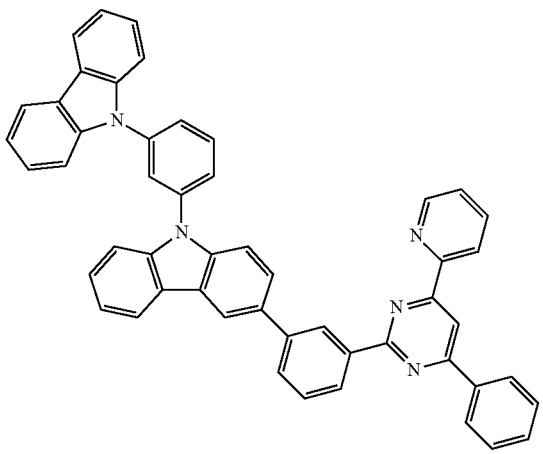
A-16
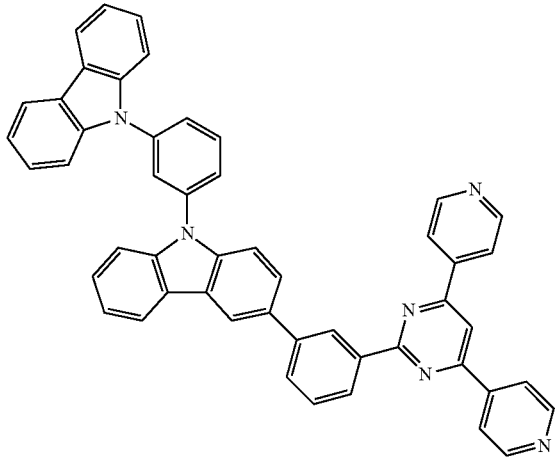
A-14
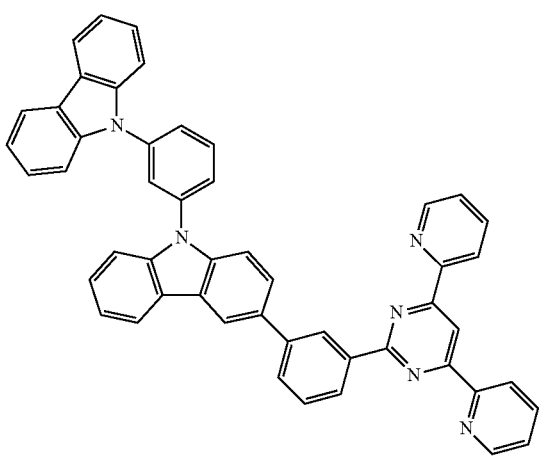
A-17
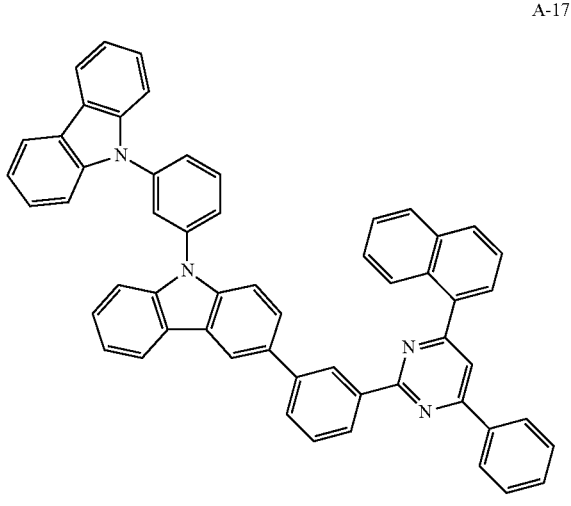
A-15
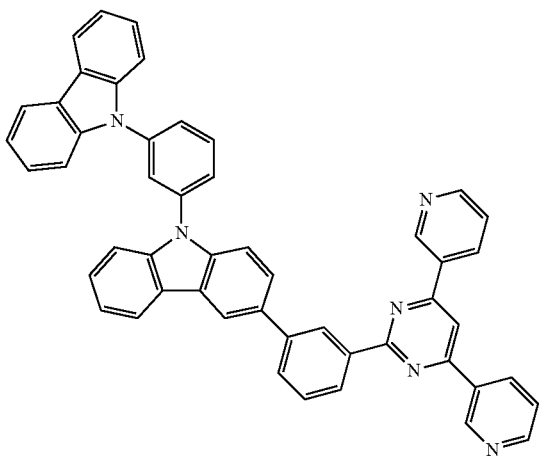
A-18
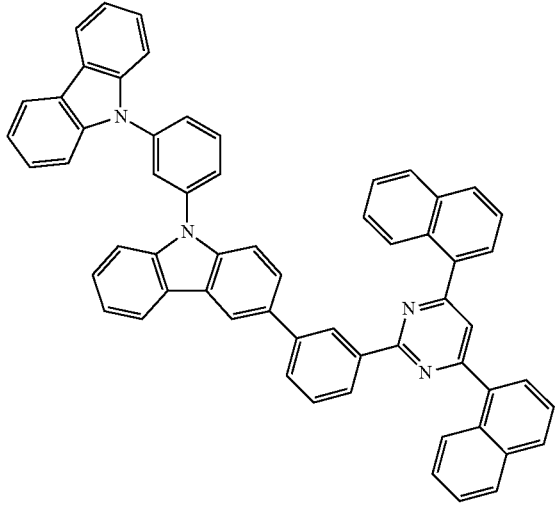

A-19
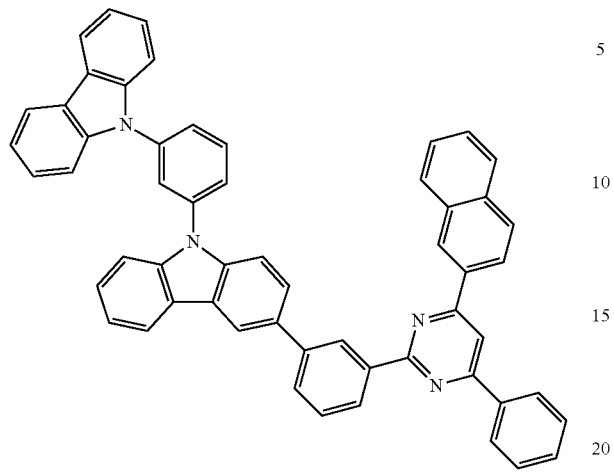
A-22
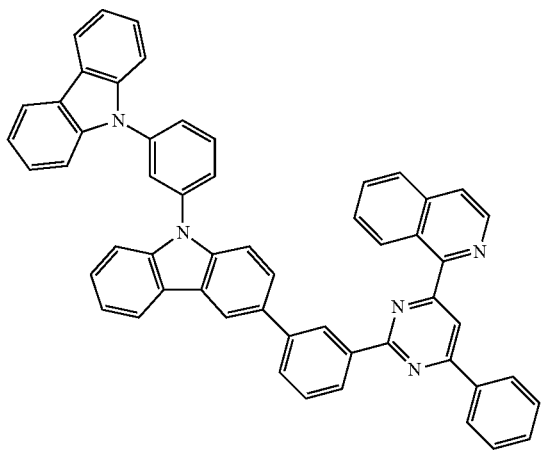
A-20
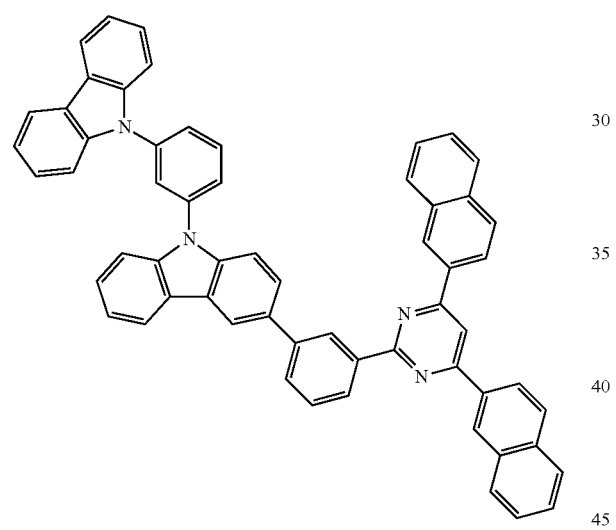
A-23
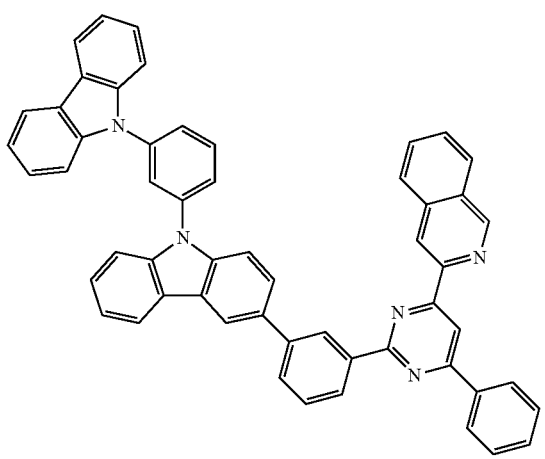
A-21
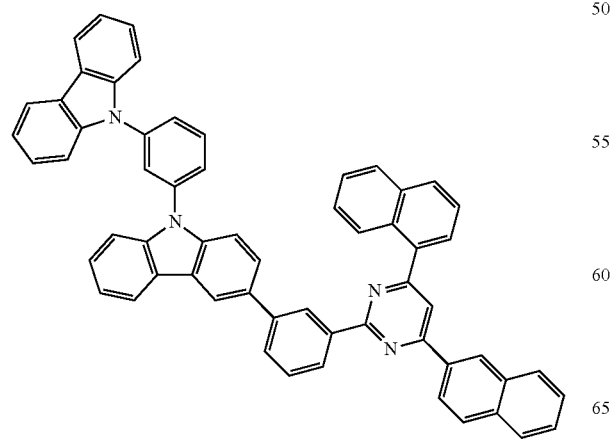
A-24
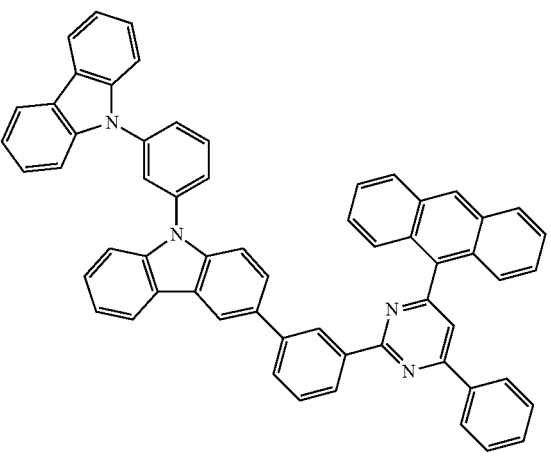

A-25
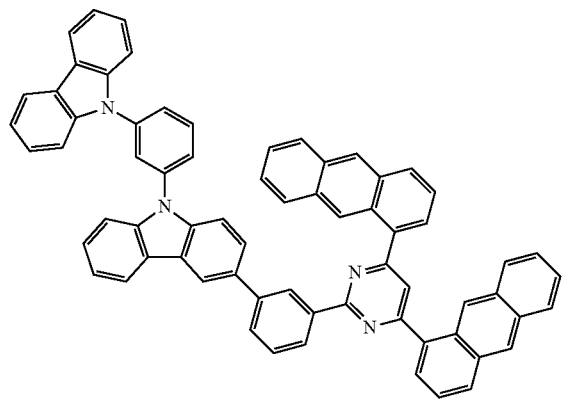
A-26
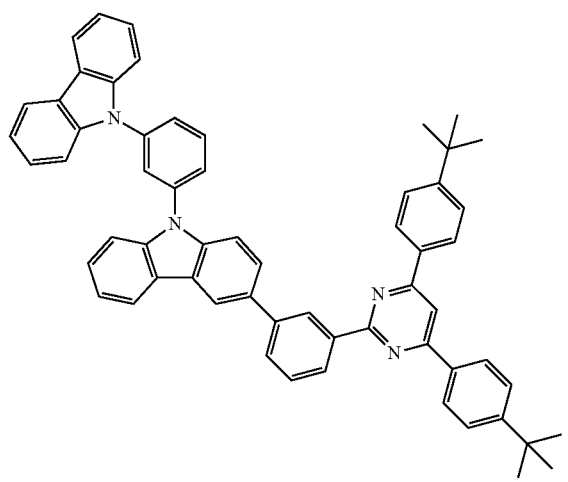
A-27
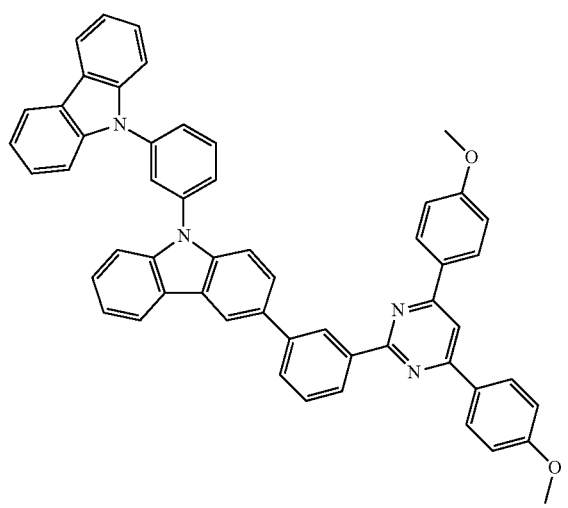
A-28
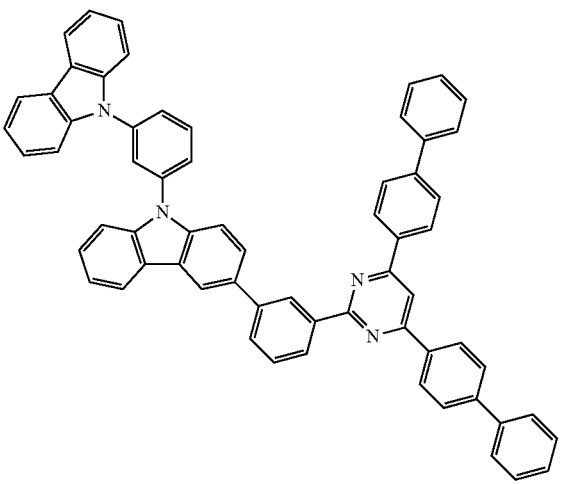
A-29
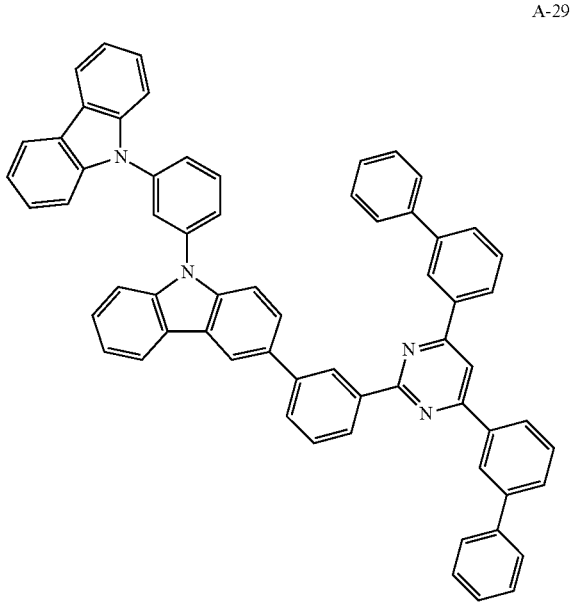
A-30
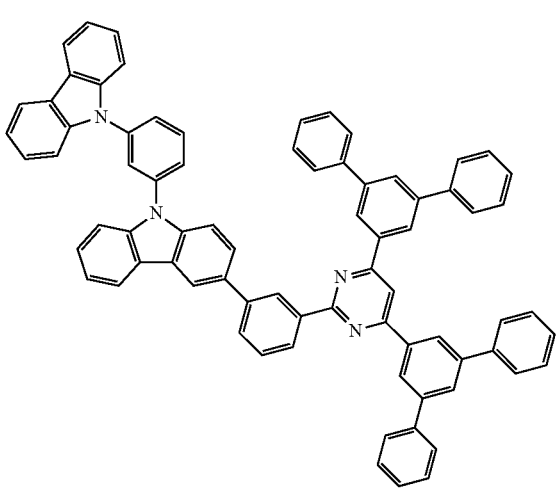

A-31
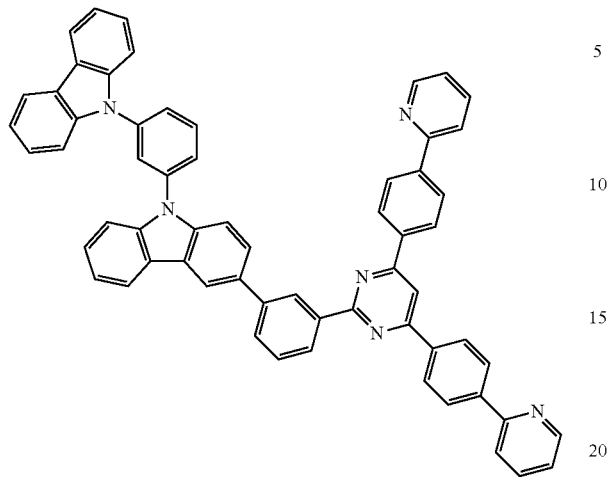
A-32
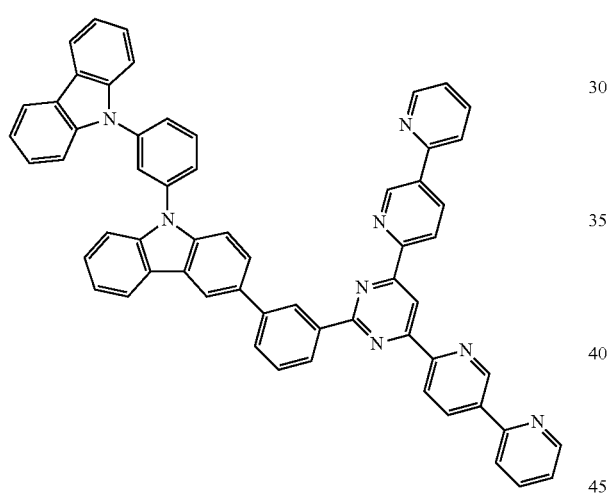
A-33
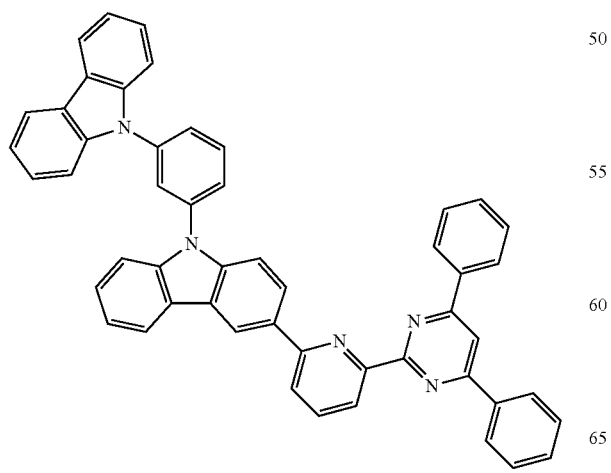
A-34
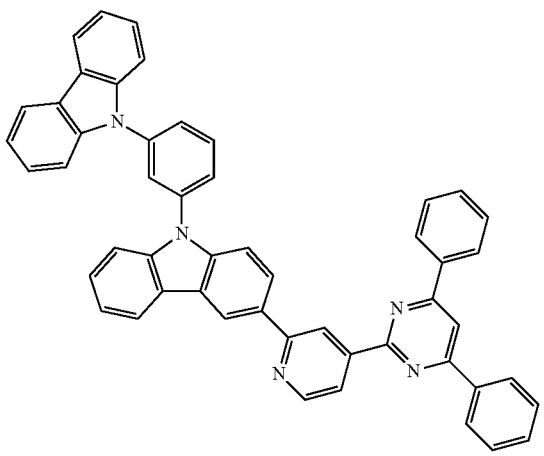
A-35
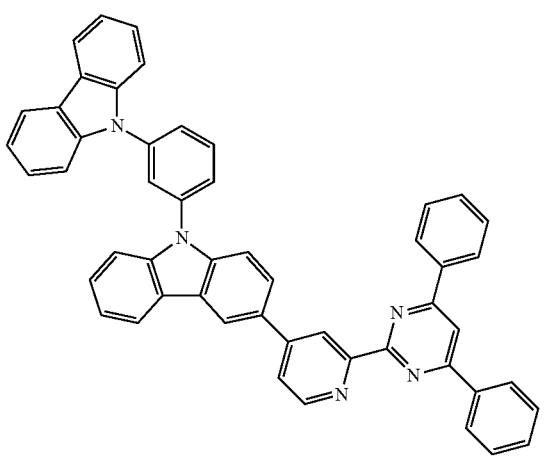
A-36
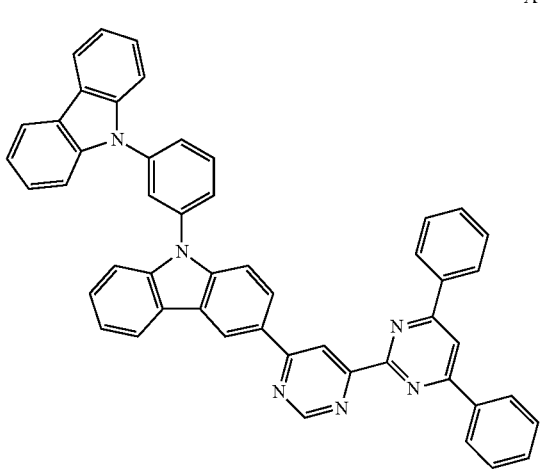

-continued
A-37
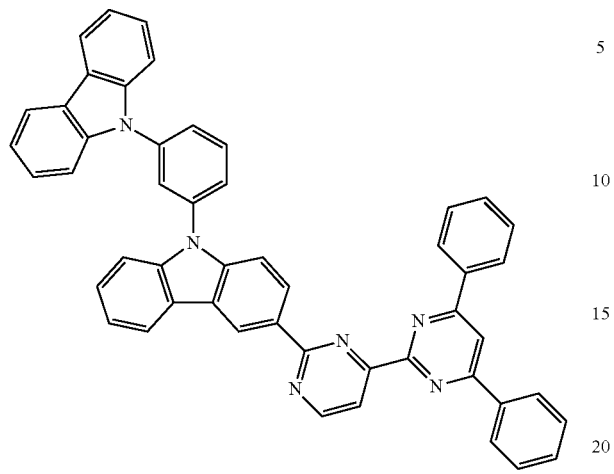
A-38
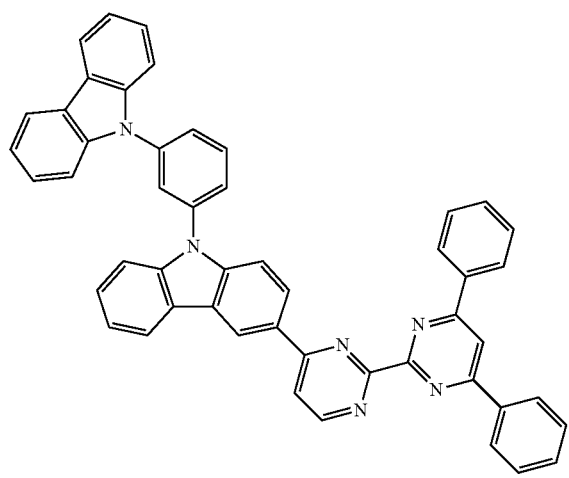
A-39
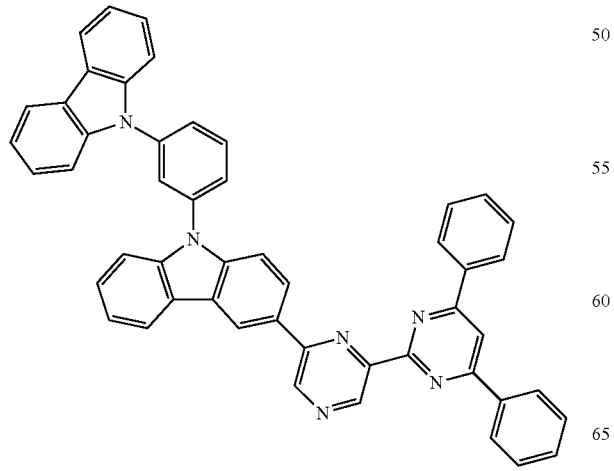
A-40
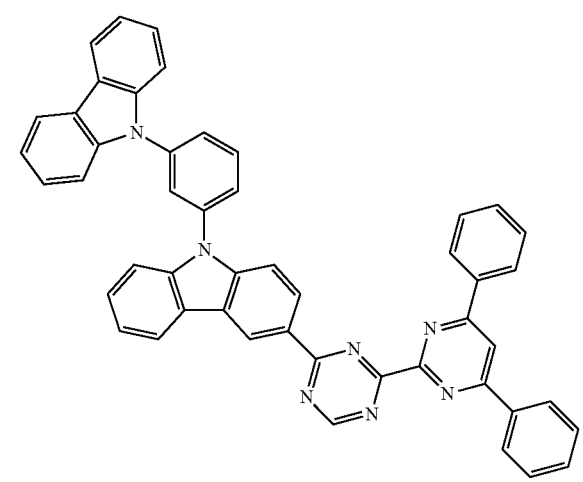
A-41
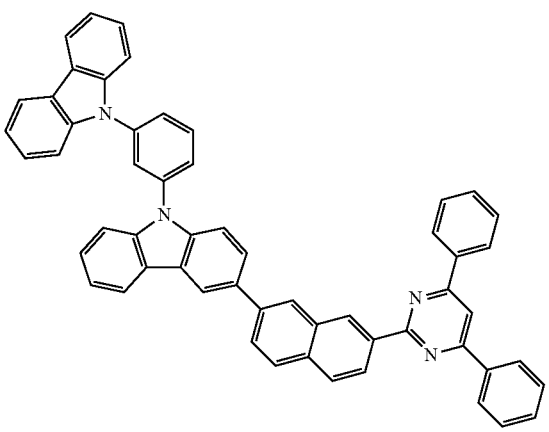
A-42
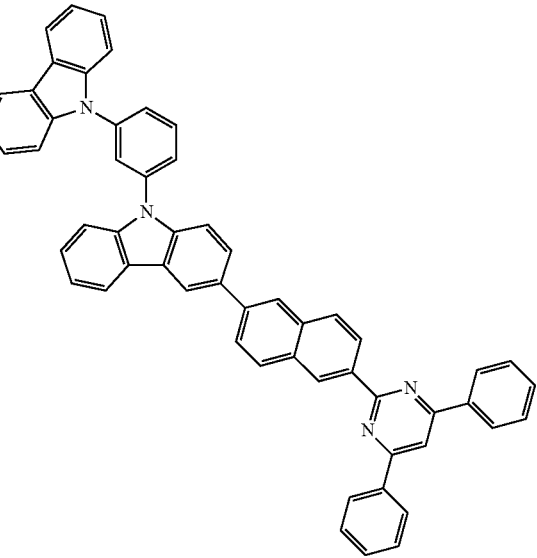

A-43
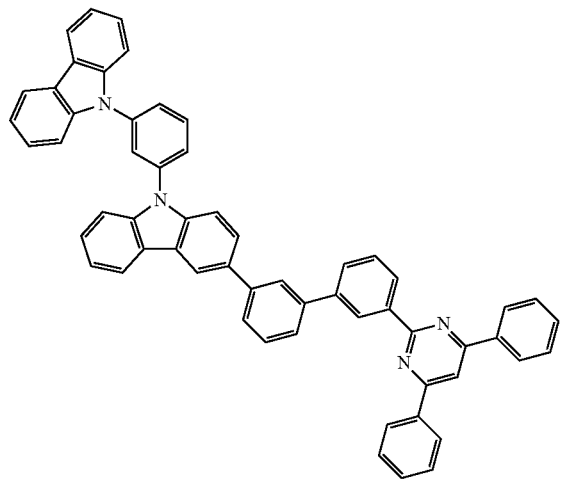
A-44
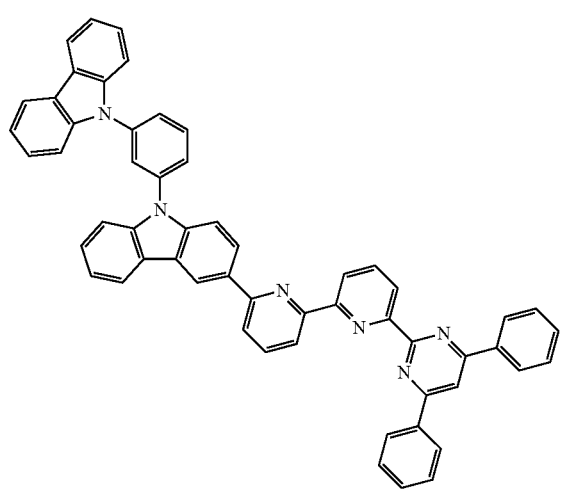
A-45
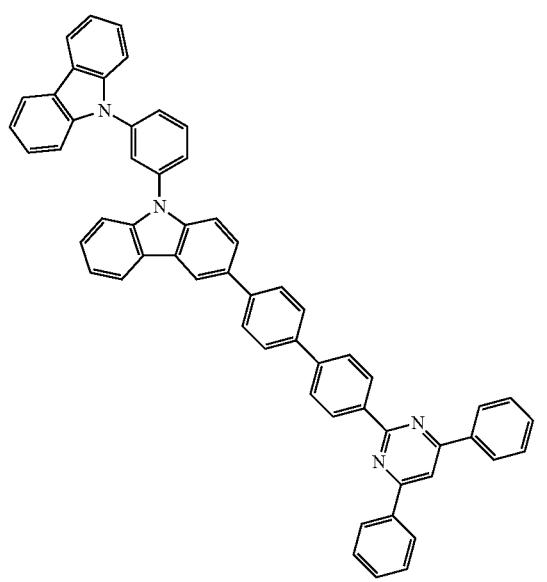
A-46
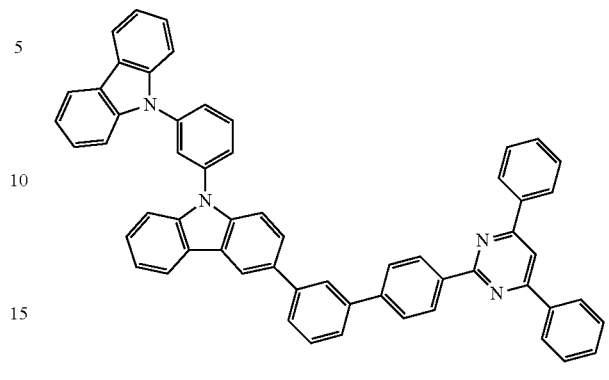
A-47
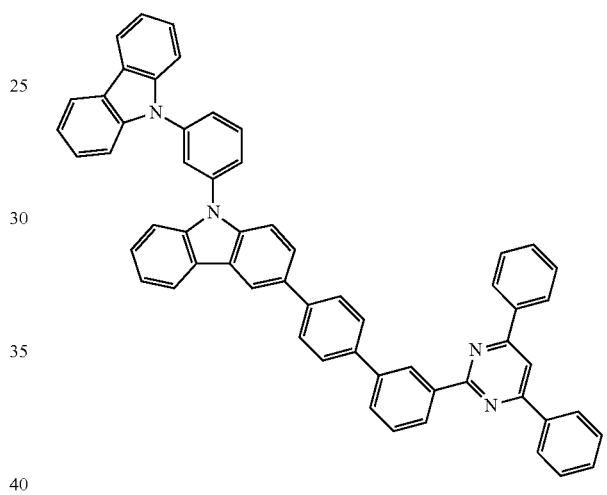
A-48
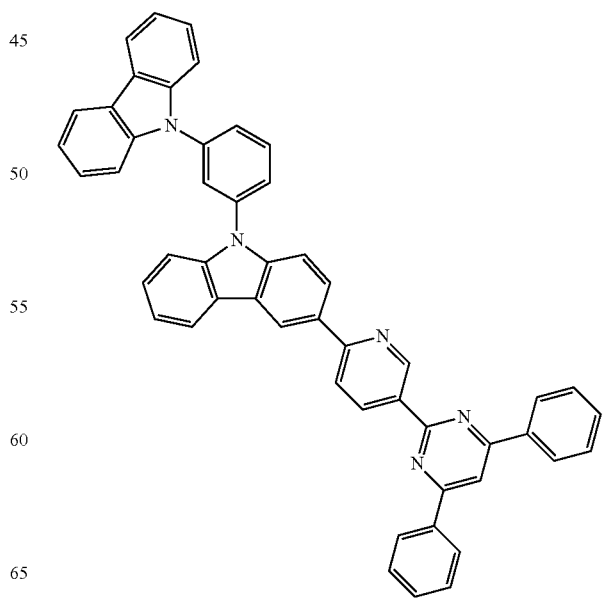

A-49
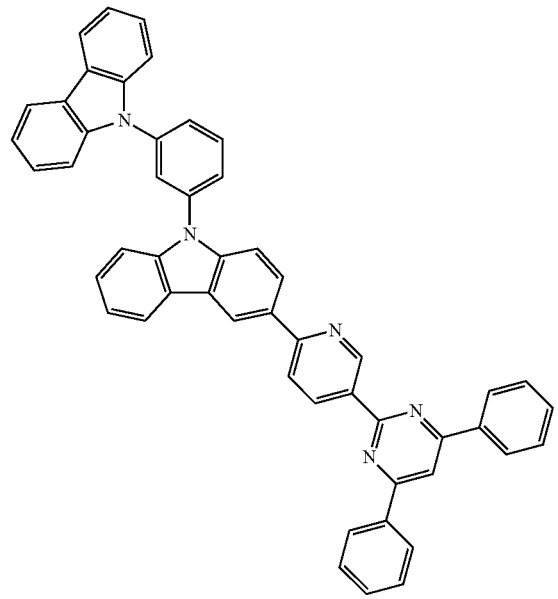
A-51
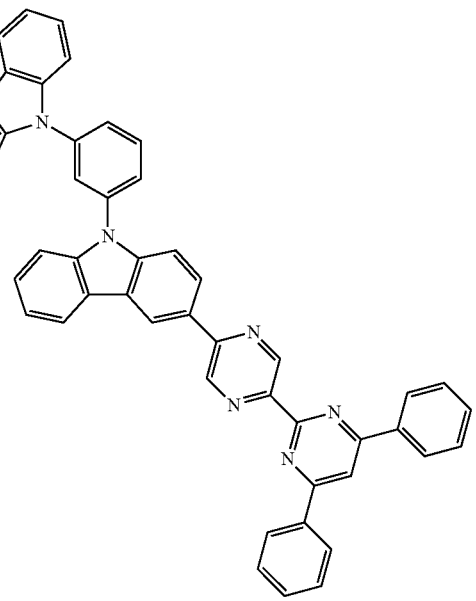
A-50
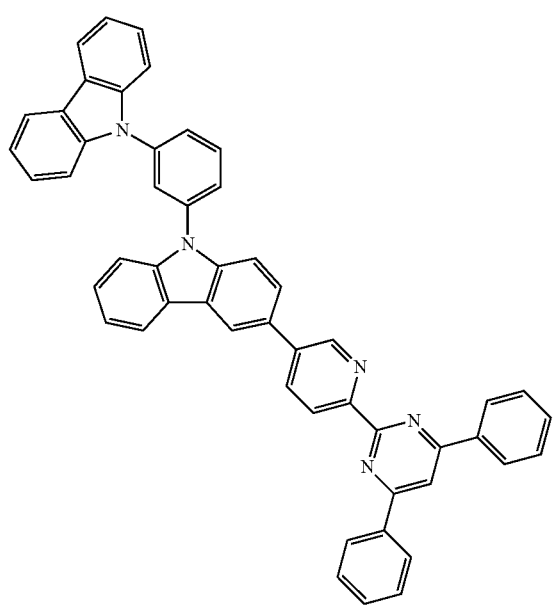
A-52
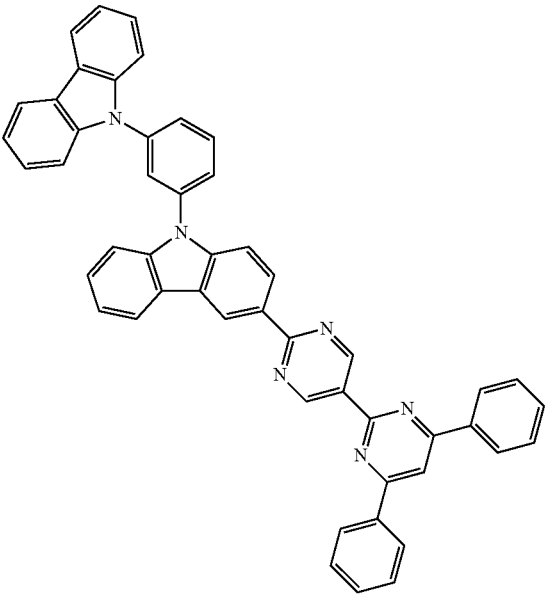

A-53
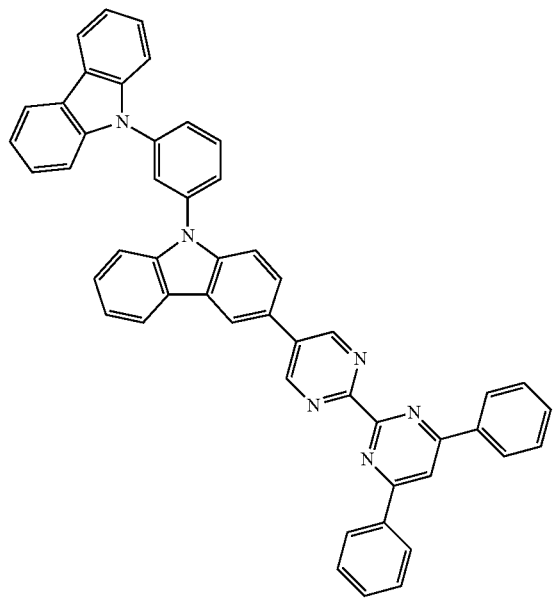
A-54
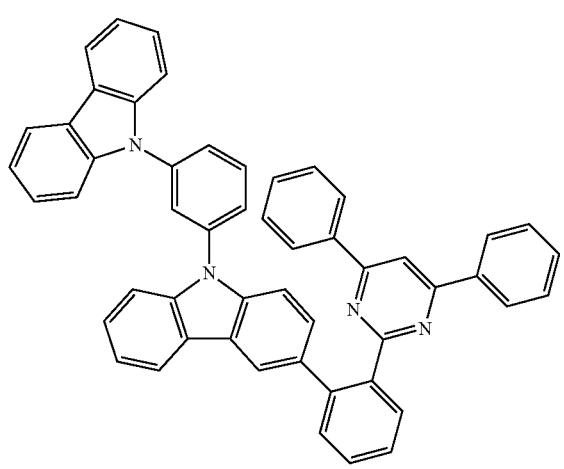
A-55
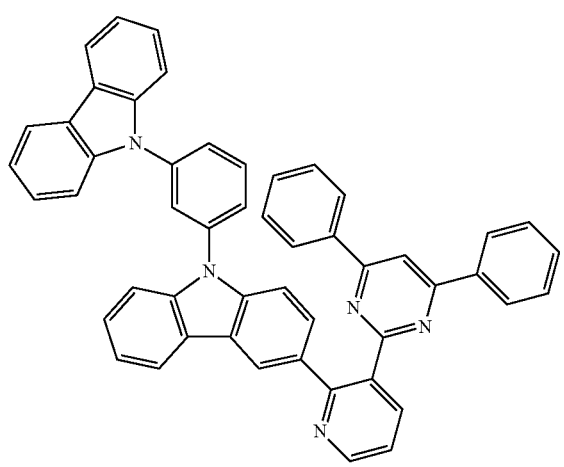
A-56
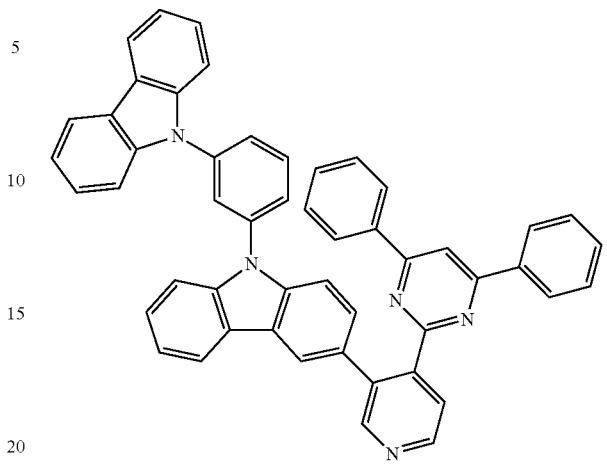
A-57
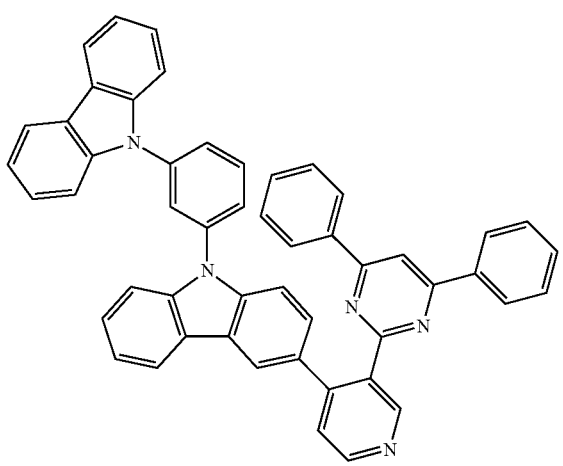
A-58
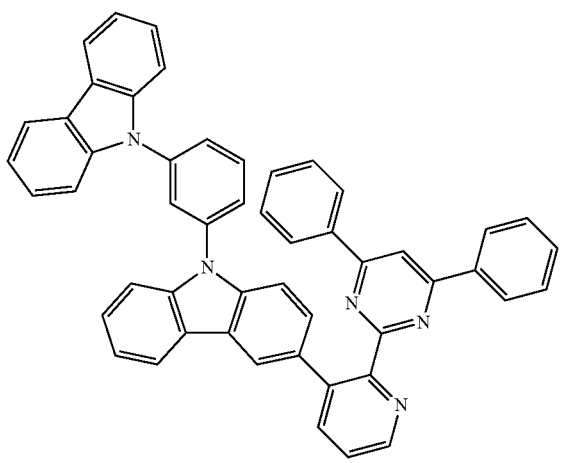

A-59
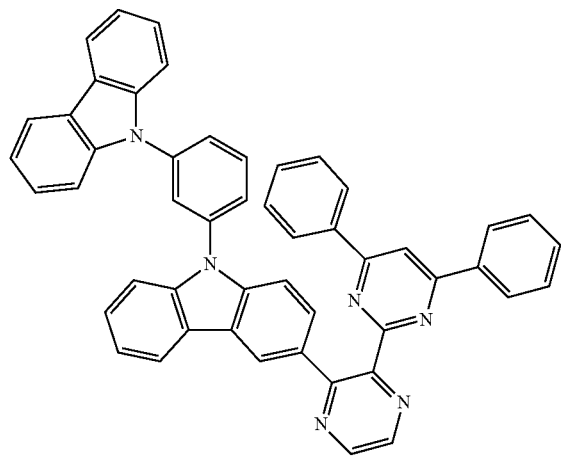
A-62
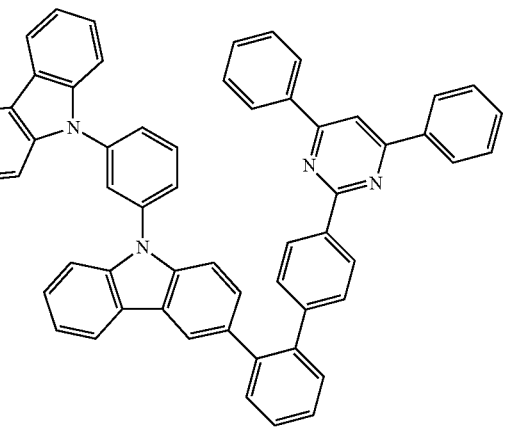
A-60
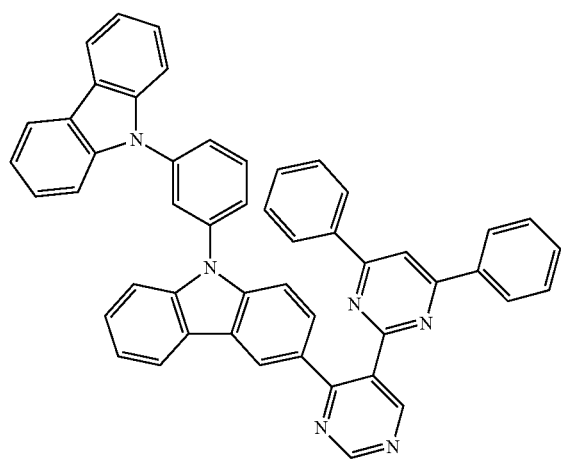
A-63
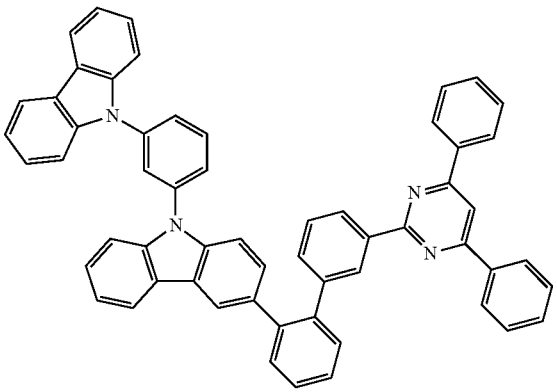
A-61
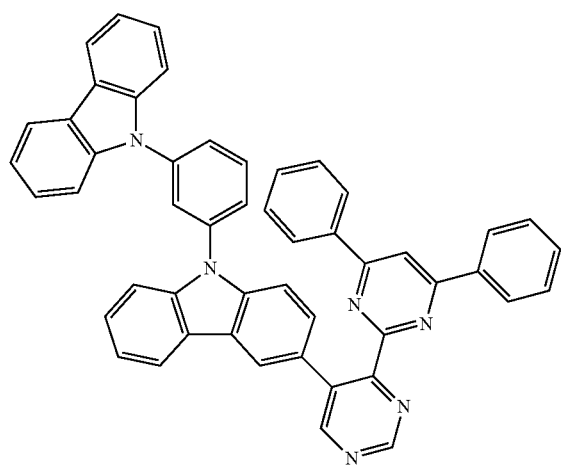
A-64
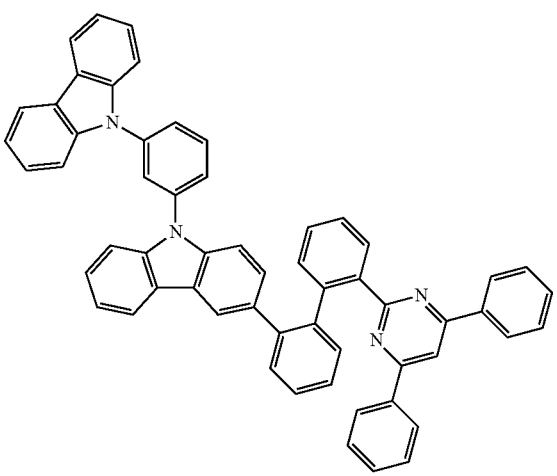

A-65
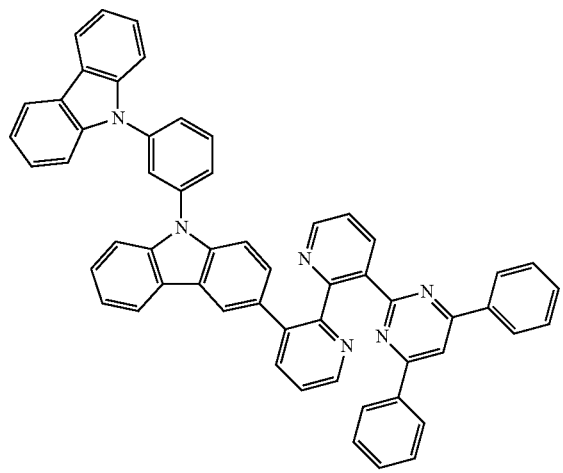
A-66
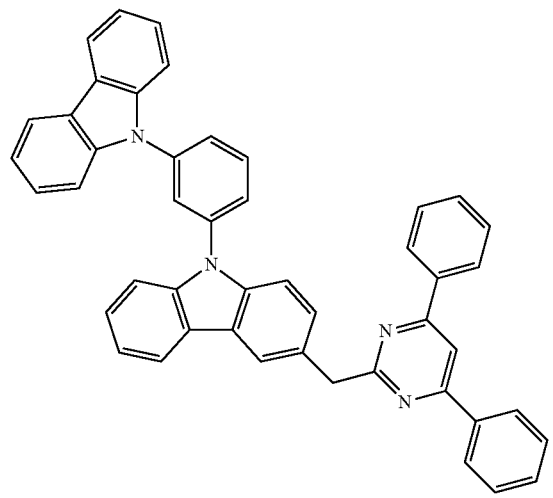
A-67
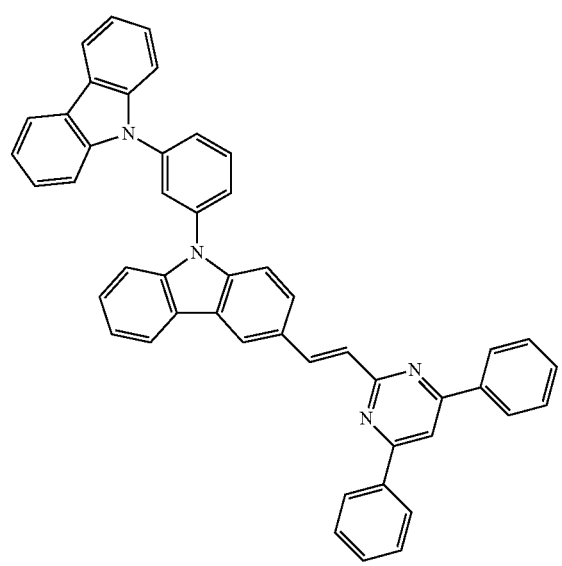
A-68
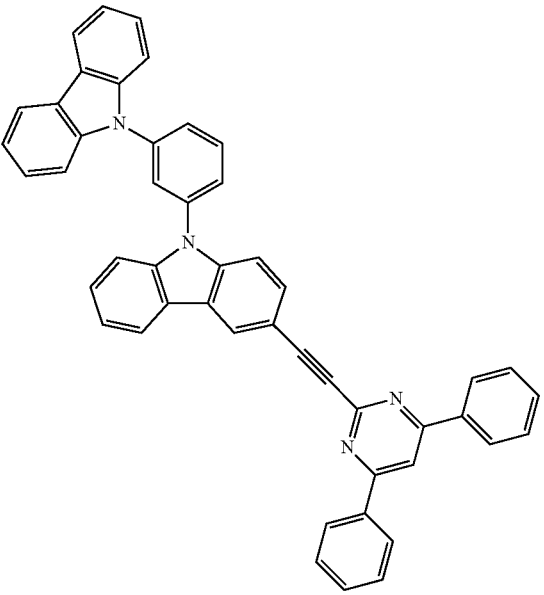
A-69
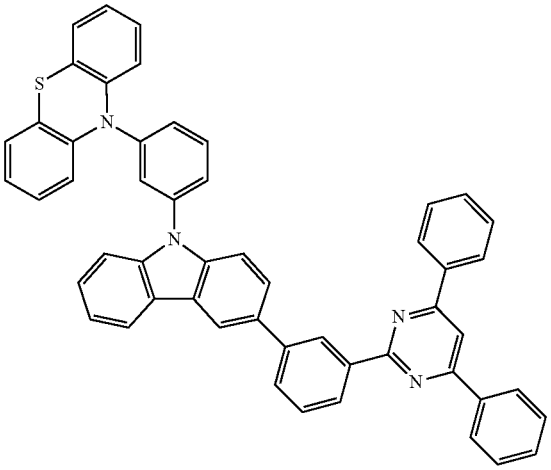
A-70
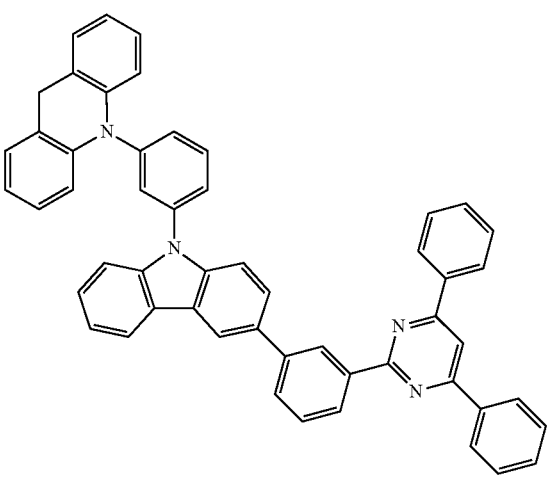

A-71
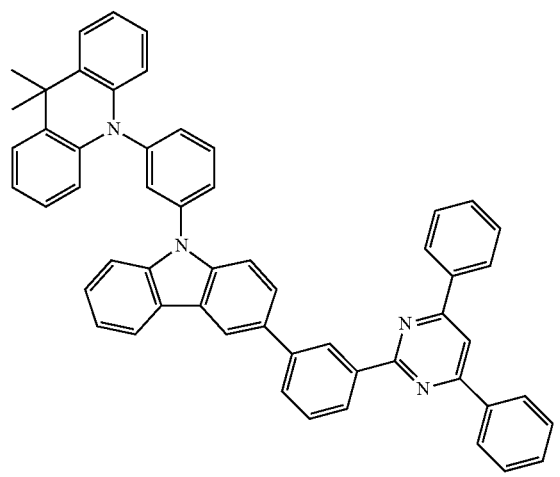
A-74
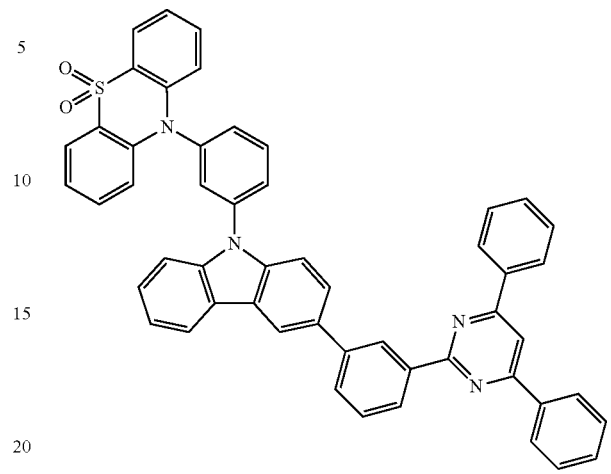
A-72
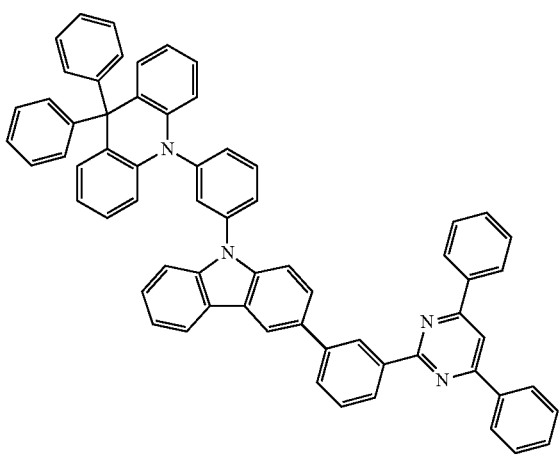
A-75
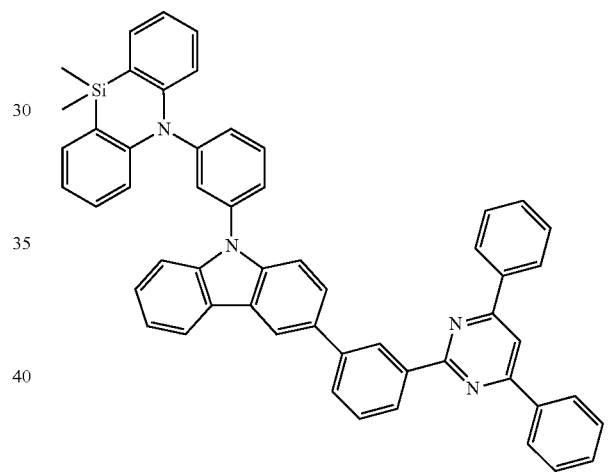
A-73
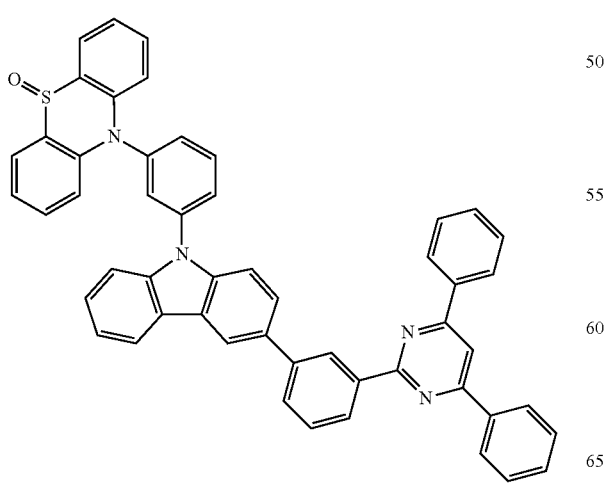
A-76
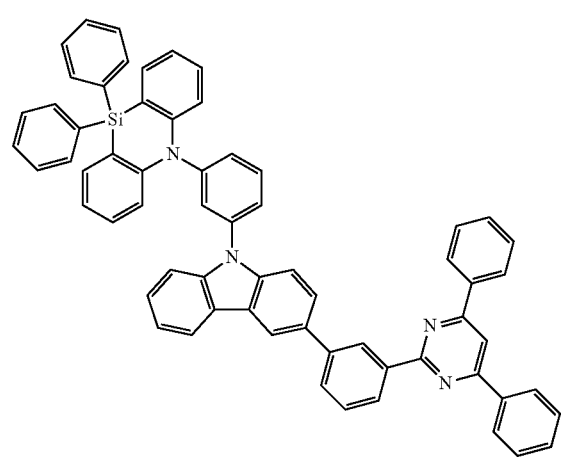

-continued
A-77
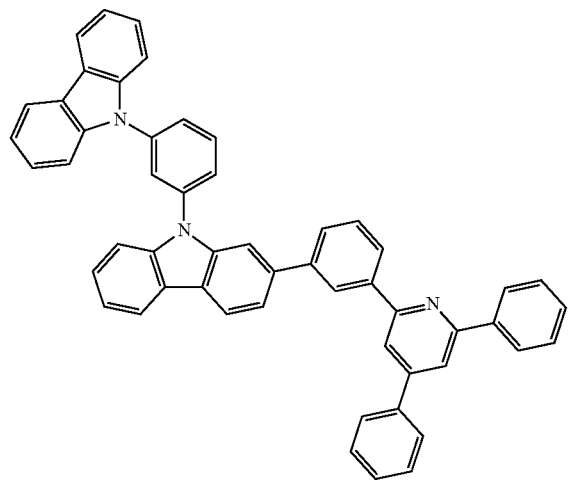
A-78
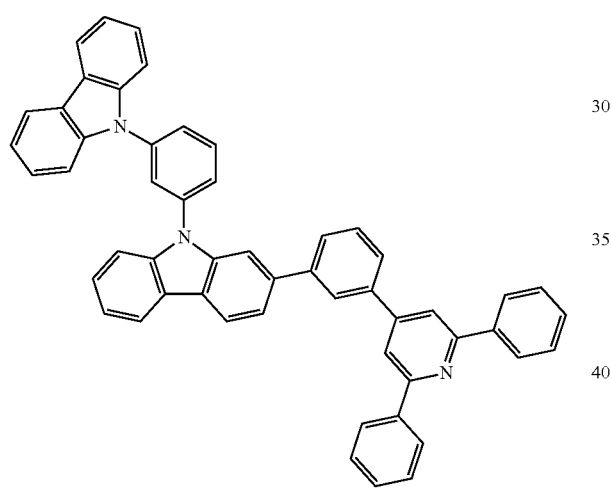
A-79
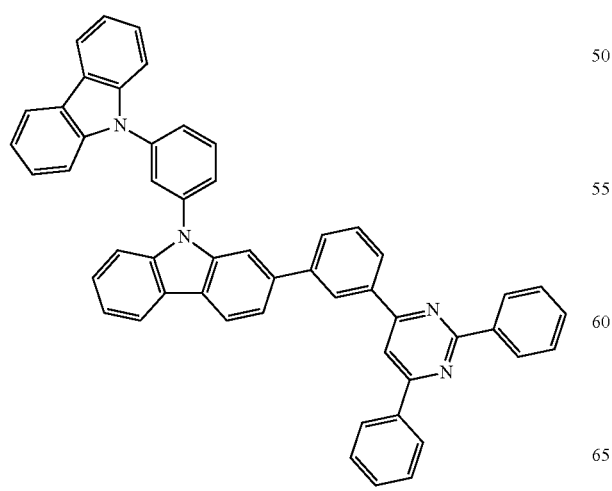
-continued
A-80
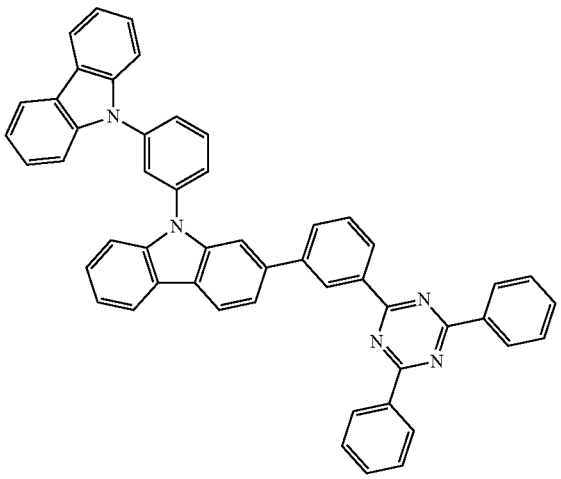
A-81
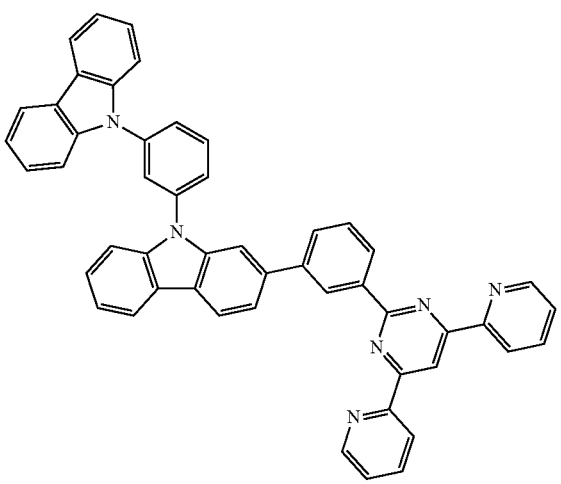
A-82
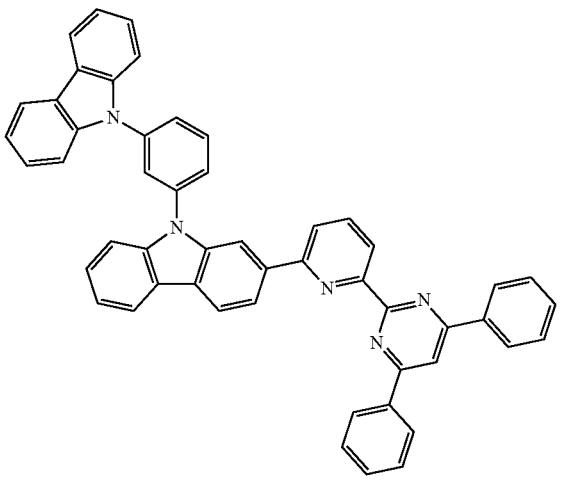

A-83
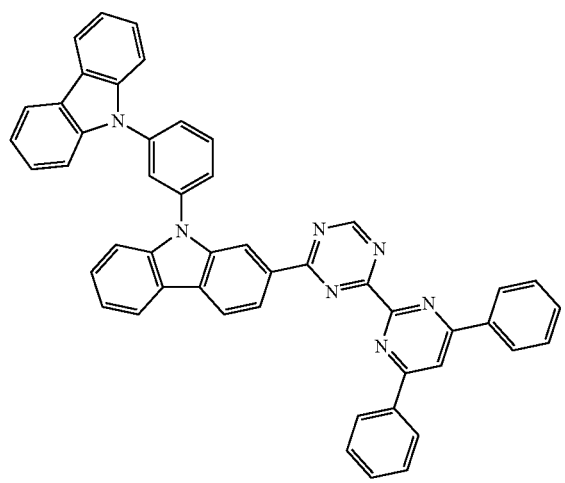
A-84
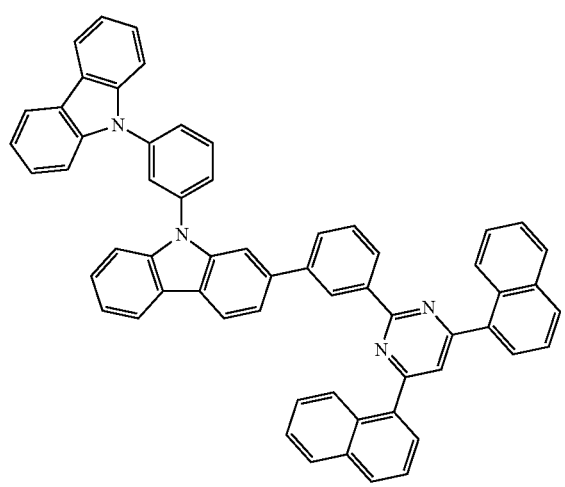
A-85
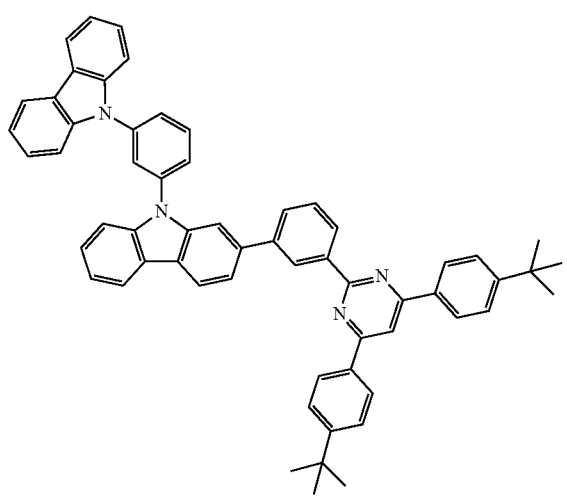
A-86
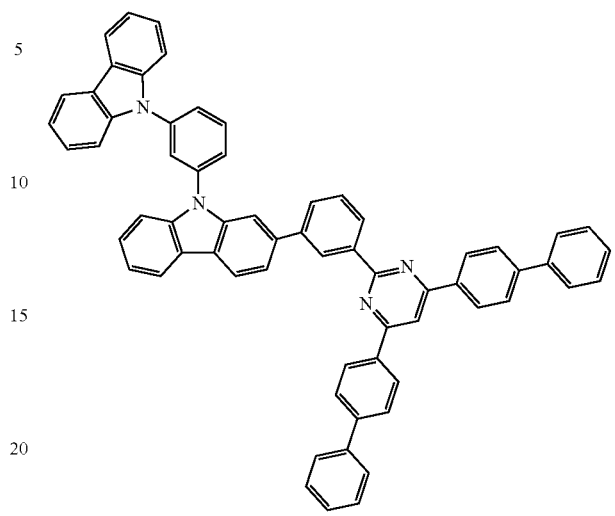
A-87
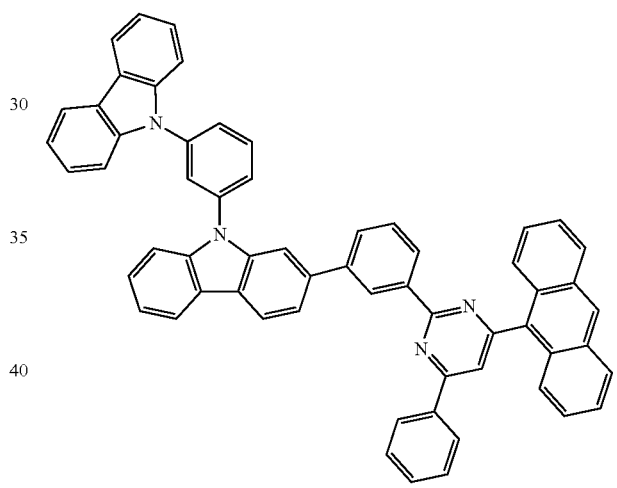
A-88
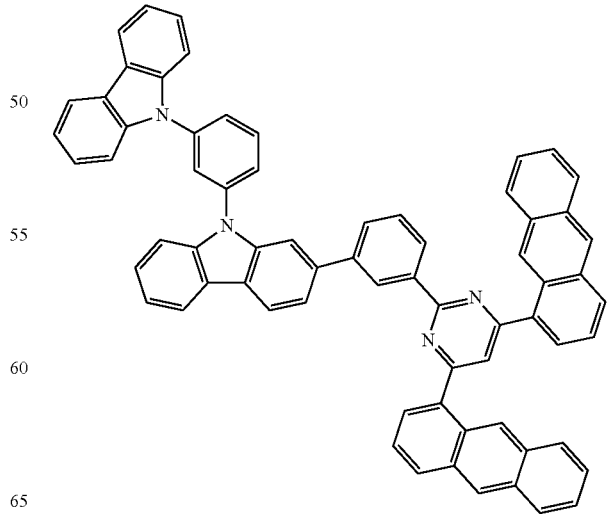

-continued
A-89
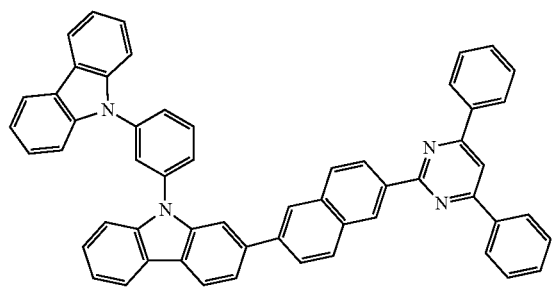
A-90
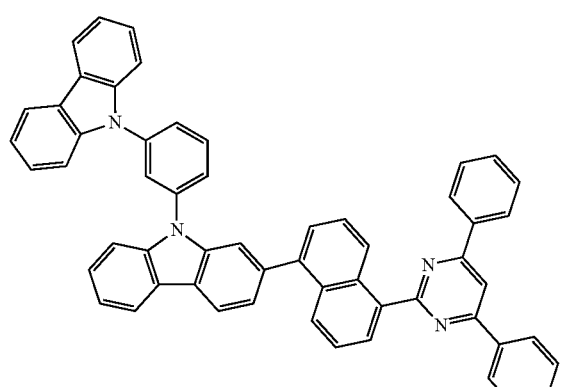
A-91
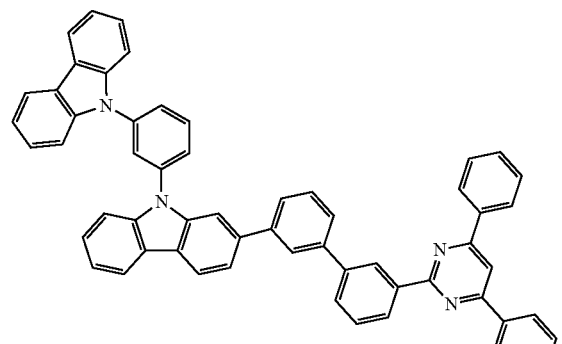
A-92
-continued
A-93
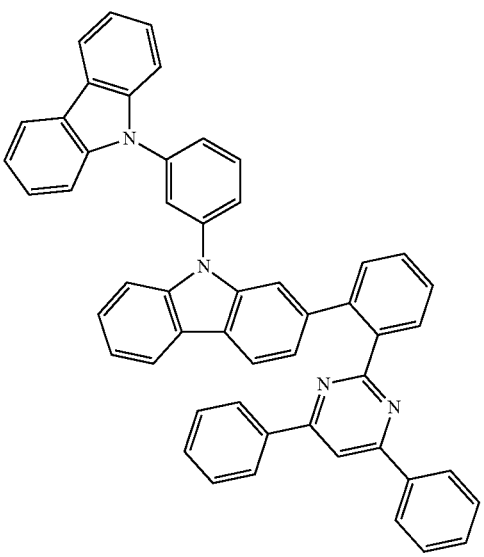
A-94
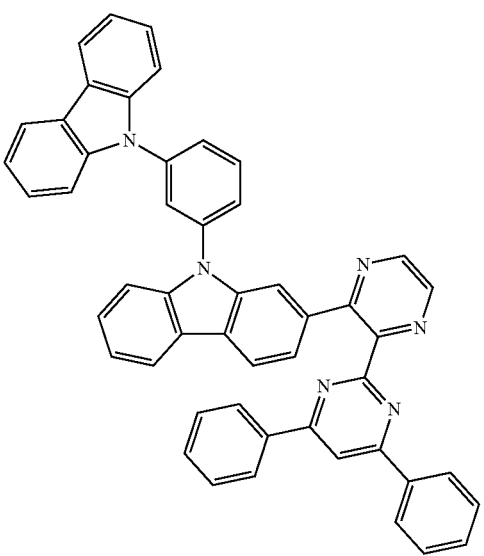
A-95
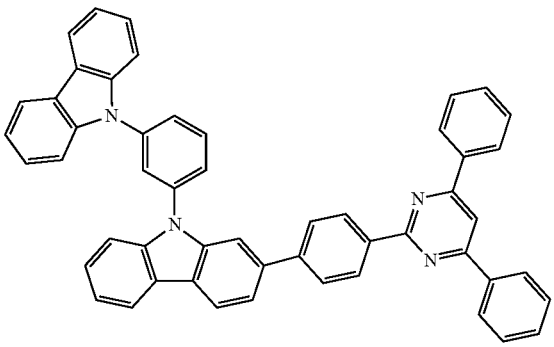

A-96
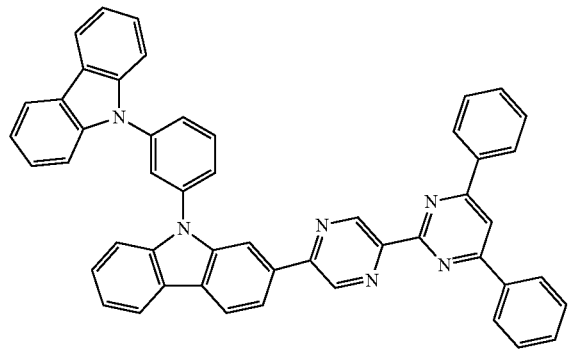
A-99
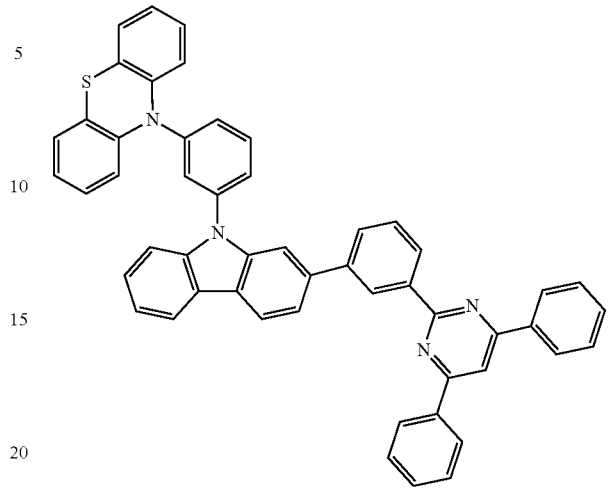
A-97
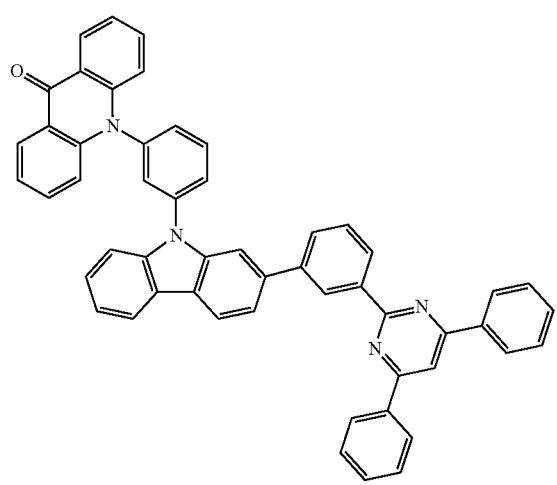
A-100
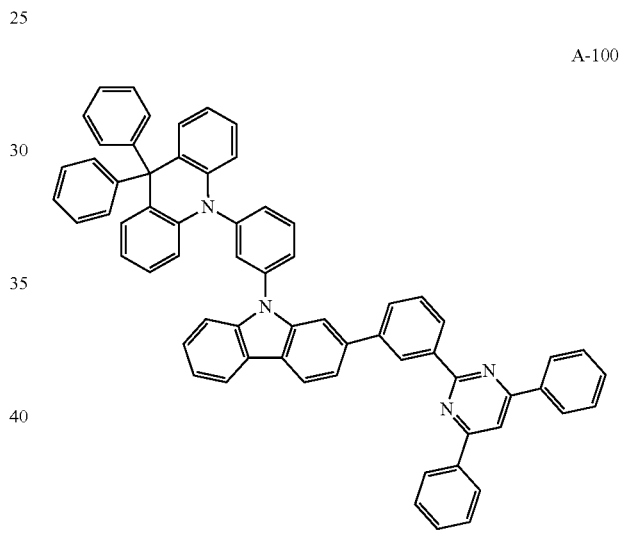
A-98
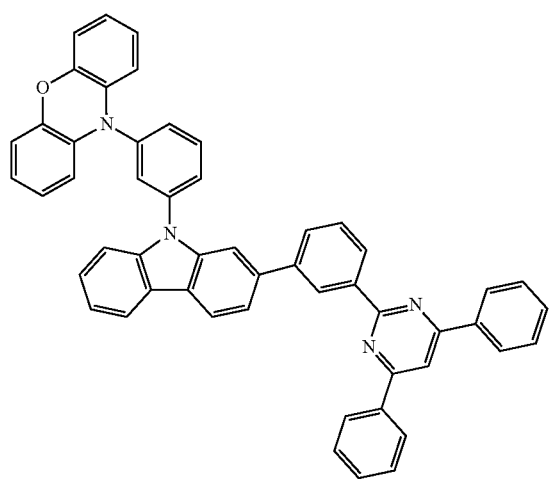
A-101
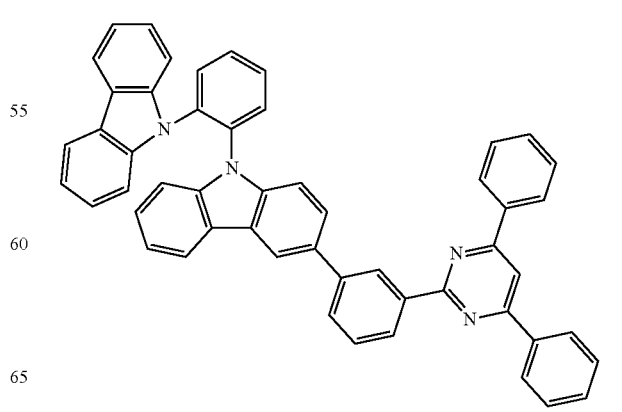

A-102
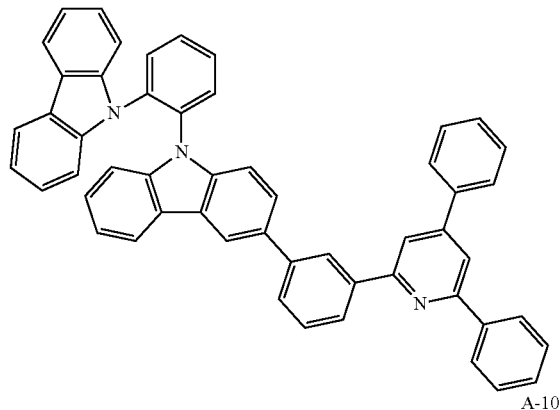
A-103
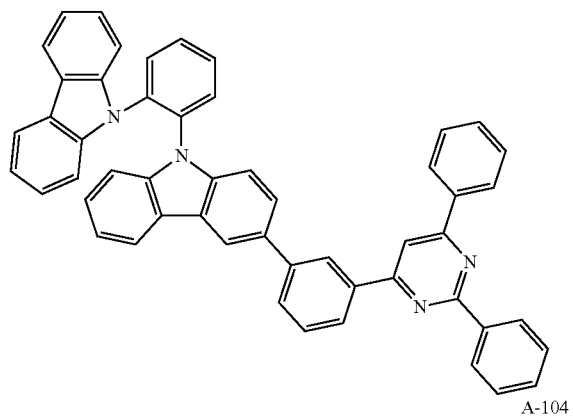
A-104
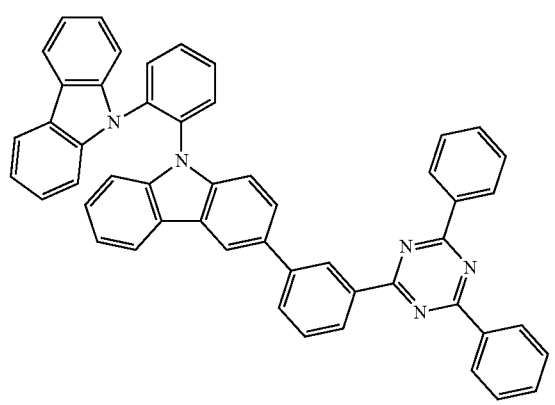
A-105
A-106
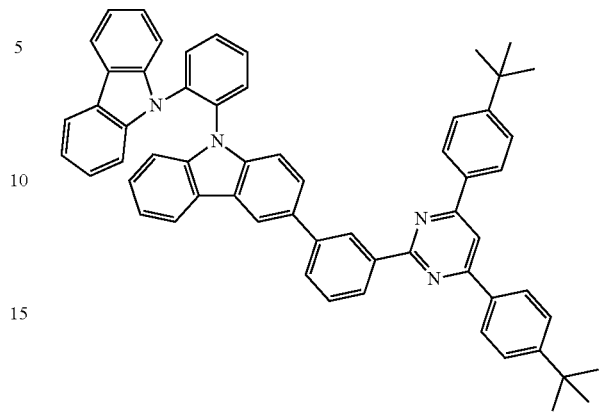
A-107
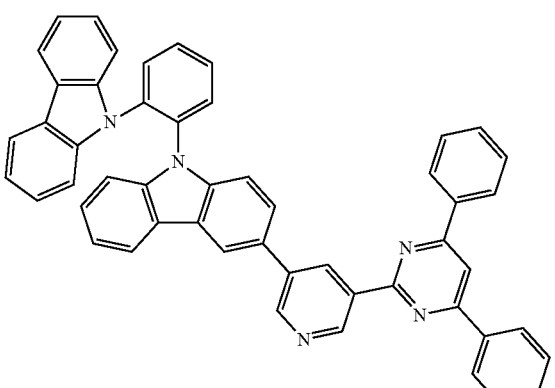
A-108
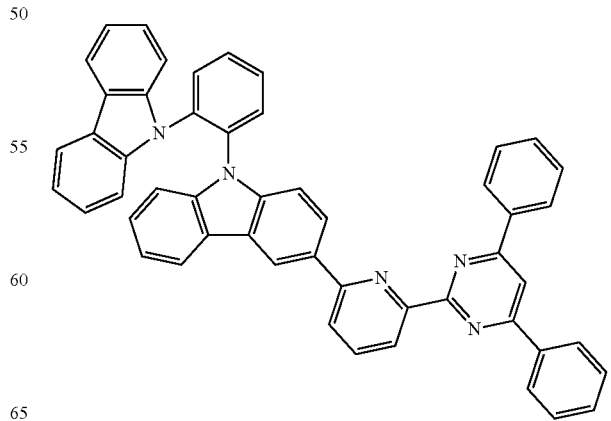

A-109
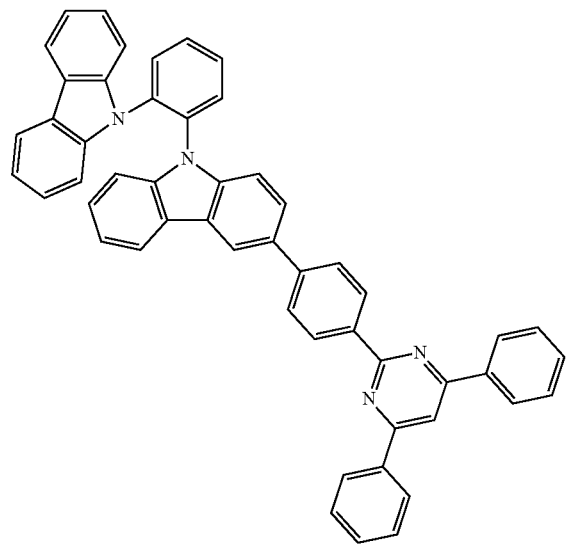
A-110
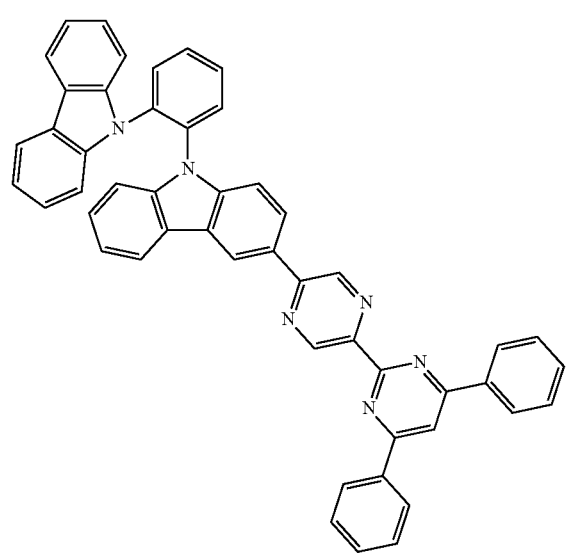
A-111
A-112
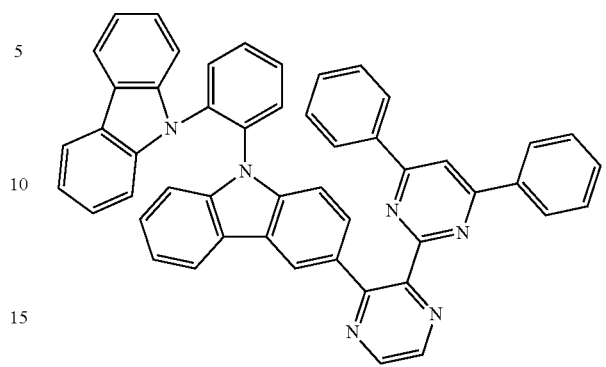
A-113
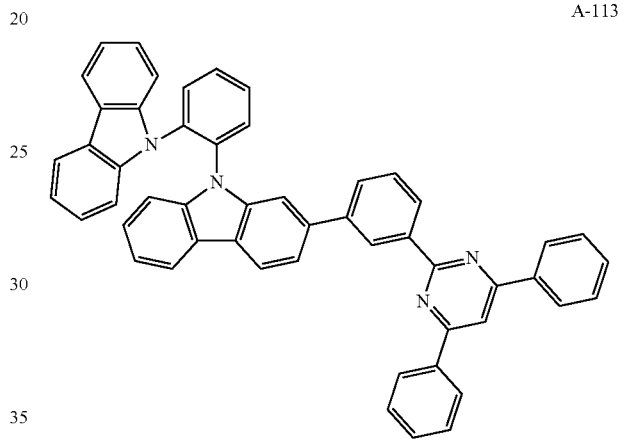
A-114
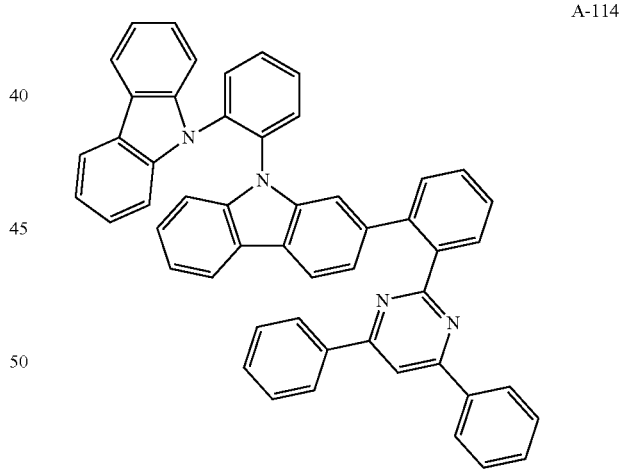
A-115
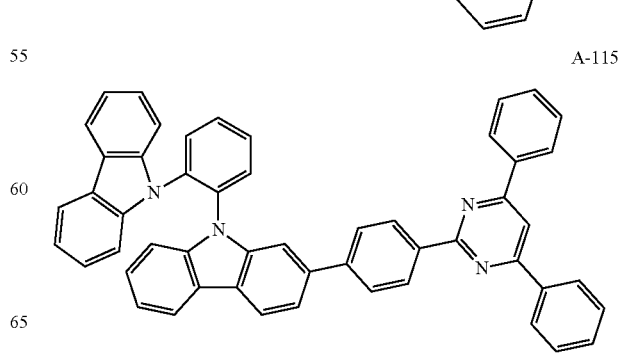

-continued
A-116
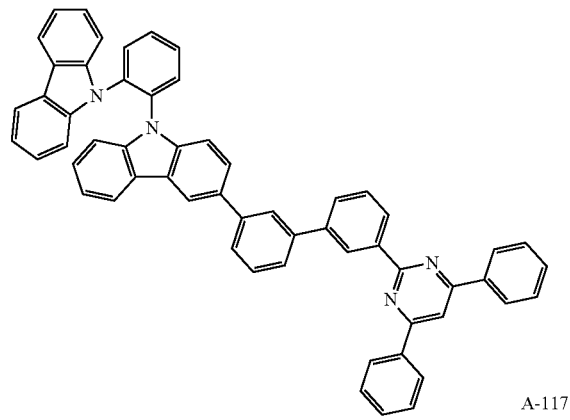
A-117
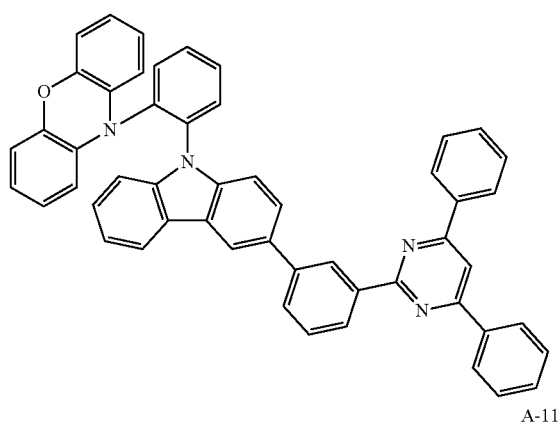
A-118
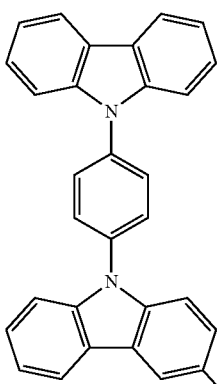
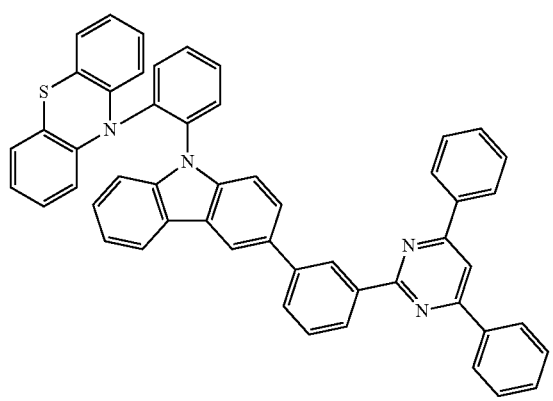
A-119
-continued
A-120
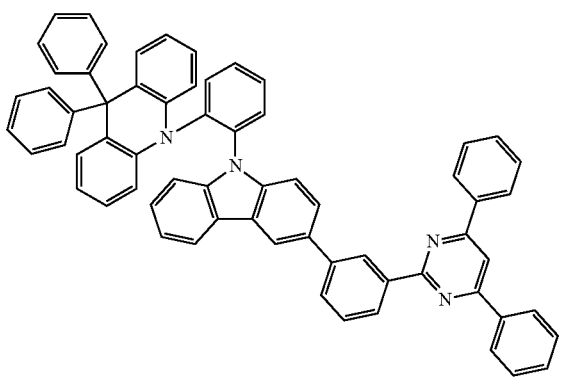
A-121
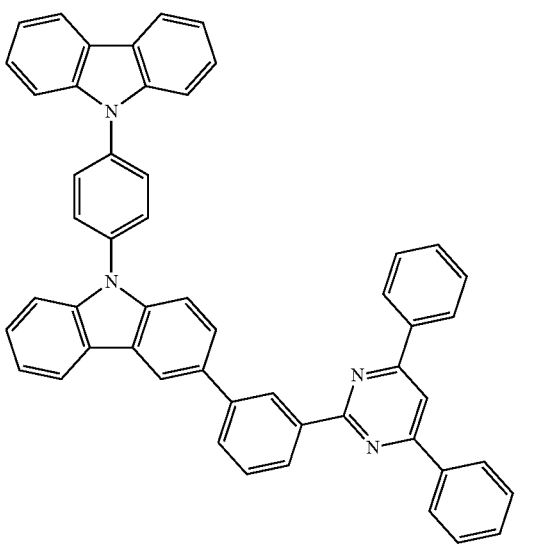
A-122
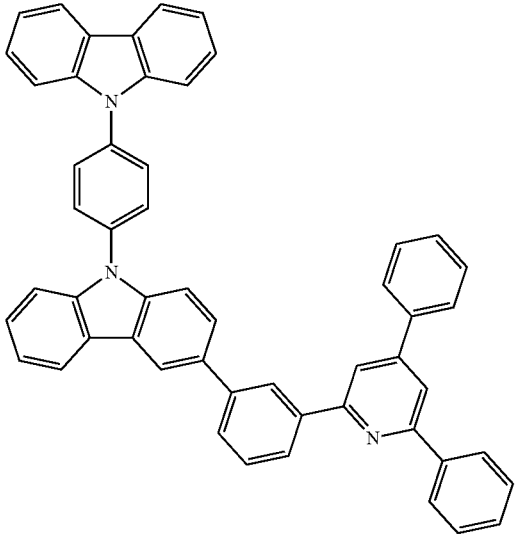

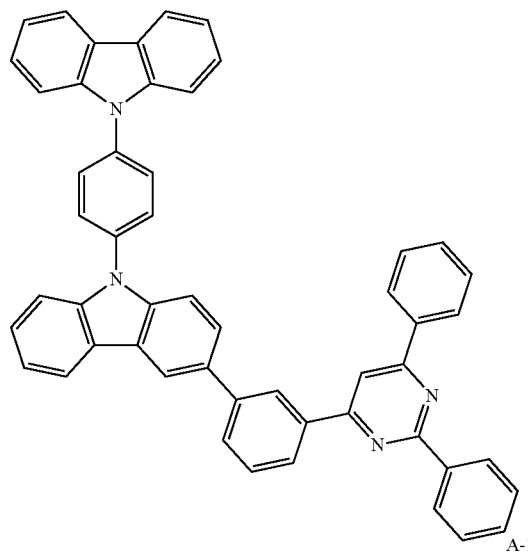
A-123
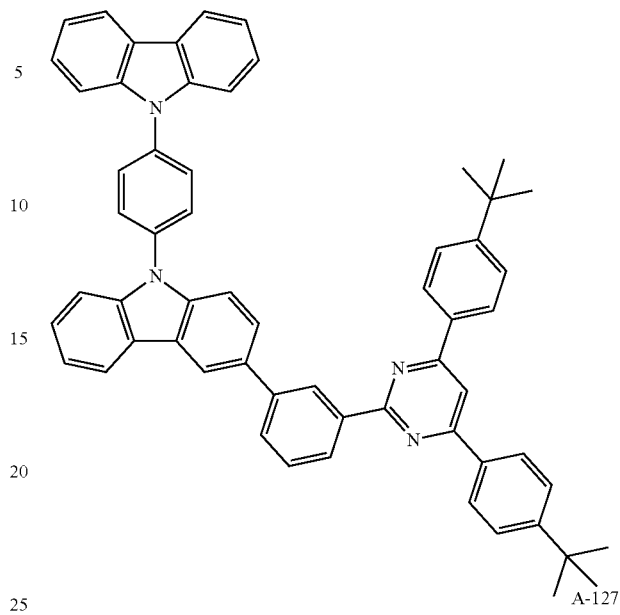
A-126
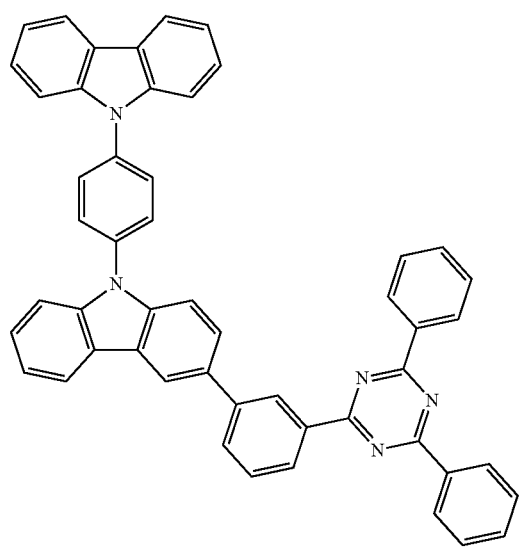
A-124
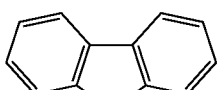
A-125
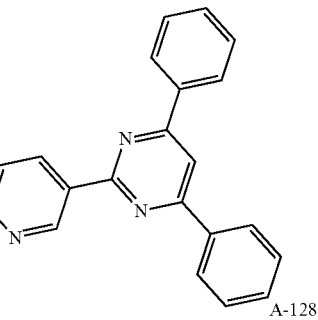
A-127
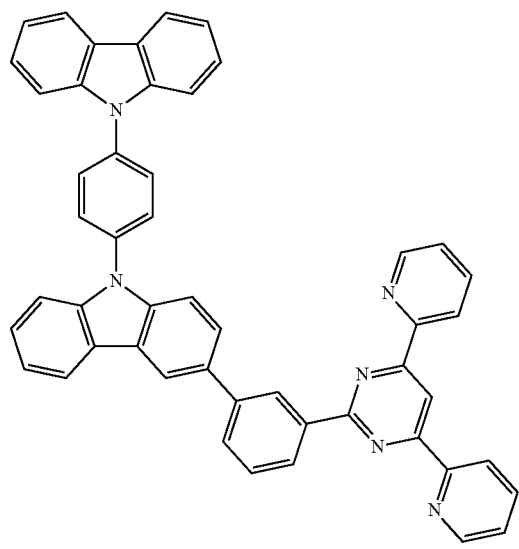
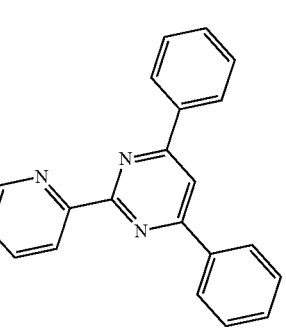
A-128

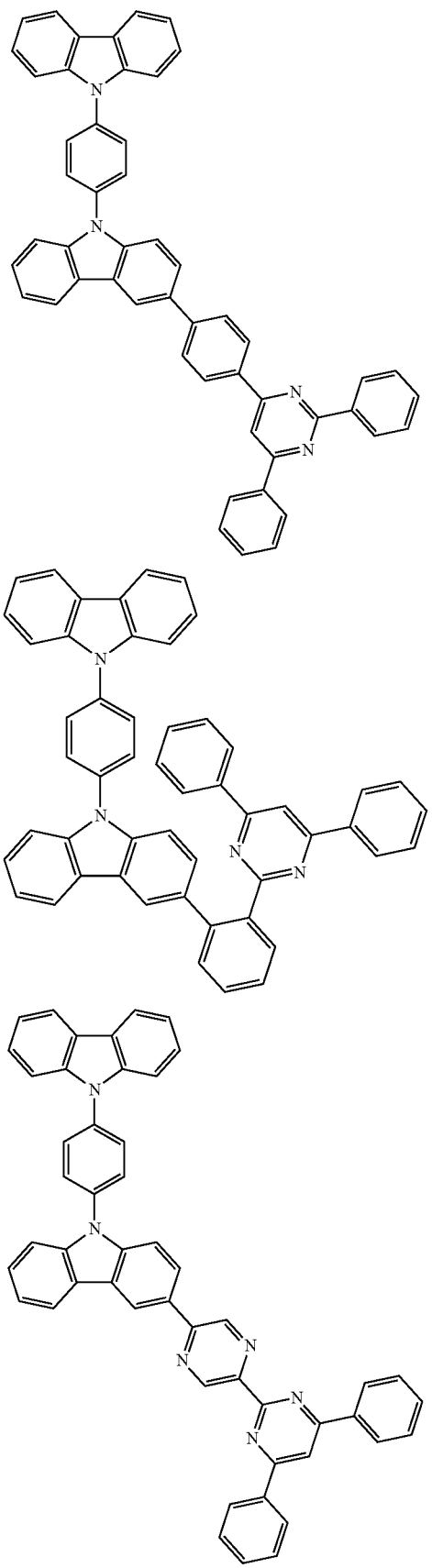
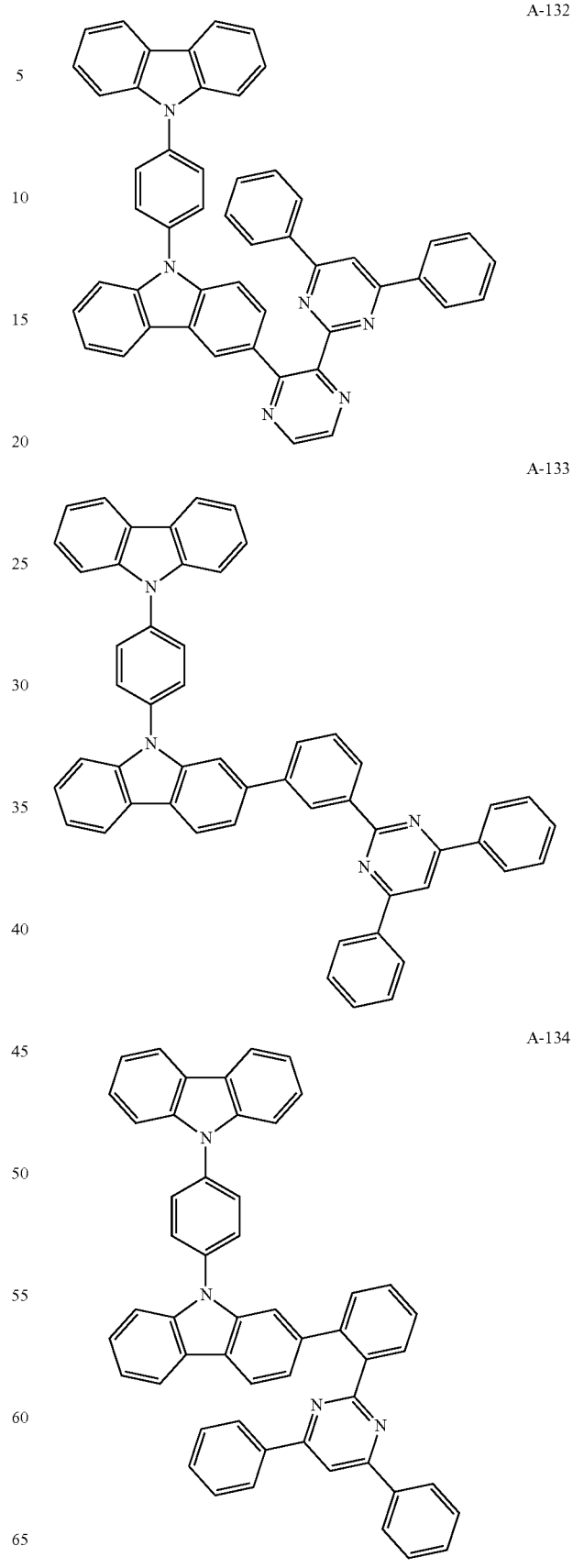

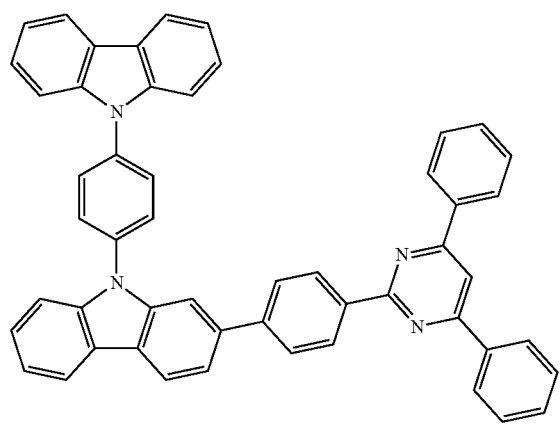
A-135
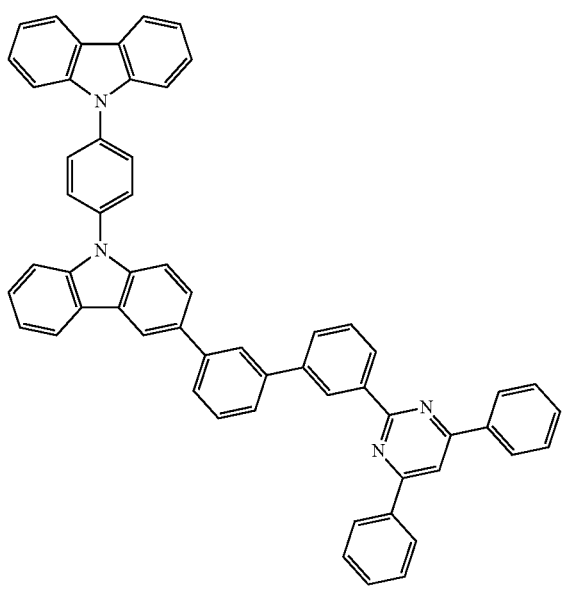
A-136
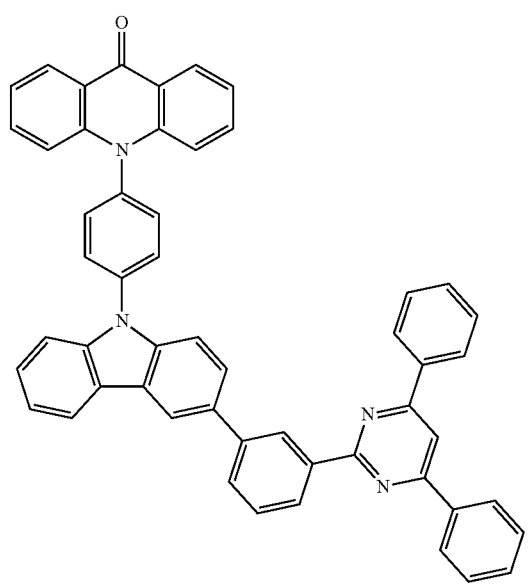
A-137
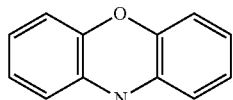
A-138
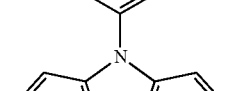
A-139
A-140

The organic optoelectronic device may be selected from an organic photoelectric device, an organic light emitting diode, an organic solar cell, an organic transistor, an organic photoconductor drum, and an organic memory device.

According to another embodiment, an organic light emitting diode including an anode, a cathode, and at least one organic thin layer between the anode and the cathode is provided. At least one organic thin layer includes the compound for an organic optoelectronic device described above.

The organic thin layer may be selected from an emission layer, a hole transport layer (HTL), a hole injection layer (HIL), an electron transport layer (ETL), an electron injection layer (EIL), a hole blocking layer, and a combination thereof.

The compound for an organic optoelectronic device may be included in an emission layer.

The compound for an organic photoelectric device may be used as a phosphorescent or fluorescent host material in an emission layer.

According to yet another embodiment, a display device including the organic light emitting diode is provided.

BRIEF DESCRIPTION OF THE DRAWINGS

The above and other aspects, advantages and features of this disclosure will become more apparent by describing in further detail exemplary embodiments thereof with reference to the accompanying drawings, in which.

DETAILED DESCRIPTION

Figure 1:
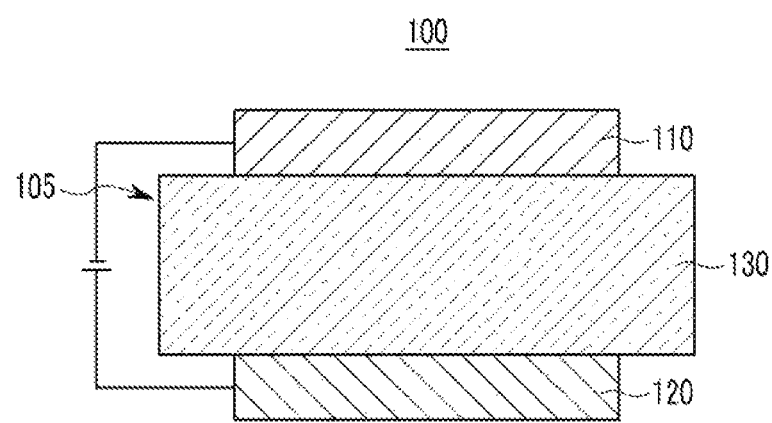
FIGS. 1 to 5 are cross-sectional views showing exemplary embodiments of organic light emitting diodes including an exemplary embodiment of a compound for an organic optoelectronic device.

Exemplary embodiments will hereinafter be described in detail. However, these embodiments are only exemplary, and the present disclosure is not limited thereto but rather is defined by the scope of the appended claims.

It will be understood that when an element is referred to as being "on" another element, it may be directly on the other element or intervening elements may be present therebetween. In contrast, when an element is referred to as being "directly on" another element, there are no intervening elements present. It will be understood that, although the terms first, second, third etc. may be used herein to describe various elements, components, regions, layers and/or sections, there elements, components, regions, layers and/or sections should not be limited by these terms. These terms are only used to distinguish one element, component, region, layer or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a", "an" and "the" are intended to include the plural forms as well, unless the context clearly indicates otherwise. The term "or" means "and/or." As used herein, the term "and/or" includes any and all combinations of one or more of the associated listed items. Expressions such as "at least one of," when preceding a list of elements, modify the entire list of elements and do not modify the individual elements of the list.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may typically have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

As used herein, when specific definition is not otherwise provided, the term "substituted" refers to a group or moiety substituted with deuterium, a halogen, a hydroxy group, an amino group, a substituted or unsubstituted C1 to C30 amine group, a nitro group, a substituted or unsubstituted C3 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C10 trifluoroalkyl group such as a trifluoromethyl group, and the like, or a cyano group instead of at least one hydrogen of a substituting group or compound.

Two adjacent substituents may be selected from an amino group, a substituted or unsubstituted C1 to C20 amine group, a nitro, a substituted or unsubstituted C3 to C40 silyl group, a C1 to C30 alkyl group, a C1 to C10 alkylsilyl group, a C3 to C30 cycloalkyl group, a C6 to C30 aryl group, a C1 to C20 alkoxy group, or a trifluoroalkyl group such as a trifluoromethyl group, and the two substituents may be fused to each other to provide a ring having 3 to 8 atoms in the ring.

As used herein, when specific definition is not otherwise provided, the term "hetero" refers to a substituent, group, or compound including 1 to 3 hetero atoms selected from N, O, S, and P, and remaining carbons in one functional group.

As used herein, when a definition is not otherwise provided, the term "combination thereof" when used in the context of substituents or groups refers to at least two substituents or groups bound to each other by a linker, or at least two substituents or groups condensed to each other.

In the specification, when a definition is not otherwise provided, the term "alkyl group" may refer to an aliphatic hydrocarbon group. The alkyl group may be a saturated group without any alkene group or alkyne group.

The alkyl group may be branched, linear, or cyclic. The alkyl group may have the specified number of carbon atoms. More specifically, the alkyl group may be a C1 to C10 alkyl group or a C1 to C6 alkyl group. For example, the C1 to C4 alkyl group may have 1 to 4 carbon atoms, and may be selected from methyl, ethyl, propyl, iso-propyl, n-butyl, iso-butyl, sec-butyl, and t-butyl. Examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

The "alkenyl group" may refer to a substituent of at least one carbon-carbon double bond of at least two carbons.

The "alkynyl group" may refer to a substituent of at least one carbon-carbon triple bond of at least two carbons.

The term "alkenylene group" may refer to a straight or branched chain, divalent hydrocarbon group having at least one carbon-carbon double bond (e.g., ethenylene (—HC=CH—)).

The term "alkylene group" may refer to a straight or branched chain, saturated, divalent aliphatic hydrocarbon group, (e.g., methylene (—$CH_2$—) or, propylene (—$(CH_2)_3$—)).

The term "aromatic group" may refer to a substituent including all elements of the cycle having p-orbitals which form conjugation. Examples may include an aryl group and a heteroaryl group.

The "aryl group" may refer to a monocyclic or fused ring polycyclic (i.e., rings sharing adjacent pairs of carbon atoms) substituent.

The term "heteroaryl group" may refer to an aryl group including 1 to 3 hetero atoms selected from N, O, S, and P as ring member(s). The heteroaryl group may be a fused ring cyclic group where each cycle may include the 1 to 3 heteroatoms.

The term "arylene group" may refer to a divalent group formed by the removal of two hydrogen atoms from one or more rings of an arene, wherein the hydrogen atoms may be removed from the same or different rings (e.g., phenylene or napthylene).

The term "heteroarylene group" may refer to a divalent radical formed by the removal of two hydrogen atoms from one or more rings of a heteroaryl moiety, wherein the hydrogen atoms may be removed from the same or different rings (preferably the same ring), each of which rings may be aromatic or nonaromatic.

The term "alkoxy group" may refer to an alkyl group that is linked via an oxygen (i.e., alkyl-O—), for example methoxy, ethoxy, and sec-butyloxy groups.

The term "aryloxy group" may refer to an aryl group that is linked via an oxygen (i.e., aryl-O—).

The term "silyl group" may refer to —$SiR_3$ wherein each R is independently a substituted or unsubstituted alkyl.

The term "silyloxy group" may refer to a silyl group that is linked via an oxygen (i.e., silyl-O—).

The term "alkoxycarbonylamino group" may refer to a group represented by —NHCOO-alkyl in which alkyl is as defined herein.

The term "aryloxycarbonylamino group" may refer to a group represented by —NHCOO-aryl in which aryl is as defined herein.

The term "alkoxycarbonyl group" may refer to an —C(O)—O-alkyl group in which alkyl is as defined herein.

The term "acyl group" may refer to the group —C(O)—R where R is H, C1-C20 alkyl, C2-C20 alkenyl, C2-C20 alkynyl, heterocycloalkyl, aryl, heteroaryl, alkyl aryl, alkyl heteroaryl, alkenyl aryl, alkenyl heteroaryl, alkynyl aryl, alkynyl heteroaryl.

The term "heterocycloalkyl" may refer to a non-aromatic monocyclic or polycyclic ring comprising carbon and hydrogen atoms and at least one heteroatom ring member.

The term "alkyl aryl" may refer to an alkyl group covalently linked to a substituted or unsubstituted aryl group that is linked to a compound.

The term "alkyl heteroaryl" may refer to an alkyl group covalently linked to a substituted or unsubstituted heteroaryl group that is linked to a compound.

The term "alkenyl aryl" may refer to an alkenyl group covalently linked to a substituted or unsubstituted aryl group that is linked to a compound.

The term "alkenyl heteroaryl" may refer to an alkenyl group covalently linked to a substituted or unsubstituted heteroaryl group that is linked to a compound.

The term "alkynyl aryl" may refer to an alkynyl group covalently linked to a substituted or unsubstituted aryl group that is linked to a compound.

The term "alkynyl heteroaryl" may refer to an alkynyl group covalently linked to a substituted or unsubstituted heteroaryl group that is linked to a compound.

The term "acyloxy group" may refer to a group represented by —OC(O)R where R is H, C1-C20 alkyl, C2-C20 alkenyl, C2-C20 alkynyl, heterocycloalkyl, aryl, heteroaryl, alkyl aryl, alkyl heteroaryl, alkenyl aryl, alkenyl heteroaryl, alkynyl aryl, alkynyl heteroaryl.

The term "acylamino group" may refer to a group represented by —NRC(O)R' where each R and R' is independently H, C1-C20 alkyl, C2-C20 alkenyl, C2-C20 alkynyl, heterocycloalkyl, aryl, heteroaryl, alkyl aryl, alkyl heteroaryl, alkenyl aryl, alkenyl heteroaryl, alkynyl aryl, alkynyl heteroaryl.

The term "sulfonyl group" may refer to a group represented by —$SO_2$—R wherein R is selected from H, aryl, heteroaryl, C1 to C20 alkyl, C1 to C20 alkyl substituted with halogens, C2-C20 alkenyl, C2-C20 alkynyl, heterocycloalkyl, aryl, heteroaryl, alkyl aryl, alkyl heteroaryl, alkenyl aryl, alkenyl heteroaryl, alkynyl aryl, alkynyl heteroaryl.

The term "sulfamoylamino group" may refer to a group represented by —NH—$SO_2$—$NR_1R_2$, wherein $R_1$ and $R_2$ are independently hydrogen, an alkyl, or an aryl.

The term "alkylthiol" may refer to -alkyl-SH in which alkyl is as defined herein.

The term "arylthiol" may refer to -aryl-SH in which aryl is as defined herein.

The term "heterocyclothiol" may refer to -heterocyclic group-SH in which heterocyclic group is a monocyclic or polycyclic ring comprising at least one heteroatom ring member.

The term "ureide" may refer to the group —C(O)NRC(O)NR'R" where each R, R', R" is independently H, C1-C20 alkyl, C2-C20 alkenyl, C2-C20 alkynyl, heterocycloalkyl, aryl, heteroaryl, alkyl aryl, alkyl heteroaryl, alkenyl aryl, alkenyl heteroaryl, alkynyl aryl, alkynyl heteroaryl.

The term "amino" as used herein may refer to a group of the formula (—$NH_2$).

The term "substituted or unsubstituted C1 to C20 amine group" as used herein may refer to a group of the formula —$N(R)_2$, wherein one R group may be hydrogen, and the other or both R groups may be the same or different substituted or unsubstituted C1-C20 alkyl or C6-C20 aryl.

In this specification, the term "hole properties" may refer to a characteristic that a hole formed in the positive electrode is easily injected into the emission layer and transported in the emission layer due to a conductive characteristic according to HOMO level. More specifically, the hole properties are similar to electron-repelling properties.

In this specification, the term "electronic properties" may refer to a characteristic that an electron formed in the negative electrode is easily injected into the emission layer and transported in the emission layer due to a conductive characteristic according to LUMO level. More specifically, the electronic properties are similar to electron-attracting properties.

A compound for an organic optoelectronic device according to an embodiment has a structure including two fused rings linked to a phenylene core. The structure may selectively include various substituents.

The compound may be used a light emitting material, a hole injection material, or a hole transport material of an organic optoelectronic device. Particularly, it may be adapted for use as an electron injection material or an electron transport material.

The compound for an organic optoelectronic device includes a core part and various substituents for substituting the core part, and thus may have various energy band gaps.

The compound may have an appropriate energy level depending on the substituents, and thus may fortify electron transport capability and hole transport capability of an organic optoelectronic device and bring about excellent effects in terms of efficiency and driving voltage, and may also have excellent electrochemical and thermal stability and thus improve life-span characteristics during the operation of the organic optoelectronic device.

According to an embodiment, a compound for an organic optoelectronic device represented by the following Chemical Formula 1 is provided.

Chemical Formula 1

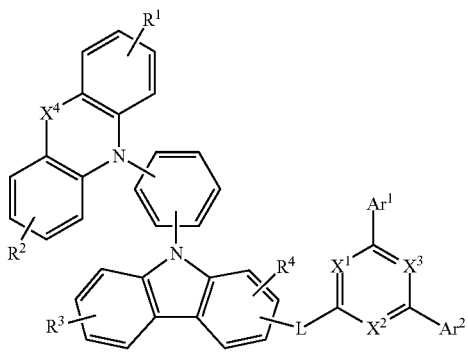

In Chemical Formula 1, $X^1$ to $X^3$ are independently —C(R')— or —N—, provided that at least one of $X^1$ to $X^3$ is —N—, $X^4$ is a single bond, —C(R')(R")—, —O—, —S—, —S(=O)—, —S(=O)$_2$—, —Si(R')(R")—, or —C(C=O)—, $R^1$ to $R^4$, R', and R" are independently hydrogen, deuterium, a halogen, a cyano group, a hydroxyl group, an amino group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, L is a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or a combination thereof, and $Ar^1$ and $Ar^2$ are independently a substituted or unsubstituted C6 to C30 aryl group or a substituted or unsubstituted C2 to C30 heteroaryl group.

The $X^4$ may be selected from the above examples depending on desired characteristics of the compound.

Specific examples of the $Ar^1$ and $Ar^2$ are independently a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof, but are not limited thereto.

A total conjugation length of the compound may be controlled by selecting L appropriately, and thereby bandgap of triplet energy may be adjusted. Accordingly, a material needed for an organic optoelectronic device may be realized. In addition, ortho, para, or meta binding positions may adjust the triplet energy bandgap.

Examples of the L may include a substituted or unsubstituted phenylene group, a substituted or unsubstituted biphenylene group, a substituted or unsubstituted terphenylene group, a substituted or unsubstituted naphthylene group, a substituted or unsubstituted anthracenylene group, a substituted or unsubstituted phenanthrylene group, a substituted or unsubstituted pyrenylene group, a substituted or unsubstituted fluorenylene group, a substituted or unsubstituted p-terphenyl group, a substituted or unsubstituted m-terphenyl group, a substituted or unsubstituted pyrenylene group, and the like.

More specifically, the L may be a substituted or unsubstituted C2 to C30 heteroarylene group.

Examples of the substituted or unsubstituted C2 to C30 heteroarylene group may include a quinolinylene group, an isoquinolinylene group, a pyridinylene group, a pyrimidinylene group, a triazinylene group, a pyrrolylene group, a pyrazolylene group, an imidazolylene group, an imidazoliylene group, a pyrazinylene group, an indolylene group, a furylylene group, an indazolylene group, a thiophenylene group, a benzothiophenylene group, an isothiazolylene group, and the like.

The compound for an organic optoelectronic device may be represented by the following Chemical Formula 2.

Chemical Formula 2

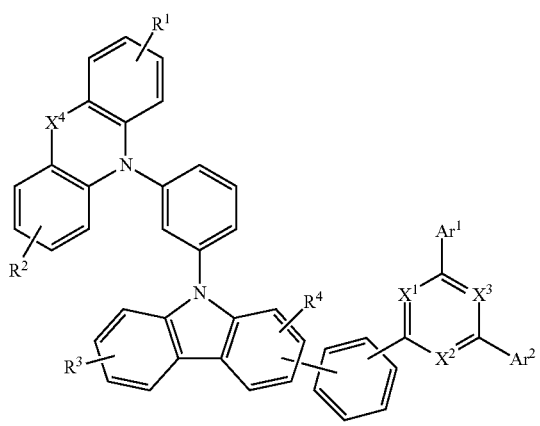

In Chemical Formula 2, $X^1$ to $X^3$ are independently —C(R')— or —N—, provided that at least one of $X^1$ to $X^3$ is —N—, $X^4$ is a single bond, —C(R')(R'')—, —O—, —S—, —S(=O)—, —S(=O)$_2$—, —SiR'R''—, or —C(C=O)—, $R^1$ to $R^4$, R', and R'' are independently hydrogen, deuterium, a halogen, a cyano group, a hydroxyl group, an amino group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and $Ar^1$ and $Ar^2$ are independently a substituted or unsubstituted C6 to C30 aryl group or a substituted or unsubstituted C2 to C30 heteroaryl group.

In the Chemical Formula 2, when two fused rings are linked to a phenylene core at a meta position to provide a kink structure, high solubility and triplet energy due to a decreased conjugation length may be provided.

The compound for an organic optoelectronic device may be represented by the following Chemical Formula 3.

Chemical Formula 3

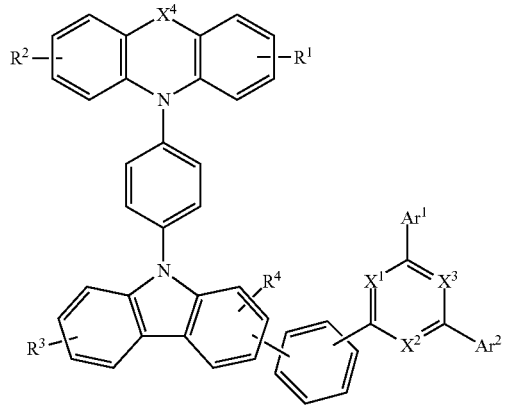

In Chemical Formula 3, $X^1$ to $X^3$ are independently CR' or N, provided that at least one of $X^1$ to $X^3$ is N, $X^4$ is a single bond, —CR'R''—, —O—, —S—, —S(=O)—, —S(=O)$_2$—, —SiR'R''—, or —C(C=O)—, $R^1$ to $R^4$, R', and R'' are independently hydrogen, deuterium, a halogen, a cyano group, a hydroxyl group, an amino group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and $Ar^1$ and $Ar^2$ are independently a substituted or unsubstituted C6 to C30 aryl group or a substituted or unsubstituted C2 to C30 heteroaryl group.

In the above Chemical Formula 3, when the two fused rings are linked to the phenylene core at a para position, the compound may have improved stability.

The compound for an organic optoelectronic device may be represented by the following Chemical Formula 4.

Chemical Formula 4

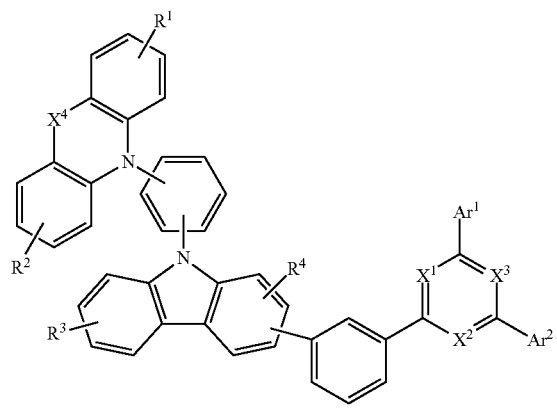

In Chemical Formula 4, $X^1$ to $X^3$ are independently —C(R')— or —N—, provided that at least one of $X^1$ to $X^3$ is —N—, $X^4$ is a single bond, —C(R')(R")—, —O—, —S—, —S(=O)—, —S(=O)$_2$—, —Si(R')(R")—, or —C(C=O)—, $R^1$ to $R^4$, R', and R" are independently hydrogen, deuterium, a halogen, a cyano group, a hydroxyl group, an amino group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and $Ar^1$ and $Ar^2$ are independently a substituted or unsubstituted C6 to C30 aryl group or a substituted or unsubstituted C2 to C30 heteroaryl group.

In the Chemical Formula 4, when L is phenylene, and two substituents are linked to the phenylene at a meta position, the compound has a kink structure and thus may have high solubility and triplet energy due to decreased conjugation length.

The compound for an organic optoelectronic device may be represented by the following Chemical Formula 5.

Chemical Formula 5

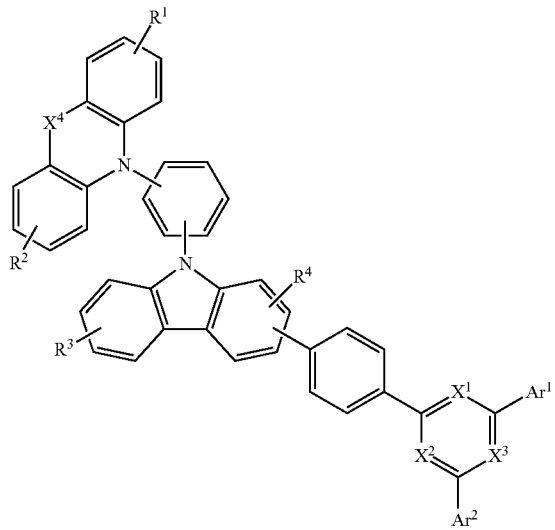

In Chemical Formula 5, $X^1$ to $X^3$ are independently —C(R')— or —N—, provided that at least one of $X^1$ to $X^3$ is —N—, $X^4$ is a single bond, —C(R')(R")—, —O—, —S—, —S(=O)—, —S(=O)$_2$—, —Si(R')(R")—, or —C(C=O)—, $R^1$ to $R^4$, R', and R" are independently hydrogen, deuterium, a halogen, a cyano group, a hydroxyl group, an amino group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and $Ar^1$ and $Ar^2$ are independently a substituted or unsubstituted C6 to C30 aryl group or a substituted or unsubstituted C2 to C30 heteroaryl group.

In the Chemical Formula 5, when L is phenylene, and two substituents are linked to the phenylene at a para position, the compound may have improved structural stability.

The compound for an organic optoelectronic device may be represented by the following Chemical Formula 6, but is not limited thereto.

Chemical Formula 6

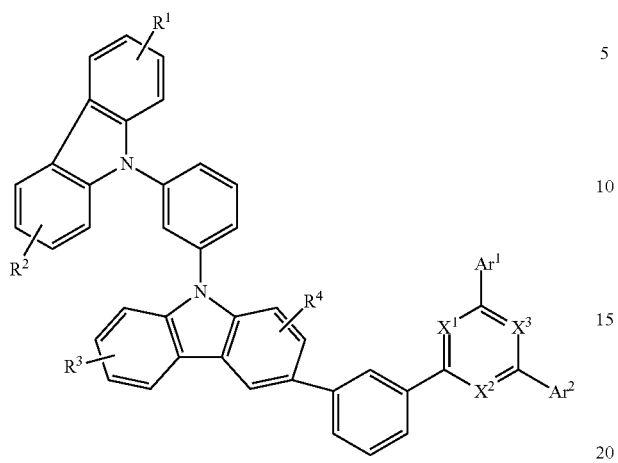

In Chemical Formula 6, $X^1$ to $X^3$ are independently —C(R')— or —N—, provided that at least one of $X^1$ to $X^3$ is —N—, $R^1$ to $R^4$ and R' are independently hydrogen, deuterium, a halogen, a cyano group, a hydroxyl group, an amino group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and $Ar^1$ and $Ar^2$ are independently a substituted or unsubstituted C6 to C30 aryl group or a substituted or unsubstituted C2 to C30 heteroaryl group.

Figure 6:
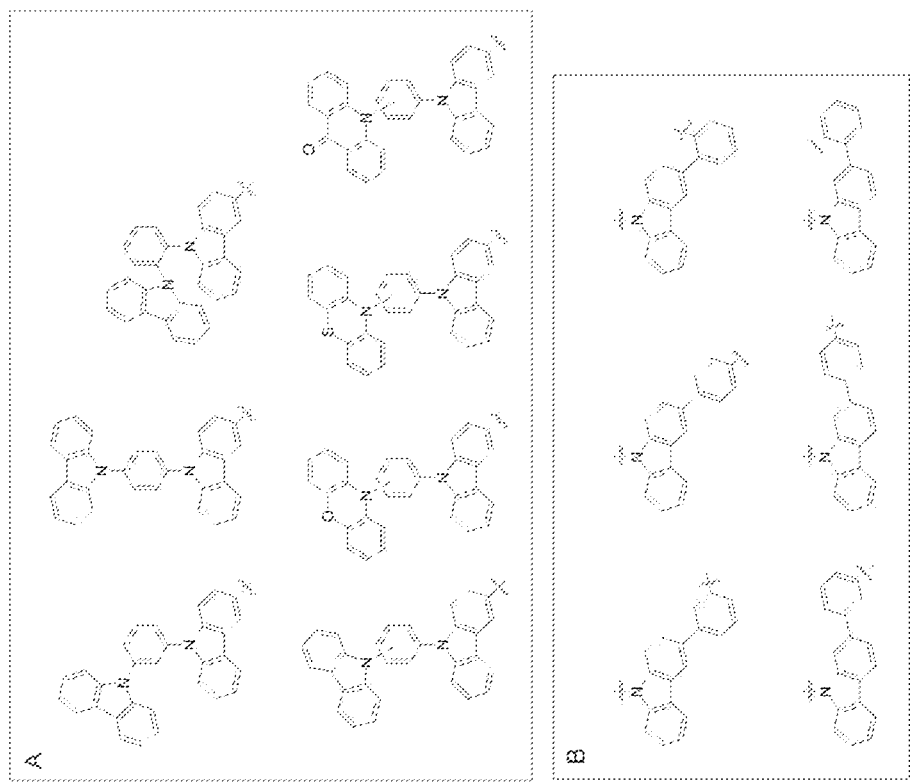
FIG. 6 shows examples of compounds for an organic optoelectronic device according to an embodiment.
Figure 6:
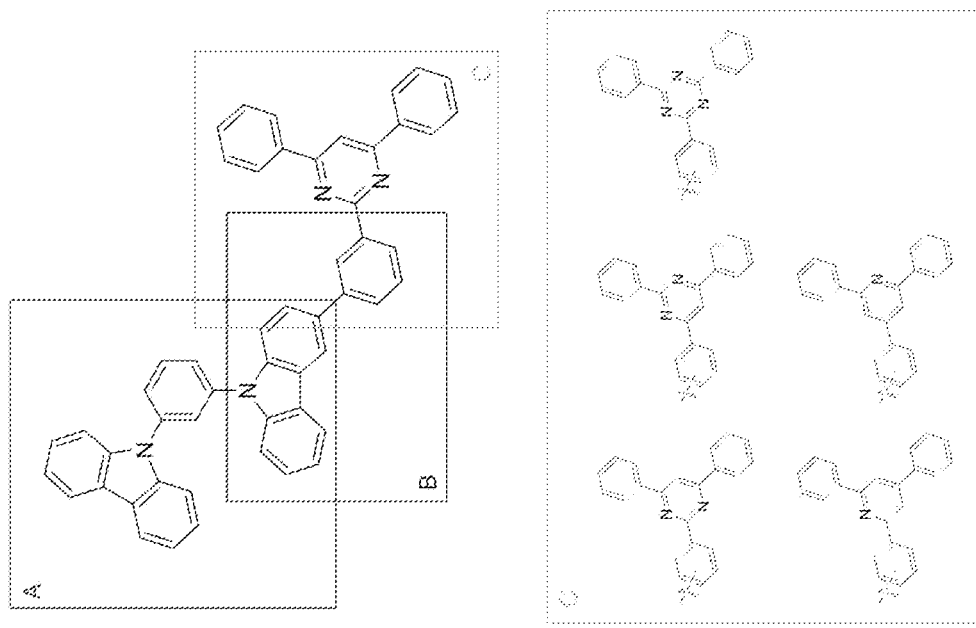

The compound for an organic optoelectronic device may be divided into A, B, and C parts, and each possible functional group of the A, B, and C parts are exemplified in FIG. 6. However, the compound is not limited thereto.

The Chemical Formula in FIG. 6 shows an example of a compound for an organic optoelectronic device according to an embodiment. Three moieties, A, B, and C of the compound are identified, and alternative moieties for each of these is further shown. All combinations of moieties A, B, and C may be used as a compound for an organic optoelectronic device according to an embodiment.

The compound for an organic optoelectronic device may include the following compounds of Formulae A-1 to A-140, but is not limited thereto.

A-1

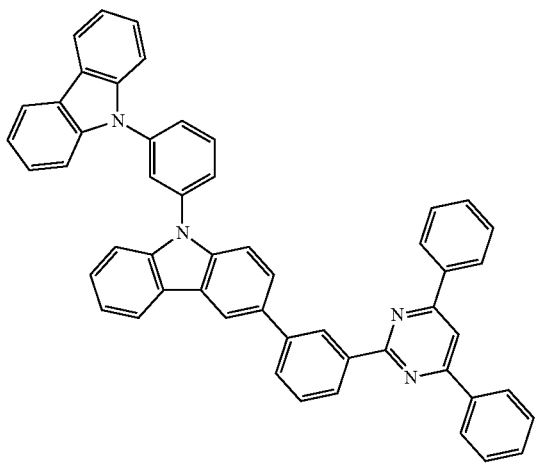

A-2

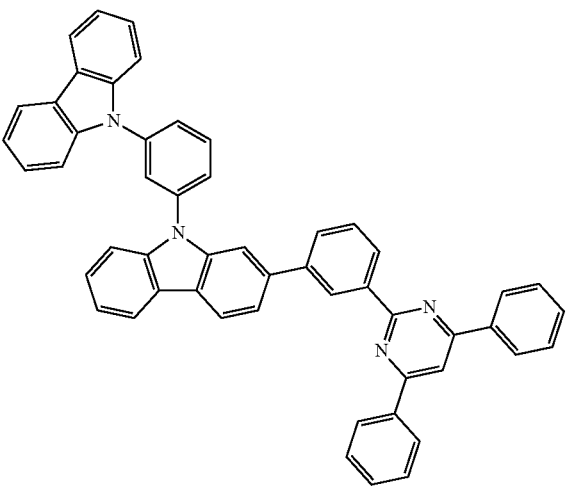

A-3

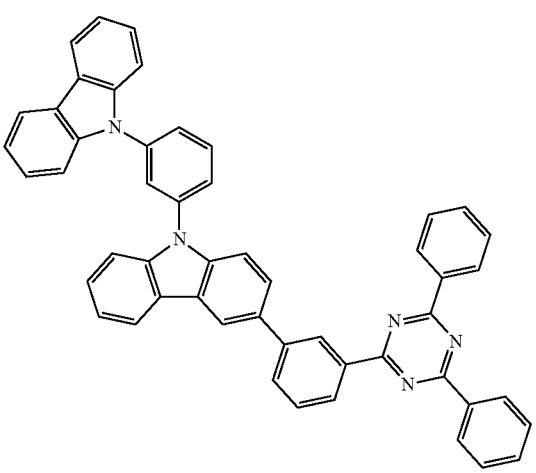

A-4
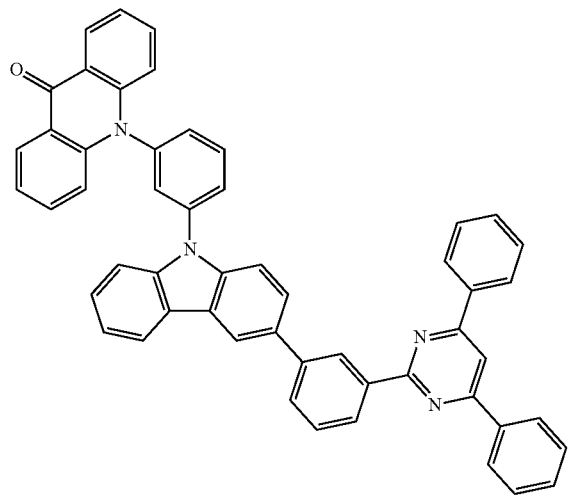
A-5
A-6
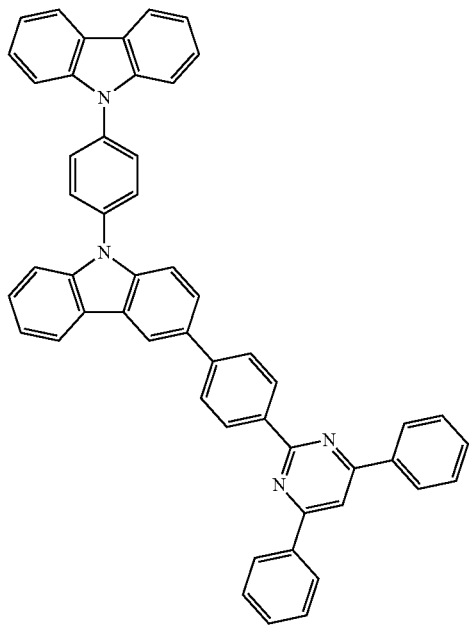
A-7
A-8
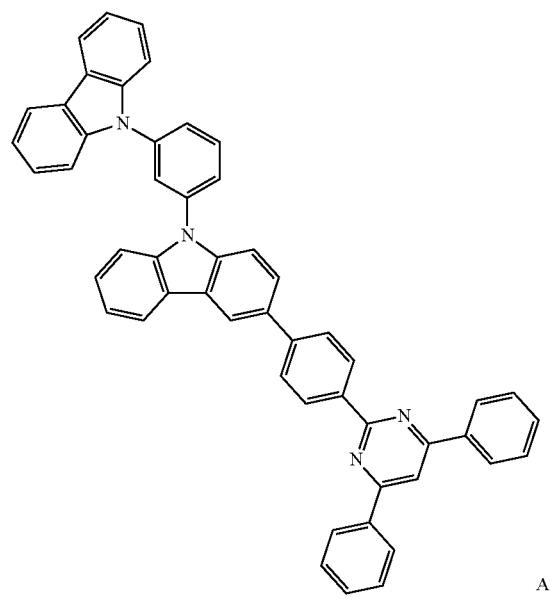
A-9
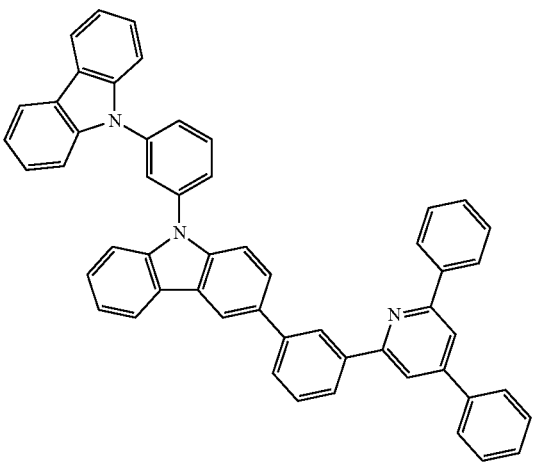

A-10
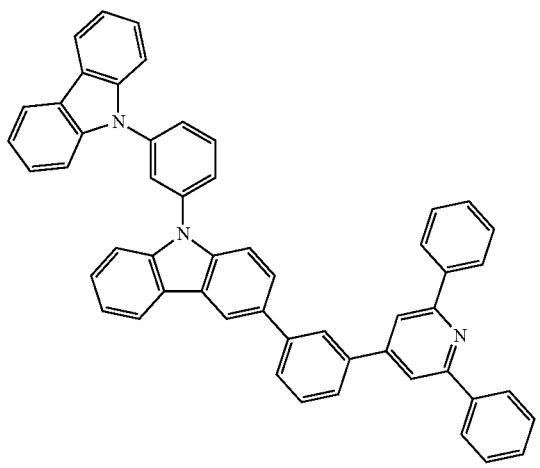
A-13
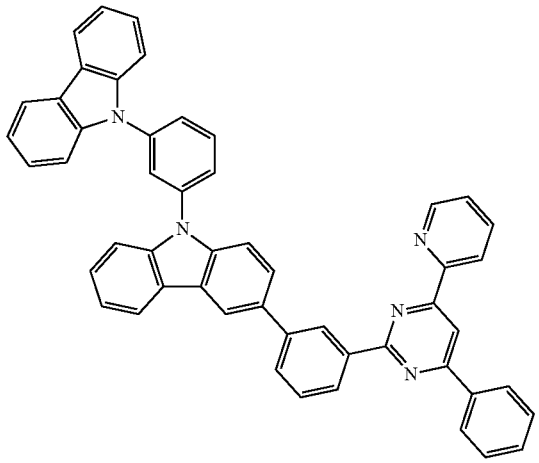
A-11
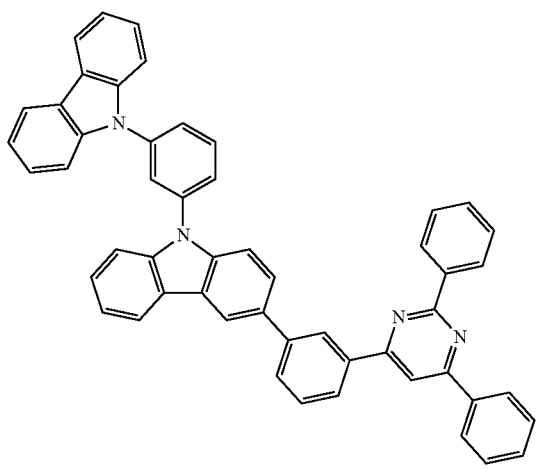
A-14
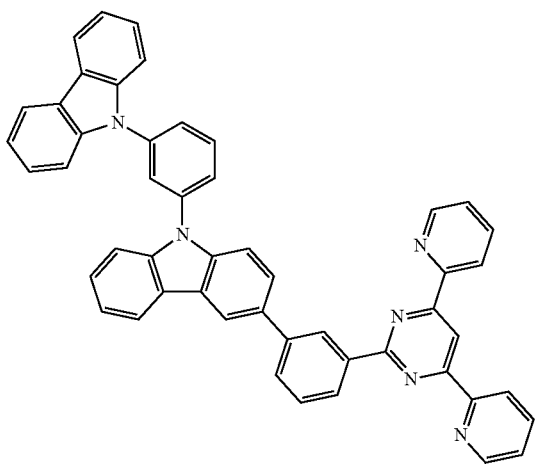
A-12
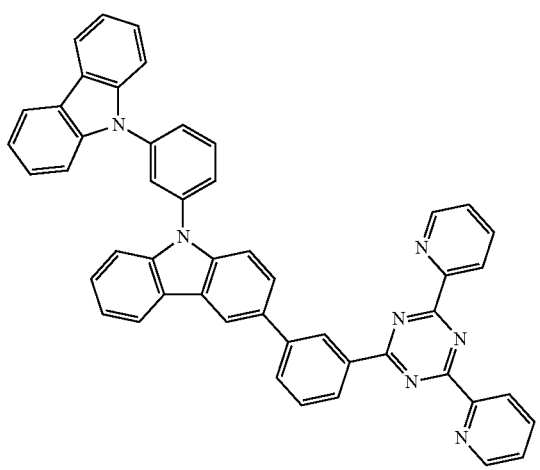
A-15
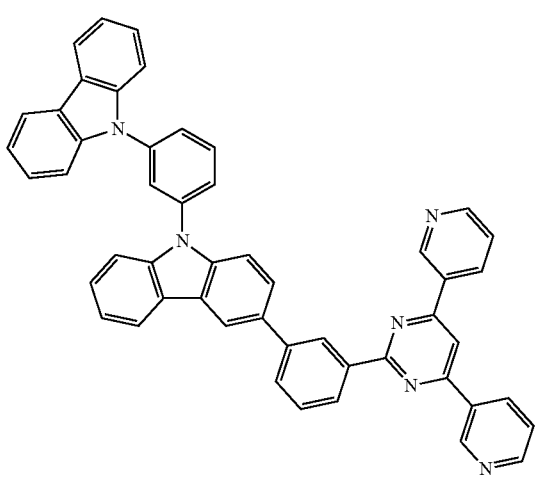

A-16
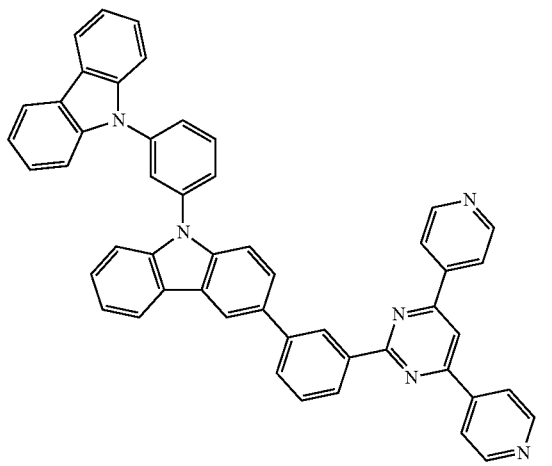
A-17
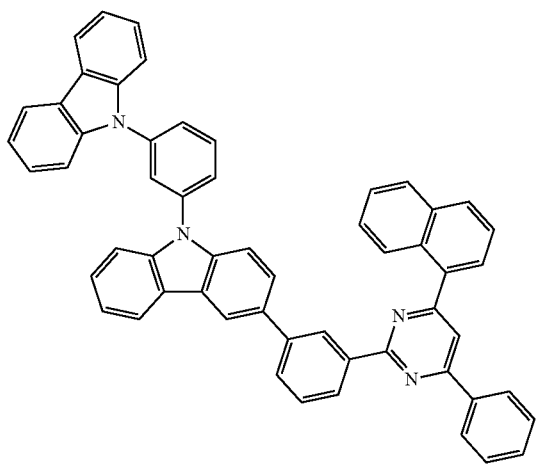
A-18
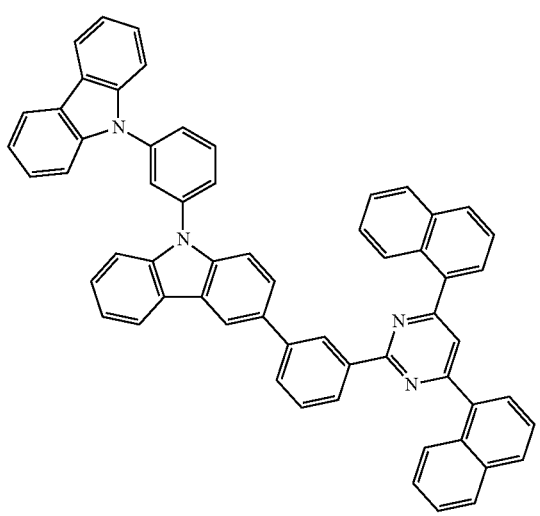
A-19
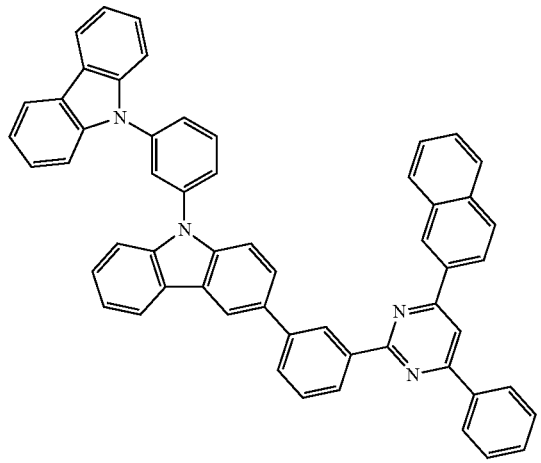
A-20
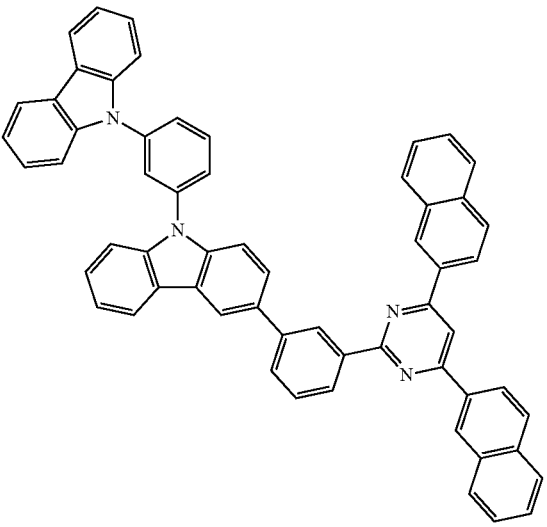
A-21
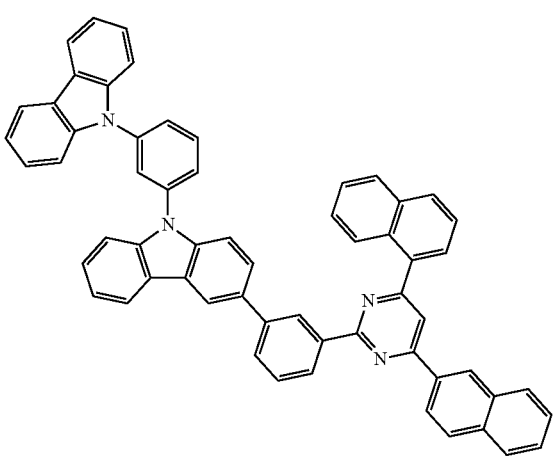

A-22
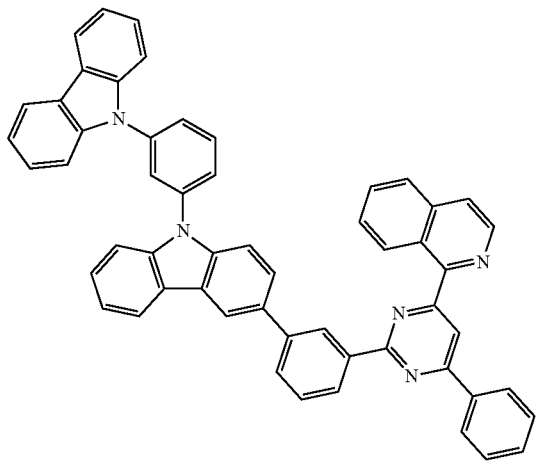
A-23
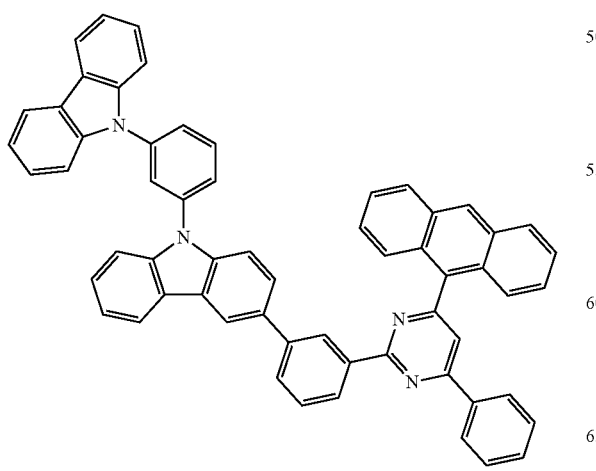
A-24
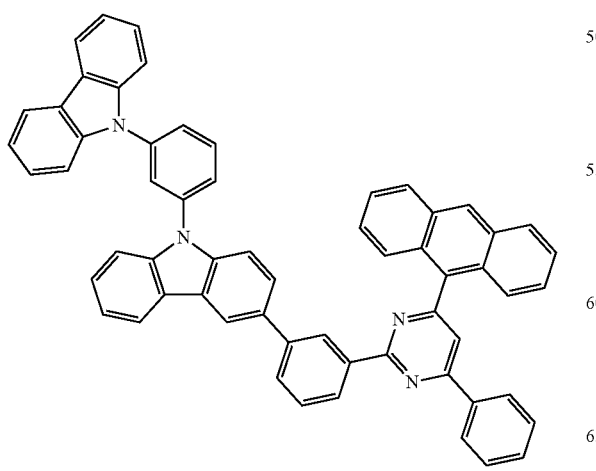
A-25
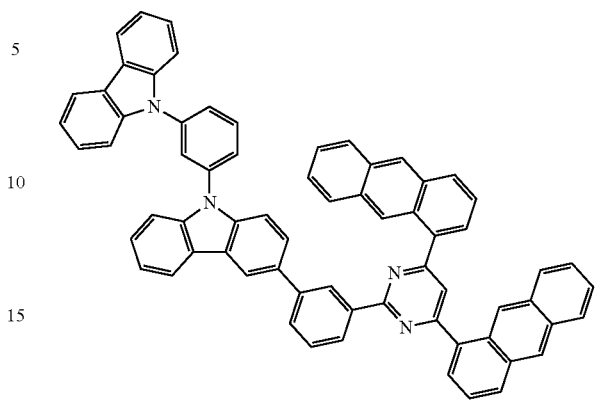
A-26
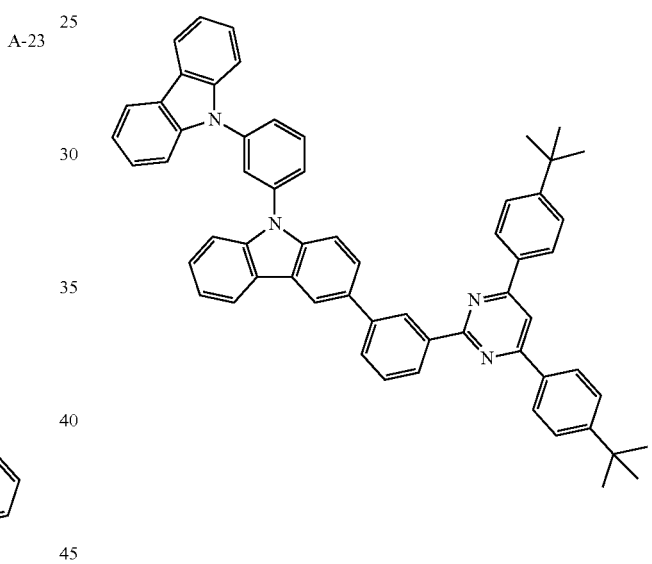
A-27
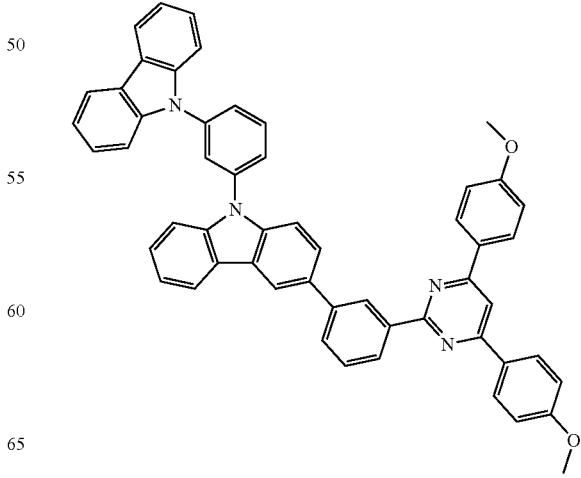

A-28
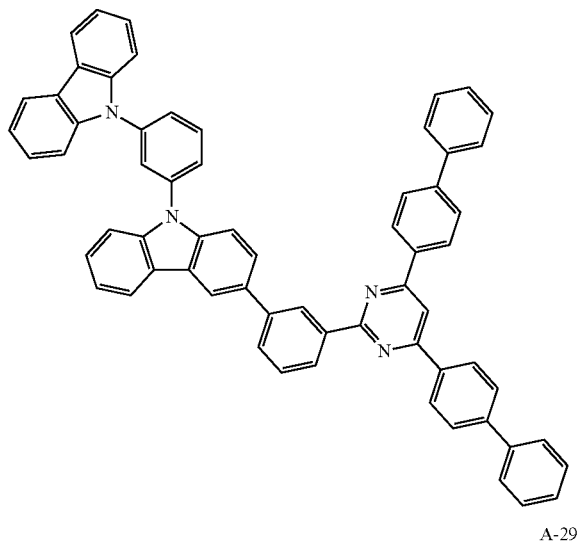
A-29
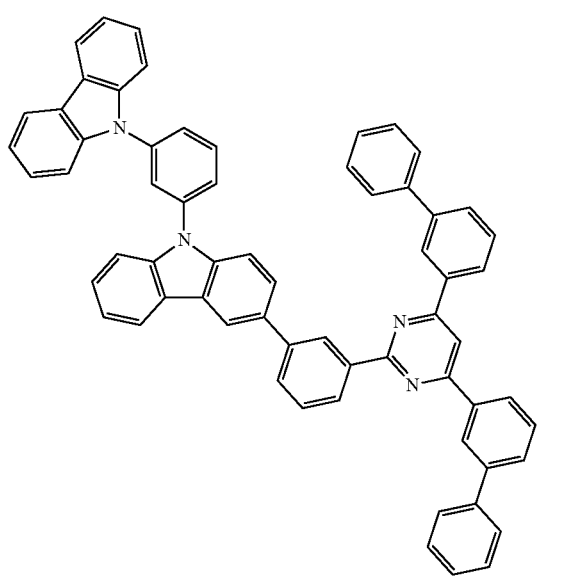
A-30
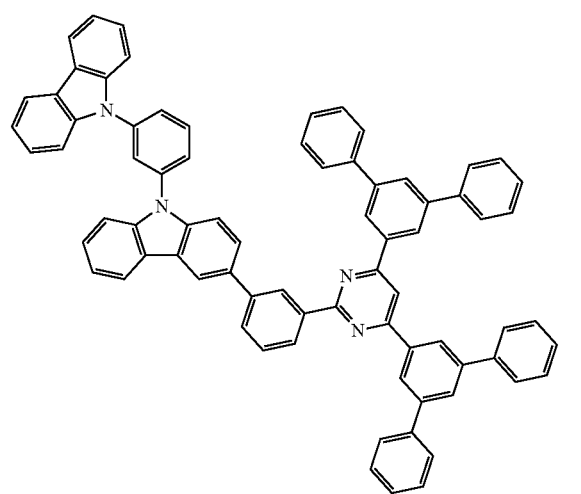
A-31
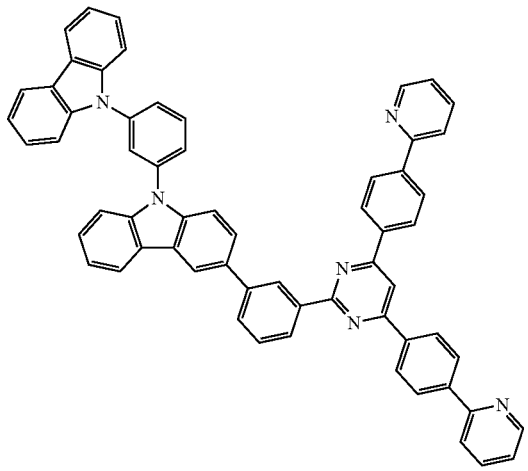
A-32
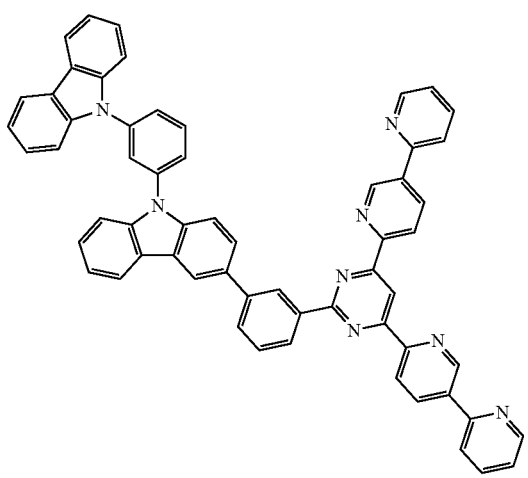
A-33
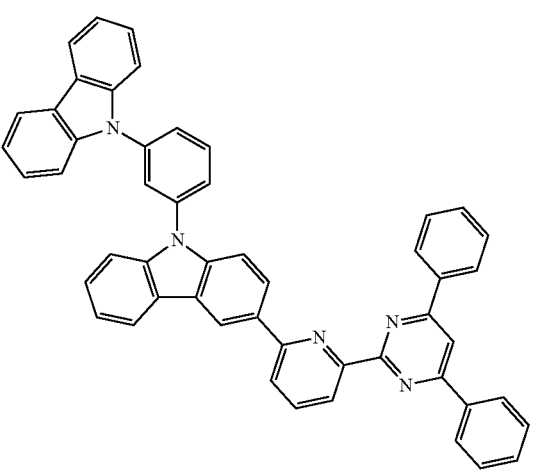

A-34
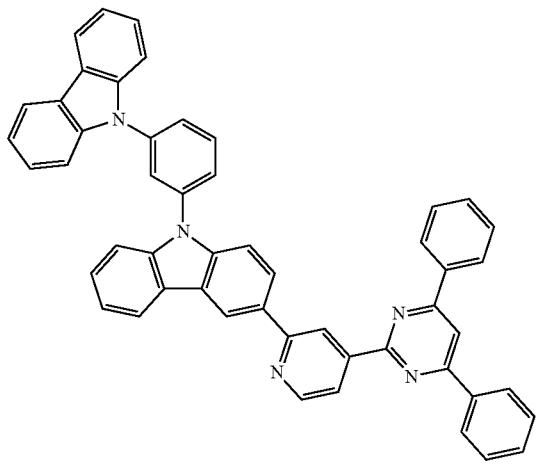
A-35
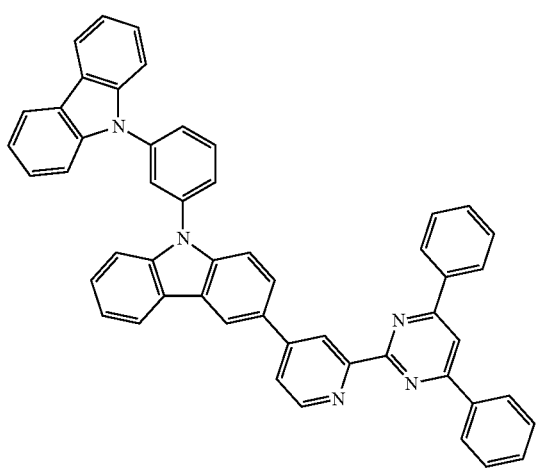
A-36
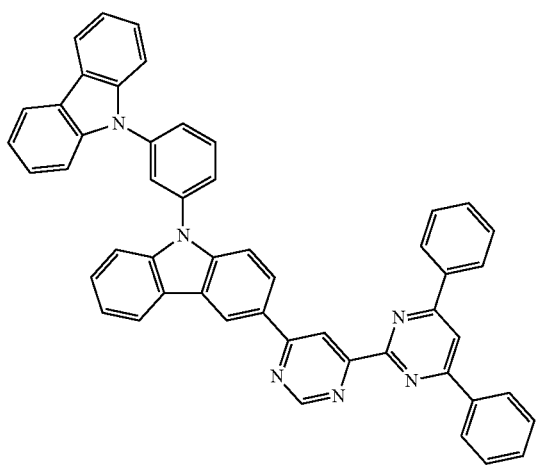
A-37
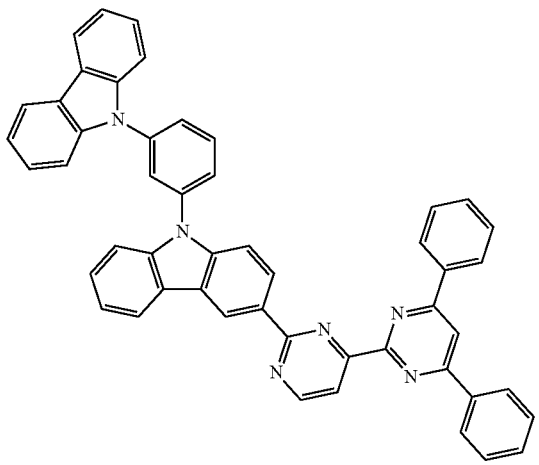
A-38
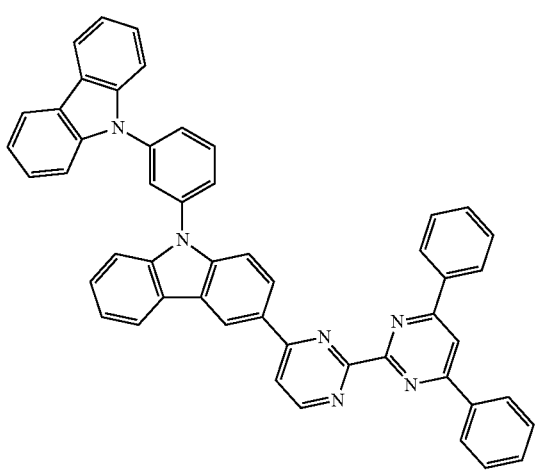
A-39
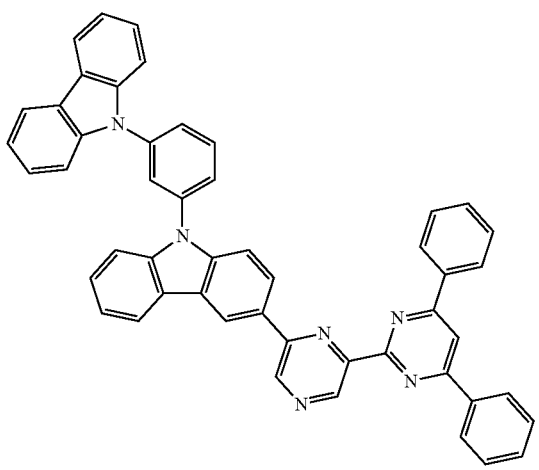

A-40
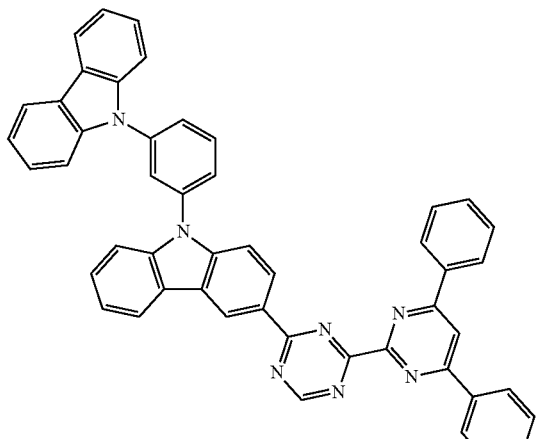
A-41
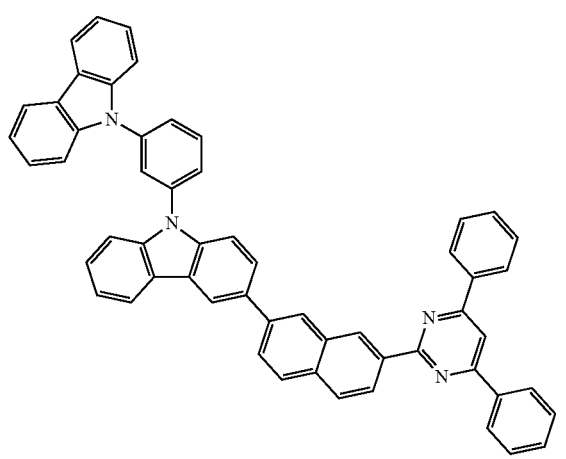
A-42
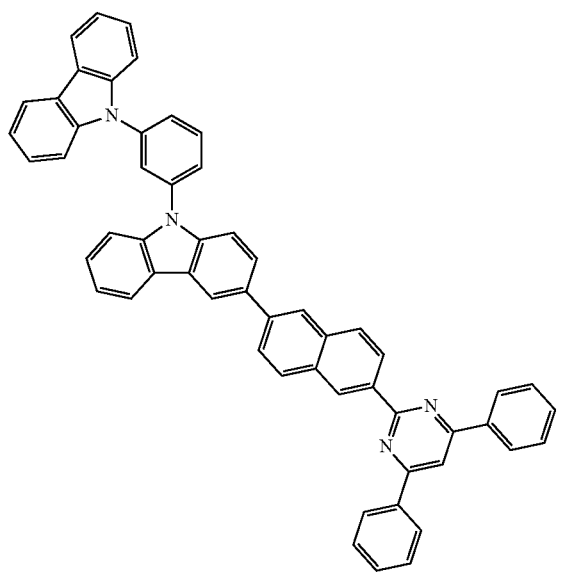
A-43
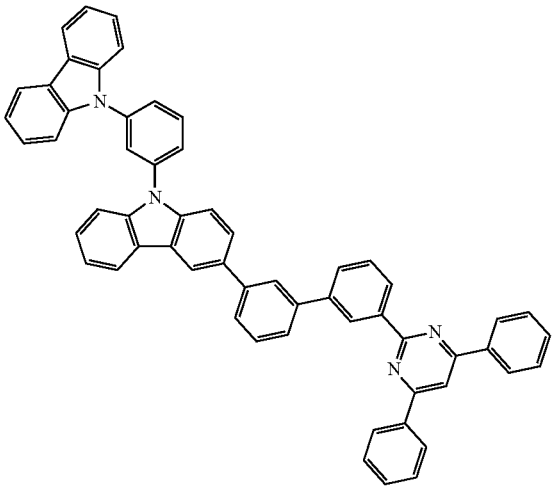
A-44
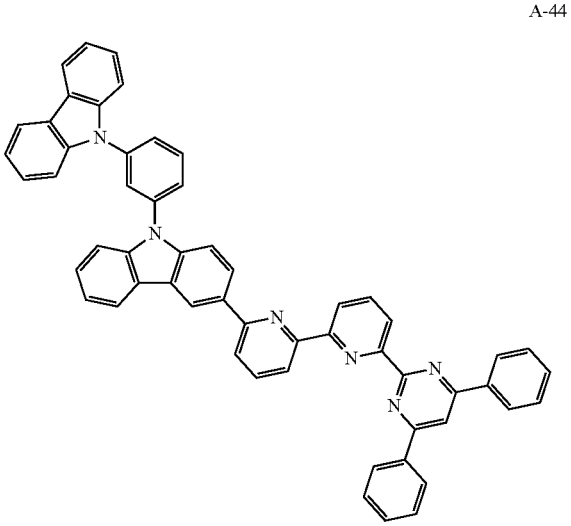
A-45
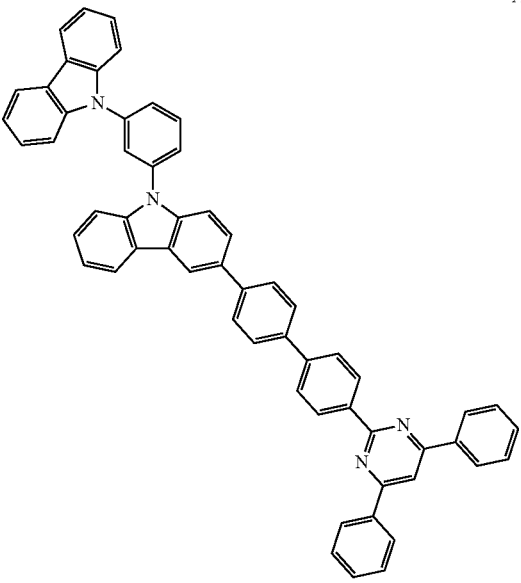

A-46
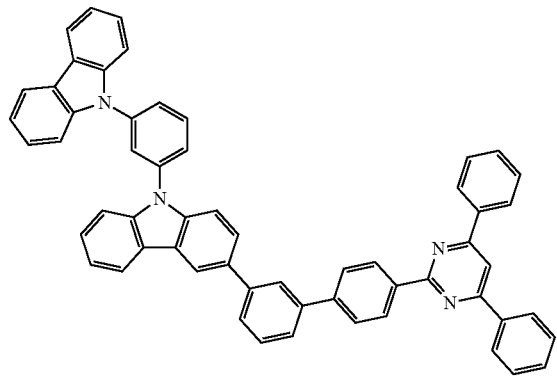
A-47
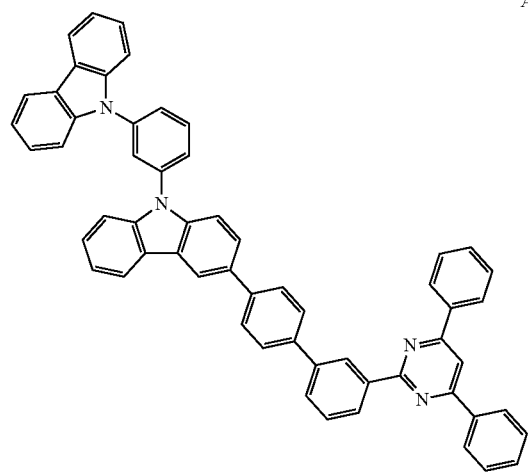
A-48
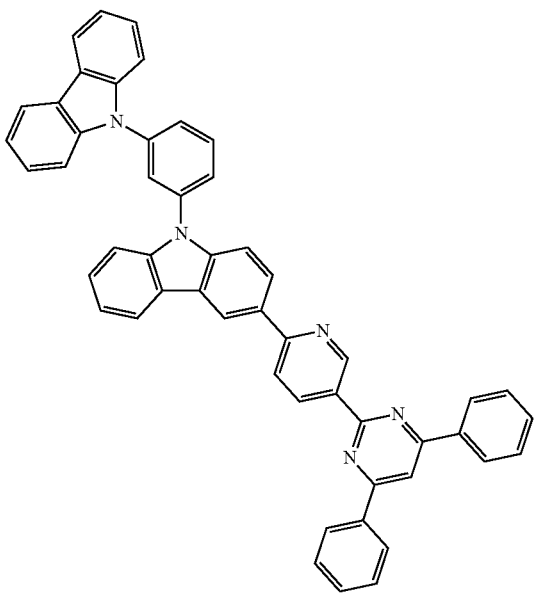
A-49
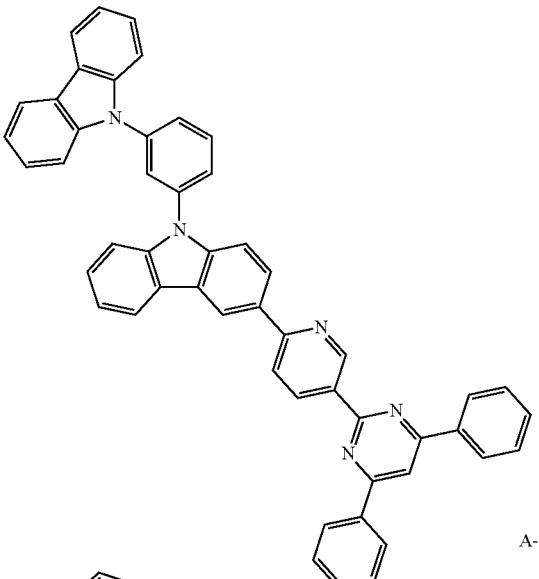
A-50
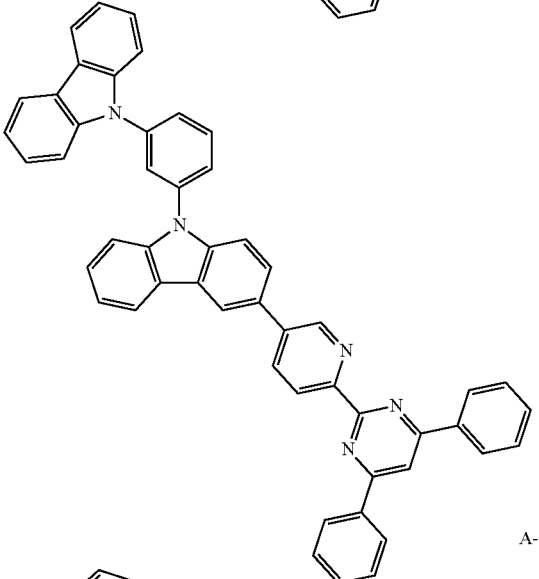
A-51
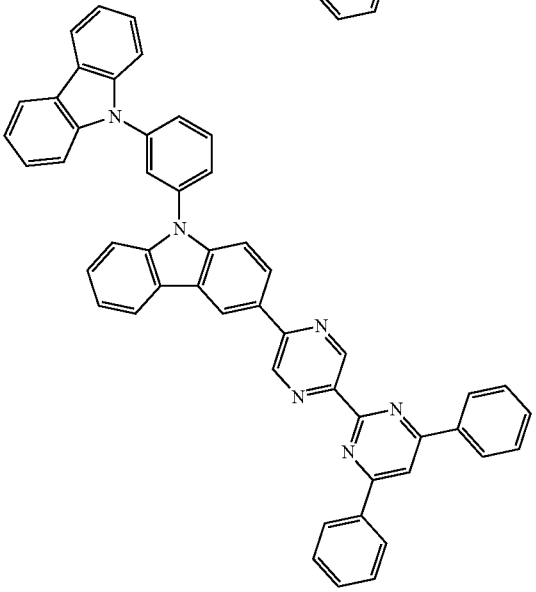

A-52
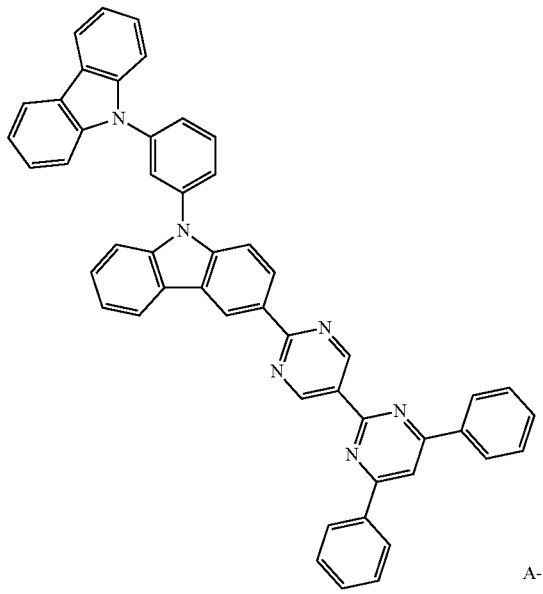
A-53
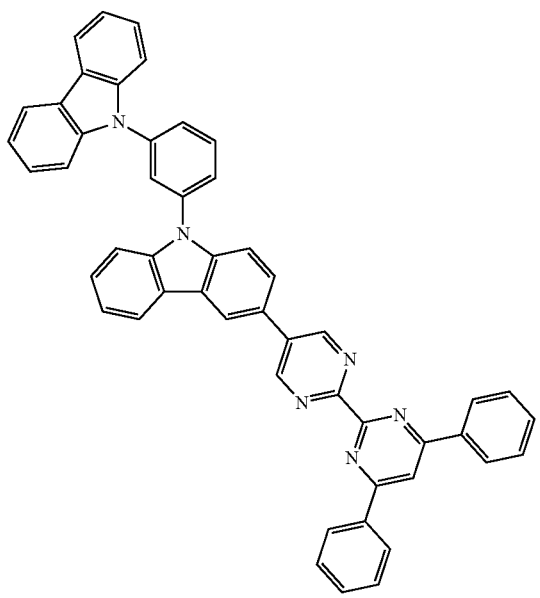
A-54
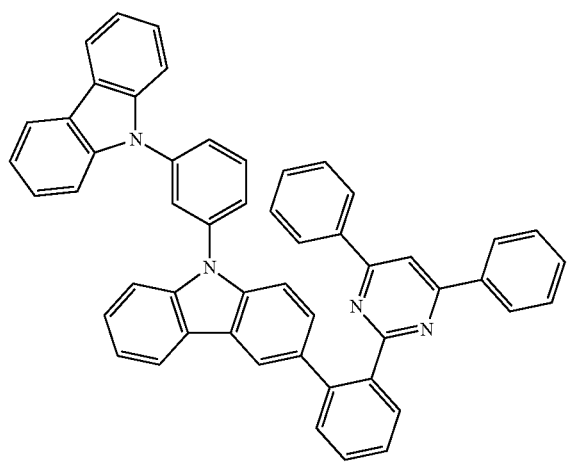
A-55
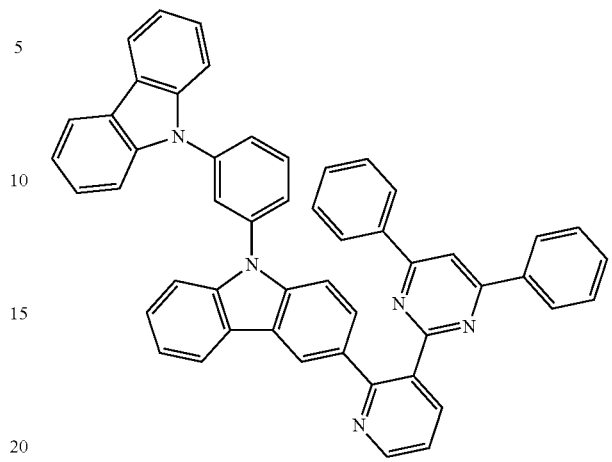
A-56
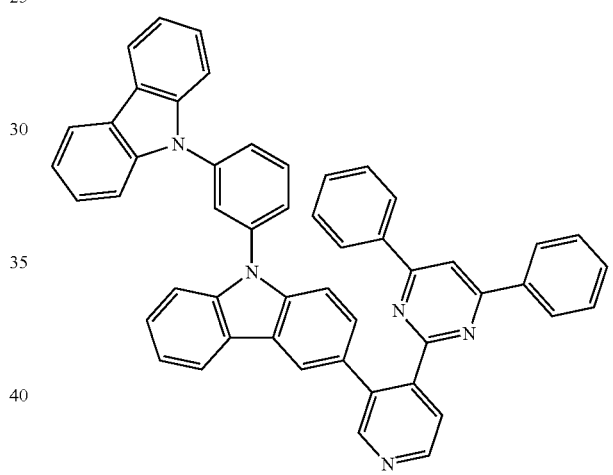
A-57
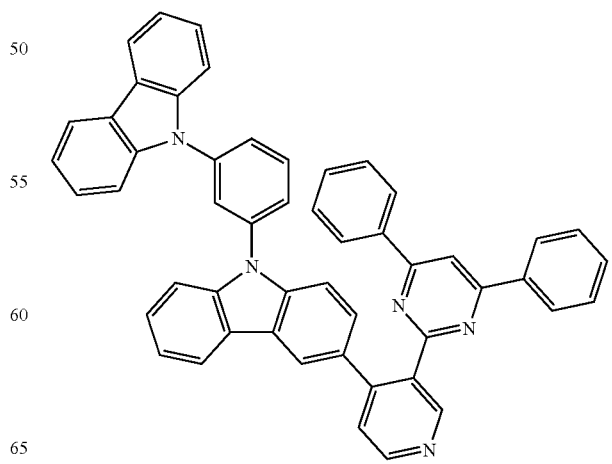

-continued
A-58
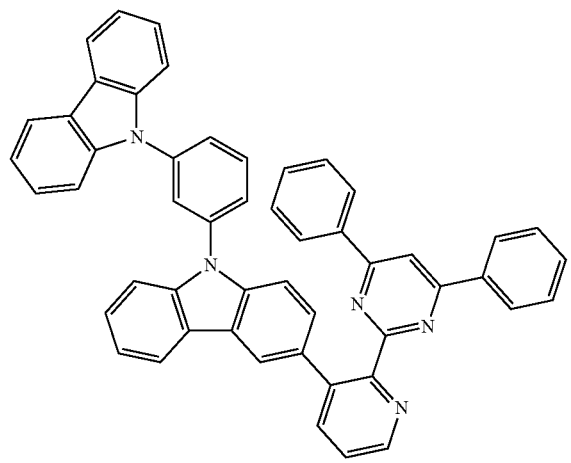
A-59
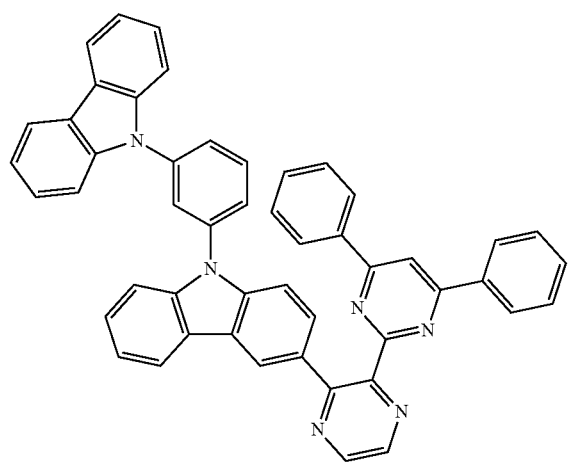
A-60
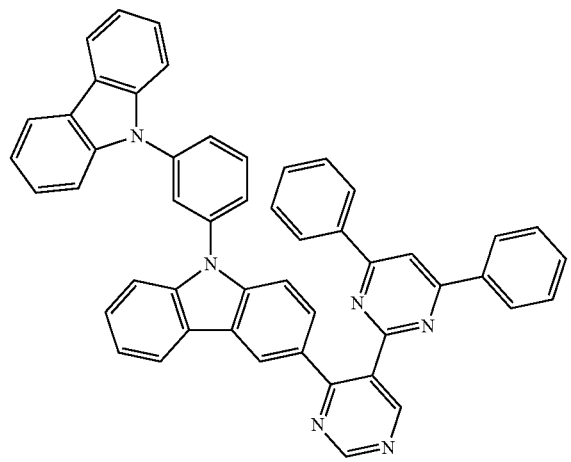
-continued
A-61
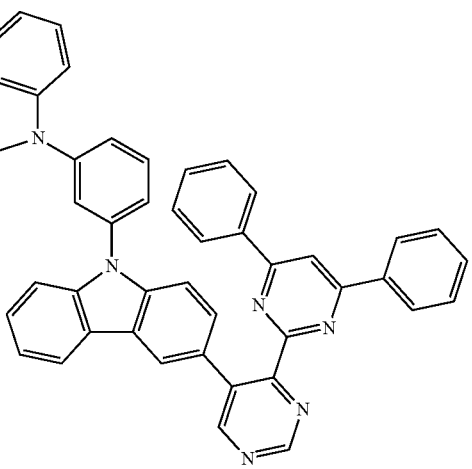
A-62
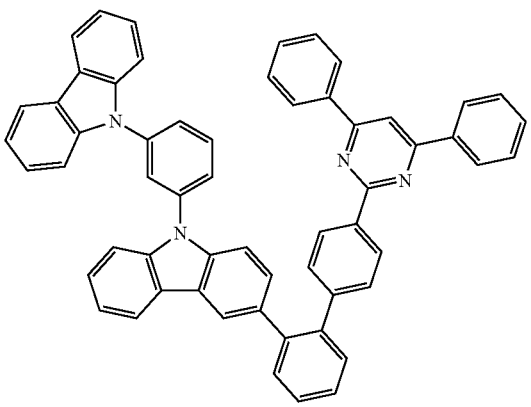
A-63
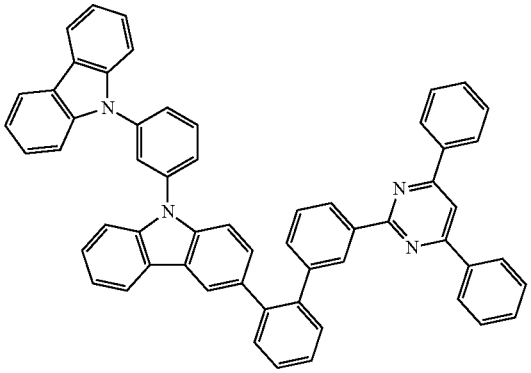

-continued
A-64
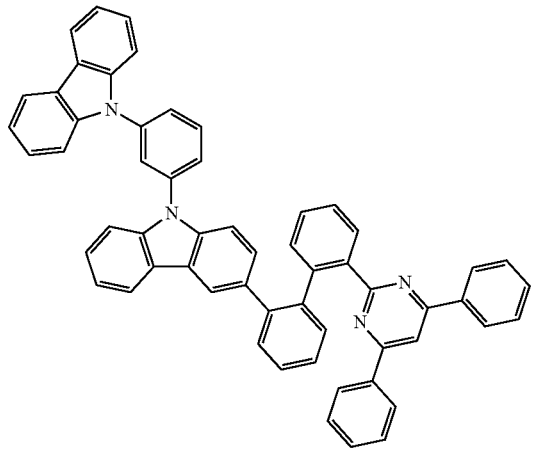
A-65
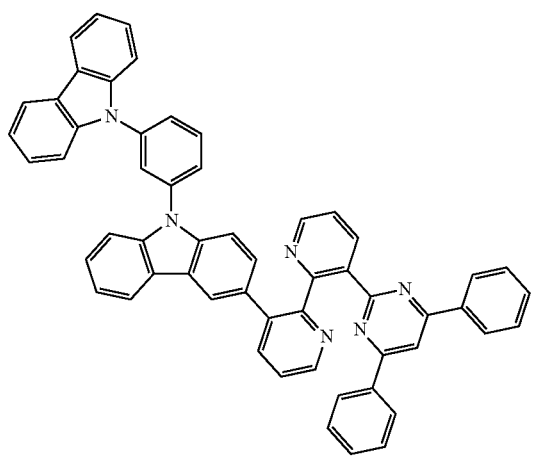
A-66
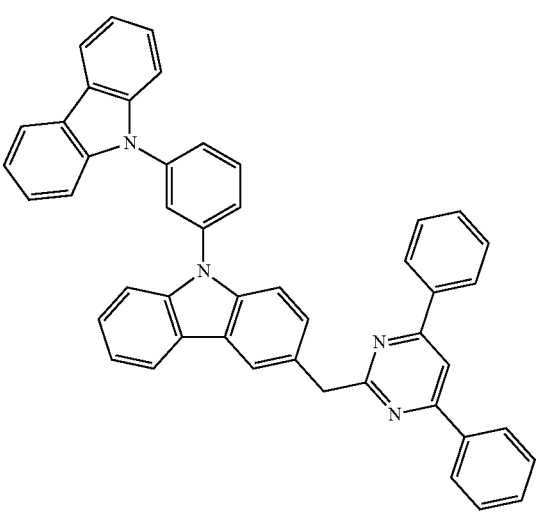
-continued
A-67
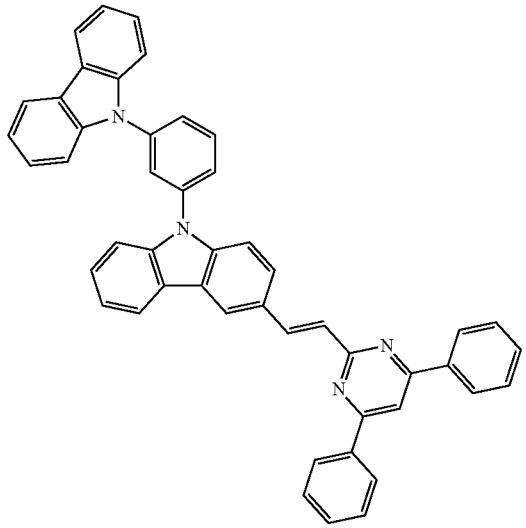
A-68
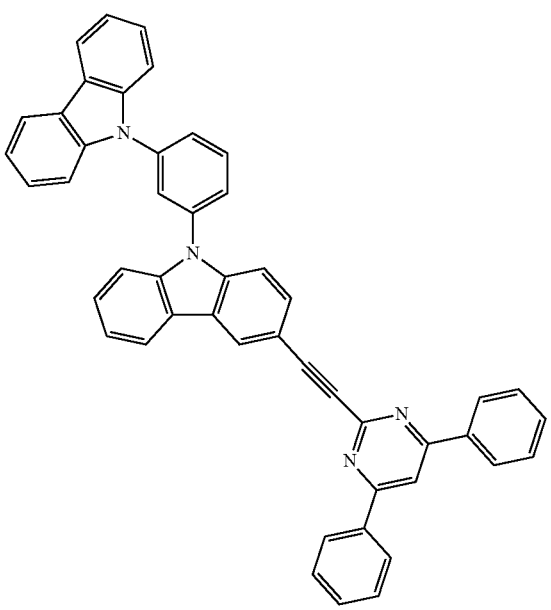
A-69
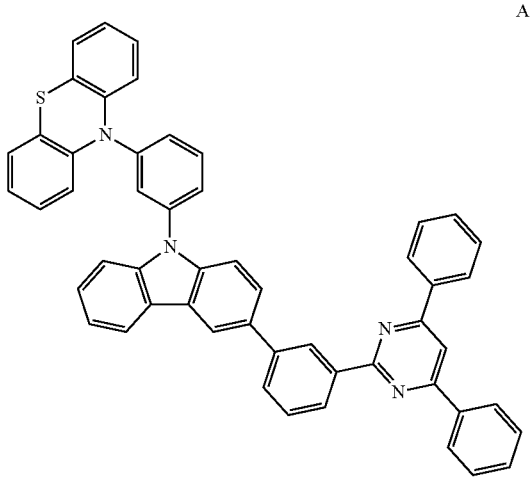

A-70
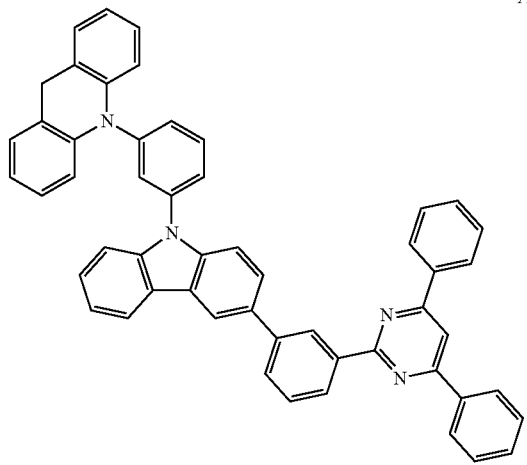
A-71
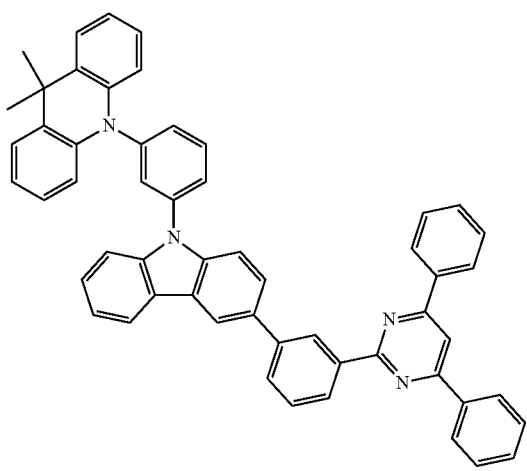
A-72
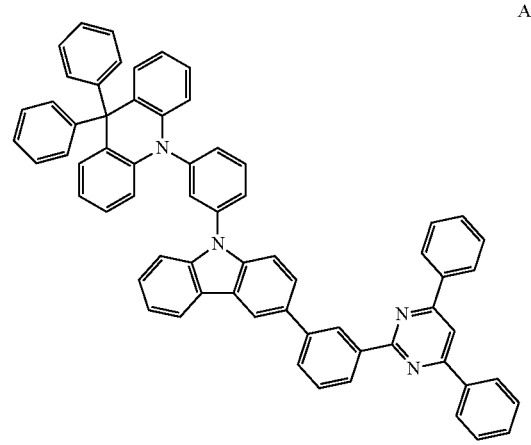
A-73
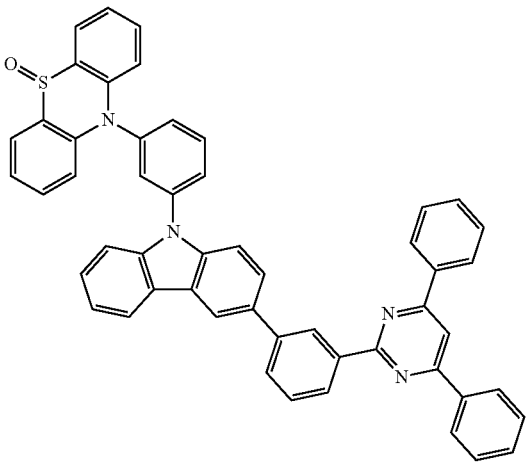
A-74
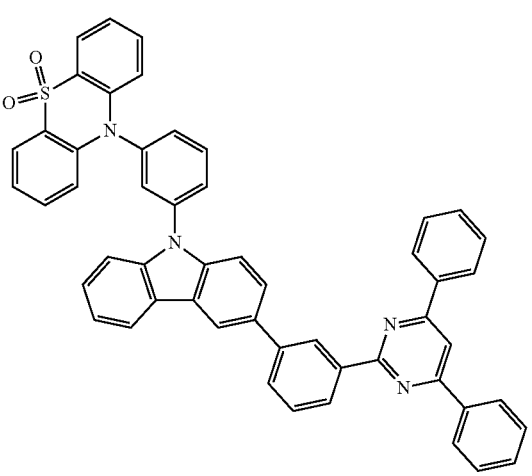
A-75
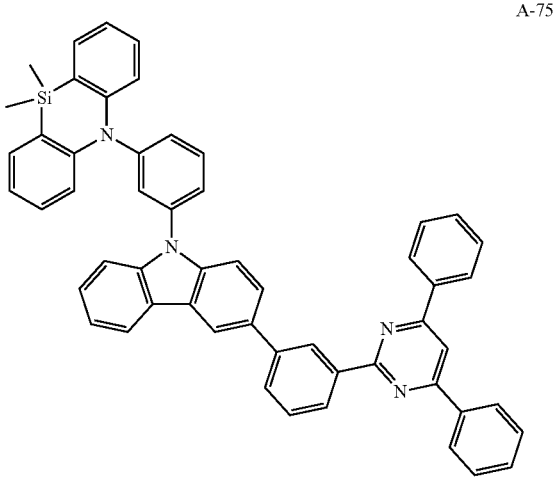

A-76
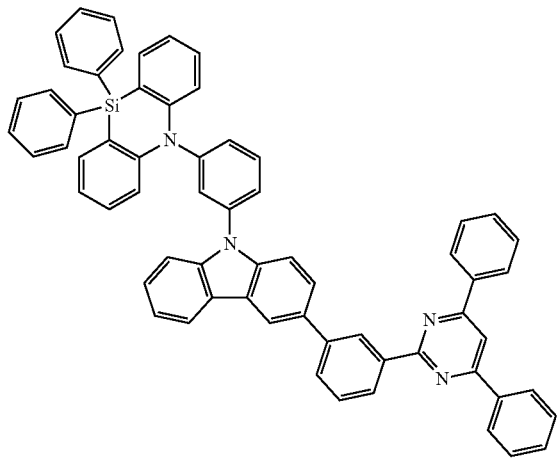
A-77
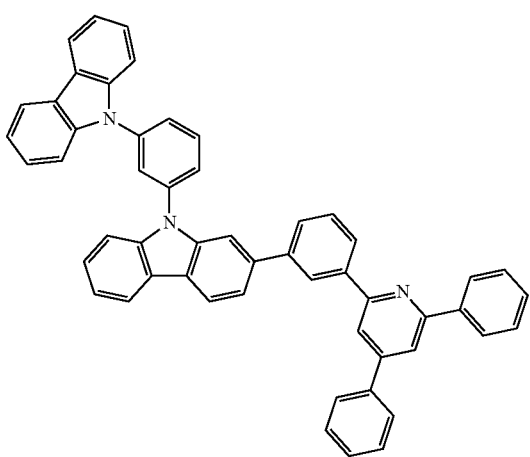
A-78
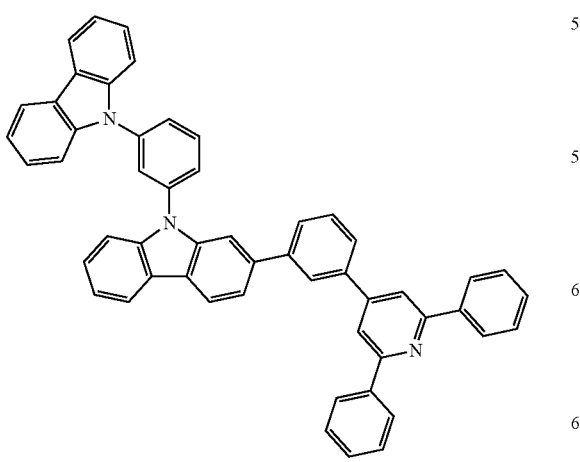
A-79
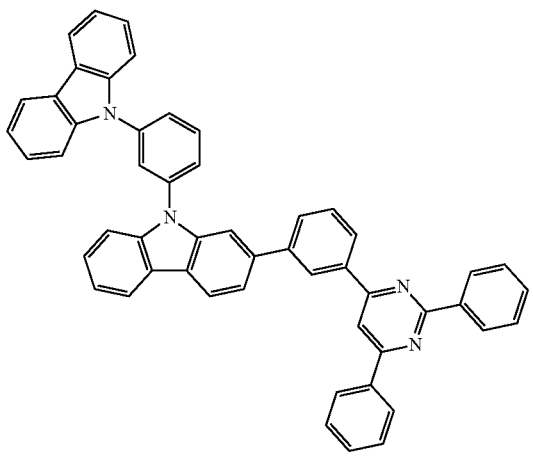
A-80
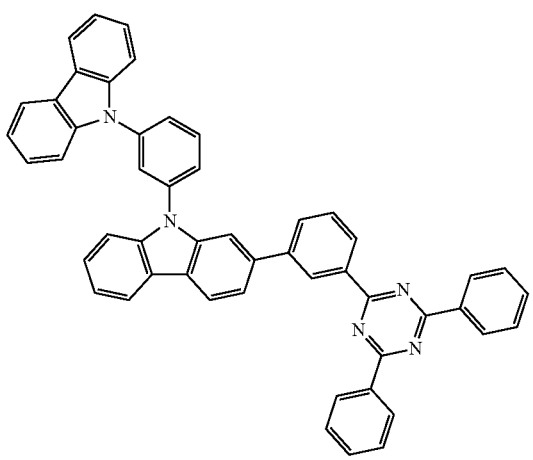
A-81
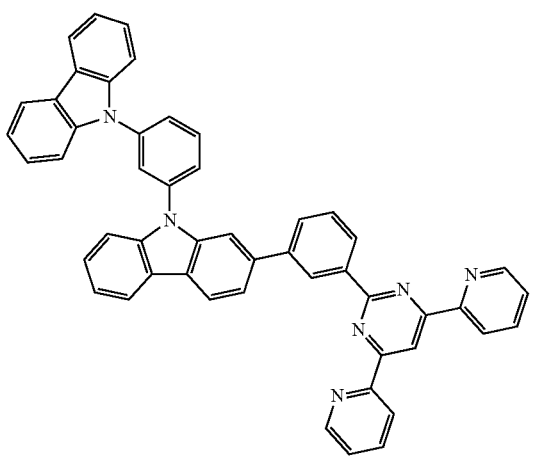

A-82
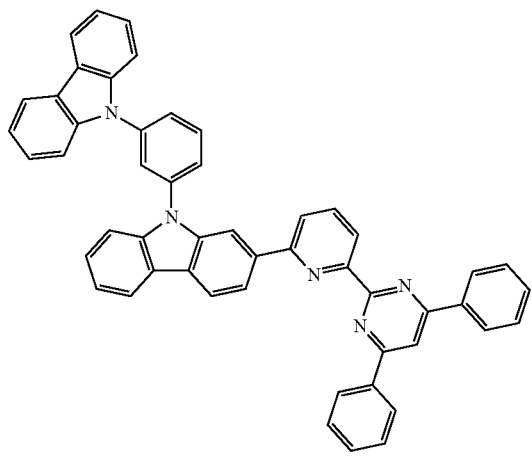
A-85
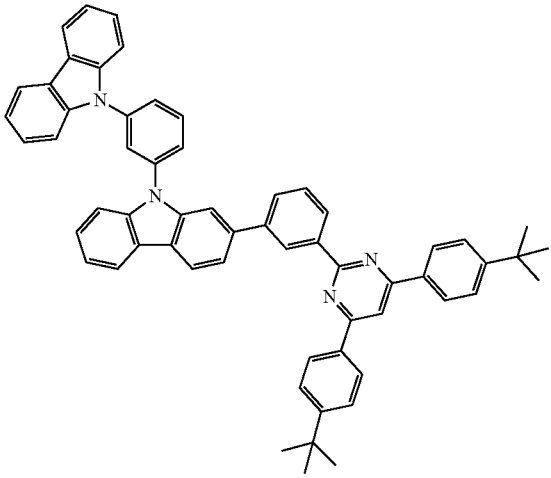
A-83
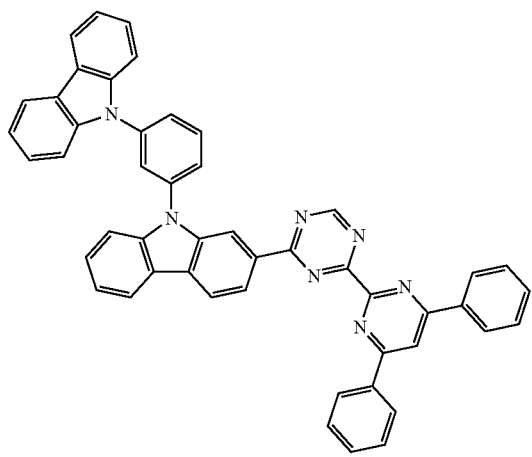
A-86
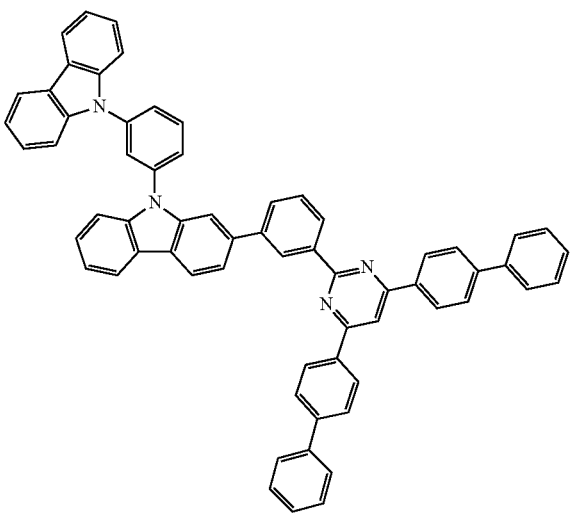
A-84
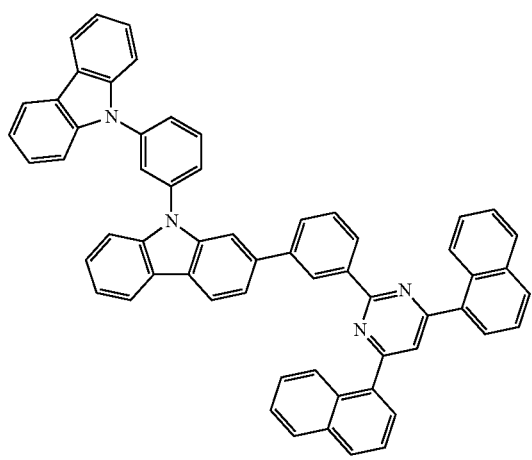
A-87
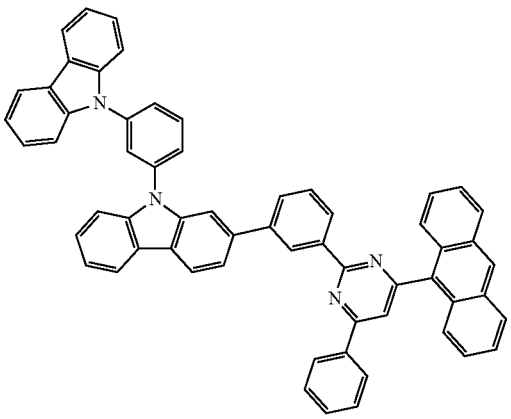

A-88
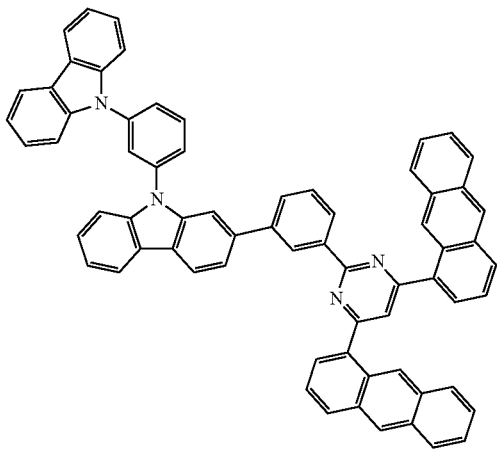
A-89
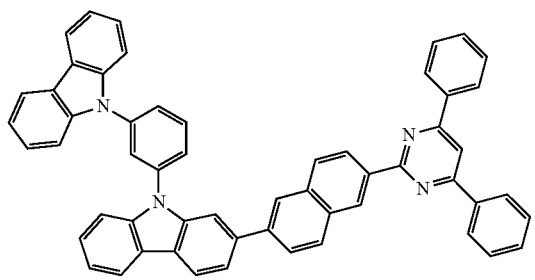
A-90
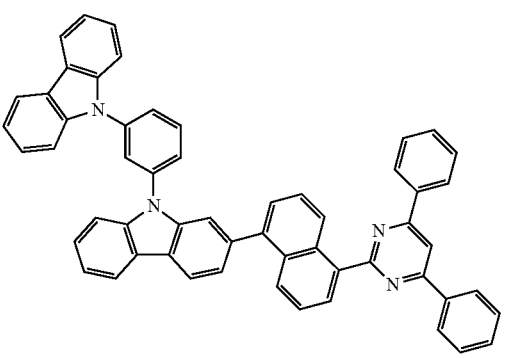
A-91
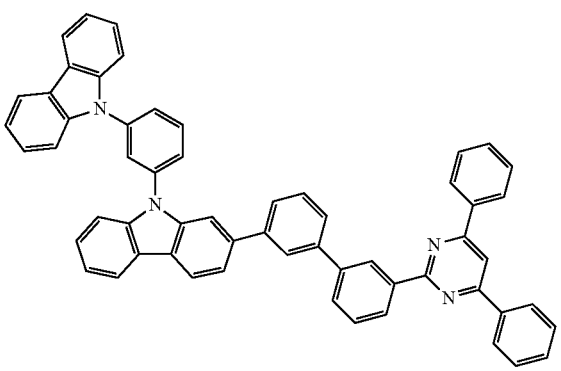
A-92
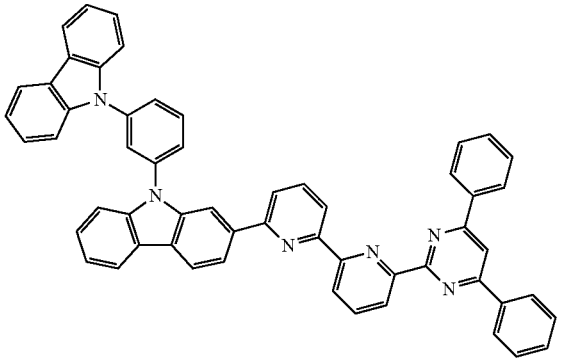
A-93
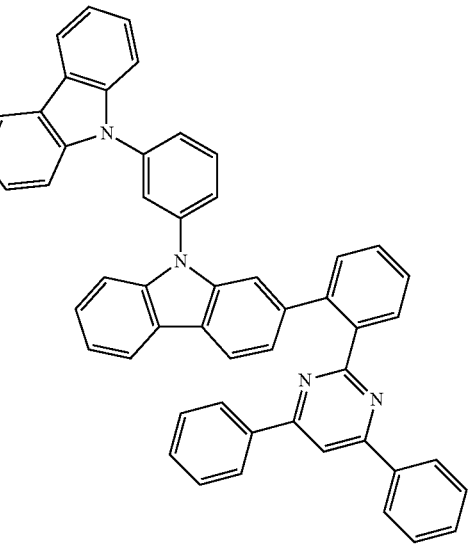
A-94
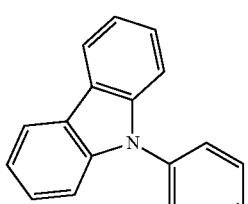
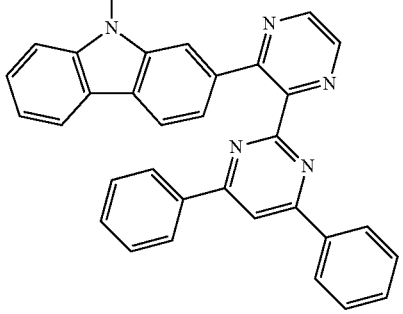

A-95
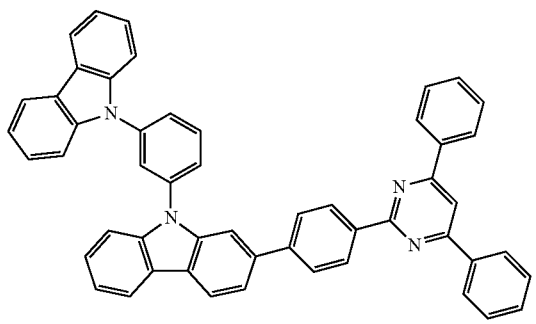
A-96
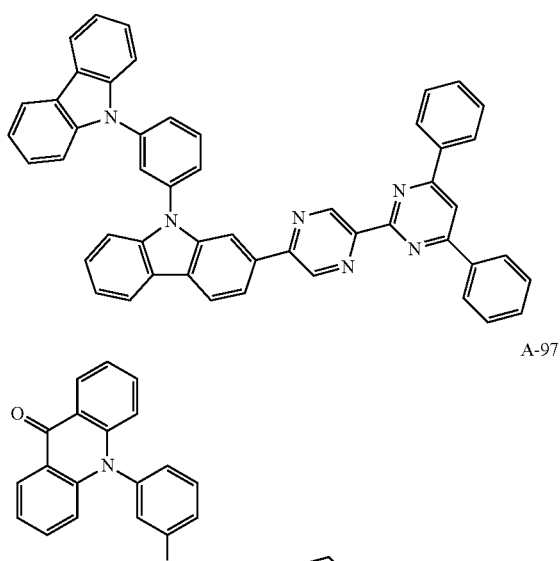
A-97
A-98
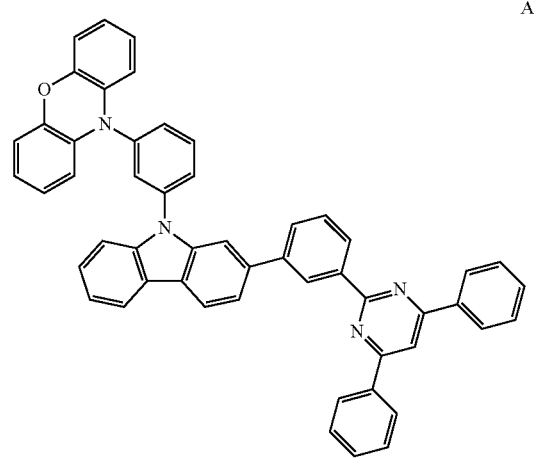
A-99
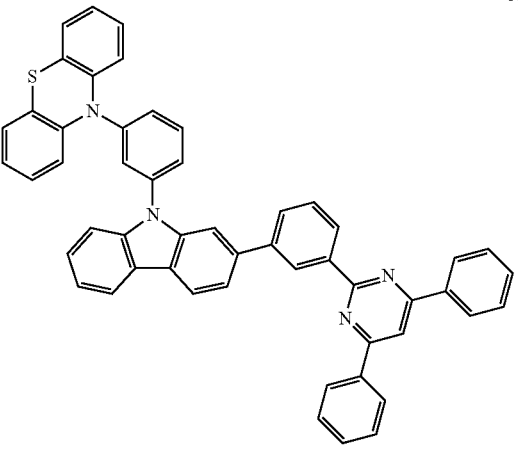
A-100
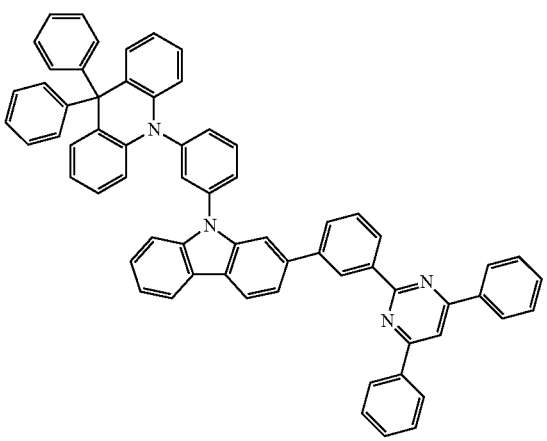
A-101
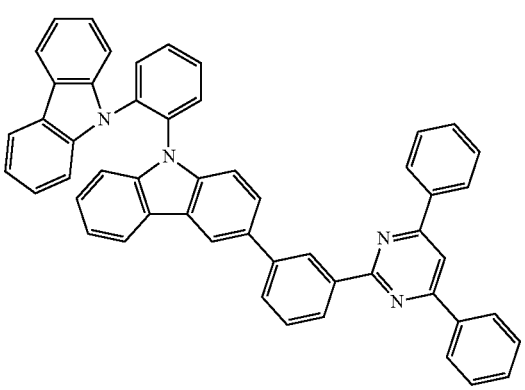

A-102
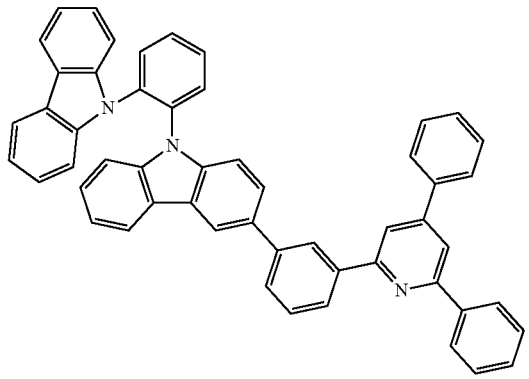
A-103
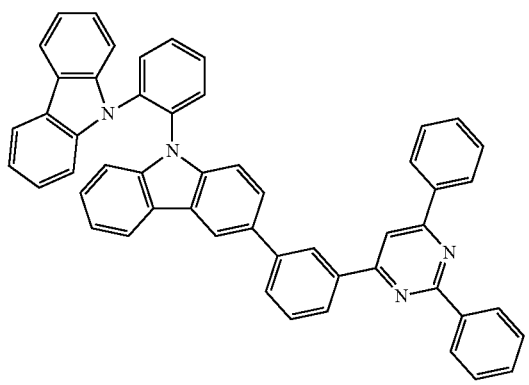
A-104
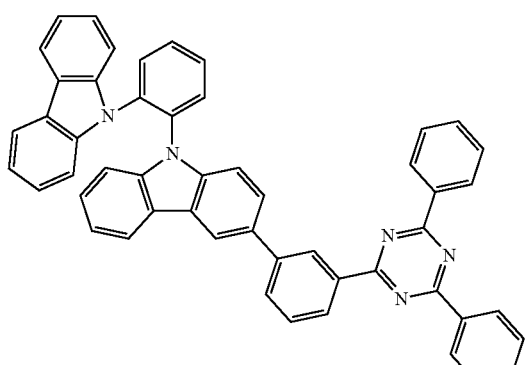
A-105
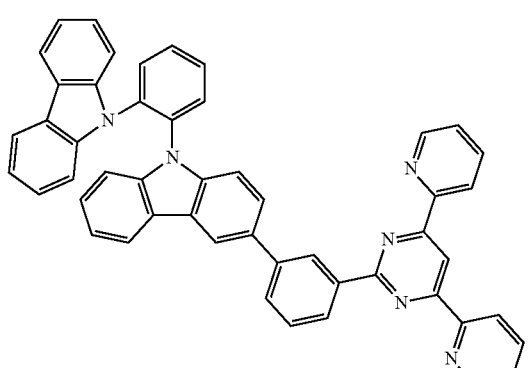
A-106
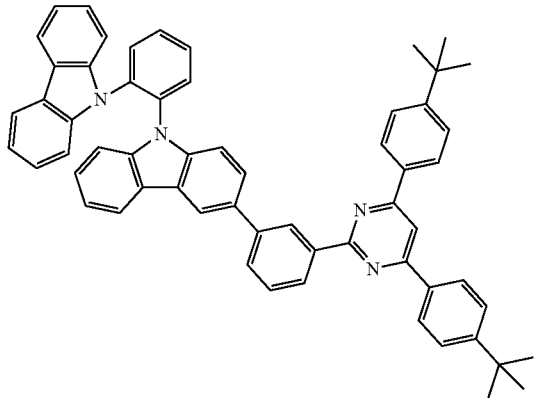
A-107
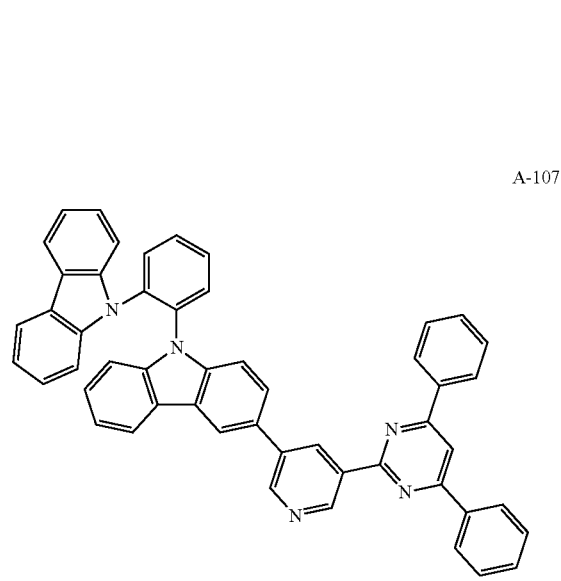
A-108
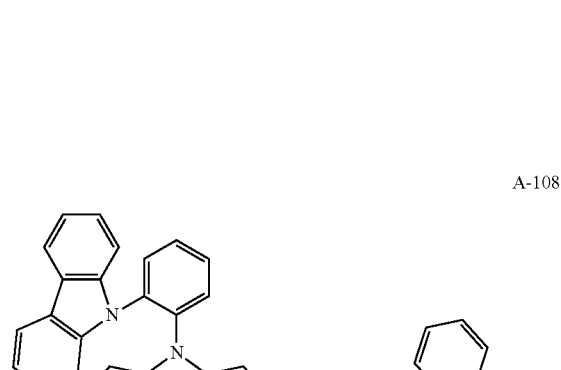
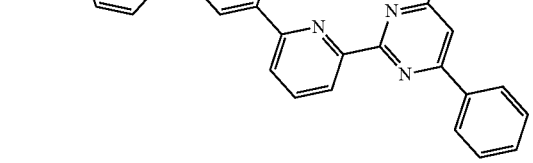

A-109
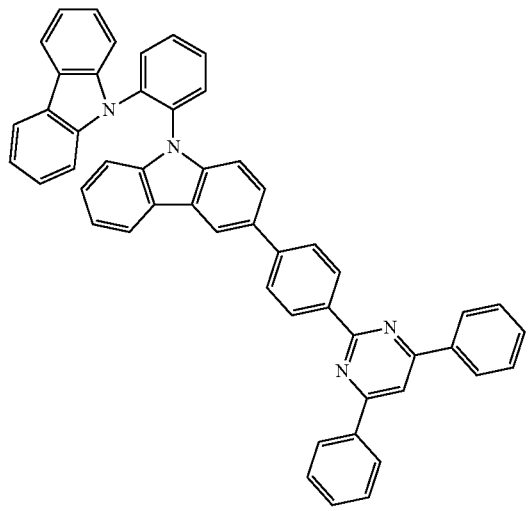
A-110
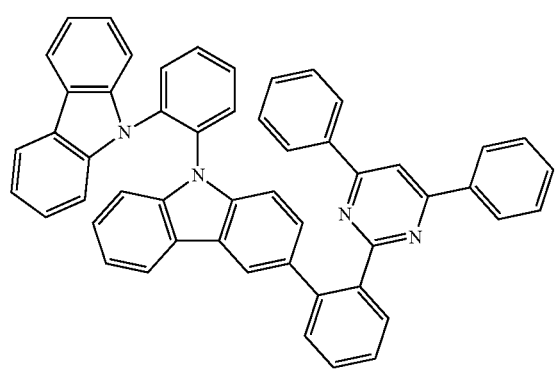
A-111
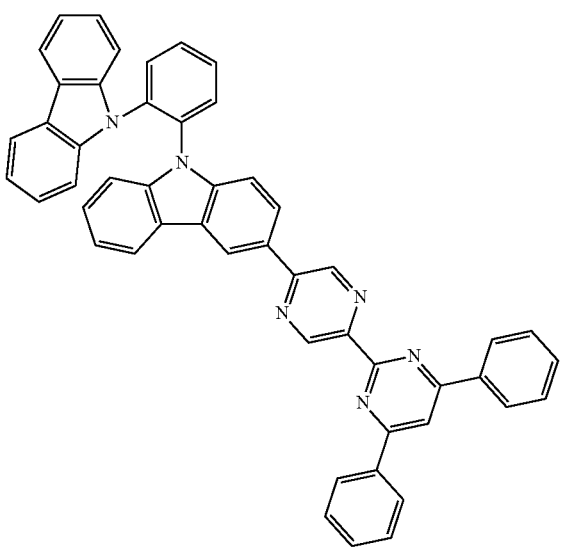
A-112
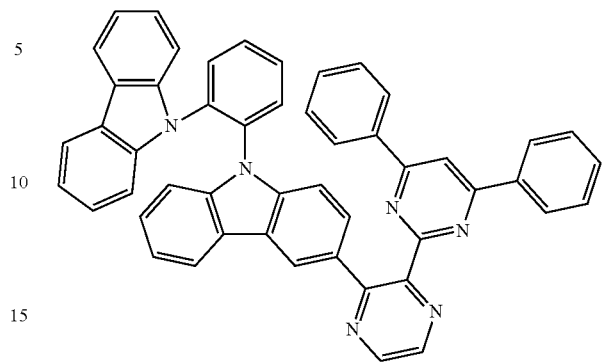
A-113
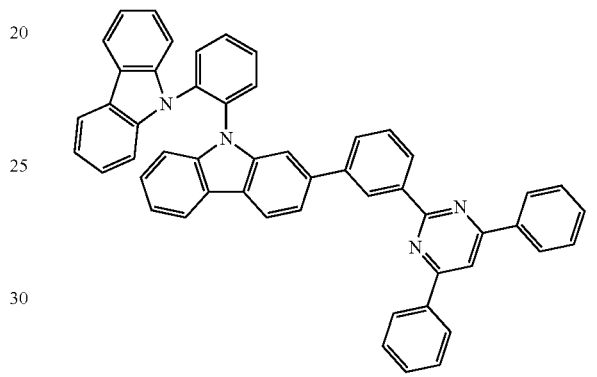
A-114
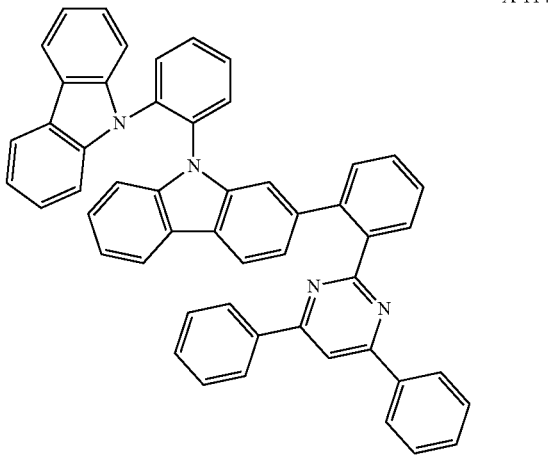
A-115
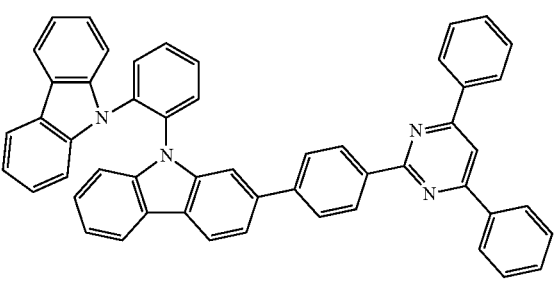

A-116
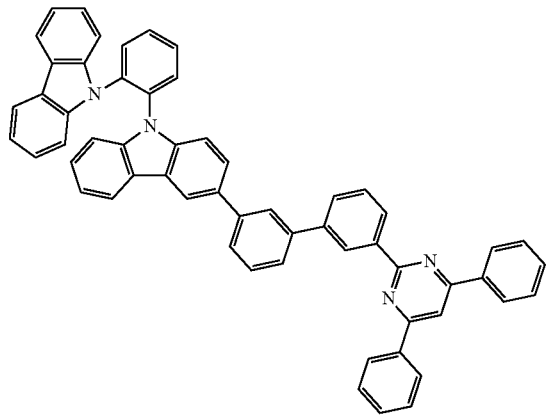
A-117
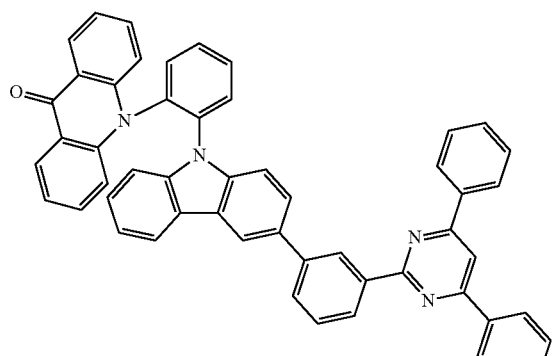
A-118
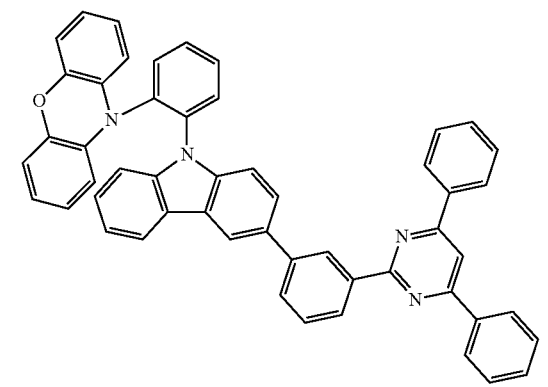
A-119
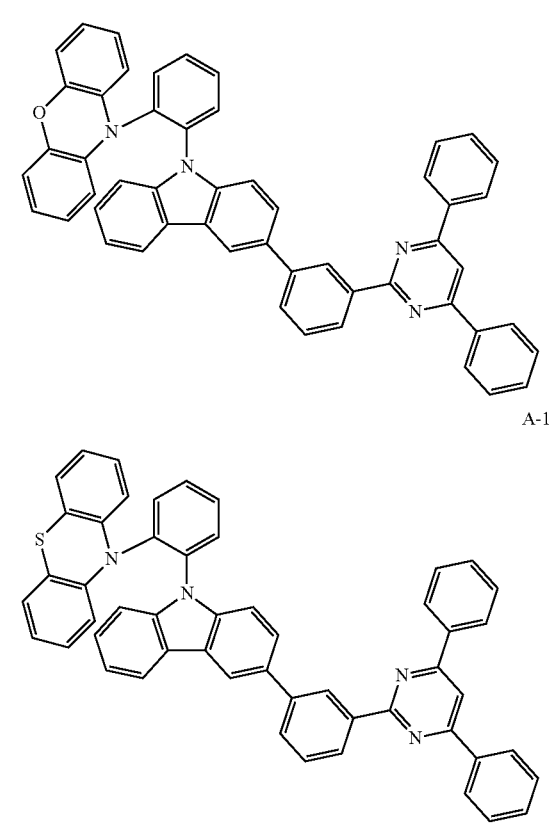
A-120
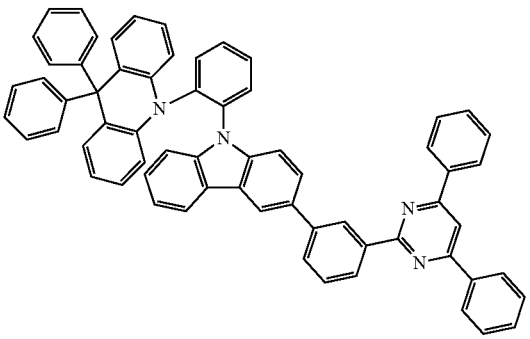
A-121
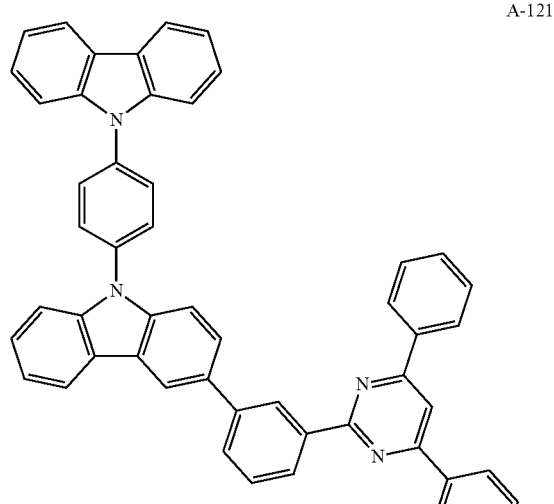
A-122
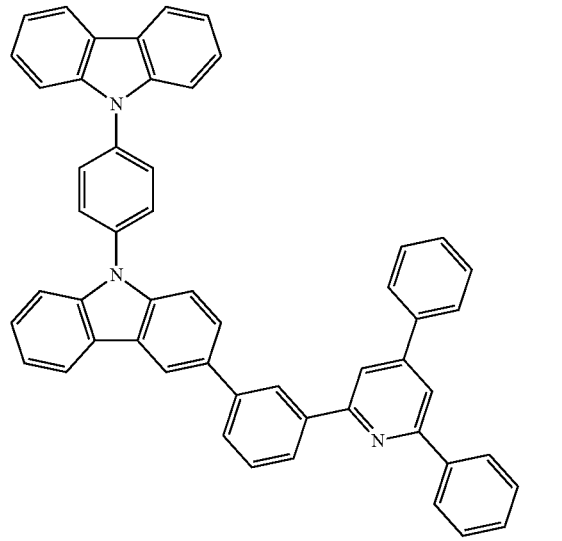

A-123
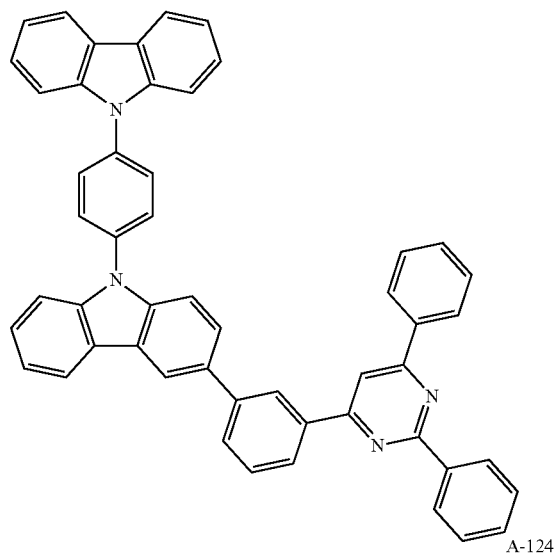
A-124
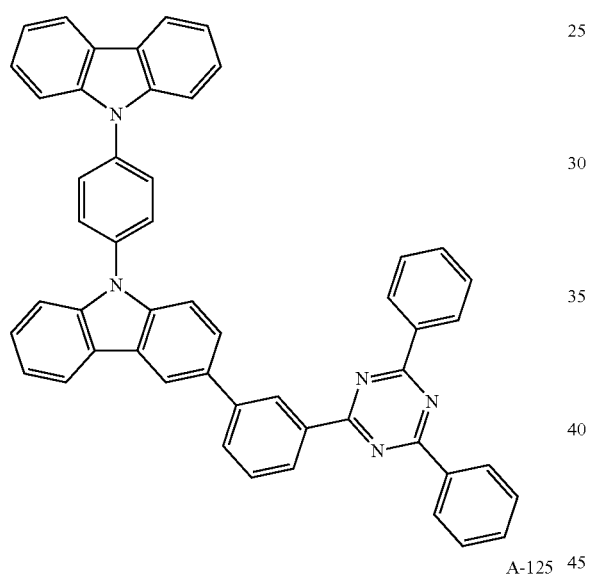
A-125
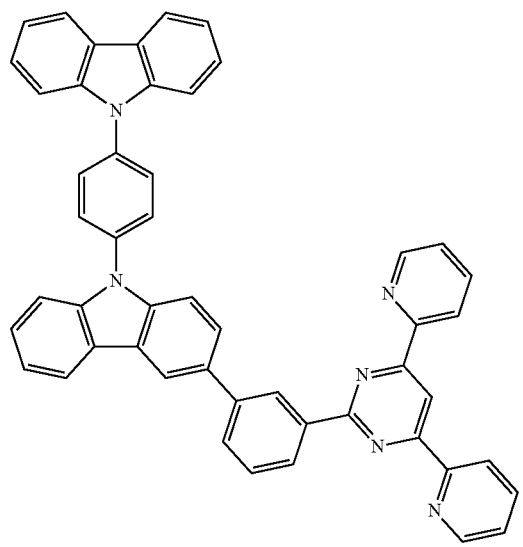
A-126
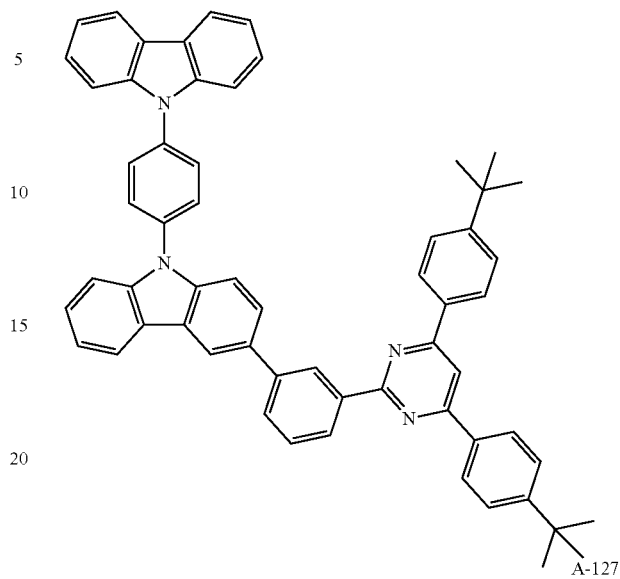
A-127
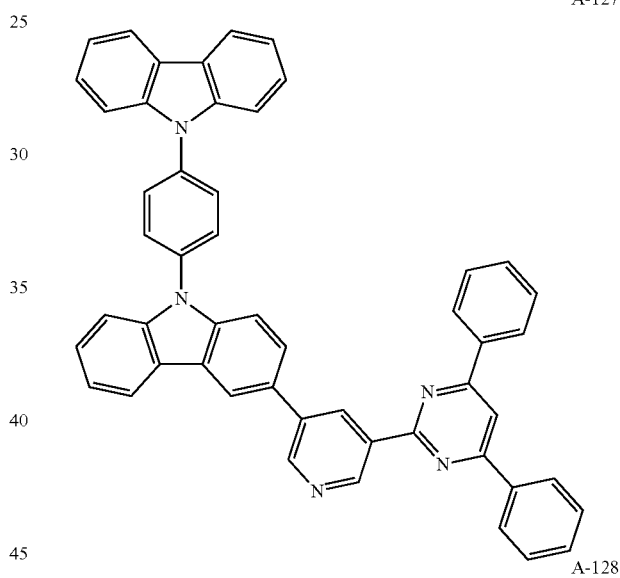
A-128
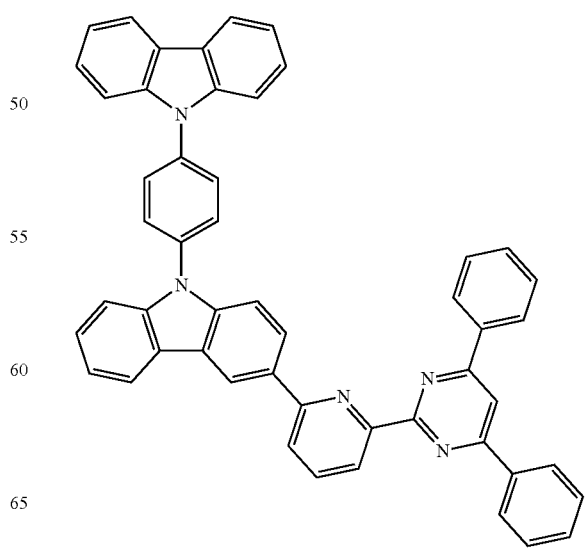

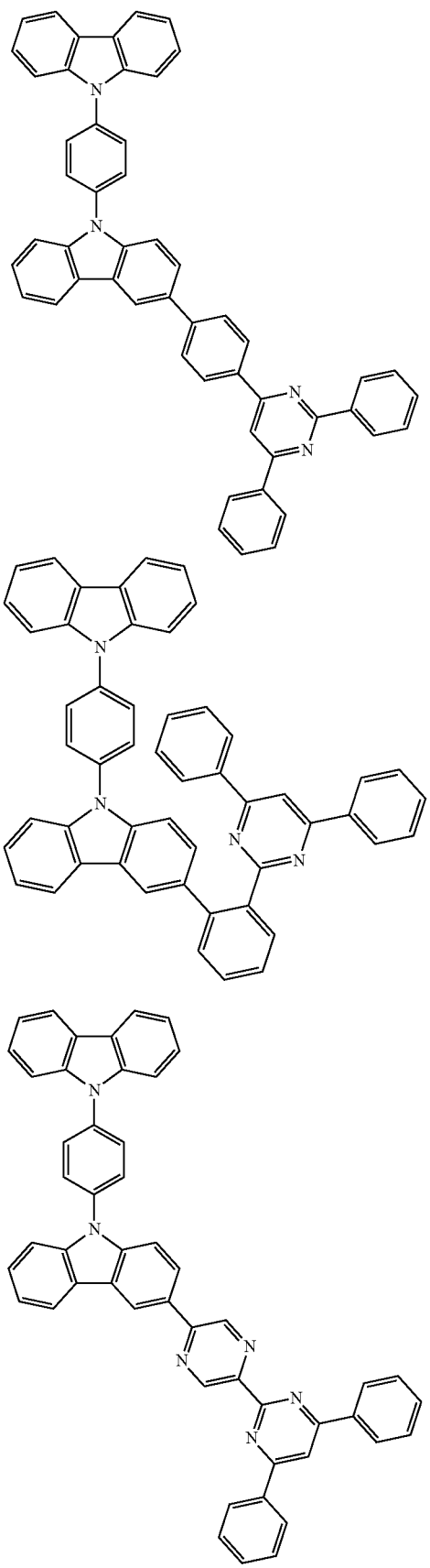
A-129
A-130
A-131
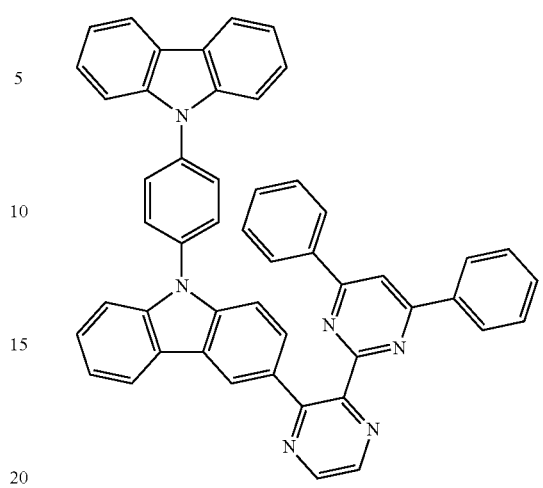
A-132
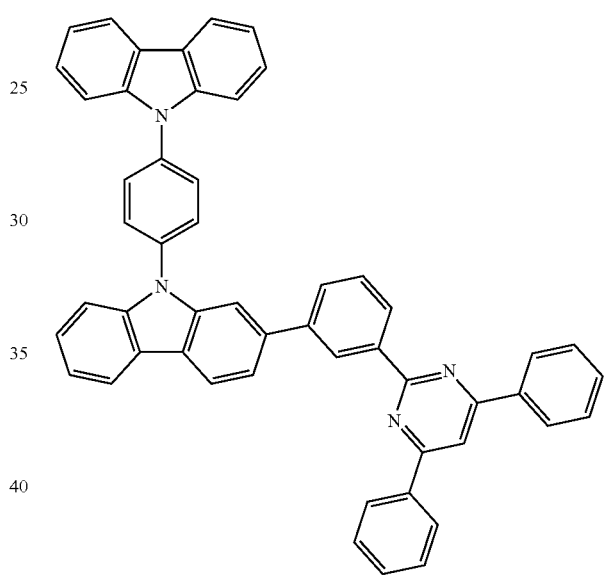
A-133
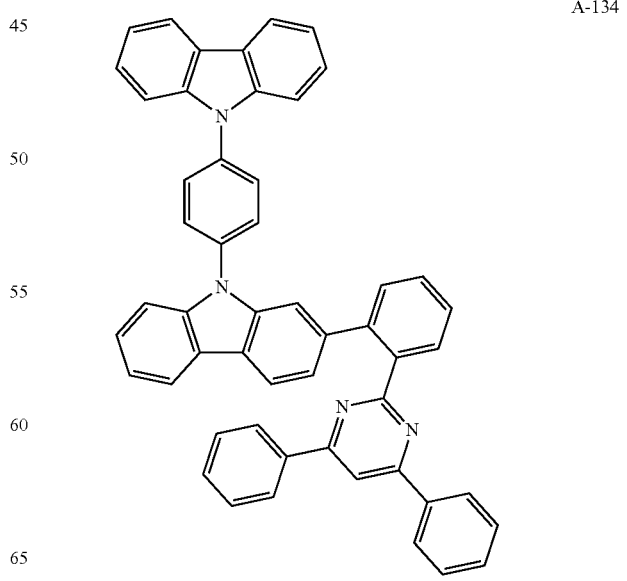
A-134

A-135
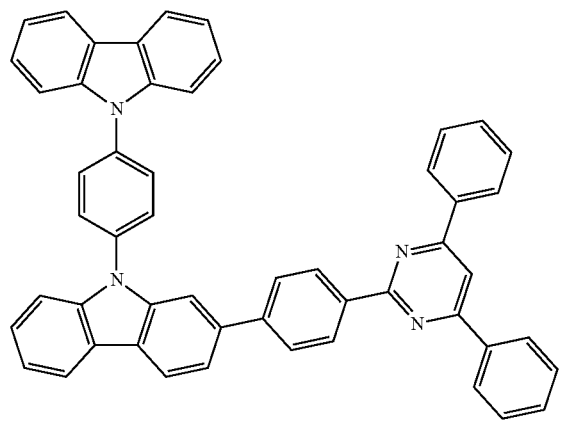
A-138
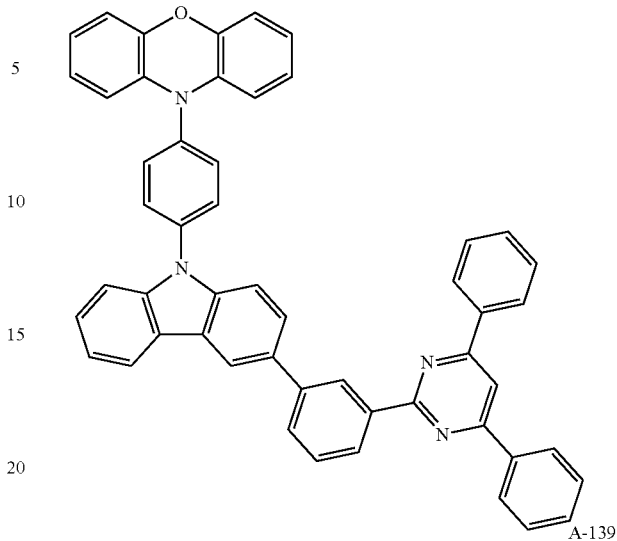
A-136
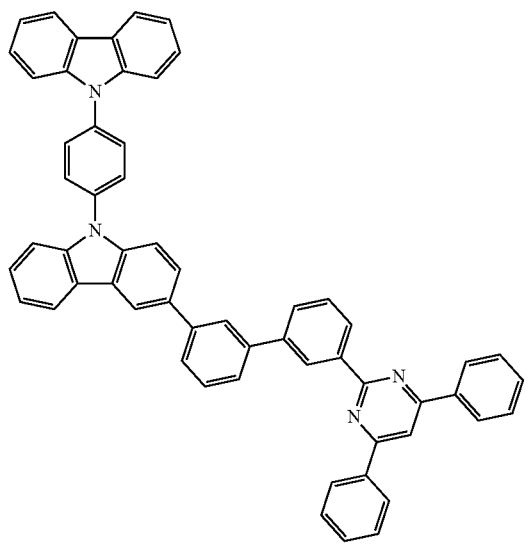
A-139
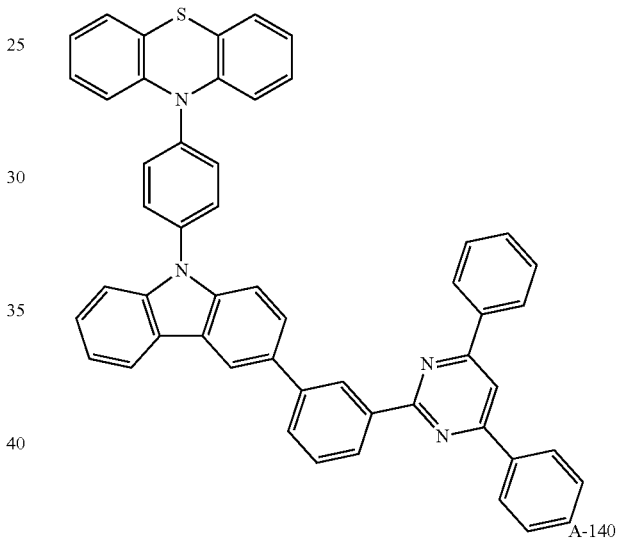
A-137
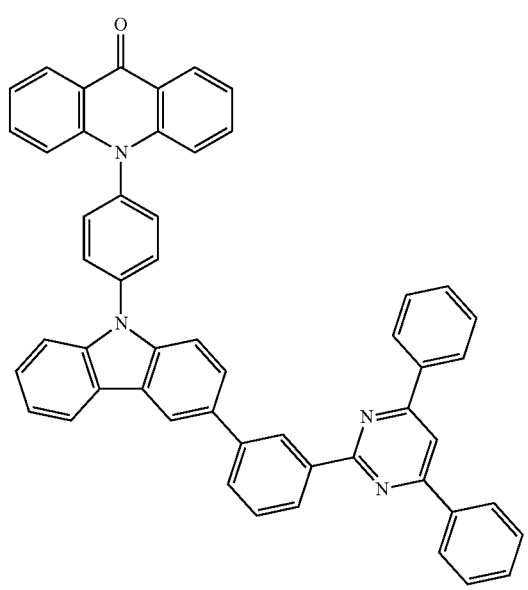
A-140
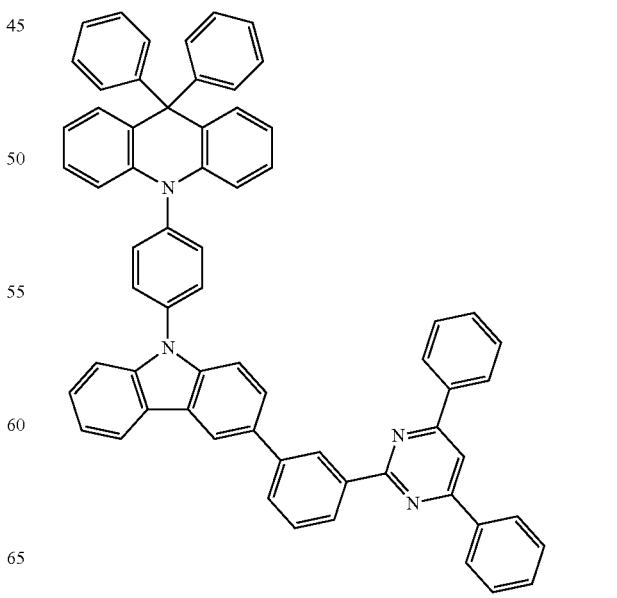

According to the embodiment, the compound includes a functional group having the desired electron attracting or withdrawing properties when both the electron and the hole properties are required, and thus the compounds may effectively improve the life-span of an organic light emitting diode and decrease a driving voltage thereof.

The compound for an organic optoelectronic device has a maximum light emitting wavelength in a range of about 320 to about 500 nm and a triplet excited energy (T1) ranging from greater than or equal to about 2.0 eV, and specifically, from about 2.0 to about 4.0 eV, and thus may efficiently transport a host charge having high triplet excited energy to a dopant and increase luminous efficiency of the dopant, and is also freely adjusted regarding HOMO and LUMO energy levels and decreases a driving voltage, and accordingly may be used as a host material or a charge transport material.

In addition, the compound for an organic optoelectronic device has photoactive and electrical activities, and thus may be used as a nonlinear optic material, an electrode material, a discolored material, or used in a light switch, a sensor, a module, a wave guide, an organic transistor, a laser, a light absorbent, a dielectric material, a separating membrane, and the like.

The compound for an organic optoelectronic device including the above compounds has a glass transition temperature of greater than or equal to 90° C., 100° C., or 110° C. and a thermal decomposition temperature of greater than or equal to 400° C., 420° C., or 450° C. indicating improved thermal stability. Thereby, it is possible to produce an organic optoelectronic device having high efficiency.

The compound for an organic optoelectronic device including the above compounds may play a role of emitting light or injecting and/or transporting electrons, and may also act as a light emitting host with an appropriate dopant. In other words, the compound for an organic optoelectronic device may be used as a phosphorescent or fluorescent host material, a blue light emitting dopant material, or an electron transport material.

Since the compound for an organic optoelectronic device according to an embodiment is used for an organic thin layer, it may improve the life-span characteristic, efficiency characteristic, electrochemical stability, and thermal stability of an organic photoelectric device, and decrease the driving voltage.

Further, according to another embodiment, an organic optoelectronic device that includes the compound for an organic optoelectronic device is provided. The organic optoelectronic device may include an organic photoelectric device, an organic light emitting diode, an organic solar cell, an organic transistor, an organic photoconductor drum, an organic memory device, and the like. For example, the compound for an organic optoelectronic device according to an embodiment may be included in an electrode or an electrode buffer layer in an organic solar cell to improve the quantum efficiency, and it may be used as an electrode material for a gate, a source-drain electrode, or the like in an organic transistor.

Hereinafter, an organic light emitting diode is described.

According to another embodiment, an organic light emitting diode includes an anode, a cathode, and at least one organic thin layer between the anode and the cathode. The at least one organic thin layer may include the compound for an organic optoelectronic device according to an embodiment of the present disclosure.

The organic thin layer may include a layer selected from an emission layer, a hole transport layer (HTL), a hole injection layer (HIL), an electron transport layer (ETL), an electron injection layer (EIL), a hole blocking layer, and a combination thereof, wherein at least one of these layers includes the compound for an organic optoelectronic device. Particularly, the compound for an organic optoelectronic device may be included in a hole transport layer (HTL) or a hole injection layer (HIL). In addition, when the compound for an organic optoelectronic device is included in the emission layer, the compound for an organic optoelectronic device may be included as a phosphorescent or fluorescent host, and particularly, as a fluorescent blue dopant material.

FIGS. 1 to 5 are cross-sectional views showing exemplary embodiments of organic light emitting diodes including the exemplary embodiment of the compound for an organic optoelectronic device.

Referring to FIGS. 1 to 5, organic light emitting diodes 100, 200, 300, 400, and 500 according to an embodiment include at least one organic thin layer 105 interposed between an anode 120 and a cathode 110.

The anode 120 includes an anode material, which can help injecting the holes into the organic thin layer. The anode material includes: a metal such as nickel, platinum, vanadium, chromium, copper, zinc, and gold, or alloys thereof; a metal oxide such as zinc oxide, indium oxide, indium tin oxide (ITO), and indium zinc oxide (IZO); a combination of a metal and oxide such as $ZnO:Al$ and $SnO_2:Sb$; or a conductive polymer such as poly(3-methylthiophene), poly[3,4-(ethylene-1,2-dioxy)thiophene] (PEDT), polypyrrole, and polyaniline, but is not limited thereto. In one embodiment, it is preferable to include a transparent electrode including indium tin oxide (ITO) as an anode.

The cathode 110 includes a cathode material, which can help injecting electrons into the organic thin layer. The cathode material includes: a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, $LiO_2$/Al, LiF/Ca, LiF/Al, and $BaF_2$/Ca, but is not limited thereto. In one embodiment, it is preferable to include a metal electrode including aluminum as a cathode.

Referring to FIG. 1, the organic photoelectric device 100 includes an organic thin layer 105 including only an emission layer 130.

Figure 2:
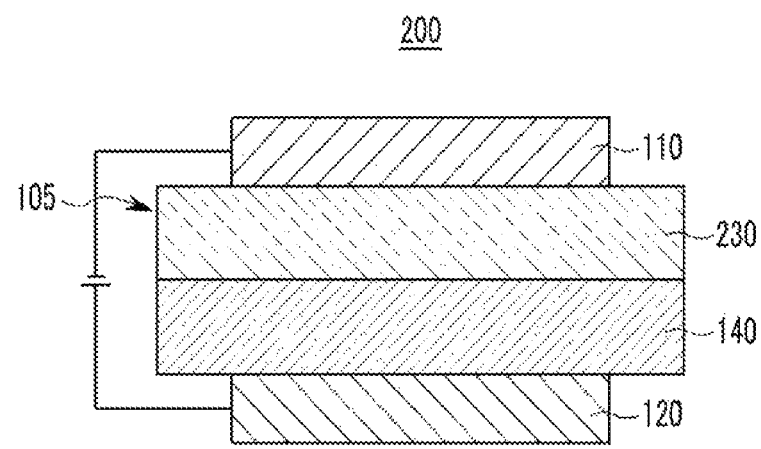

Referring to FIG. 2, a double-layered organic photoelectric device 200 includes an organic thin layer 105 including an emission layer 230 including an electron transport layer (ETL) (not shown), and a hole transport layer (HTL) 140. As shown in FIG. 2, the organic thin layer 105 includes a double layer of the emission layer 230 and the hole transport layer (HTL) 140. The emission layer 230 also functions as an electron transport layer (ETL), and the hole transport layer (HTL) 140 layer has an excellent binding property with a transparent electrode such as ITO or an excellent hole transport capability.

Figure 3:
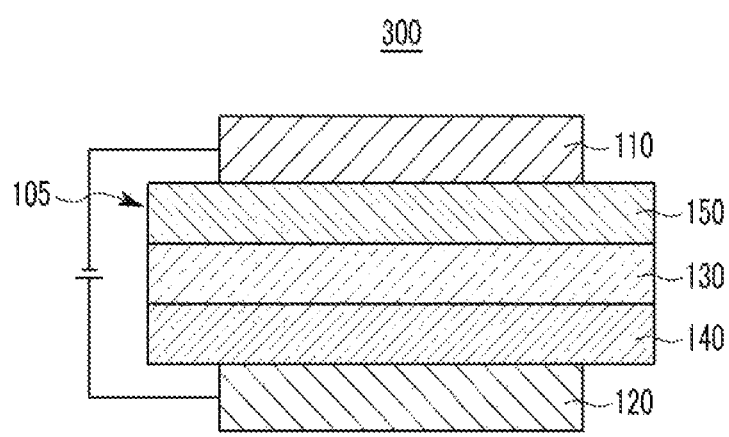

Referring to FIG. 3, a three-layered organic photoelectric device 300 includes an organic thin layer 105 including an electron transport layer (ETL) 150, an emission layer 130, and a hole transport layer (HTL) 140. The emission layer 130 is independently installed, and layers having an excellent electron transport capability or an excellent hole transport capability are separately stacked.

Figure 4:
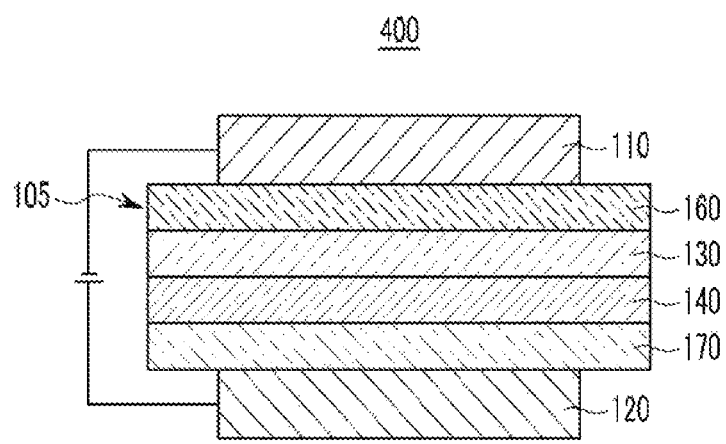

As shown in FIG. 4, a four-layered organic photoelectric device 400 includes an organic thin layer 105 including an electron injection layer (EIL) 160, an emission layer 130, a hole transport layer (HTL) 140, and a hole injection layer (HIL) 170 for adherence with the cathode of ITO.

Figure 5:
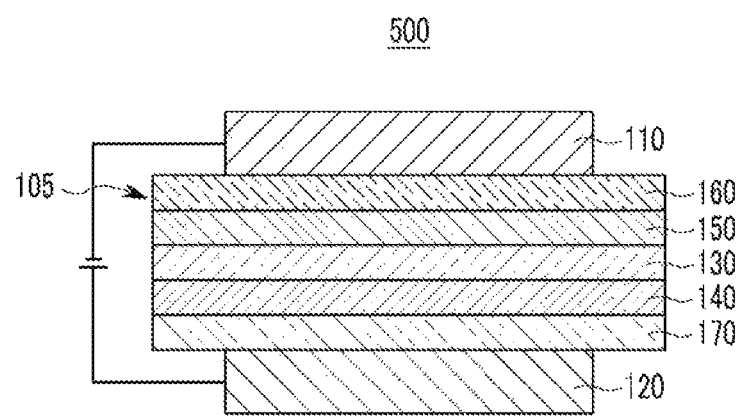

As shown in FIG. 5, a five-layered organic photoelectric device 500 includes an organic thin layer 105 including an electron transport layer (ETL) 150, an emission layer 130, a hole transport layer (HTL) 140, and a hole injection layer (HIL) 170, and further includes an electron injection layer (EIL) 160 to achieve a low voltage.

In FIGS. 1 to 5, the organic thin layer 105 including at least one selected from an electron transport layer (ETL) 150, an electron injection layer (EIL) 160, emission layers 130 and 230, a hole transport layer (HTL) 140, a hole injection layer (HIL) 170, wherein the organic thin layer includes a compound for an organic optoelectronic device. The compound for an organic optoelectronic device may be used for an electron transport layer (ETL) 150 or electron injection layer (EIL) 160. When it is used for the electron transport layer (ETL), it is possible to provide an organic photoelectric device having a simpler structure because it does not require an additional hole blocking layer (not shown).

Furthermore, when the compound for an organic photoelectric device is included in the emission layers 130 and 230, the material for the organic photoelectric device may be included as a phosphorescent or fluorescent host or a fluorescent blue dopant.

The organic light emitting diode may be fabricated by: forming an anode on a substrate; forming an organic thin layer in accordance with a dry coating method such as evaporation, sputtering, plasma plating, and ion plating, or a wet coating method such as spin coating, dipping, and flow coating; and providing a cathode thereon.

Another embodiment of the present disclosure provides a display device including the organic photoelectric device according to the above embodiment.

Hereinafter, the embodiments are illustrated in more detail with reference to examples. These examples, however, should not in any sense be interpreted as limiting the scope of the present disclosure.

PREPARATION OF COMPOUND FOR ORGANIC OPTOELECTRONIC DEVICE

Example 1

Synthesis of Compound A-1

The compound A-1 as a specific example of a compound for an organic optoelectronic device according to the present disclosure is synthesized according to the following Reaction Scheme 1.

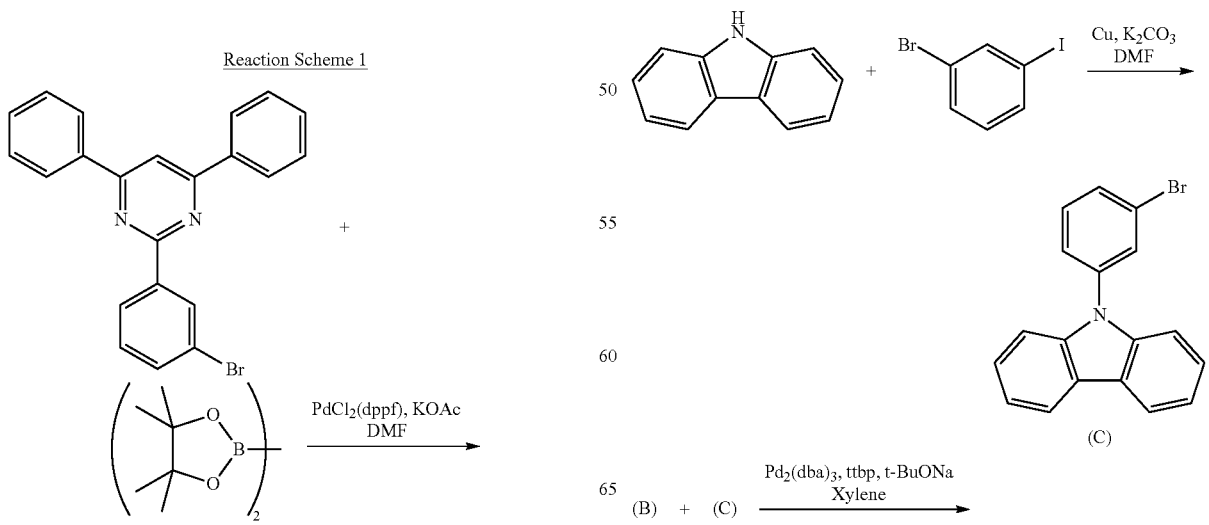

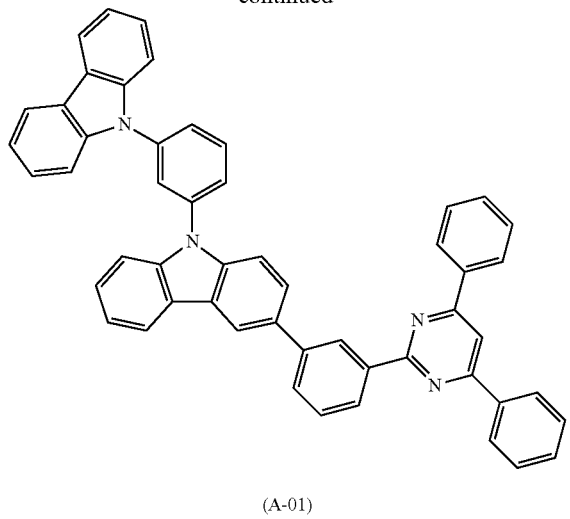

(A-01)

First Step: Synthesis of Intermediate Product (A)

5.00 g (12.9 mmol) of 2-(3-bromophenyl)-4,6-diphenylpyrimidine, 3.94 g (15.5 mmol) of bis(pinacolato)diboron, 527 mg (0.645 mmol) of PdCl$_2$(dppf).CH$_2$Cl$_2$, and 3.80 g (38.7 mmol) of potassium acetate are added to 100 mL of DMF, and the mixture is heated and agitated at 100° C. When the reaction is complete, the agitated reaction product is cooled down to room temperature, passed through silica gel, and then filtered and concentrated under a reduced pressure. The product is recrystallized and purified under an ethyl acetate/toluene condition, obtaining 4.59 g of desired intermediate product (A) (a yield of 82%).

$^1$H-NMR (300 MHz, CDCl$_3$): 9.09 (s, 1H); 8.82 (dt, 1H); 8.31-8.28 (m, 4H); 8.00 (s, 1H), 7.97 (dt, 1H); 7.60-7.50 (m, 7H); 1.99 (s, 12H)

Second Step: Synthesis of Intermediate Product (B)

1.80 g (4.14 mmol) of the intermediate A, 1.02 g (4.14 mmol) of 3-bromocarbazole, 478 mg (0.414 mmol) of tetrakis(triphenylphosphine)palladium(0) (Pd(PPh$_3$)$_4$), and 1.72 g (12.4 mmol) of potassium carbonate are added to a mixed solution of 8 mL of toluene, 8 mL of tetrahydrofuran, and 8 mL of water. The mixture is refluxed and agitated. When the reaction is complete, the resulting product is cooled down to room temperature, extracted to remove an aqueous solution layer, passed through silica gel, and then filtered and concentrated under a reduced pressure. The obtained product is separated through silica gel column chromatography (ethyl acetate:n-hexane=1:5 v/v), obtaining 1.43 g of desired intermediate product (B) (a yield of 73%).

$^1$H-NMR (300 MHz, CDCl$_3$): 9.04 (s, 1H); 8.72 (d. 1H); 8.42 (s, 1H); 8.33-8.31 (m, 4H); 8.16 (t, 2H); 8.06 (s, 1H); 7.84-7.81 (m, 2H); 7.66 (d, 1H); 7.60-7.50 (m, 6H); 7.48-7.44 (m, 2H); 7.27-7.24 (m, 2H)

Third Step: Synthesis of Intermediate Product (C)

2.00 g (12.0 mmol) of carbazole, 2.02 mL (15.8 mmol) of 1-bromo-3-iodobenzene, 2.29 g (36.0 mmol) of copper (Cu), and 4.98 g (36.0 mmol) of calcium carbonate are added to 30 mL of DMF. The mixture is heated and agitated at 130° C. When the reaction is complete, the agitated mixture is cooled down to room temperature, diluted with ethyl acetate, passed through silica gel, and then filtered and concentrated under a reduced pressure. The product is separated through silica gel column chromatography (ethyl acetate:n-hexane=1:20 v/v), obtaining 3.80 g of desired intermediate product (C) (a yield of 98%).

$^1$H-NMR (300 MHz, CDCl$_3$): 8.16-8.13 (d, 1H), 7.75-7.69 (m, 2H), 7.57-7.40 (m, 7H), 7.33-7.30 (m, 2H)

Fourth Step: Synthesis of Chemical Formula A-1

474 mg (1.00 mmol) of the intermediate (B), 387 mg (1.20 mmol) of the intermediate (C), 91.6 mg (0.10 mmol) of Pd$_2$(dba)$_3$, 100 μL (0.20 mmol) of tri-tert-butylphosphine (ttbp) (50% in toluene), and 192 mg (2.00 mmol) of sodium tert-butoxide are added to 10 mL of xylene. The mixture is heated and agitated at 145° C. When the reaction is complete, the agitated mixture is cooled down to room temperature and passed through silica gel, and then filtered and concentrated under a reduced pressure. The obtained product is separated through silica gel column chromatography (ethyl acetate:n-hexane=1:4 v/v). The separated product is recrystallized and purified under a toluene/methanol condition, obtaining 465 mg of a desired compound represented by Chemical Formula A-01 (a yield of 65%).

$^1$H-NMR (300 MHz, CDCl$_3$): 9.05 (t, 1H); 8.73 (dt, 1H); 8.50 (d, 1H); 8.34-8.30 (m, 4H); 8.23 (d, 1H); 8.17 (d. 2H); 8.06 (s, 1H); 7.88-7.83 (m, 4H); 7.77-7.72 (m, 2H); 7.69-7.63 (m, 2H); 7.61-7.52 (m, 8H); 7.50-7.43 (m, 3H); 7.33 (dd, 3H); 7.17 (d, 1H)

Example 2

Synthesis of A-2

The compound A-2 as a specific example of a compound for an organic optoelectronic device according to the present disclosure is synthesized according to the following Reaction Scheme 2.

Reaction Scheme 2

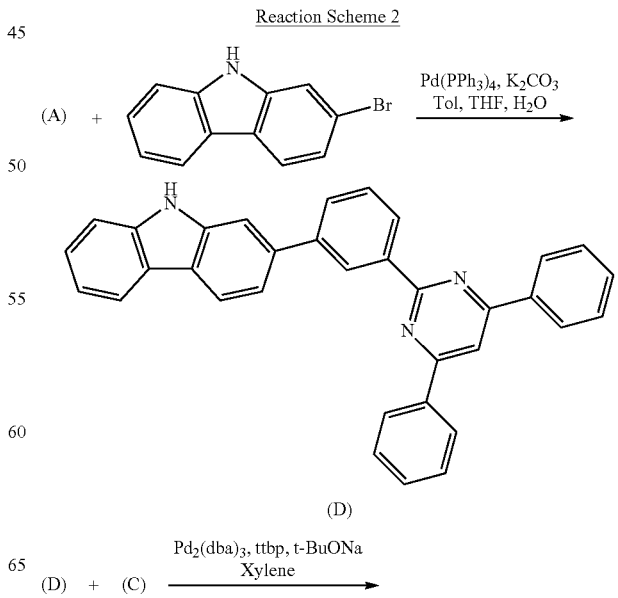

-continued

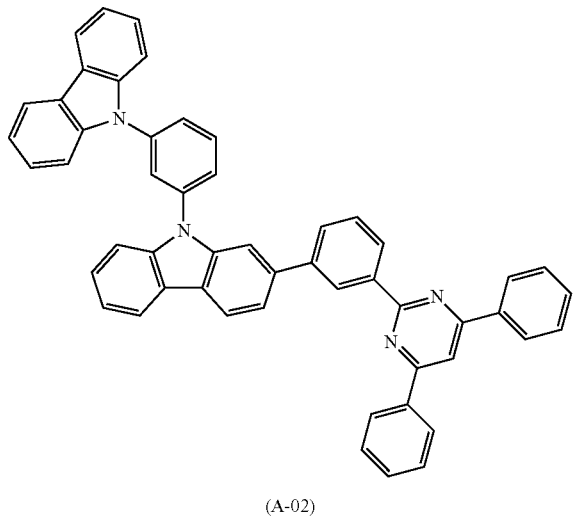

(A-02)

Reaction Scheme 3

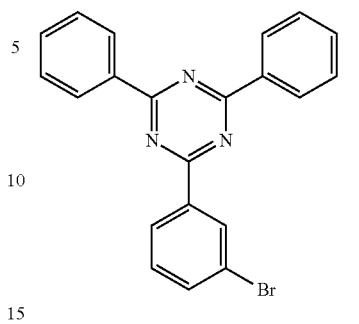

+

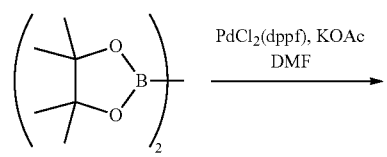

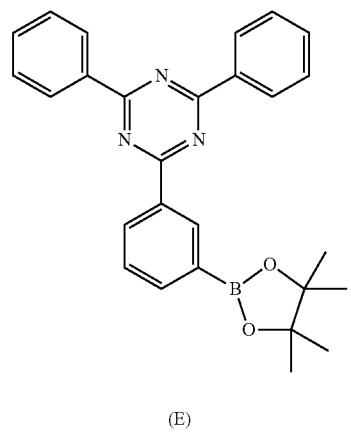

(E)

First Step: Synthesis of Intermediate Product (D)

1.80 g (4.14 mmol) of the intermediate A, 1.02 g (4.14 mmol) of 2-bromocarbazole, 478 mg (0.414 mmol) of tetrakis(triphenylphosphine)palladium(0) (Pd(PPh$_3$)$_4$), and 1.72 g (12.4 mmol) of potassium carbonate are added to a mixed solution of 8 mL of toluene, 8 mL of tetrahydrofuran, and 8 mL of water. The mixture is refluxed and agitated. When the reaction is complete, the agitated mixture is cooled down to room temperature, extracted to remove an aqueous solution layer, passed through silica gel, and then filtered and concentrated under a reduced pressure. The resulting product is separated through silica gel column chromatography (ethyl acetate:n-hexane=1:5 v/v), obtaining 1.52 g of desired intermediate product (D) (a yield of 78%).

Second Step: Synthesis of Chemical Formula A-2

474 mg (1.00 mmol) of the intermediate (D), 387 mg (1.20 mmol) of the intermediate (C), 91.6 mg (0.10 mmol) of Pd$_2$(dba)$_3$, 100 μL (0.20 mmol) of tri-tert-butylphosphine (ttbp) (50% in toluene), and 192 mg (2.00 mmol) of sodium tert-butoxide are added to 10 mL of xylene. The mixture is heated and agitated at 145° C. When the reaction is complete, the agitated mixture is cooled down to room temperature, passed through silica gel, and then filtered and concentrated under a reduced pressure. The resulting product is separated through silica gel column chromatography (ethyl acetate:n-hexane=1:4 v/v). The obtained product is recrystallized and purified under a toluene/methanol condition, obtaining 515 mg of a desired compound represented by Chemical Formula A-2 (a yield of 72%).

Example 3

Synthesis of A-3

The compound A-3 as a specific example of a compound for an organic optoelectronic device according to the present disclosure is synthesized according to the following Reaction Scheme 3.

(E) +

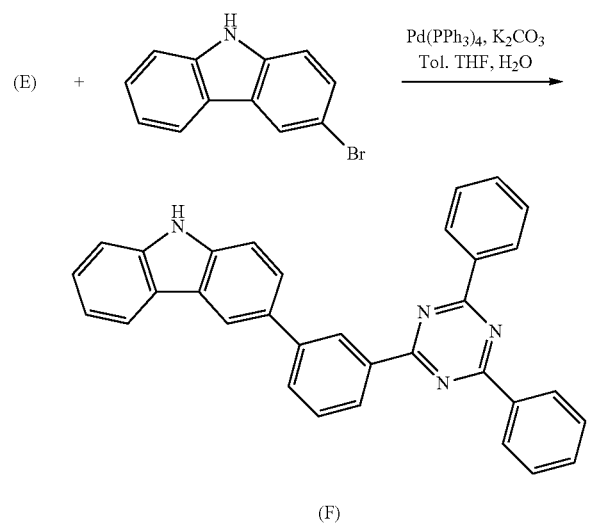

(F)

(F) + (C)

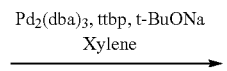

119
-continued

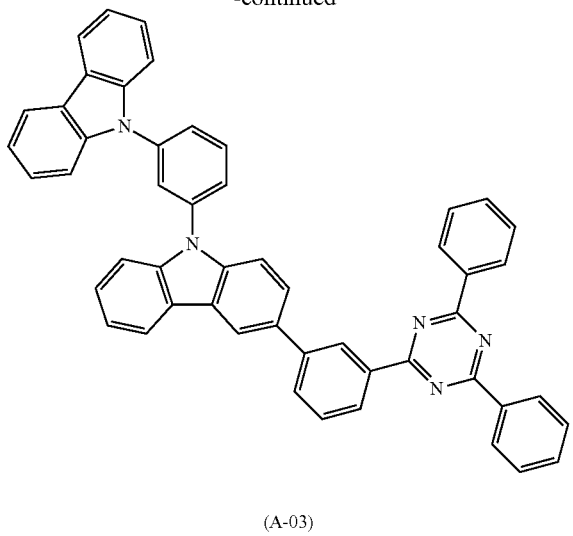

(A-03)

First Step: Synthesis of Intermediate Product (E)

5.00 g (12.9 mmol) of 2-(3-bromophenyl)-4,6-diphenyl-1,3,5-triazine), 3.94 g (15.5 mmol) of bis(pinacolato)diboron, 527 mg (0.645 mmol) of $PdCl_2(dppf).CH_2Cl_2$, and 3.80 g (38.7 mmol) of potassium acetate are added to 100 mL of DMF. The mixture is heated and agitated at 100° C. When the reaction is complete, the agitated mixture is cooled down to room temperature and passed through silica gel, and then filtered and concentrated under a reduced pressure. The product is recrystallized and purified under an ethyl acetate/toluene condition, obtaining 4.25 g of desired intermediate product (E) (a yield of 76%).

Second Step: Synthesis of Intermediate Product (F)

2.00 g (4.59 mmol) of the intermediate (E), 1.13 g (4.59 mmol) of 3-bromocarbazole, 530 mg (0.459 mmol) of tetrakis(triphenylphosphine)palladium(0) $(Pd(PPh_3)_4)$, and 1.91 g (13.8 mmol) of potassium carbonate are added to a mixed solution of 10 mL of toluene, 10 mL of tetrahydrofuran, and 10 mL of water, and the mixture is refluxed and agitated. When the reaction is complete, the agitated mixture is cooled down to room temperature, extracted to remove an aqueous solution layer, passed through silica gel, and then filtered and concentrated under a reduced pressure. The product is separated through silica gel column chromatography (ethyl acetate:n-hexane=1:4<v/v>), obtaining 1.50 g of desired intermediate product (F) (a yield of 69%).

Third Step: Synthesis of Chemical Formula A-3

475 mg (1.00 mmol) of the intermediate (F), 387 mg (1.20 mmol) of the intermediate (C), 91.6 mg (0.100 mmol) of $Pd_2(dba)_3$, 100 µL (0.20 mmol) of tri-tert-butylphosphine (ttbp) (50% in toluene), and 192 mg (2.00 mmol) of sodium tert-butoxide are added to 10 mL of xylene. The mixture is heated and agitated at 145° C. When the reaction is complete, the agitated mixture is cooled down to room temperature and passed through silica gel, and then filtered and concentrated under a reduced pressure. The product is separated through silica gel column chromatography (ethyl acetate:n-hexane=1:3 <v/v>). The separated product is recrystallized and purified under a toluene/methanol condition, obtaining 422 mg of a desired compound represented by Chemical Formula A-3 (a yield of 59%).

Example 4

Synthesis of A-4

The compound A-4 as a specific compound for an organic optoelectronic device according to the present disclosure is synthesized according to the following Reaction Scheme 4.

Reaction Scheme 4

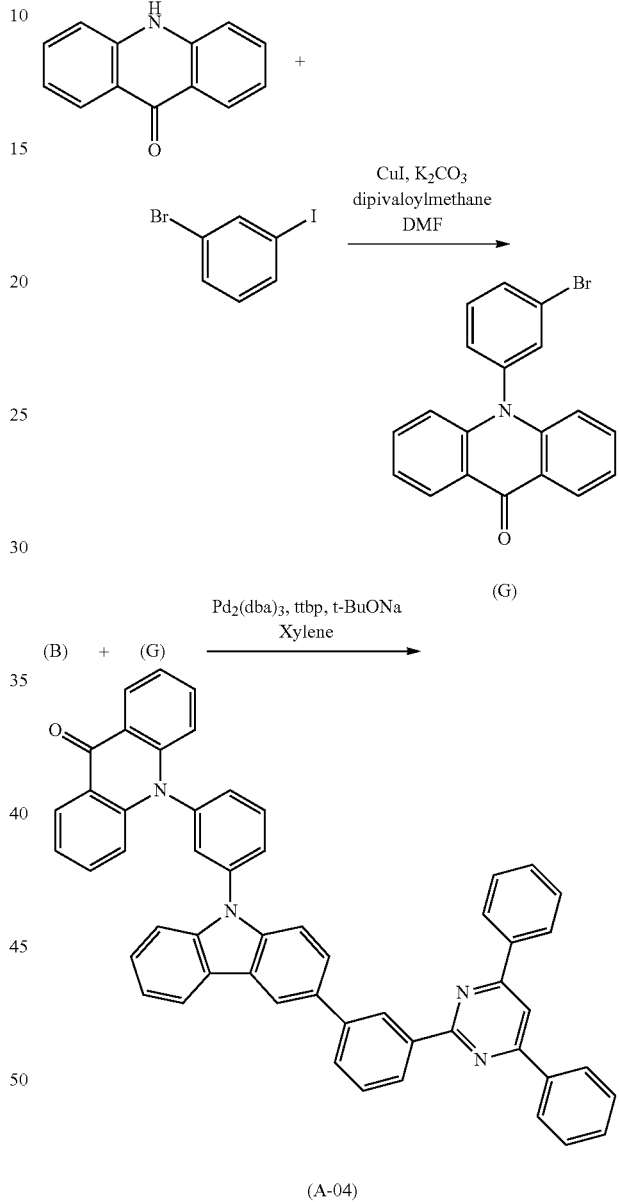

(A-04)

First Step: Synthesis of Intermediate Product (G)

2.00 g (10.2 mmol) of acridone, 1.95 mL (15.3 mmol) of 1-bromo-3-iodobenzene, 1.06 mL (5.10 mmol) of dipivaloylmethane, 389 mg (2.04 mmol) of cuprous iodide (CuI), and 2.82 g (20.4 mmol) of calcium carbonate are added to 50 mL of DMF. The mixture is refluxed and agitated. When the reaction is complete, the agitated mixture is cooled down to room temperature, diluted with ethyl acetate, and passed through silica gel, and then filtered and concentrated under a reduced pressure filter. The product is separated through silica gel column chromatography (ethyl acetate:n-hexane=1:10 <v/v>), obtaining 2.85 g of desired intermediate product (G) (a yield of 80%).

Second Step: Synthesis of Chemical Formula A-4

474 mg (1.00 mmol) of the intermediate (B), 420 mg (1.20 mmol) of the intermediate (G), 91.6 mg (0.10 mmol) of Pd$_2$(dba)$_3$, 100 μL (0.20 mmol) of tri-tert-butylphosphine (ttbp) (50% in toluene), and 192 mg (2.00 mmol) of sodium tert-butoxide are added to 10 mL of xylene, and the mixture is heated and agitated at 145° C. When the reaction is complete, the agitated mixture is cooled down to room temperature, passed through silica gel, and then filtered and concentrated under a reduced pressure. The obtained product is separated through silica gel column chromatography (ethyl acetate:n-hexane=1:3 <v/v>). The separated product is recrystallized and purified under a toluene/methanol condition, obtaining 387 mg of a compound represented by Chemical Formula A-4 (a yield of 52%).

Example 5

Synthesis of A-5

The compound A-5 as specific example of a compound for an organic optoelectronic device is synthesized according to the following Reaction Scheme 5.

First Step: Synthesis of Intermediate Product (H)

2.00 g (10.9 mmol) of phenoxazine, 2.08 mL (16.4 mmol) of 1-bromo-3-iodobenzene, 2.08 g (32.7 mmol) of copper (Cu), and 4.52 g (32.7 mmol) of calcium carbonate are added to 30 mL of DMF, and the mixture is heated and agitated at 130° C. When the reaction is complete, the agitated mixture is cooled down to room temperature, diluted with ethyl acetate, and passed through silica gel, and then filtered and concentrated under a reduced pressure. The obtained product is separated through silica gel column chromatography (ethyl acetate:n-hexane=1:20 <v/v>), obtaining 1.52 g of a desired compound, an intermediate product (H) (a yield of 41%).

$^1$H-NMR (300 MHz, CDCl$_3$): 7.62 (ddd, 1H); 7.53 (t, 1H); 7.47 (t, 1H); 7.31 (ddd, 1H); 6.71-6.58 (m, 8H); 5.92 (dd, 2H)>

Second Step: Synthesis of Chemical Formula A-5

474 mg (1.00 mmol) of the intermediate (B), 406 mg (1.20 mmol) of the intermediate (H), 91.6 mg (0.10 mmol) of Pd$_2$(dba)$_3$, 100 μL of (0.20 mmol) of tri-tert-butylphosphine (ttbp) (50% in toluene), and 192 mg (2.00 mmol) of sodium tert-butoxide are added to 10 mL of xylene, and the mixture is heated and agitated at 145° C. When the reaction is complete, the agitated mixture is cooled down to room temperature, passed through silica gel, and then filtered and concentrated under a reduced pressure. The obtained product is separated through silica gel column chromatography (ethyl acetate:n-hexane=1:5 <v/v>). The separated product is recrystallized and purified under a toluene/methanol condition, obtaining 497 mg of a compound represented by Chemical Formula A-5 (a yield of 68%).

$^1$H-NMR (300 MHz, CDCl$_3$): 9.04 (t. 1H); 8.73 (dt, 1H); 8.48 (d. 1H); 8.33-8.30 (m, 4H); 8.23 (d, 1H); 8.05 (s, 1H); 7.89-7.76 (m, 4H); 7.68-7.65 (m, 2H); 7.63-7.52 (m, 6H); 7.49-7.43 (m, 2H); 7.36-7.31 (m, 1H); 7.25-7.16 (m, 2H); 6.75-6.67 (m, 6H); 6.17-6.11 (m, 2H)>

Example 6

Synthesis of A-6

The compound A-6 as a specific compound for an organic optoelectronic device according to the present disclosure is synthesized according to the following Reaction Scheme 6.

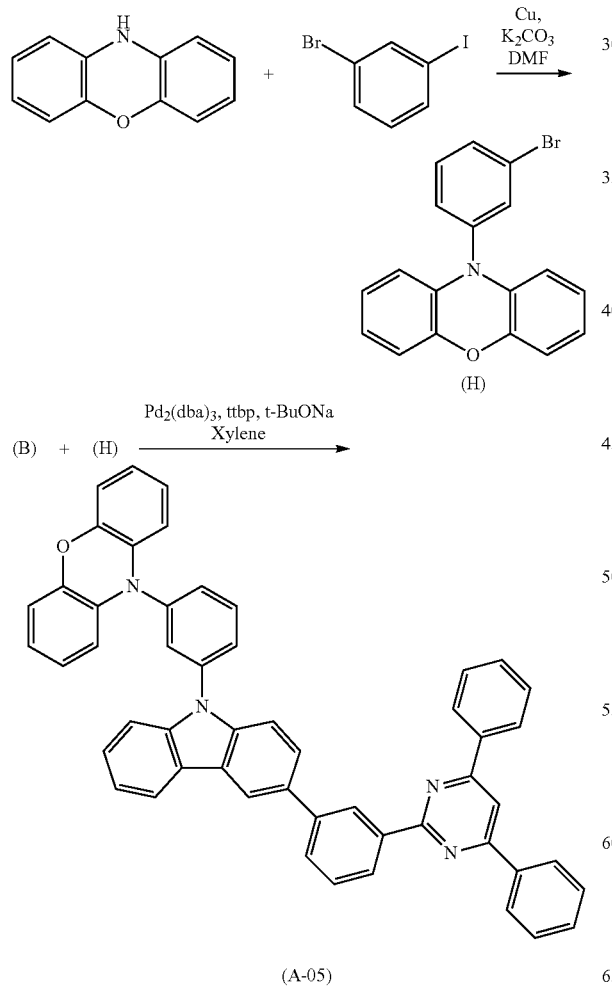

Reaction Scheme 5

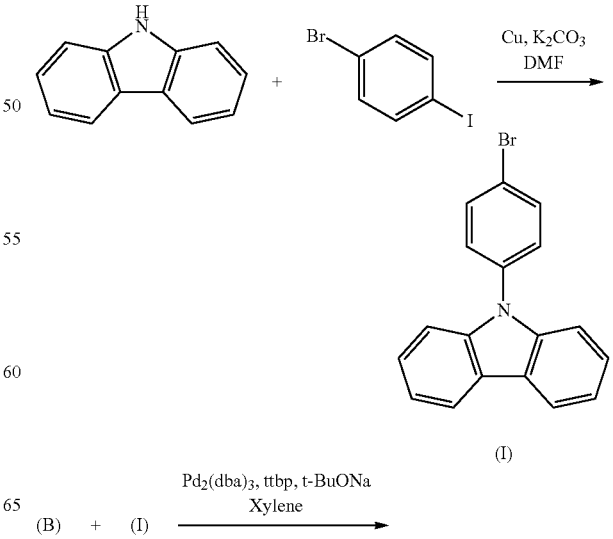

Reaction Scheme 6

-continued

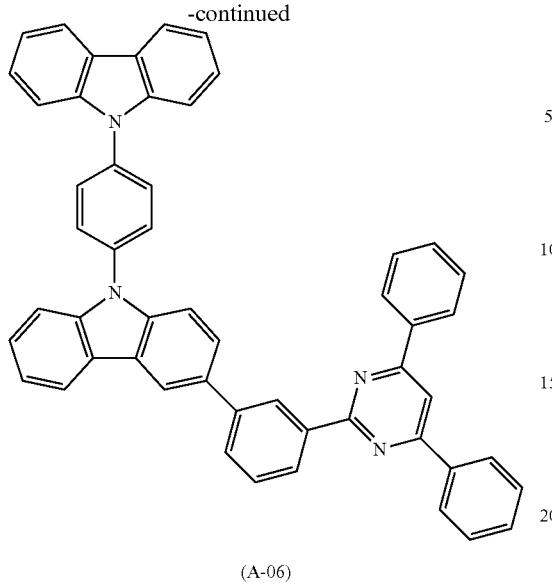

(A-06)

First Step: Synthesis of Intermediate Product (I)

2.00 g (12.0 mmol) of carbazole, 2.02 mL (15.8 mmol) of 1-bromo-3-iodobenzene, 2.29 g (36.0 mmol) of copper (Cu), and 4.98 g (36.0 mmol) of calcium carbonate are added to 30 mL of DMF, and the mixture is heated and agitated at 130° C. When the reaction is complete, the agitated mixture is cooled down to room temperature, diluted with ethyl acetate, and passed through silica gel, and then filtered and concentrated under a reduced pressure. The obtained product is separated through silica gel column chromatography (ethyl acetate:n-hexane=1:20 <v/v>), obtaining 3.68 g of a desired compound, an intermediate product (I) (a yield of 95%).

$^1$H-NMR (300 MHz, CDCl$_3$): 8.22 (d, 2H); 7.84-7.76 (m, 2H); 7.55-7.41 (m, 6H); 7.39-7.31 (m, 2H)>

Second Step: Synthesis of Chemical Formula A-6

474 mg (1.00 mmol) of the intermediate (B), 387 mg (1.20 mmol) of the intermediate (I), 91.6 mg (0.10 mmol) of Pd$_2$(dba)$_3$, 100 μL (0.20 mmol) of tri-tert-butylphosphine (ttbp) (50% in toluene), and 192 mg (2.00 mmol) of sodium tert-butoxide are added to 10 mL of xylene, and the mixture is heated and agitated at 145° C. When the reaction is complete, the agitated mixture is cooled down to room temperature, passed through silica gel, and then filtered and concentrated under a reduced pressure. The obtained product is separated through silica gel column chromatography (ethyl acetate:n-hexane=1:4 <v/v>). The separated product is recrystallized and purified under a toluene/methanol condition, obtaining 386 mg of a compound represented by Chemical Formula A-6 (a yield of 54%).

$^1$H-NMR (300 MHz, CDCl$_3$): 9.08 (t. 1H); 8.74 (dt, 1H); 8.53 (d, 1H); 8.34-8.31 (m, 4H); 8.27 (d, 1H); 8.17 (d, 2H); 8.06 (s, 1H); 7.91-7.81 (m, 6H); 7.69 (d, 2H); 7.65-7.53 (m, 8H); 7.49-7.46 (m, 3H); 7.40-7.32 (m, 3H); 7.20 (dd, 1H)>

Example 7

Synthesis of A-7

The compound A-7 as a specific compound for an organic optoelectronic device according to the present disclosure is synthesized according to the following Reaction Scheme 7.

Reaction Scheme 7

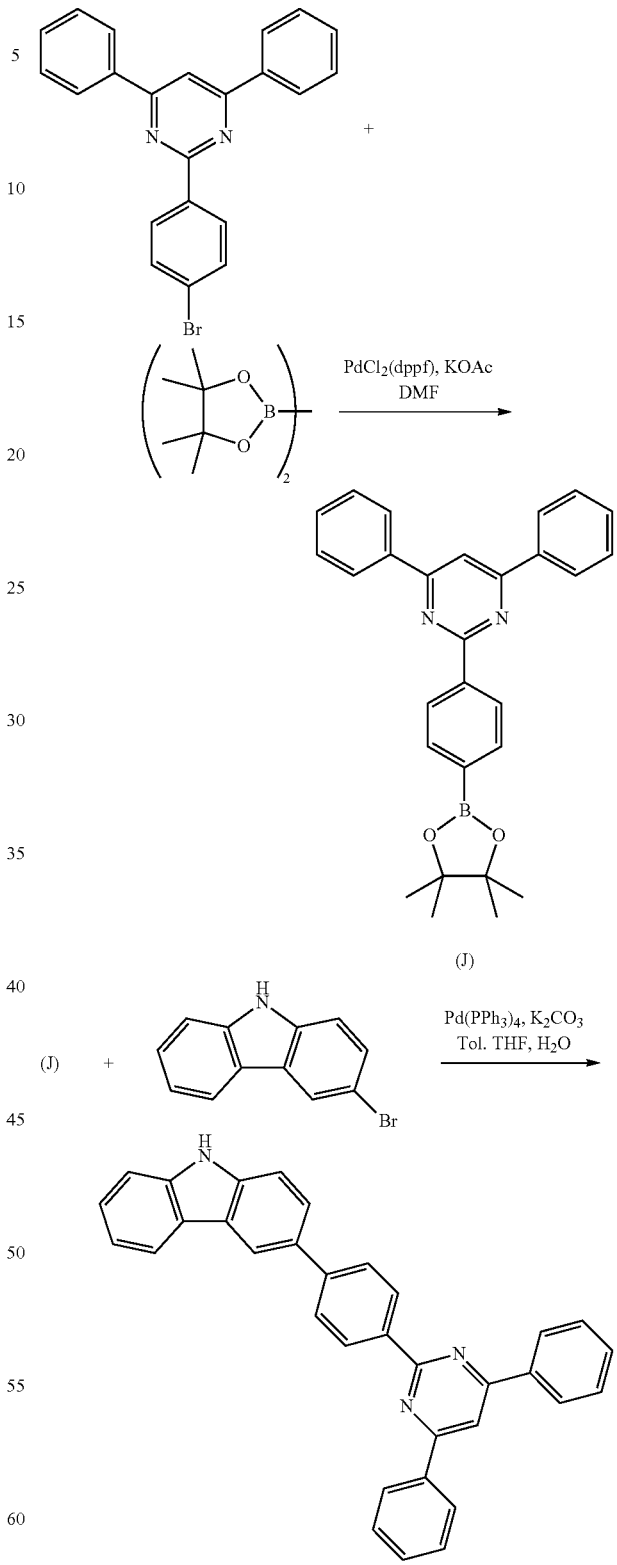

125

-continued

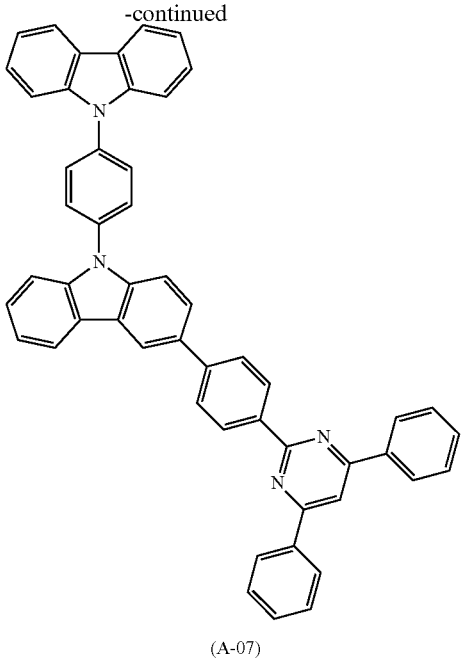

(A-07)

First Step: Synthesis of Intermediate Product (J)

5.00 g (12.9 mmol) of 2-(4-bromophenyl)-4,6-diphenylpyrimidine), 3.94 g (15.5 mmol) of bis(pinacolato)diboron, 527 mg (0.645 mmol) of $PdCl_2(dppf).CH_2Cl_2$, and 3.80 g (38.7 mmol) of potassium acetate are added to 100 mL of DMF, and the mixture is heated and agitated at 100° C. When the reaction is complete, the agitated mixture is cooled down to room temperature, passed through silica gel, and then filtered and concentrated under a reduced pressure. The obtained product is recrystallized and purified under an ethyl acetate/toluene condition, obtaining 4.81 g of a desired compound, an intermediate product (J) (a yield of 86%).

Second Step: Synthesis of Intermediate Product (K)

1.80 g (4.14 mmol) of the intermediate (J), 1.02 g (4.14 mmol) of 3-bromocarbazole, 478 mg (0.414 mmol) of tetrakis(triphenylphosphine)palladium(0) $(Pd(PPh_3)_4)$, and 1.72 g (12.4 mmol) of potassium carbonate are added to a mixed solution of 8 mL of toluene, 8 mL of tetrahydrofuran, and 8 mL of water, and the mixture is refluxed and agitated. When the reaction is complete, the agitated mixture is cooled down to room temperature, extracted to remove an aqueous solution layer, passed through silica gel, and then filtered and concentrated under a reduced pressure. The obtained product is separated through silica gel column chromatography (ethyl acetate:n-hexane=1:5 <v/v>), obtaining 1.12 g of a desired compound, an intermediate (K) (a yield of 57%).

Third Step: Synthesis of Chemical Formula A-7

474 mg (1.00 mmol) of the intermediate (K), 387 mg (1.20 mmol) of the intermediate (I), 91.6 mg (0.10 mmol) of $Pd_2(dba)_3$, 100 µL (0.20 mmol) of tri-tert-butylphosphine (ttbp) (50% in toluene), and 192 mg (2.00 mmol) of sodium tert-butoxide are added to 10 mL of xylene, and the mixture is heated and agitated at 145° C. When the reaction is complete, the agitated mixture is cooled down to room temperature, passed through silica gel, and then filtered and concentrated under a reduced pressure. The obtained product is separated through silica gel column chromatography (ethyl acetate:n-hexane=1:4 <v/v>). The separated product is recrystallized and purified under a toluene/methanol condition, obtaining 444 mg of a desired compound represented by Chemical Formula A-7 (a yield of 62%).

126

Example 8

Synthesis of A-8

The compound A-8 as a specific example of a compound for an organic optoelectronic device according to the present disclosure is synthesized according to the following Reaction Scheme 8.

Reaction Scheme 8

(K) + (C) →  $Pd_2(dba)_3$, ttbp, t-BuONa / Xylene

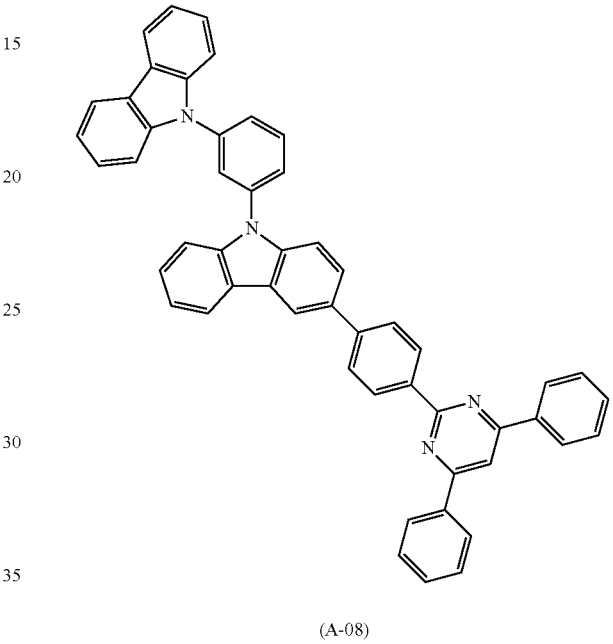

(A-08)

First Step: Synthesis of Chemical Formula A-8

474 mg (1.00 mmol) of the intermediate (K), 387 mg (1.20 mmol) of the intermediate (C), 91.6 mg (0.10 mmol) of $Pd_2(dba)_3$, 100 µL (0.20 mmol) of tri-tert-butylphosphine (ttbp) (50% in toluene), and 192 mg (2.00 mmol) of sodium tert-butoxide are added to 10 mL of xylene, and the mixture is heated and agitated at 145° C. When the reaction is complete, the agitated mixture is cooled down to room temperature, passed through silica gel, and then filtered and concentrated under a reduced pressure. The obtained product is passed through silica gel column chromatography (ethyl acetate:n-hexane=1:4 <v/v>). The separated product is recrystallized and purified under a toluene/methanol condition, obtaining 559 mg of a desired compound represented by Chemical Formula A-8 (a yield of 78%).

$^1$H-NMR (300 MHz, $CDCl_3$): 8.54 (d, 2H); 8.46 (d, 1H); 8.34-8.30 (m, 4H); 8.24 (d, 1H); 8.16 (d, 2H); 8.02 (s, 1H); 7.91-7.85 (m, 4H); 7.80 (dd, 1H); 7.72-7.69 (m, 2H); 7.60 (d, 1H); 7.59-7.53 (m, 8H); 7.49-7.40 (m, 3H); 7.37-7.28 (m, 3H); 7.25-7.16 (m, 1H)

Manufacture of Organic Light Emitting Diode

Example 9

Manufacture of Organic Light Emitting Diode

First Step: Preparation of Composition for Organic Photoelectric Device

The host compound synthesized according to Example 1 is doped with 10 wt % of $Ir(ppy)_3$, preparing a mixture for an emission layer. Then, 1 wt % of the mixture for an emission layer is dissolved in a toluene solvent, preparing a composition for an organic photoelectric device.

Second Step: Manufacture of Organic Light Emitting Diode

First, a transparent electrode substrate is fabricated by coating ITO (indium-tin oxide) on a glass substrate, cleaning it, patterning the ITO using a photosensitive resin and an etchant, and cleaning it again. Next, PEDOT (Batron P 4083, Bayer Inc.) is coated to be about 55 nm thick on the ITO and fired at 180° C. for about one hour, forming a hole injection layer (HIL). Then, the composition for an organic photoelectric device prepared in the first step is spin-coated on the hole injection layer (HIL) and fired in a vacuum oven to completely remove a solvent and form an emission layer. Herein, the composition for an emission layer is filtered through a 0.2 mm filter before the spin-coating. The emission layer is formed to be about 45 nm thick by controlling the concentration and spin-coating speed of the composition. Then, an electron transport layer (ETL) is formed by respectively vacuum-depositing ET202 and LiQ to be 15 nm thick on the emission layer with a vacuum depositor, while a vacuum degree of less than or equal to $4 \times 10^{-6}$ Torr is maintained. Next, Al is sequentially deposited to be 120 nm thick to form a negative electrode on the electron transport layer (ETL). In the deposition, the thickness and speed of the negative electrode are controlled using a crystal sensor.

The organic light emitting diode is specifically fabricated to have a structure of ITO/PEDOT:PSS (55 nm)/EML (host compound (90 wt %)+dopant compound (10 wt %), 45 nm)/ET202 (15 nm)/LiQ (15 nm)/Al (120 nm).

Example 10

Manufacture of Organic Light Emitting Diode

An organic light emitting diode is fabricated according to the same method as Example 9, except for using the host compound synthesized according to Example 2 instead of the one according to Example 1.

Example 11

Manufacture of Organic Light Emitting Diode

An organic light emitting diode is fabricated according to the same method as Example 9, except for using the host compound synthesized according to Example 3 instead of the one according to Example 1.

Example 12

Manufacture of Organic Light Emitting Diode

An organic light emitting diode is fabricated according to the same method as Example 9, except for using the host compound synthesized according to Example 4 instead of the one according to Example 1.

Example 13

Manufacture of Organic Light Emitting Diode

An organic light emitting diode is fabricated according to the same method as Example 9, except for using the host compound synthesized according to Example 5 instead of the one according to Example 1.

Example 14

Manufacture of Organic Light Emitting Diode

An organic light emitting diode is fabricated according to the same method as Example 9, except for using the host compound synthesized according to Example 6 instead of the one according to Example 1.

Example 15

Manufacture of Organic Light Emitting Diode

An organic light emitting diode is fabricated according to the same method as Example 9, except for using the host compound synthesized according to Example 7 instead of the one according to Example 1.

Example 16

Manufacture of Organic Light Emitting Diode

An organic light emitting diode is fabricated according to the same method as Example 9, except for using the host compound synthesized according to Example 8 instead of the one according to Example 1.

Comparative Example 1

Manufacture of Organic Light Emitting Diode

An organic light emitting diode is fabricated according to the same method as Example 9, except for using a mixture of PVK (polyvinylcarbazole) and PBD (2-(4-biphenyl)-5-(4-t-butylphenyl)-1,3,4-oxadiazole) represented by the following chemical formulae in a weight ratio of 1:1 as a host instead of the host compound synthesized according to Example 1.

The Ir(ppy)$_3$, PVK, and PBD used to fabricate the organic light emitting diode have the following structures.

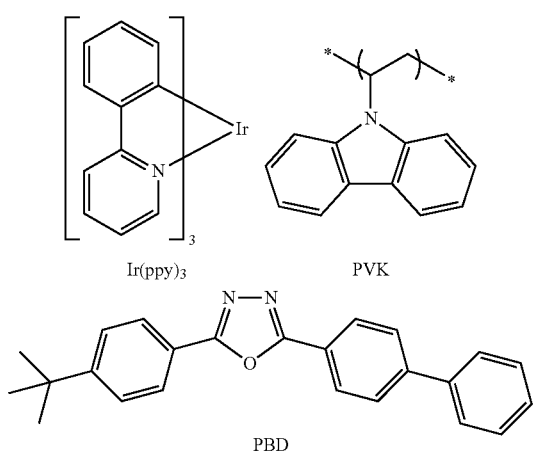

Performance Measurement of Organic Light Emitting Diode

Each organic light emitting diode according to Examples 9 to 16 and Comparative Example 1 is measured regarding current density change depending upon the voltage, luminance change, and luminous efficiency. The results are shown in the Table 1. The specific methods are as follows.

(1) Measurement of Current Density Change Depending on Voltage Change

The obtained organic light emitting diodes are measured regarding current value flowing in a unit device, while their voltages are increased from 0 V to 10 V using a current-voltage meter (Keithley 2400). The measured current value is divided by an area to calculate current density.

(2) Measurement of Luminance Change Depending on Voltage Change

The organic light emitting diodes are measured regarding luminance using a luminance meter (Minolta Cs-1000A) while their voltages are increased from 0 V to 10 V.

(3) Measurement of Luminous Efficiency

Current efficiency (cd/A) and electric power efficiency (lm/W) at the same luminance (1000 cd/m$^2$) are calculated by using luminance and current density from (1) and (2) and a voltage.

TABLE 1

Results at 1000 cd/m$^2$

| | Driving voltage (V) | Current efficiency (cd/A) | Electric power efficiency (lm/W) | EL color |
|---|---|---|---|---|
| Example 9 | 5.7 | 18.6 | 10.2 | Green |
| Example 10 | 5.5 | 17.8 | 10.2 | Green |
| Example 11 | 5.2 | 20.5 | 12.4 | Green |
| Example 12 | 5.2 | 19.4 | 11.7 | Green |
| Example 13 | 5.5 | 15.6 | 8.9 | Green |
| Example 14 | 4.9 | 27.3 | 17.5 | Green |
| Example 15 | 4.8 | 25.0 | 16.4 | Green |
| Example 16 | 5.6 | 16.7 | 9.4 | Green |
| Comparative Example 1 | 5.1 | 13.2 | 8.1 | Green |

Referring to the results in Table 1, the host materials used in Examples 9 to 16 have excellent device performance in terms of luminous efficiency and electric power efficiency compared with the one used in Comparative Example 1. Specifically, the host materials used in Example 14 and 15 have excellent device performance in terms of driving voltage, current efficiency, and electric power efficiency compared with the one according to Comparative Example 1. Accordingly, the host materials may realize an organic light emitting diode having a low voltage, high efficiency, high luminance, and a long life-span.

While this application has been described in connection with what is presently considered to be practical exemplary embodiments, it is to be understood that the application is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

What is claimed is:

1. A compound for an organic optoelectronic device represented by Chemical Formula 1:

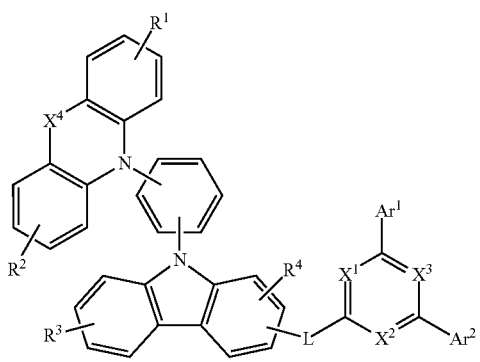

Chemical Formula 1 wherein, in Chemical Formula 1,
X$^1$ to X$^3$ are independently —C(R')— or —N—, provided that at least one of X$^1$ to X$^3$ is —N—,
X$^4$ is a single bond, —C(R')(R")—, —O—, —S—, —S(=O)—, —S(=O)$_2$—, —Si(R')(R")— or —C(=O)—,
R$^1$ to R$^4$, R', and R" are independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof,
L is a substituted or unsubstituted C2 to C20 alkenylene group, a substituted or unsubstituted C2 to C20 alkynylene group, a substituted or unsubstituted C6 to C30 arylene group, a substituted or unsubstituted C2 to C30 heteroarylene group, or combination thereof, and
Ar$^1$ and Ar$^2$ are independently a substituted or unsubstituted C6 to C30 aryl group or a substituted or unsubstituted C2 to C30 heteroaryl group.

2. The compound for an organic optoelectronic device of claim 1, wherein the $X^4$ is a single bond.

3. The compound for an organic optoelectronic device of claim 1, wherein the $X^4$ is —C(R')(R'')—.

4. The compound for an organic optoelectronic device of claim 1, wherein the $X^4$ is —O—.

5. The compound for an organic optoelectronic device of claim 1, wherein the $X^4$ is —S—.

6. The compound for an organic optoelectronic device of claim 1, wherein the $X^4$ is —C(=O)—.

7. The compound for an organic optoelectronic device of claim 1, wherein the compound for an organic optoelectronic device is represented by Chemical Formula 2:

Chemical Formula 2

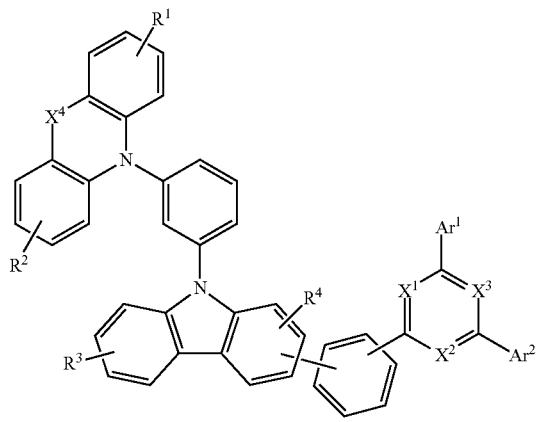

wherein, in Chemical Formula 2, $X^1$ to $X^3$ are independently —C(R')— or —N—, provided that at least one of $X^1$ to $X^3$ is —N—, $X^4$ is a single bond, —C(R')(R'')—, —O—, —S—, —S(=O)—, —S(=O)$_2$—, —Si(R')(R'')— or —C(=O)—, $R^1$ to $R^4$, R', and R'' are independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and $Ar^1$ and $Ar^2$ are independently a substituted or unsubstituted C6 to C30 aryl group or a substituted or unsubstituted C2 to C30 heteroaryl group.

8. The compound for an organic optoelectronic device of claim 1, wherein the compound for an organic optoelectronic device is represented by Chemical Formula 3:

Chemical Formula 3

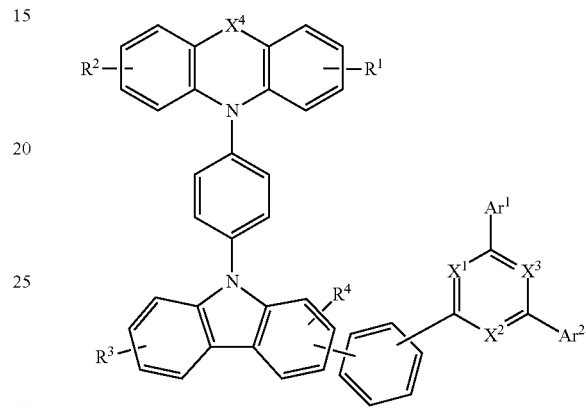

wherein, in Chemical Formula 3, $X^1$ to $X^3$ are independently —C(R')— or —N—, provided that at least one of $X^1$ to $X^3$ is —N—, $X^4$ is a single bond, —C(R')(R'')—, —O—, —S—, —S(=O)—, —S(=O)$_2$—, —Si(R')(R'')— or —C(=O)—, $R^1$ to $R^4$, R', and R'' are independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and Ar¹ and Ar² are independently a substituted or unsubstituted C6 to C30 aryl group or a substituted or unsubstituted C2 to C30 heteroaryl group.

9. The compound for an organic optoelectronic device of claim 1, wherein the compound for an organic optoelectronic device is represented by Chemical Formula 4:

Chemical Formula 4

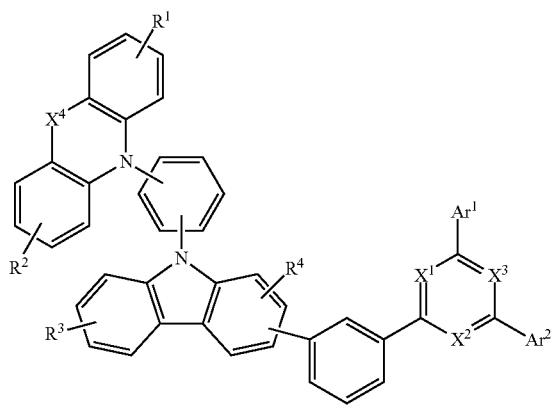

wherein, in Chemical Formula 4, $X^1$ to $X^3$ are independently —C(R')— or —N—, provided that at least one of $X^1$ to $X^3$ is —N—, $X^4$ is a single bond, —C(R')(R")—, —O—, —S—, —S(=O)—, —S(=O)₂—, —Si(R')(R")— or —C(=O)—, $R^1$ to $R^4$, R', and R" are independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and Ar¹ and Ar² are independently a substituted or unsubstituted C6 to C30 aryl group or a substituted or unsubstituted C2 to C30 heteroaryl group.

10. The compound for an organic optoelectronic device of claim 1, wherein the compound for an organic optoelectronic device is represented by Chemical Formula 5:

Chemical Formula 5

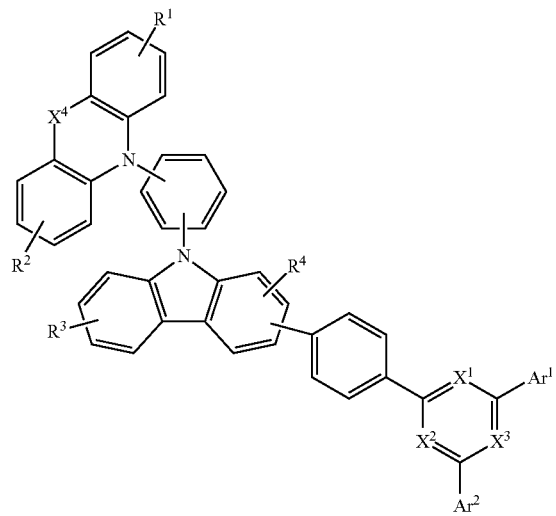

wherein, in Chemical Formula 5, $X^1$ to $X^3$ are independently —C(R')— or —N—, provided that at least one of $X^1$ to $X^3$ is —N—, $X^4$ is a single bond, —C(R')(R")—, —O—, —S—, —S(=O)—, —S(=O)₂—, —Si(R')(R")— or —C(=O)—, $R^1$ to $R^4$, R', and R" are independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and Ar¹ and Ar² are independently a substituted or unsubstituted C6 to C30 aryl group or a substituted or unsubstituted C2 to C30 heteroaryl group.

11. The compound for an organic optoelectronic device of claim 1, wherein the compound for an organic optoelectronic device is represented by Chemical Formula 6:

Chemical Formula 6

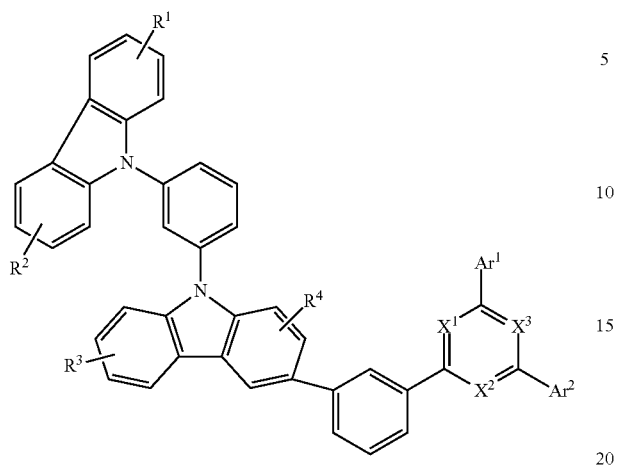

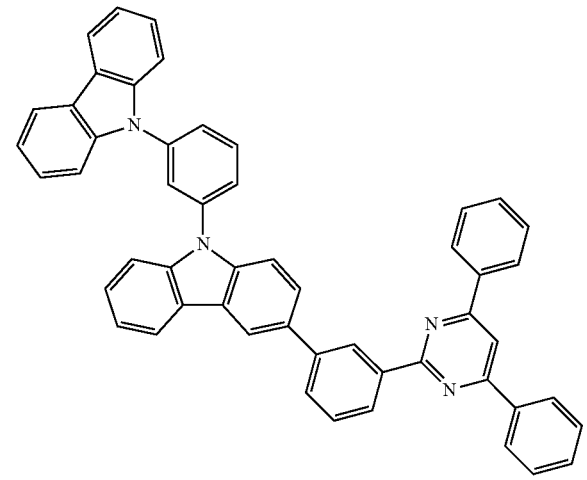

A-1

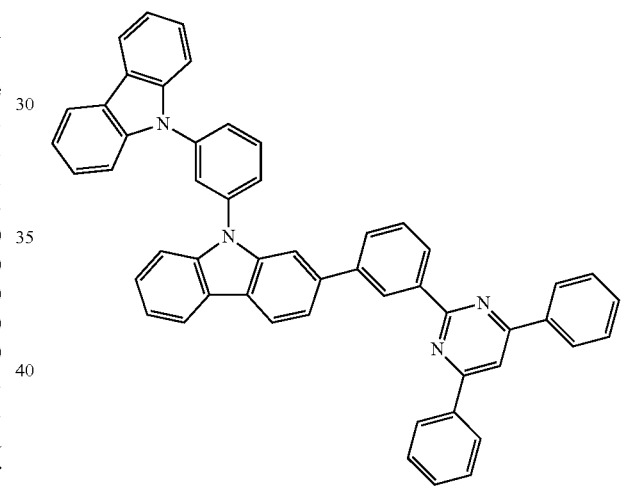

A-2

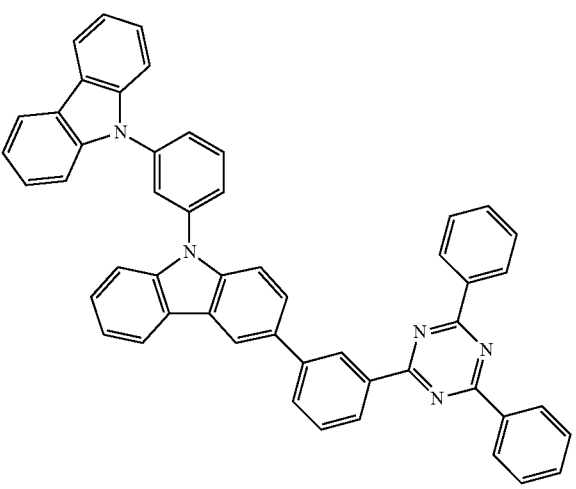

A-3 wherein, in Chemical Formula 6, $X^1$ to $X^3$ are independently —C(R')— or —N—, provided that at least one of $X^1$ to $X^3$ is —N—, $R^1$ to $R^4$ and R' are independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, and $Ar^1$ and $Ar^2$ are independently a substituted or unsubstituted C6 to C30 aryl group or a substituted or unsubstituted C2 to C30 heteroaryl group.

12. The compound for an organic optoelectronic device of claim 11, wherein the $Ar^1$ and $Ar^2$ are independently a substituted or unsubstituted C6 to C30 aryl group.

13. The compound for an organic optoelectronic device of claim 1, wherein the $X^1$ to $X^3$ are independently —C(R')— or —N— provided that two of the $X^1$ to $X^3$ are —N—.

14. The compound for an organic optoelectronic device of claim 1, which is represented by at least one of Chemical Formulas A-1 to A-140:

-continued
A-4
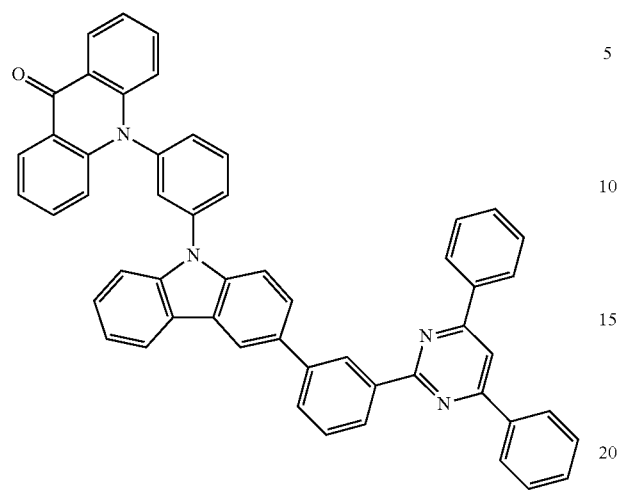
A-5
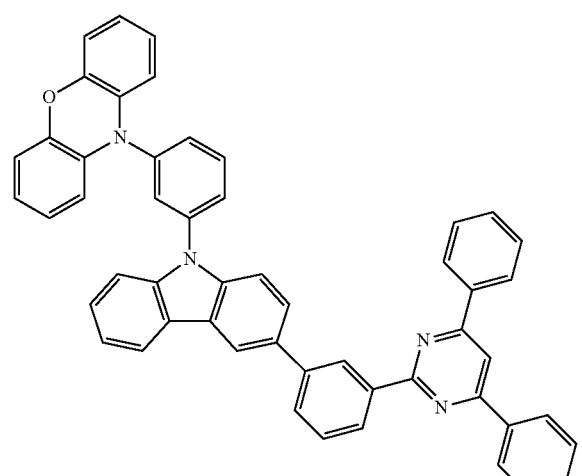
A-6
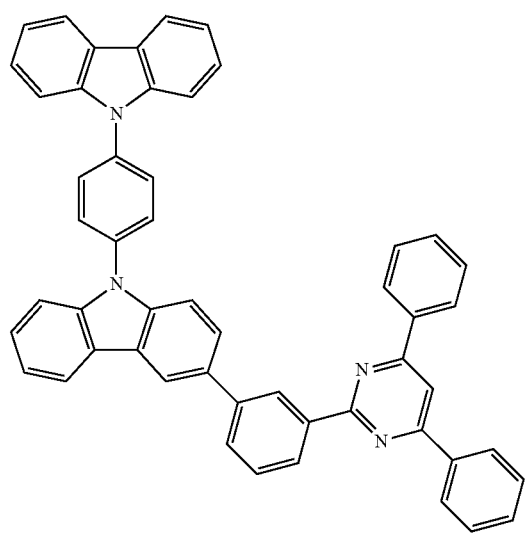
-continued
A-7
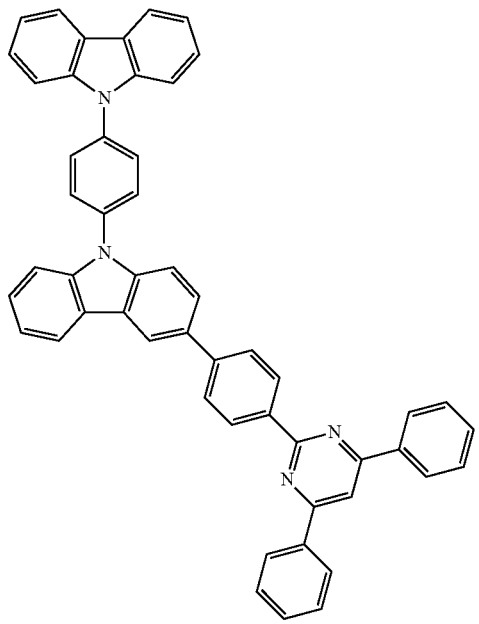
A-8
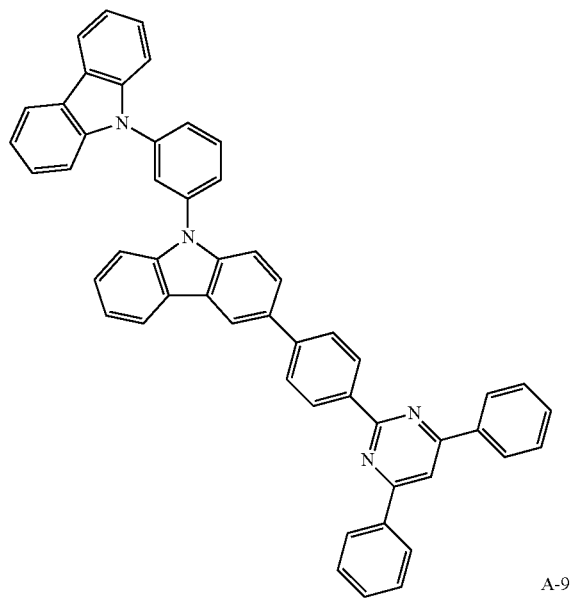
A-9
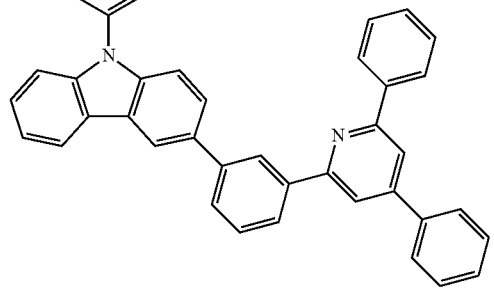

A-10
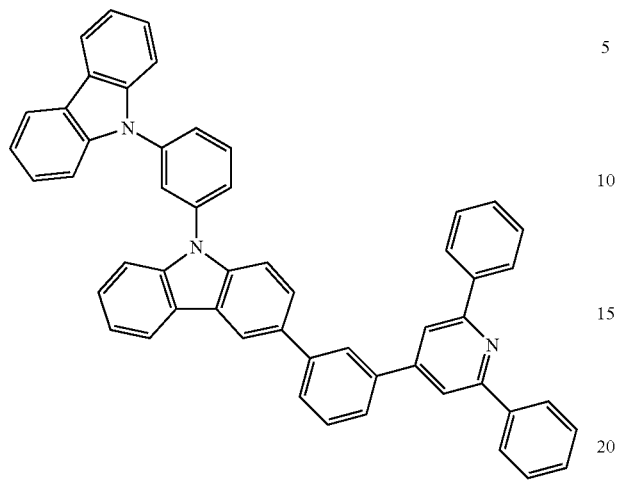
A-13
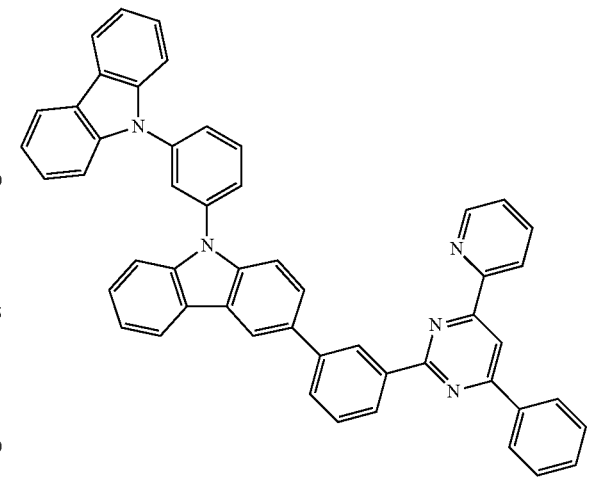
A-11
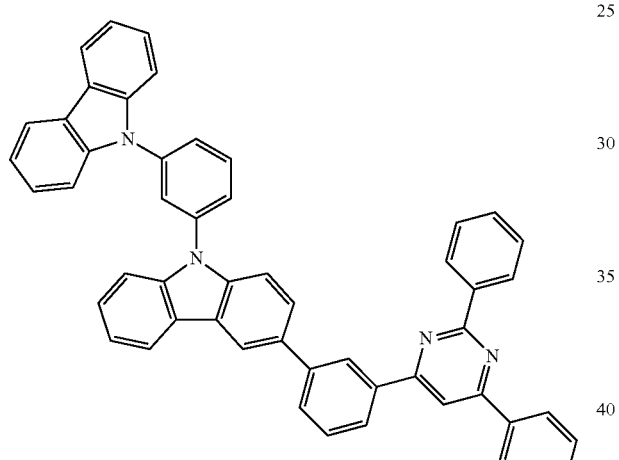
A-14
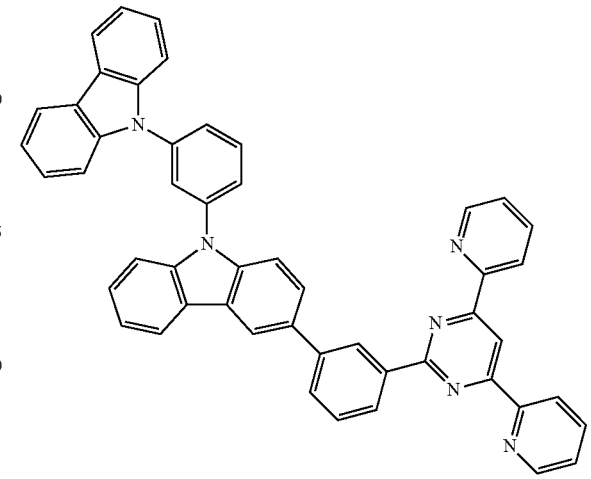
A-12
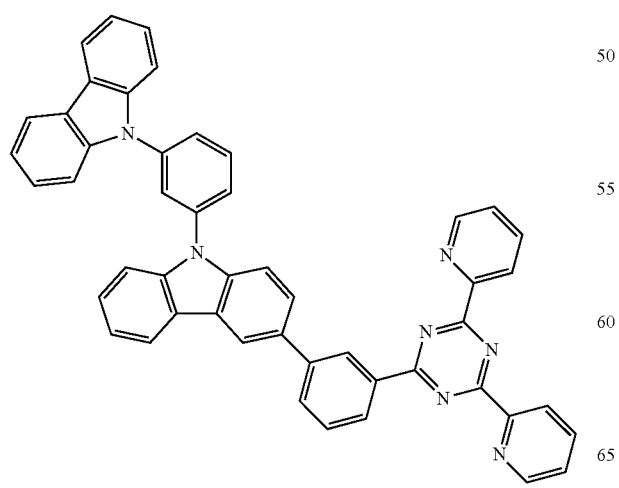
A-15
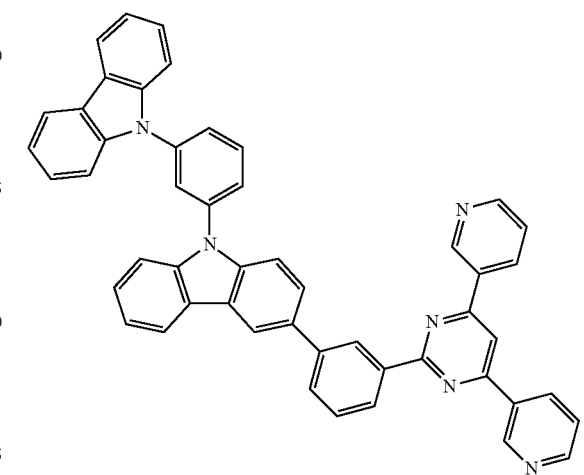

A-16
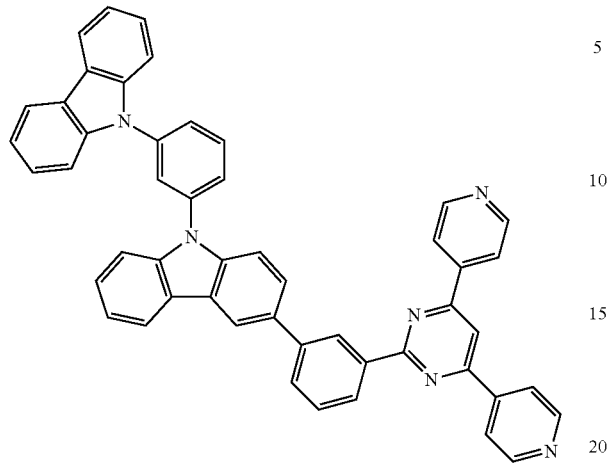
A-17
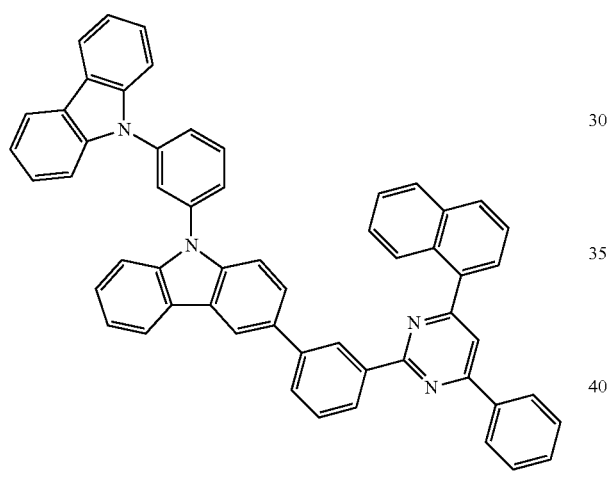
A-18
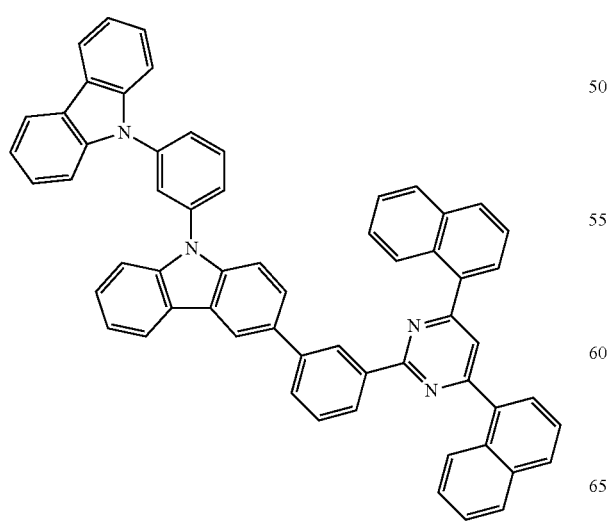
A-19
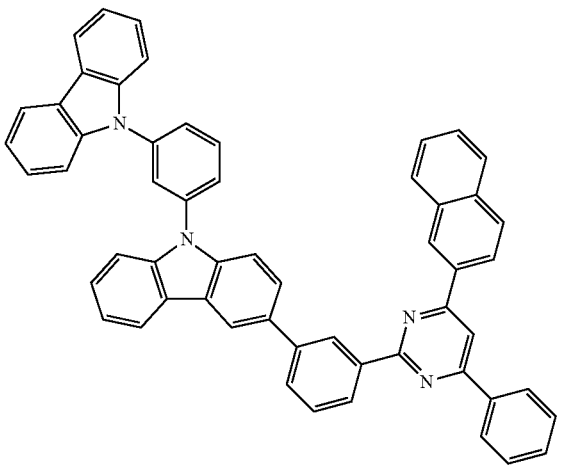
A-20
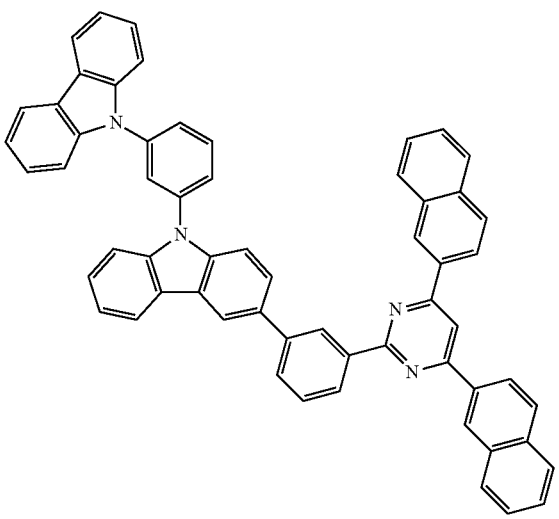
A-21
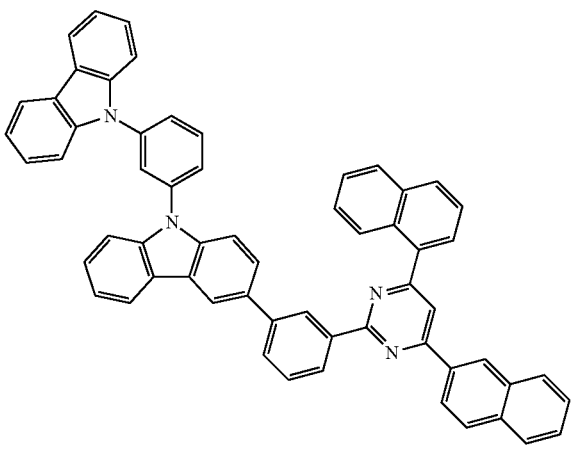

A-22
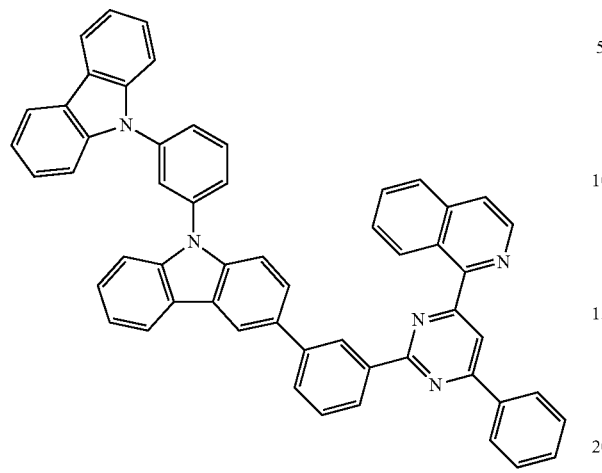
A-23
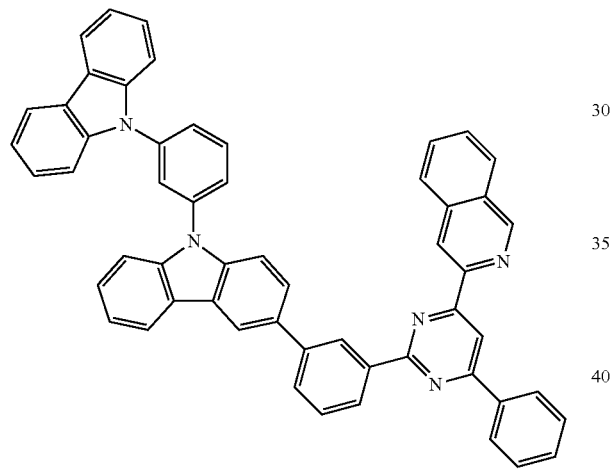
A-24
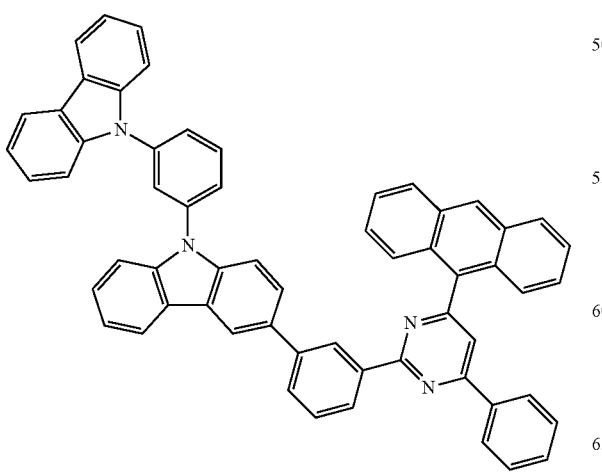
A-25
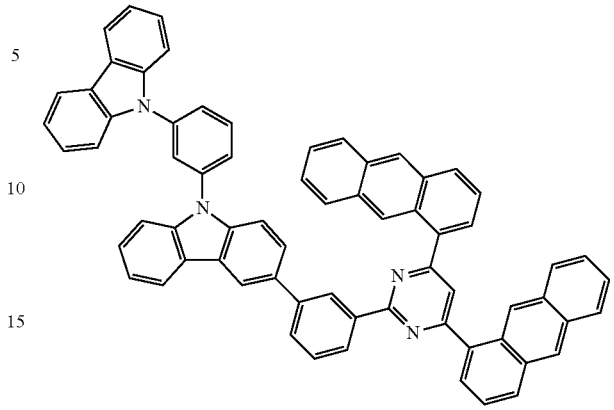
A-26
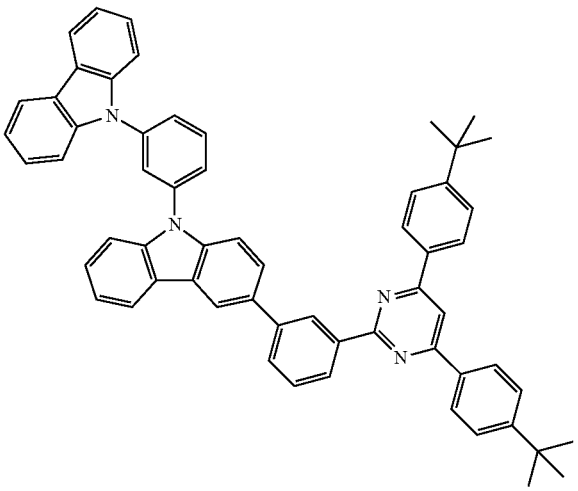
A-27
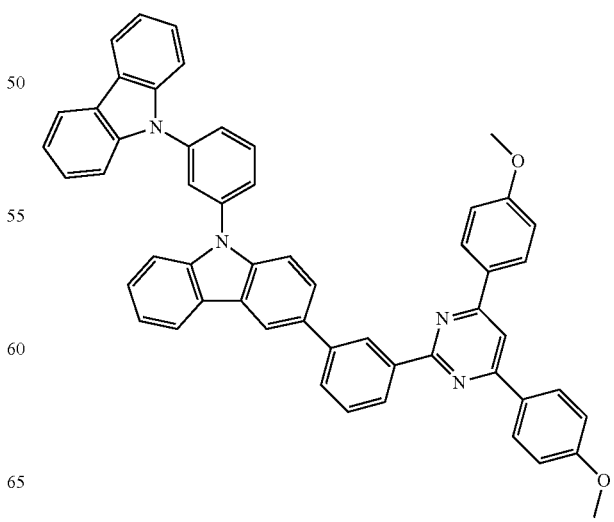

A-28
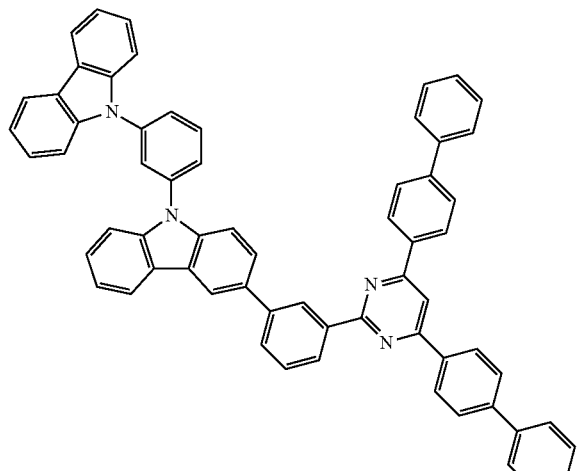
A-31
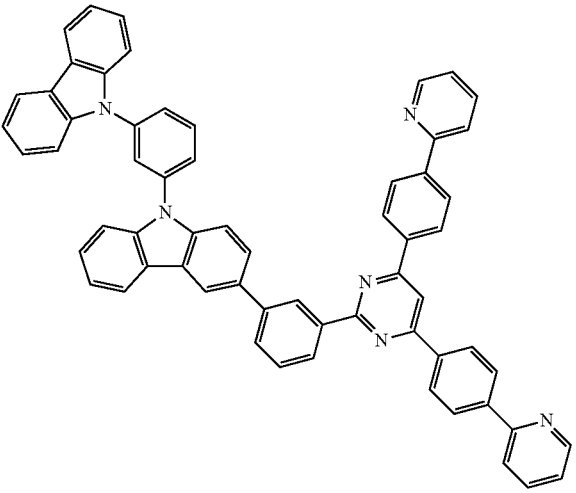
A-29
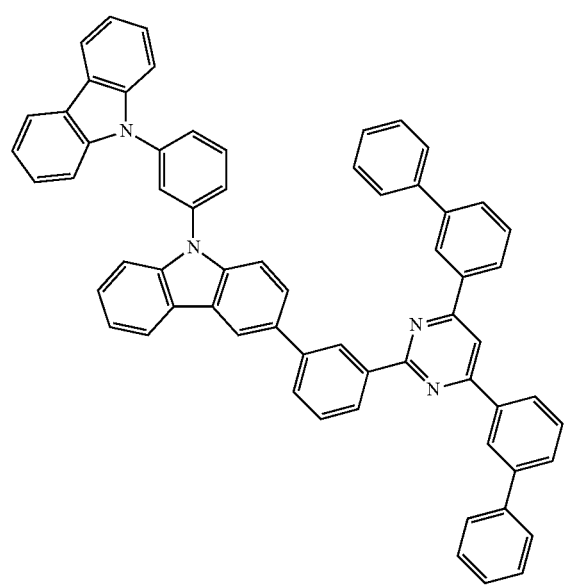
A-32
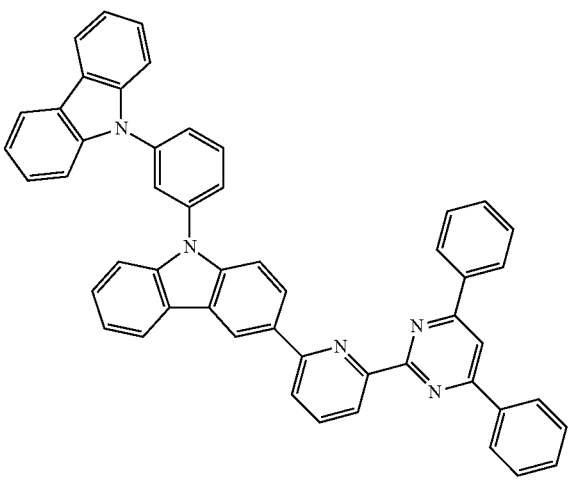
A-30
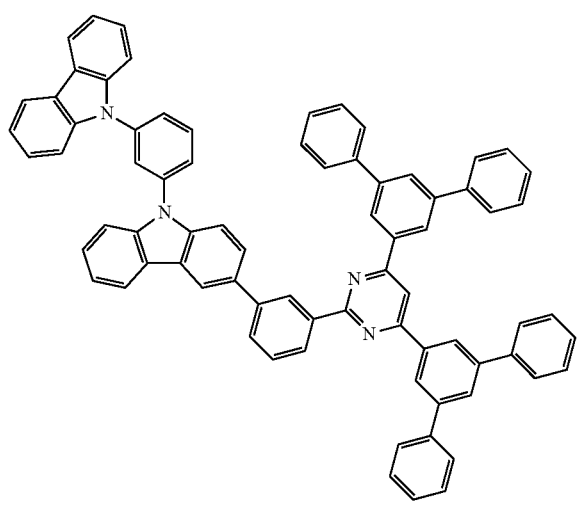
A-33

A-34
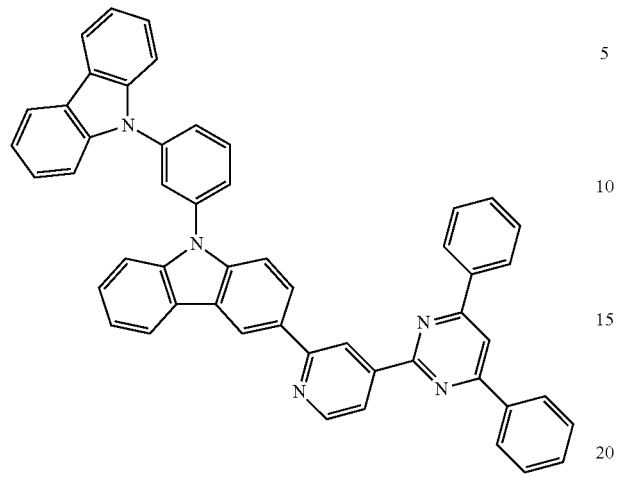
A-37
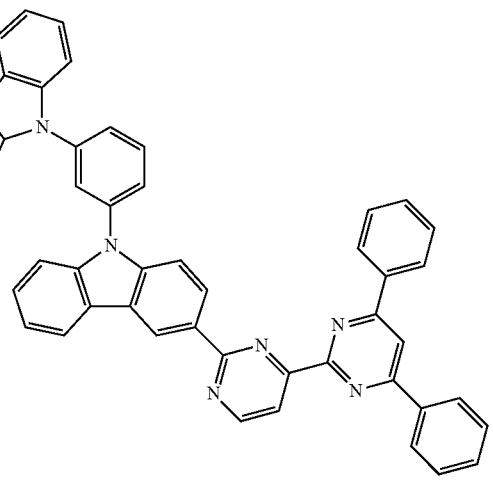
A-35
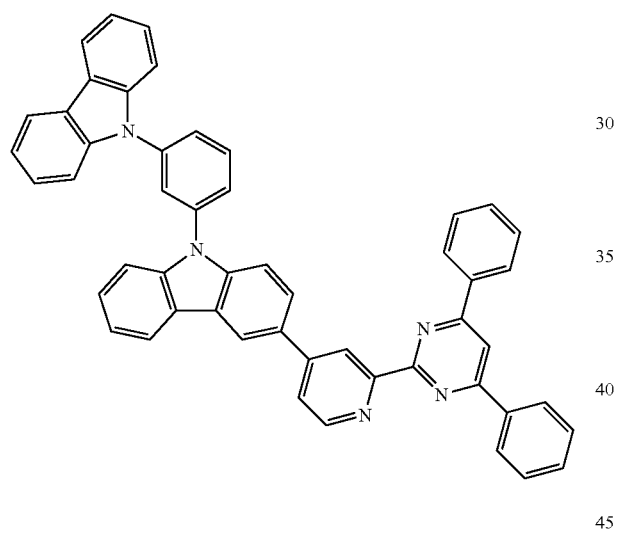
A-38
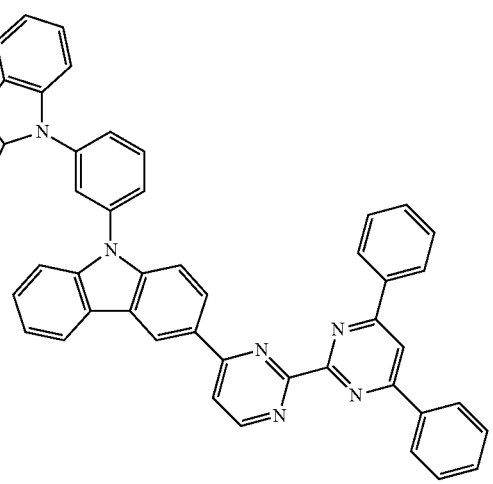
A-36
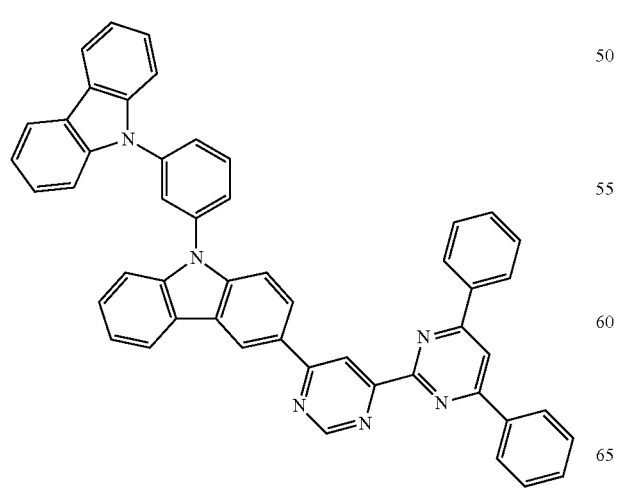
A-39
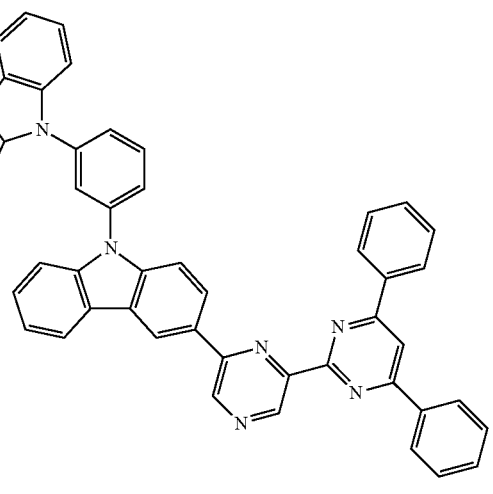

A-40
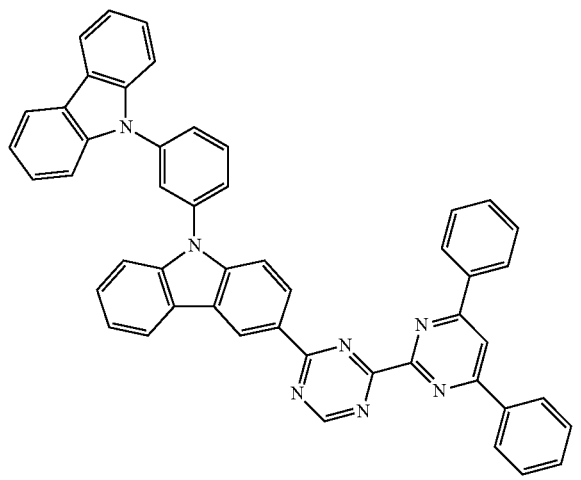
A-43
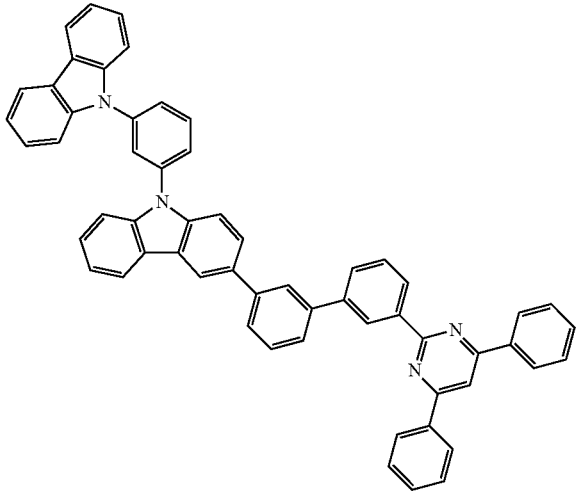
A-41
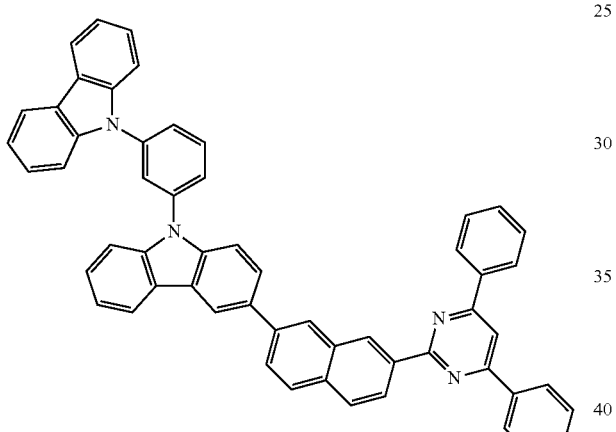
A-44
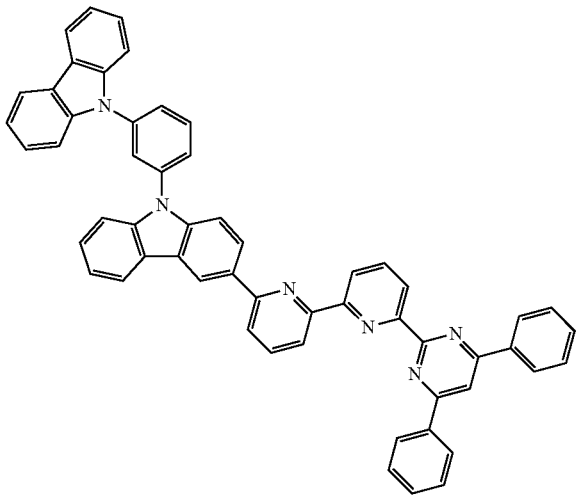
A-42
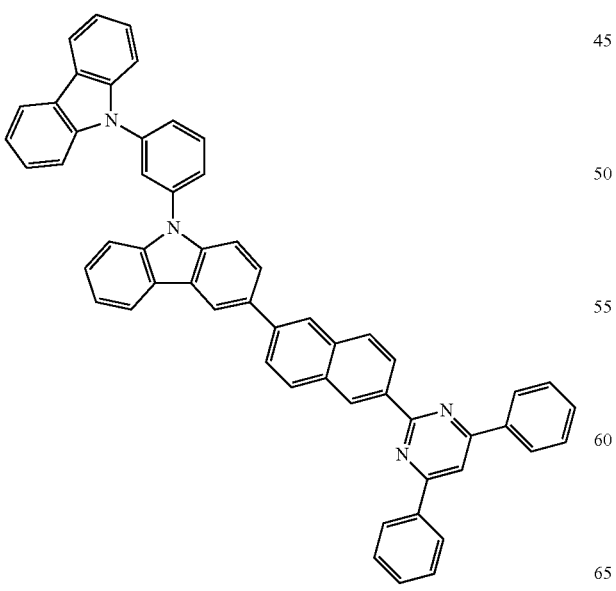
A-45
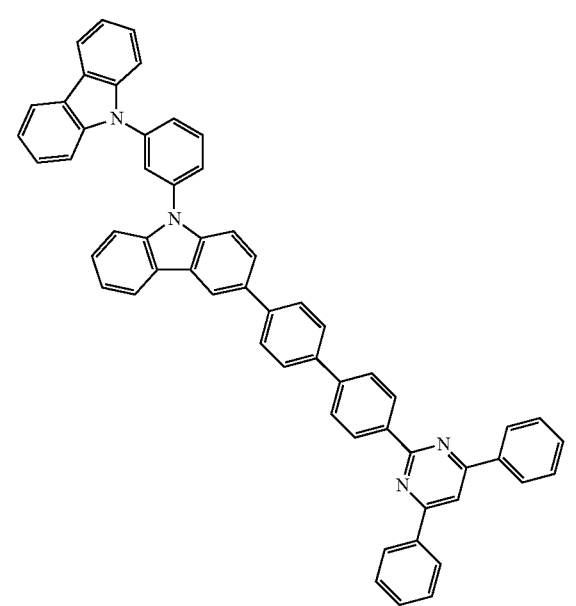

A-46
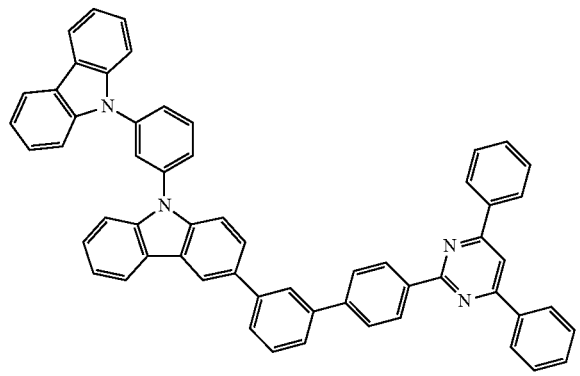
A-47
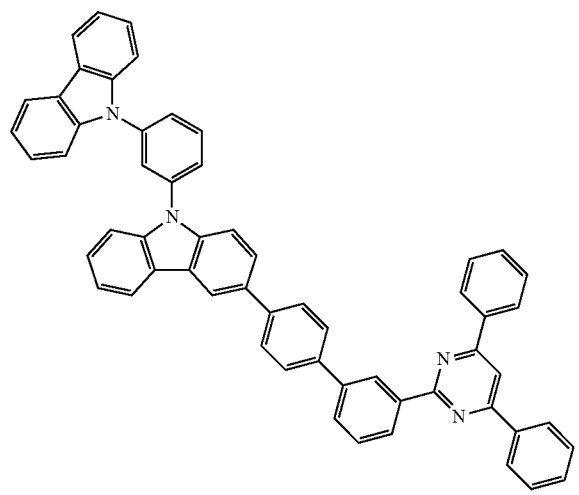
A-48
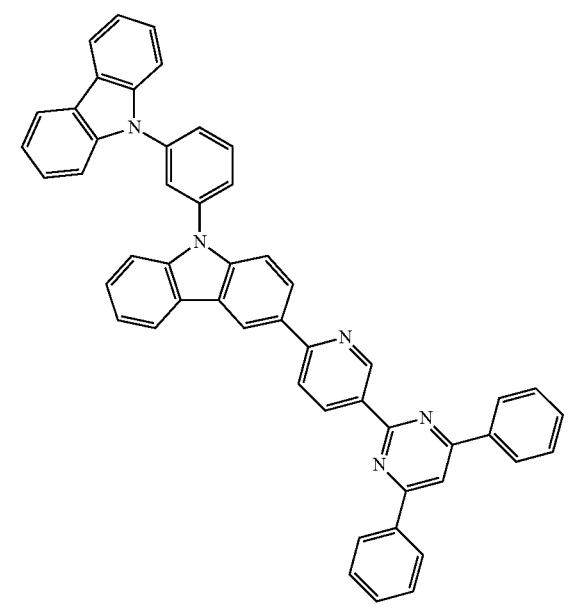
A-49
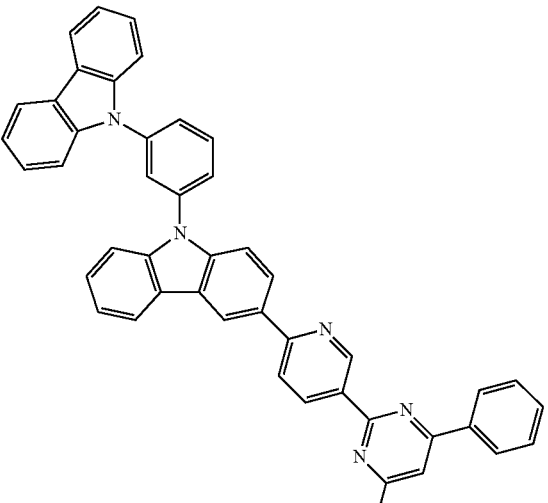
A-50
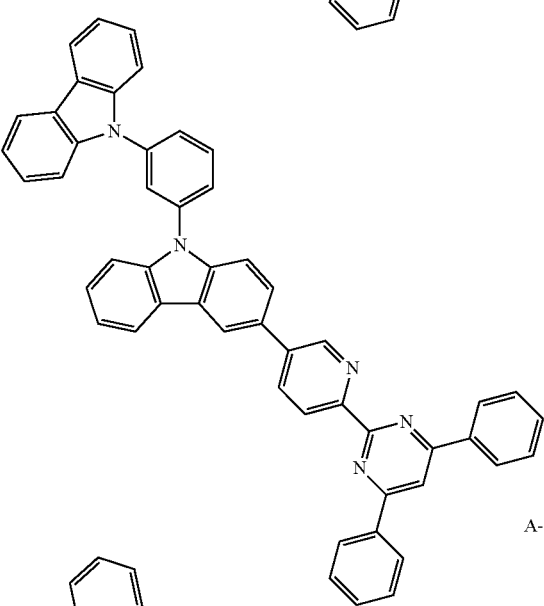
A-51
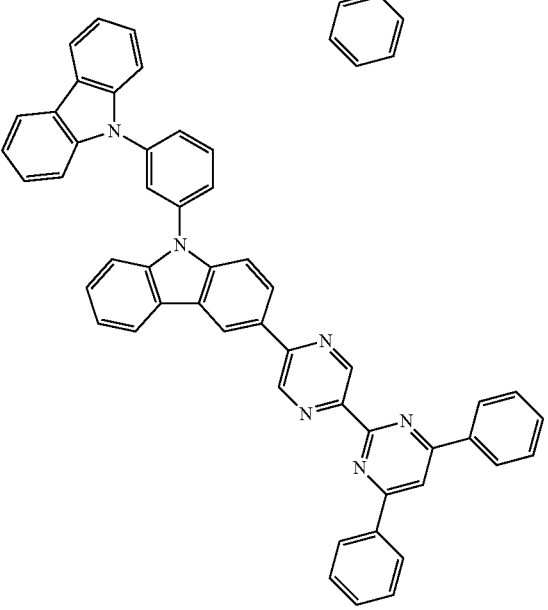

A-52
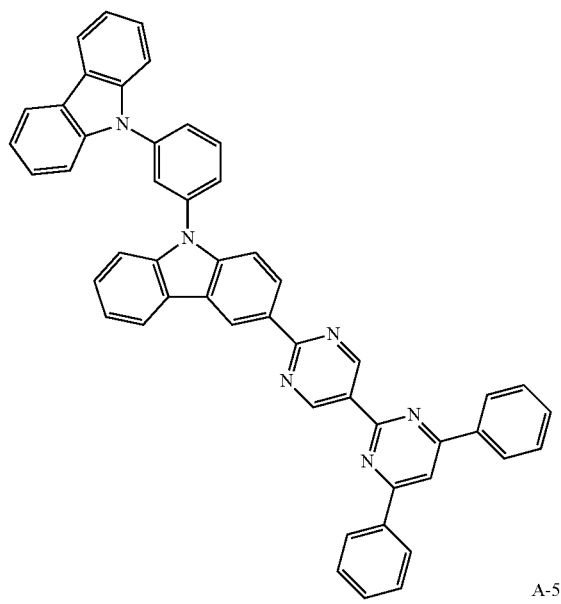
A-55
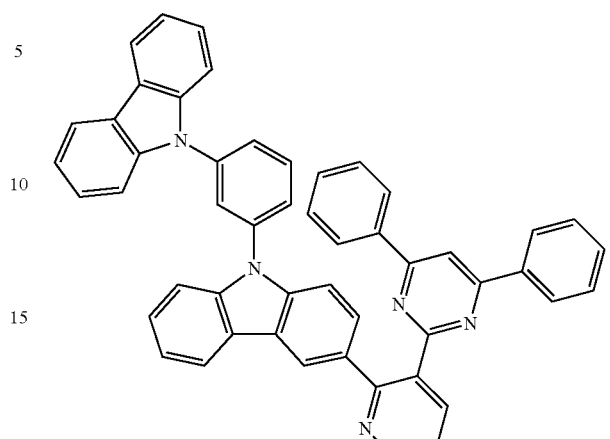
A-53
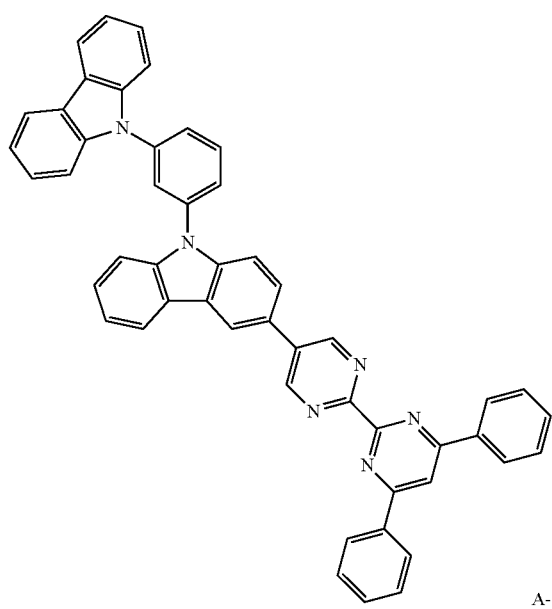
A-56
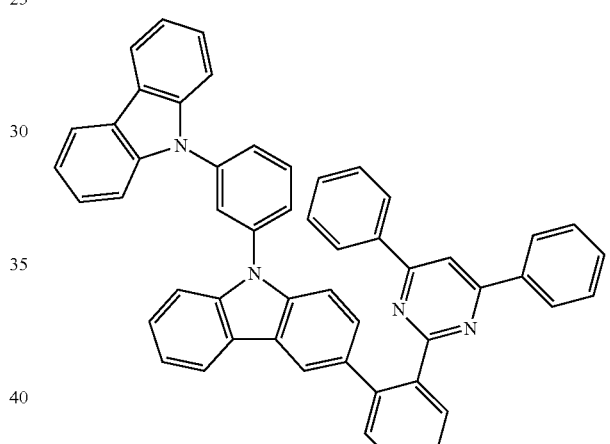
A-54
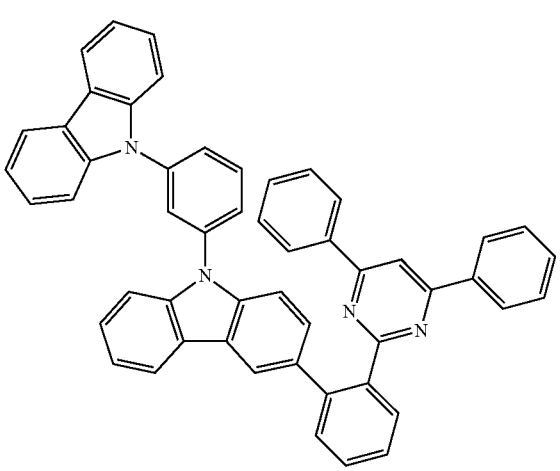
A-57
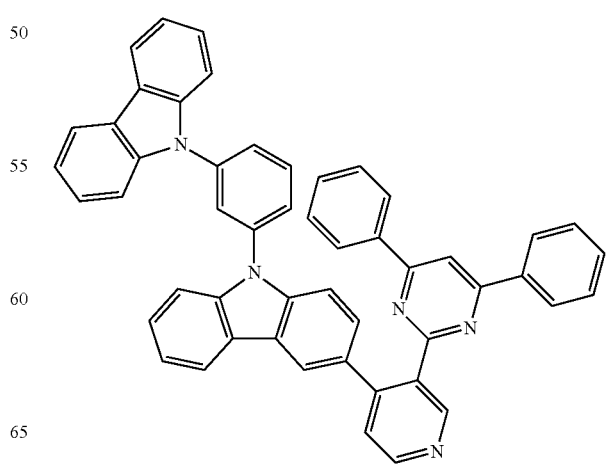

A-58
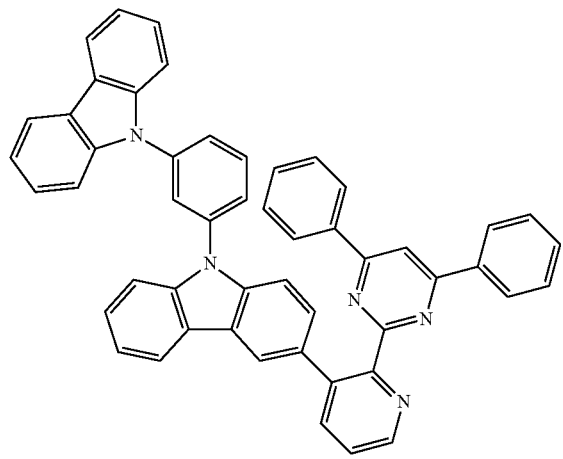
A-59
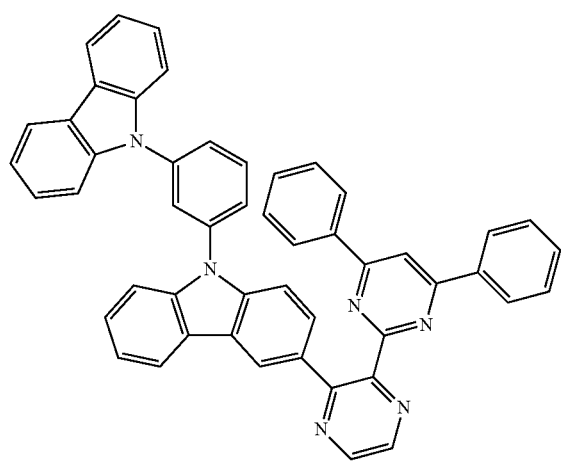
A-60
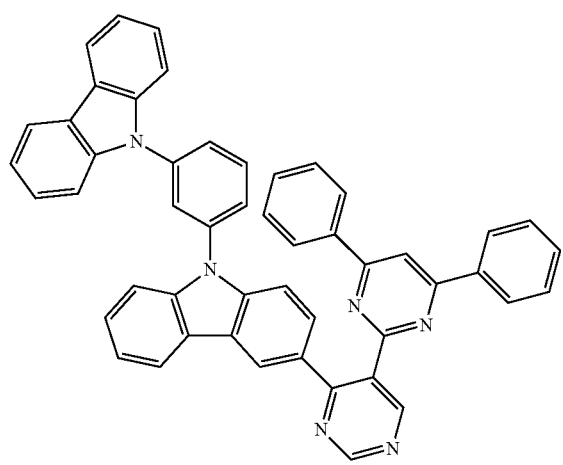
A-61
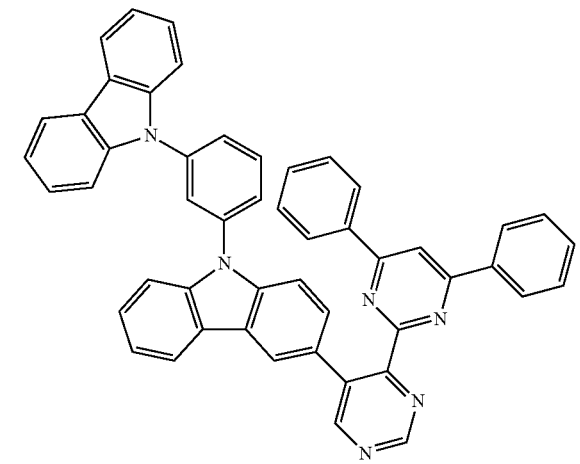
A-62
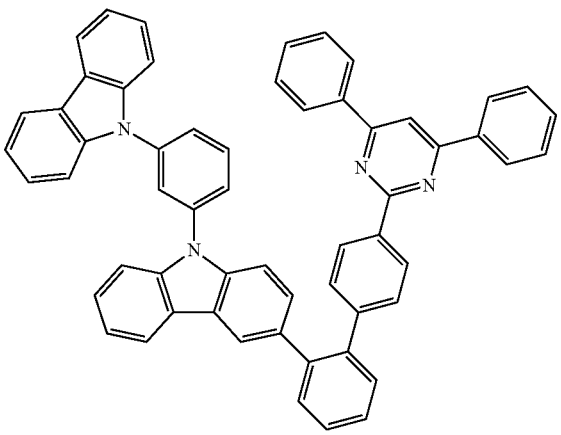
A-63
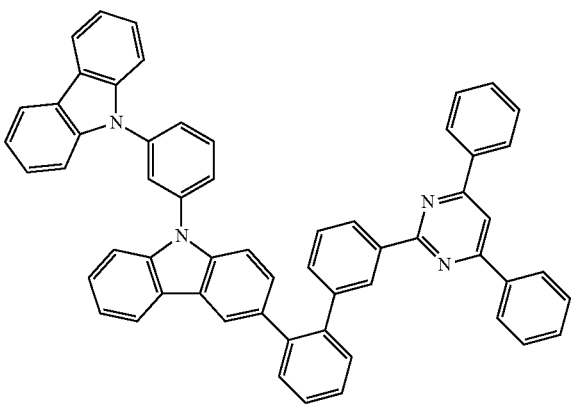

A-64
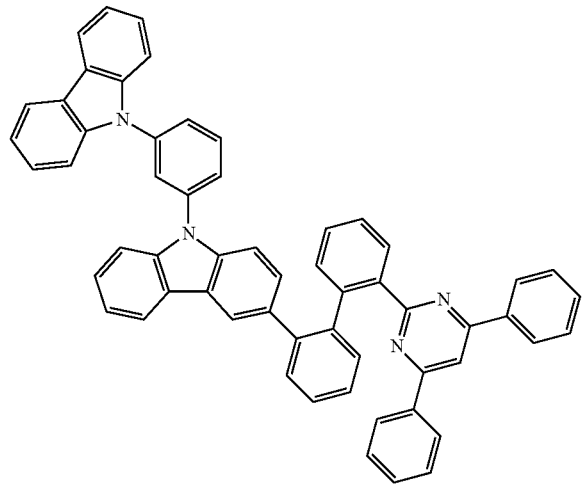
A-65
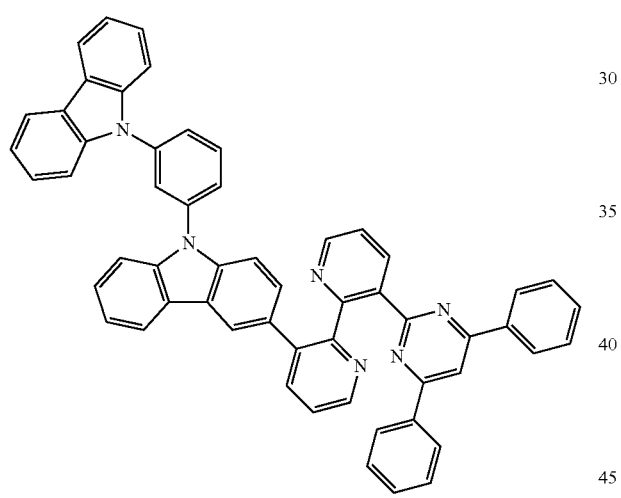
A-66
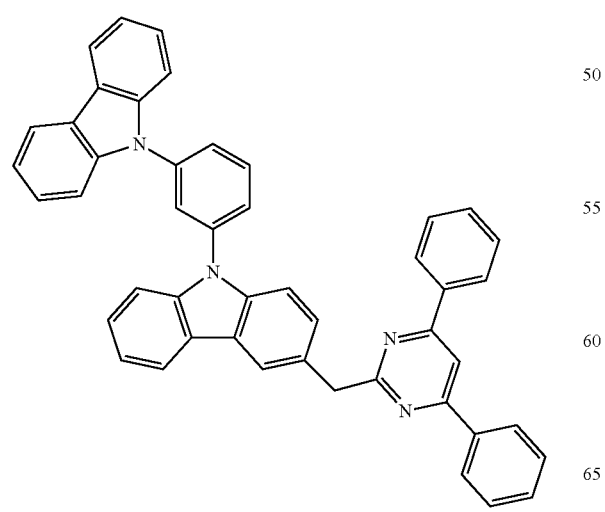
A-67
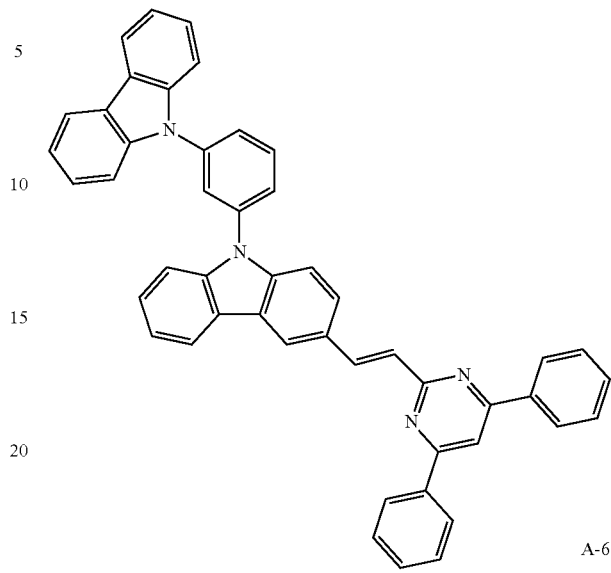
A-68
A-69
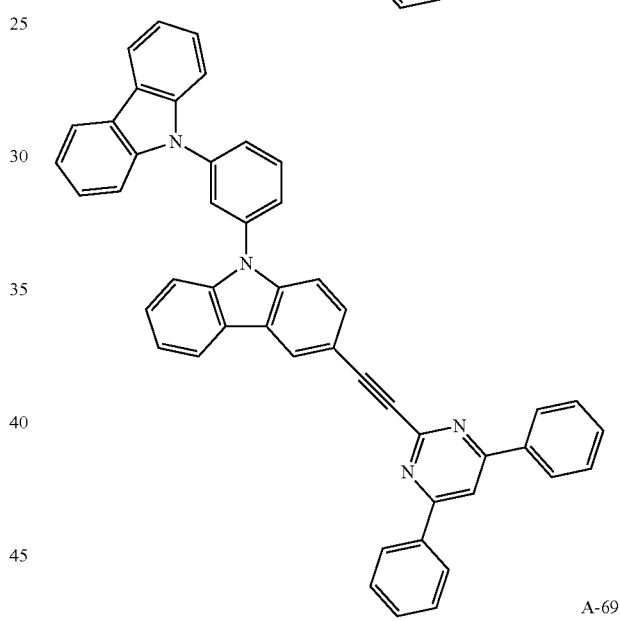

-continued
A-70
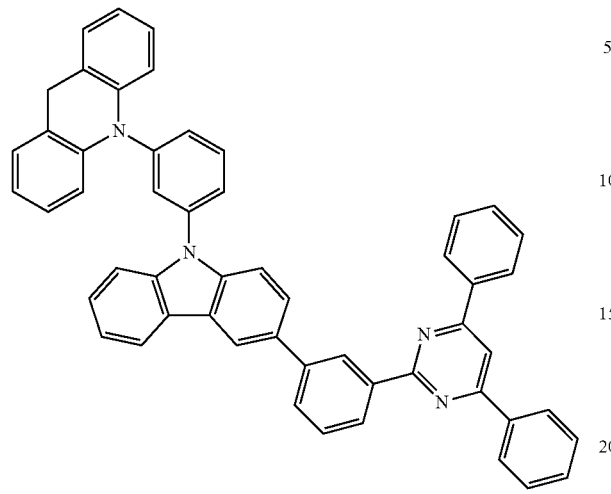
A-71
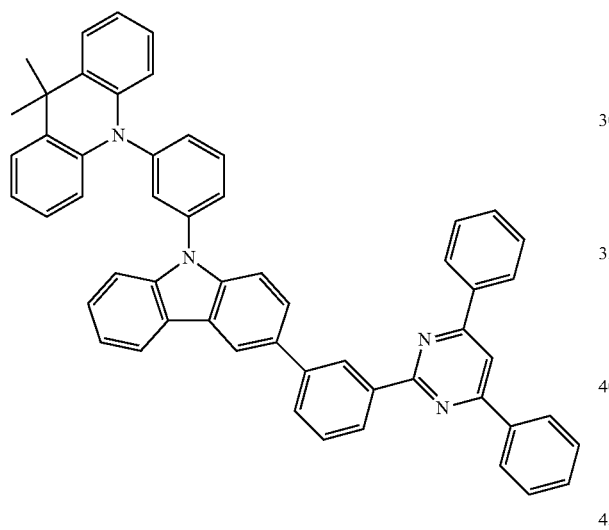
A-72
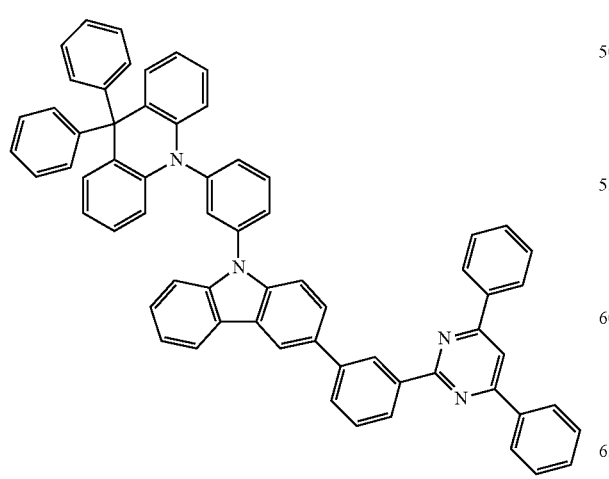
-continued
A-73
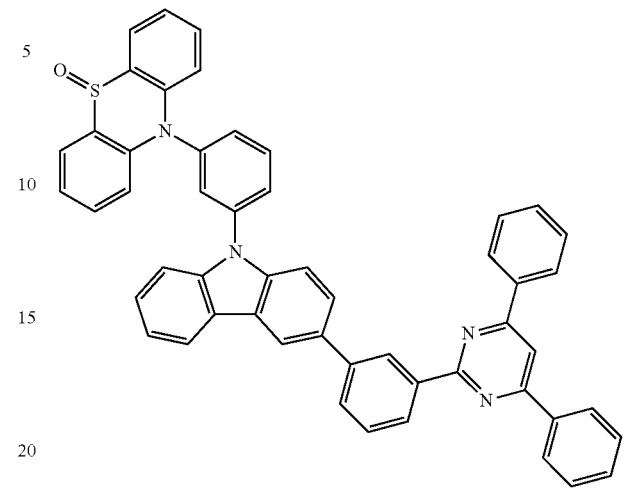
A-74
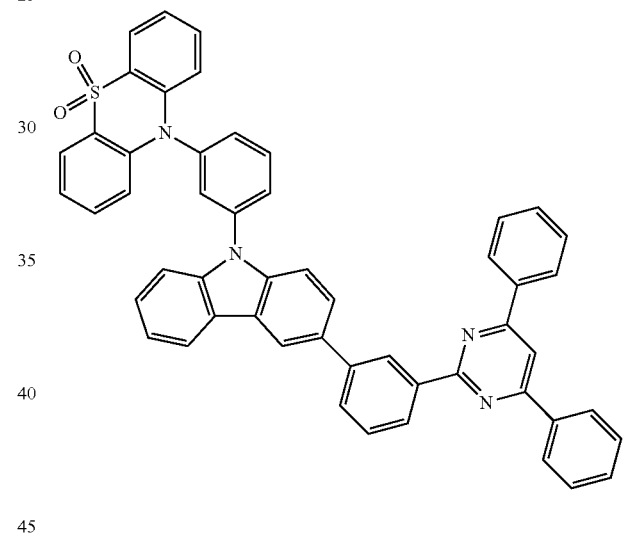
A-75
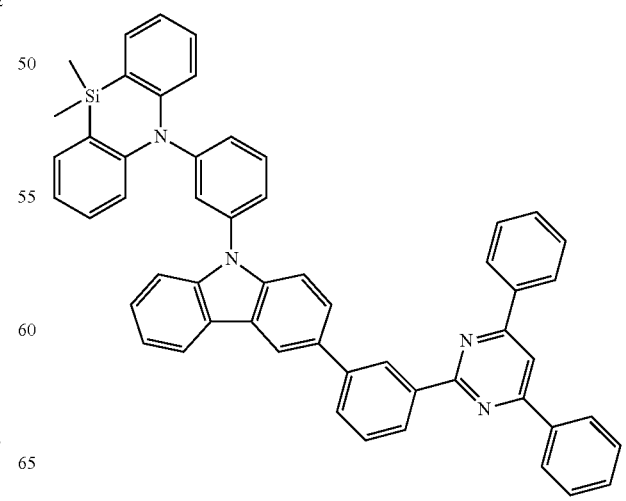

-continued
A-76
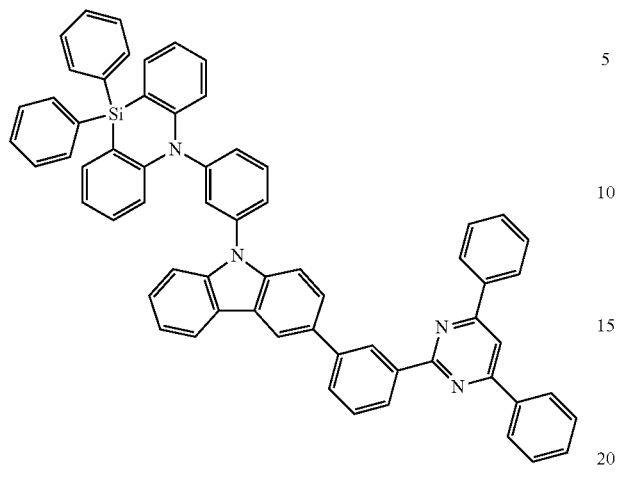
A-77
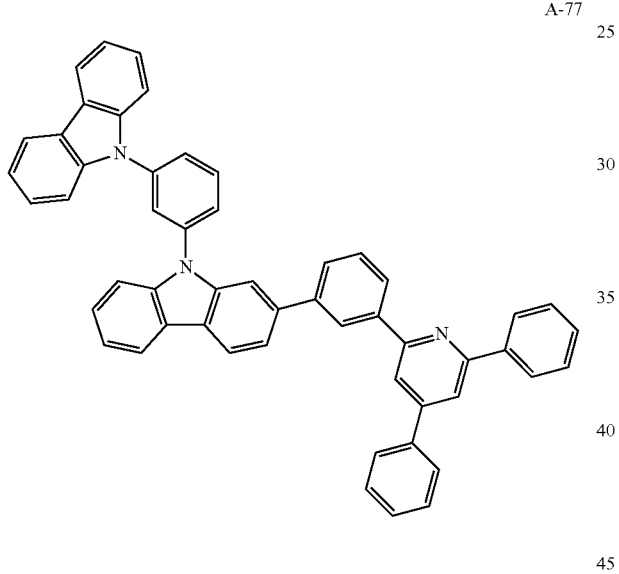
A-78
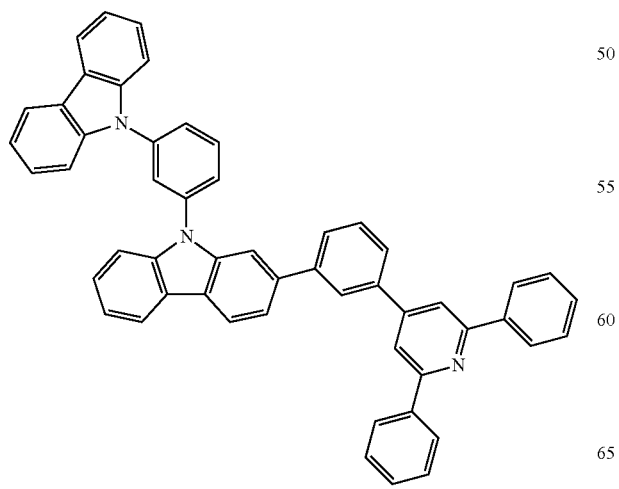
-continued
A-79
A-80
A-81
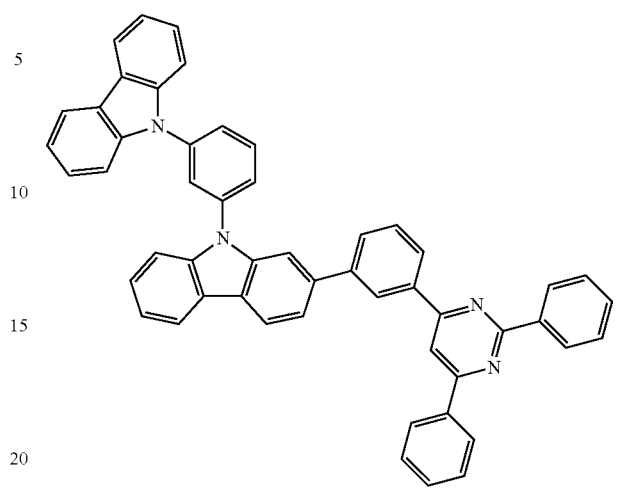

A-82
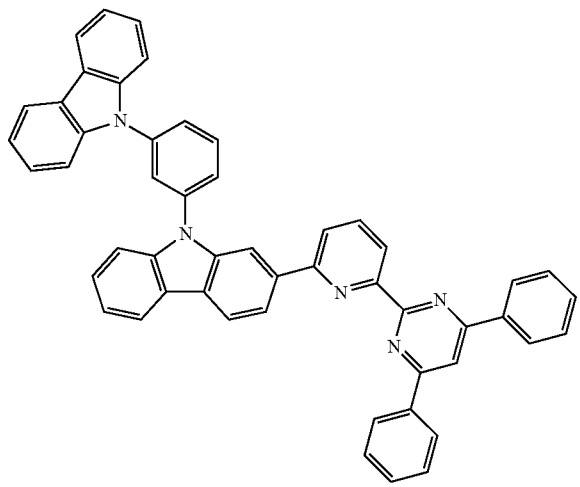
A-83
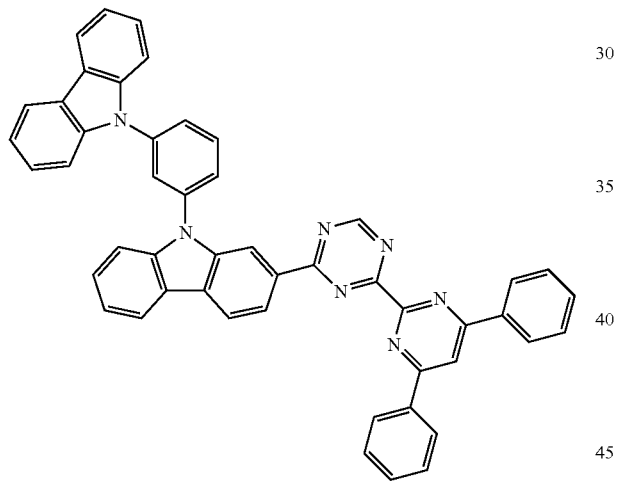
A-84
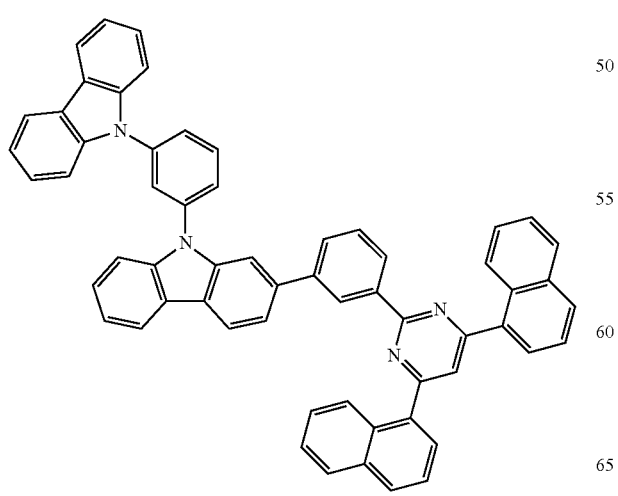
A-85
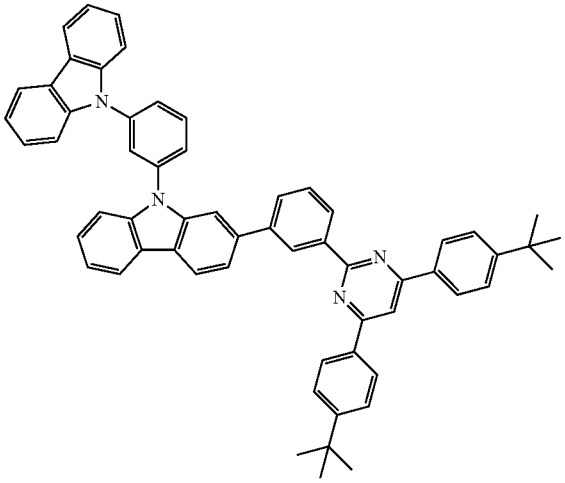
A-86
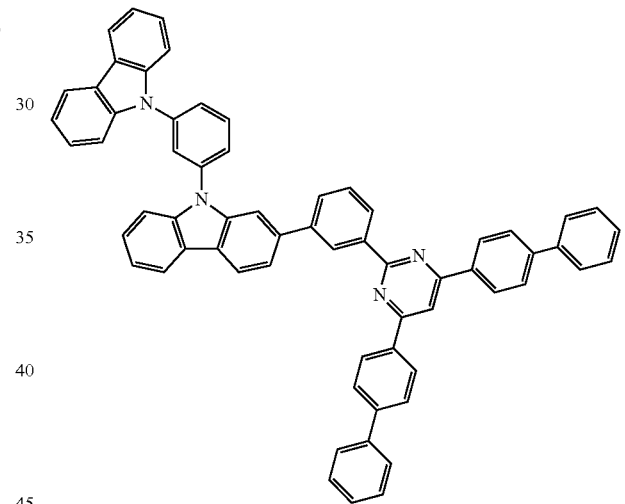
A-87
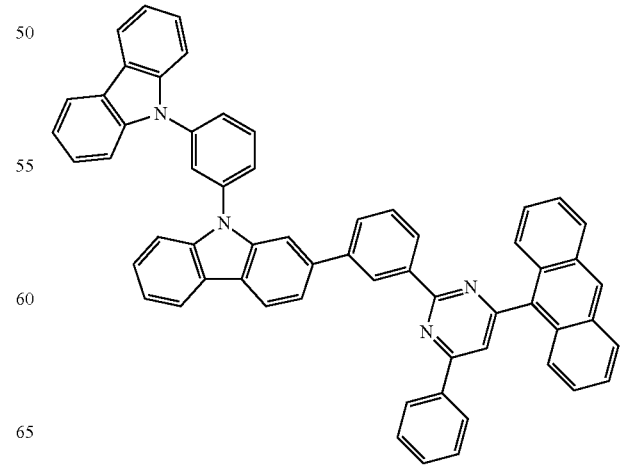

A-88
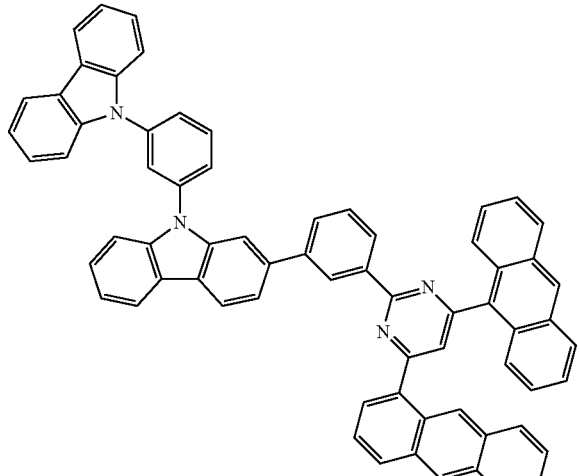
A-89
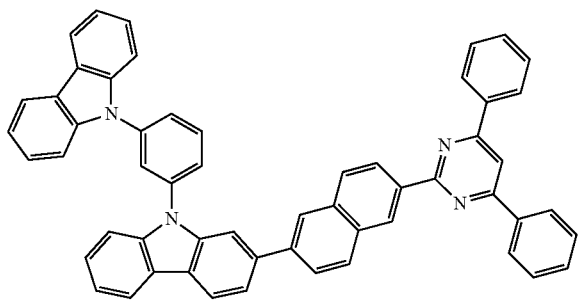
A-90
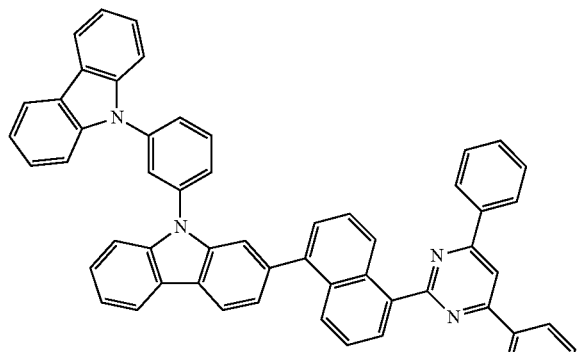
A-91
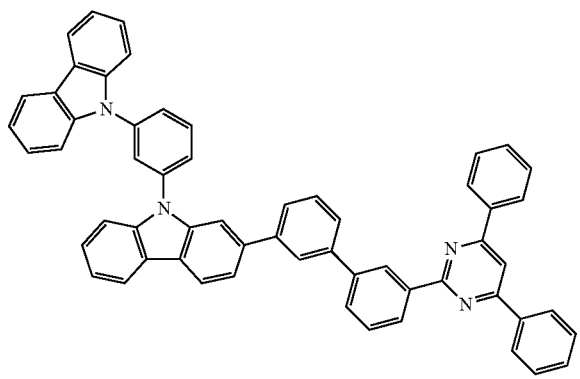
A-92
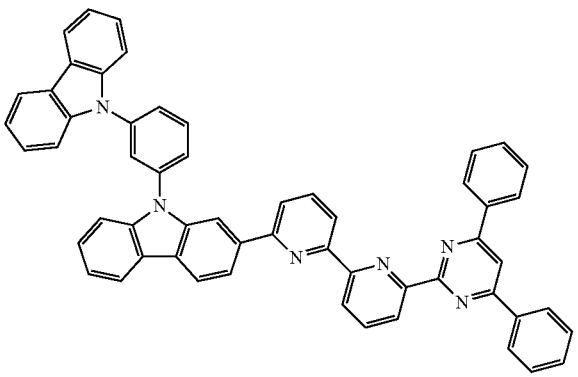
A-93
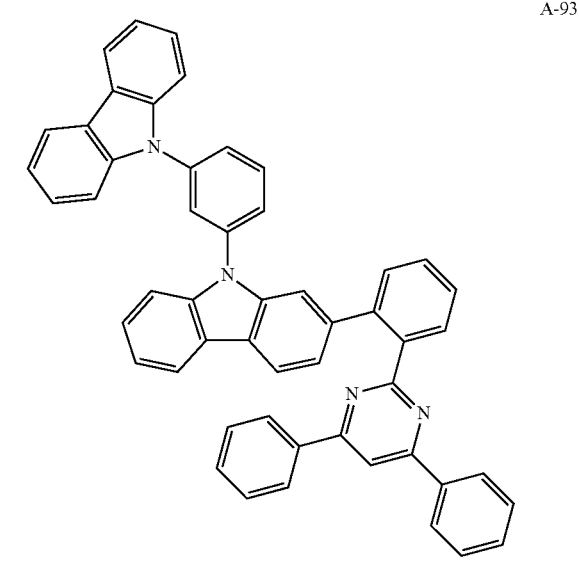
A-94
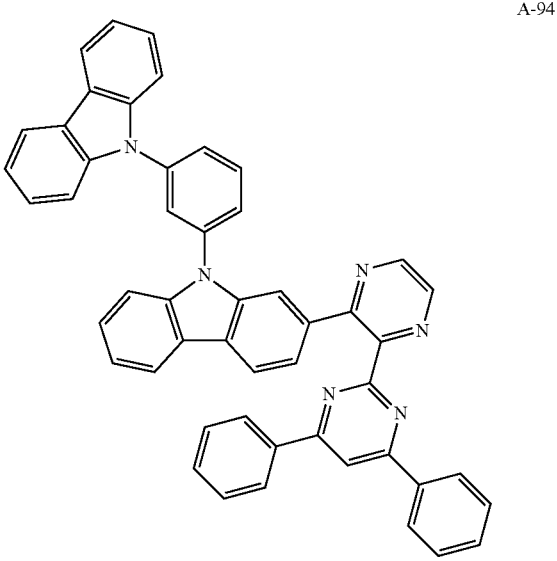

-continued
A-95
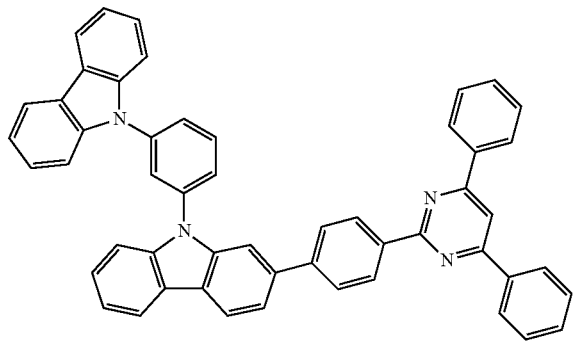
A-96
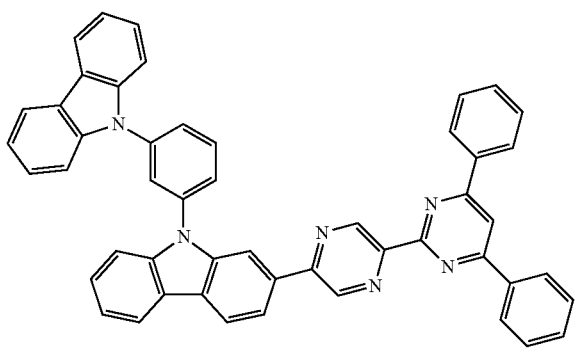
A-97
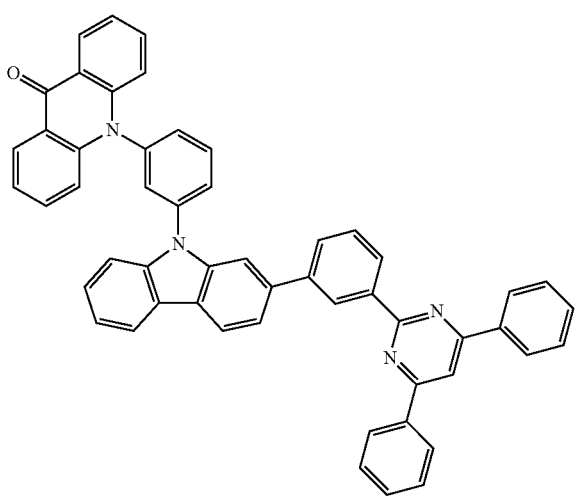
-continued
A-98
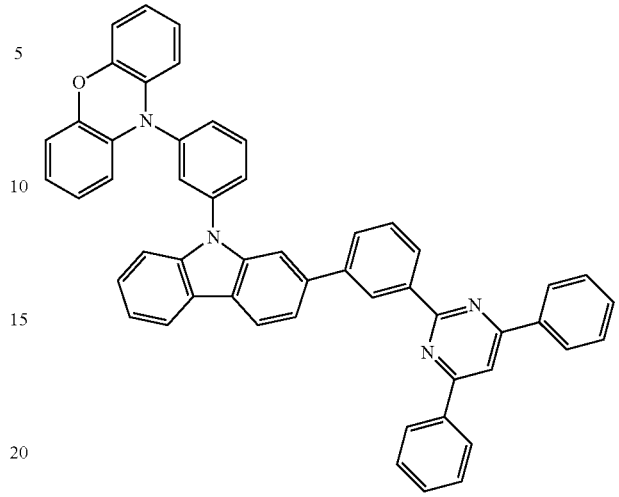
A-99
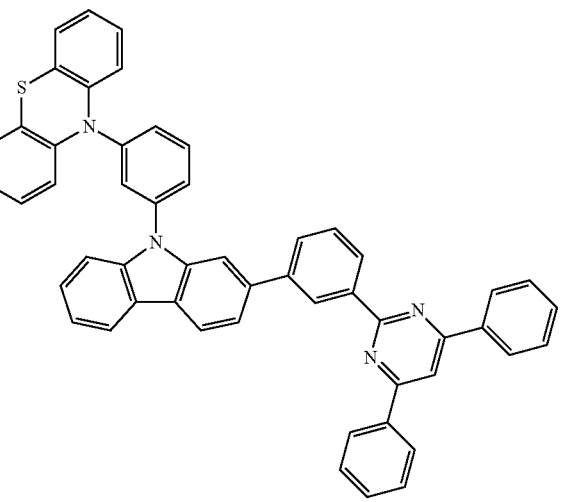
A-100
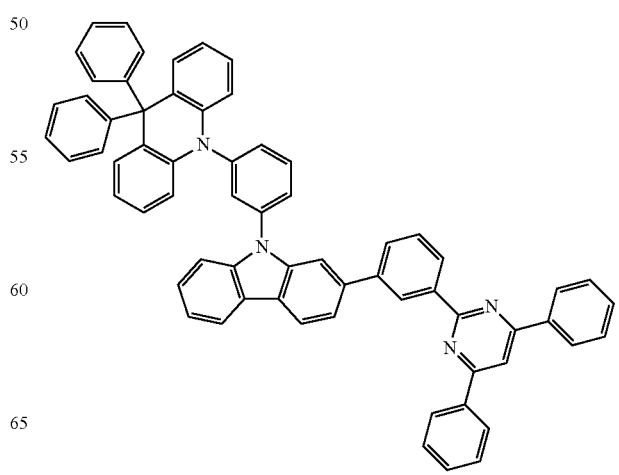

A-101
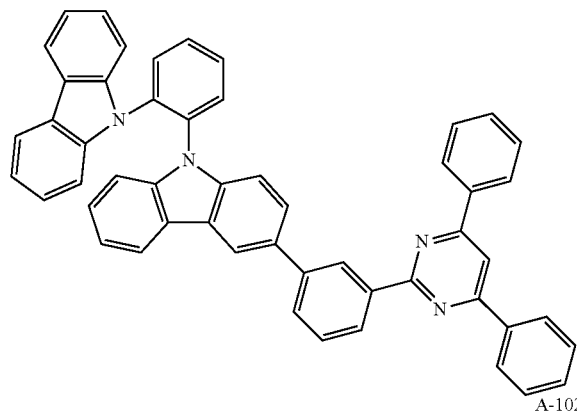
A-102
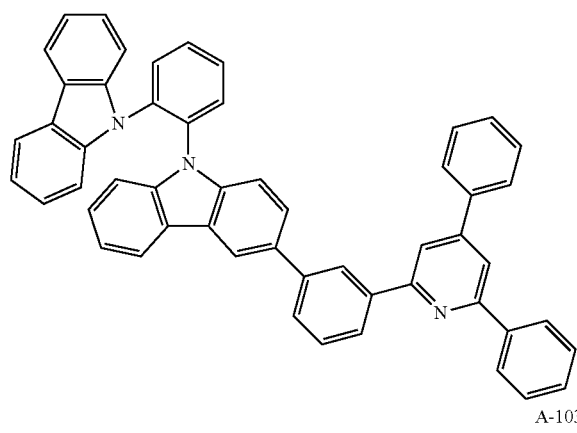
A-103
A-104
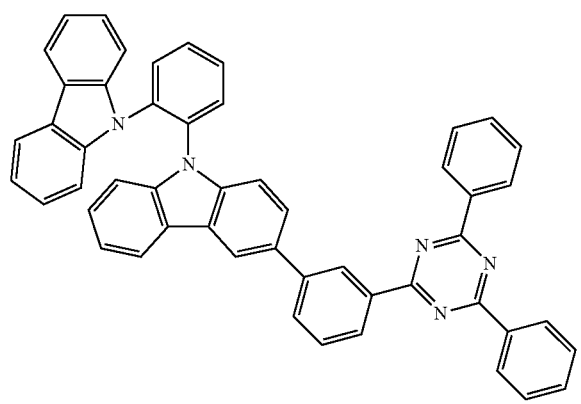
A-105
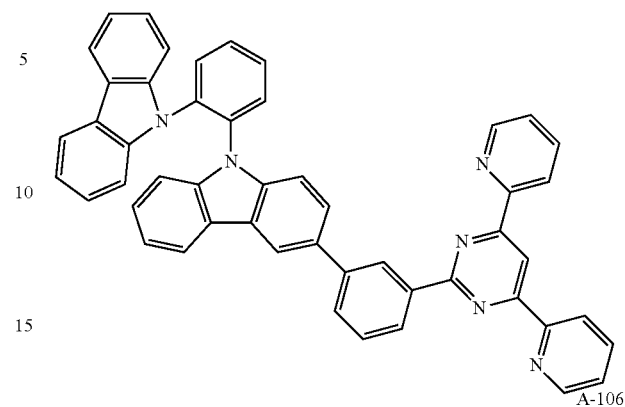
A-106
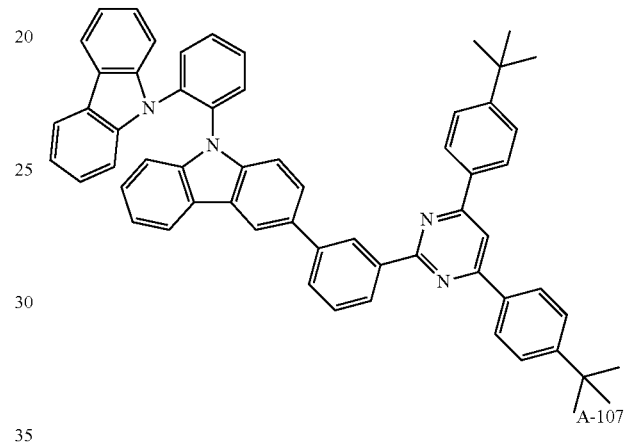
A-107
A-108
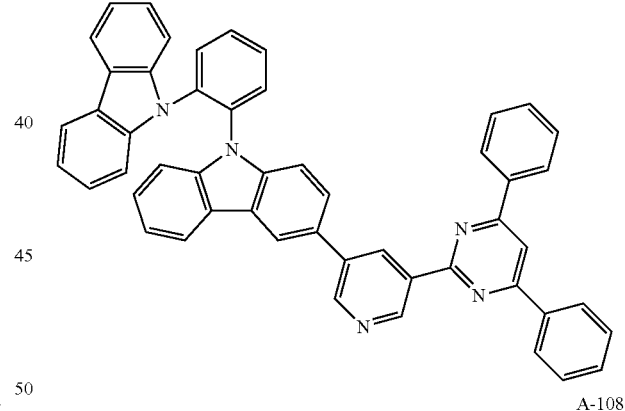
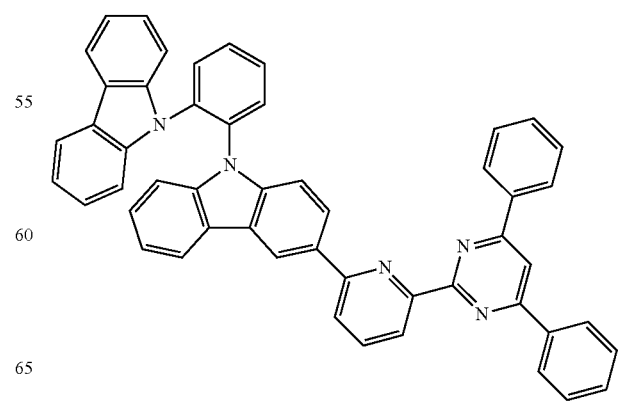

-continued
A-109
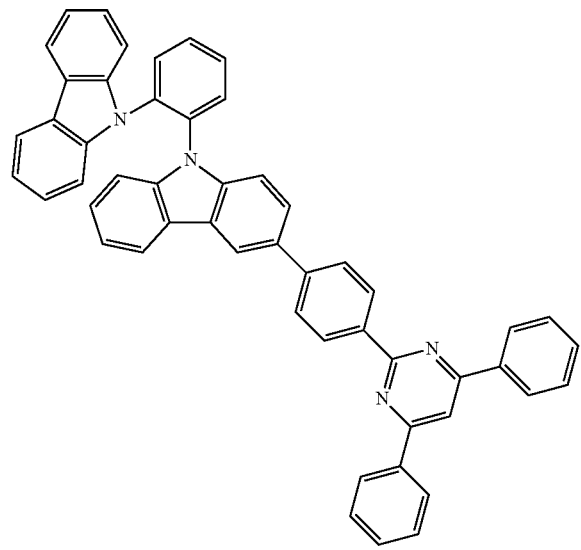
A-110
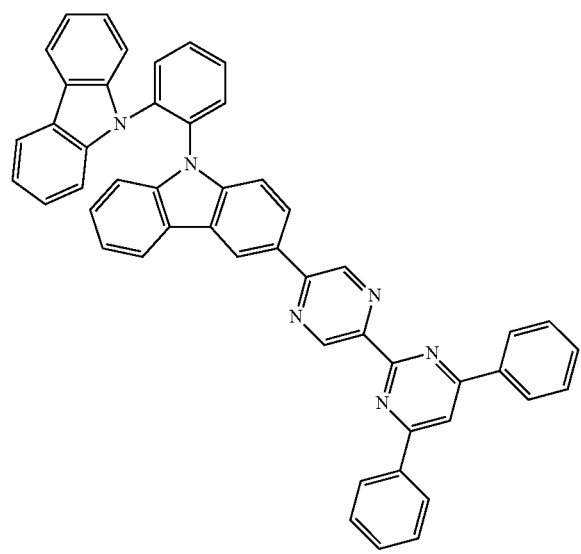
A-111
A-112
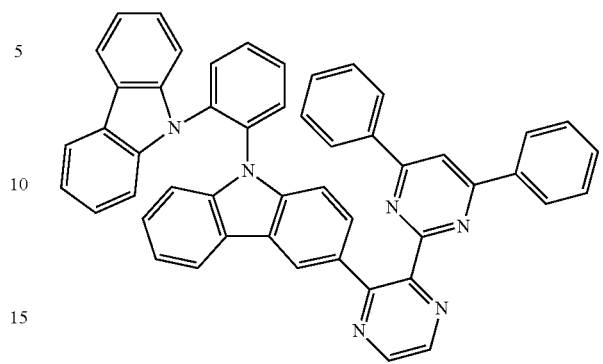
A-113
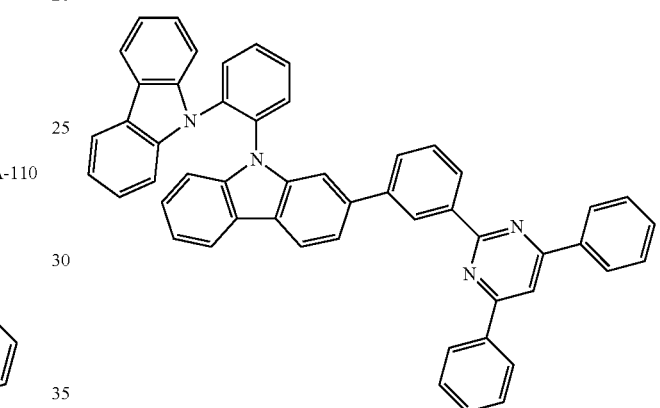
A-114
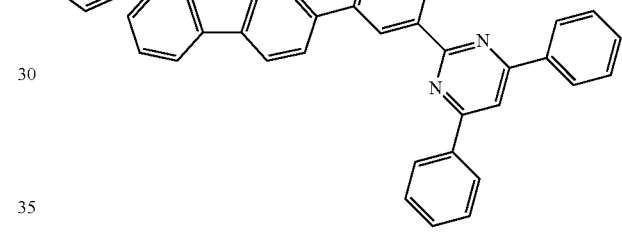
A-115
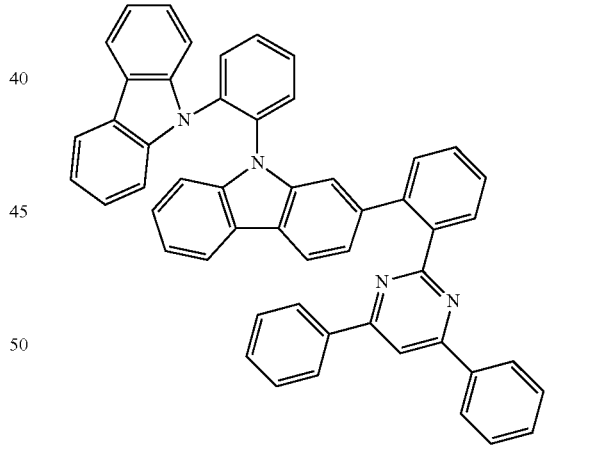

A-116
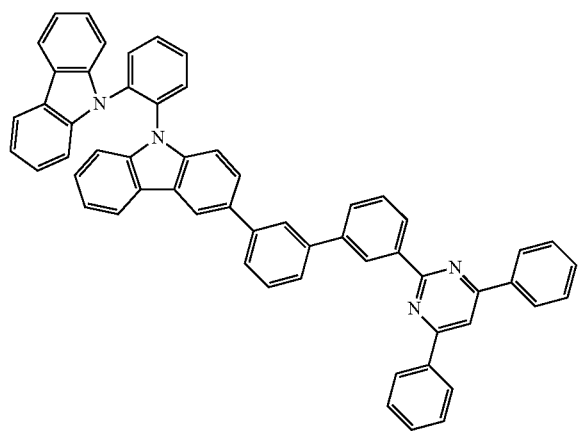
A-119
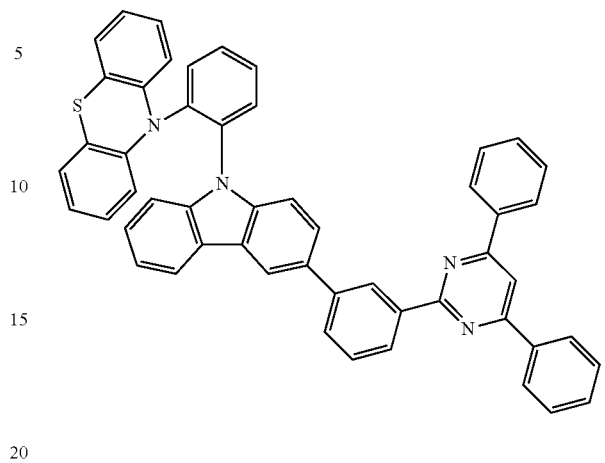
A-117
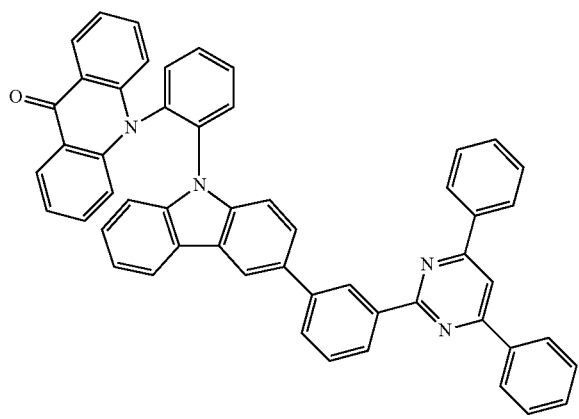
A-120
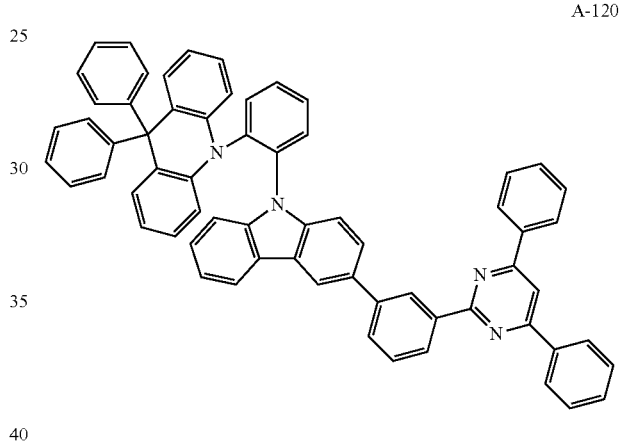
A-118
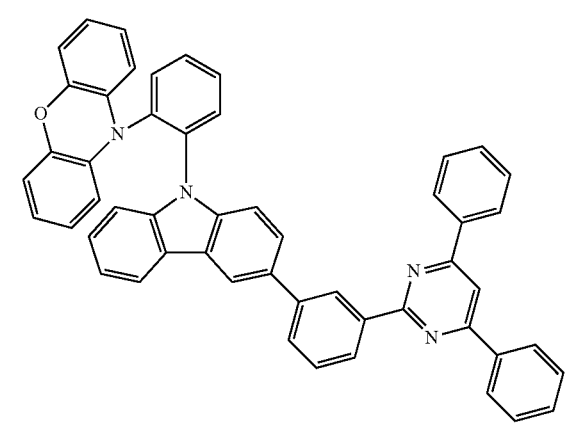
A-121
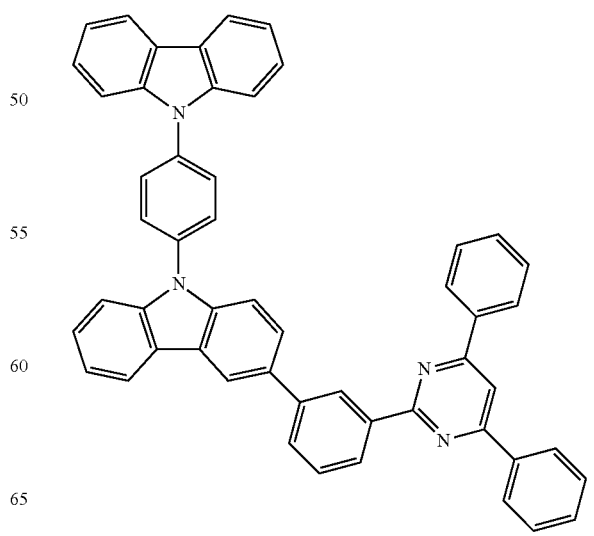

A-122
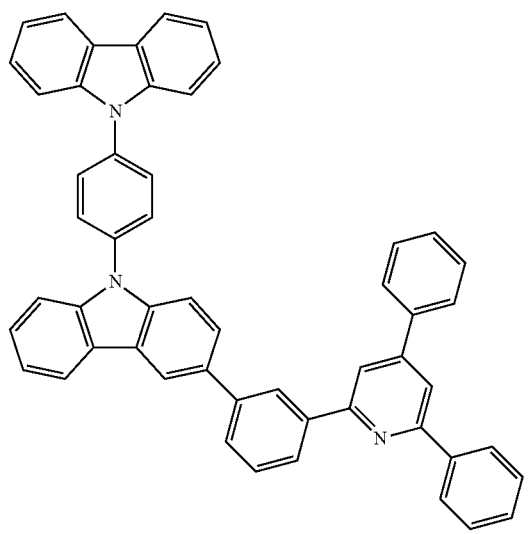
A-123
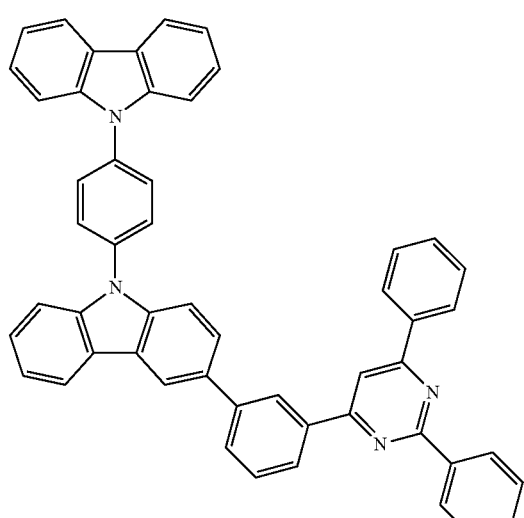
A-124
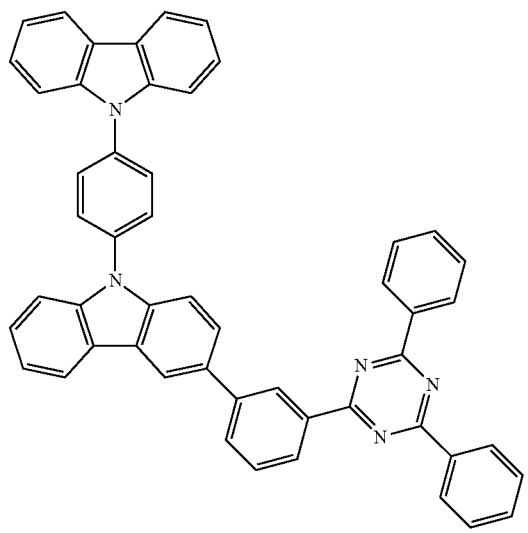
A-125
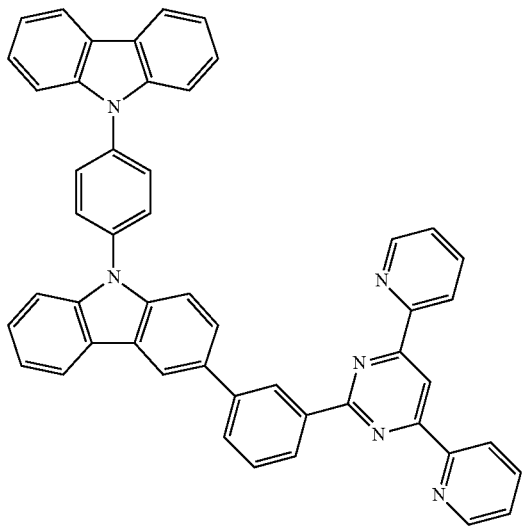
A-126
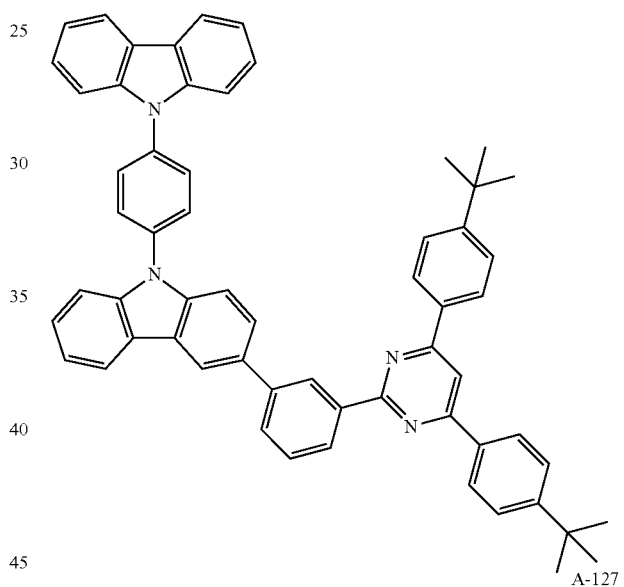
A-127
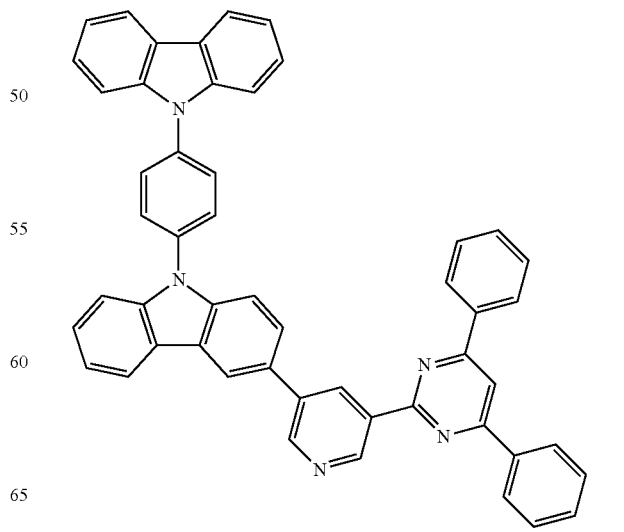

-continued
A-128
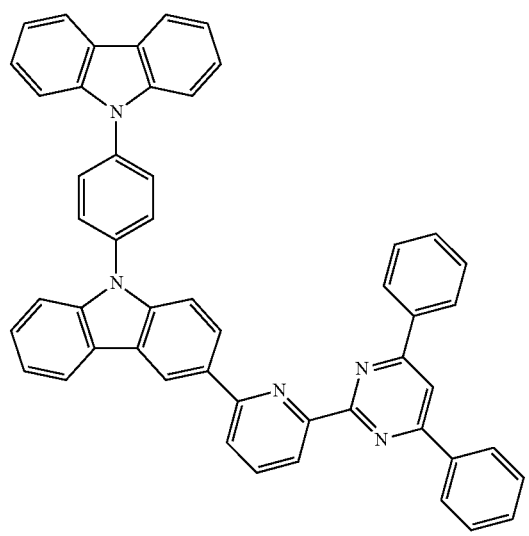
A-129
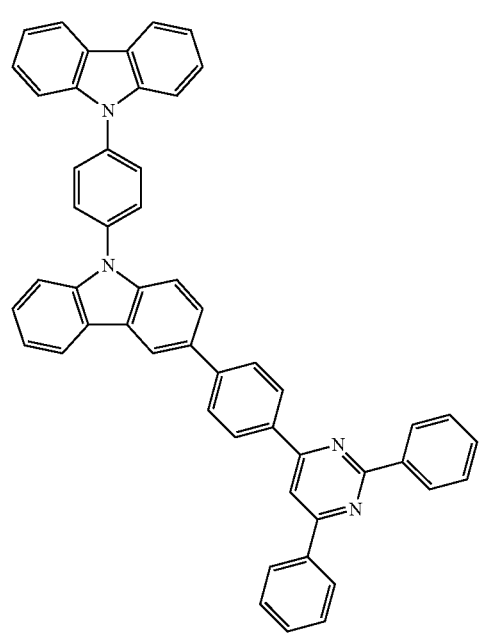
A-130
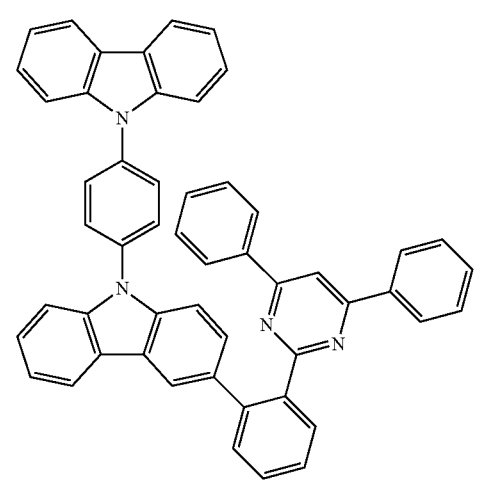
-continued
A-131
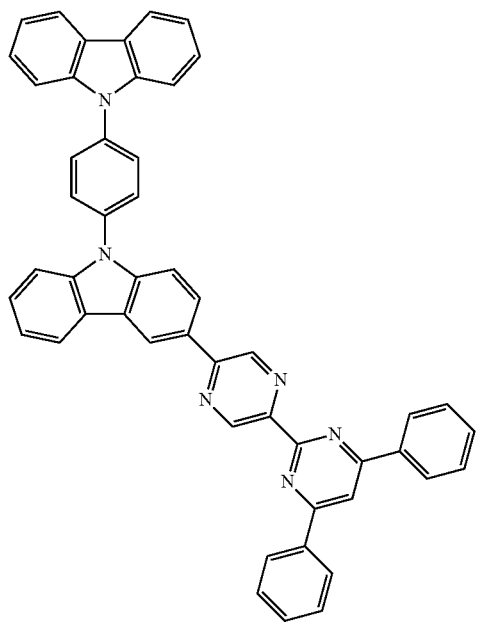
A-132
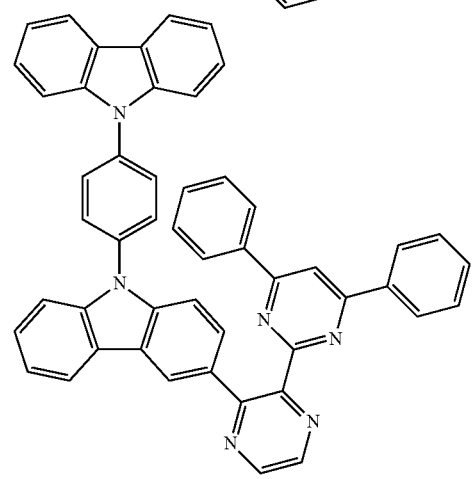
A-133
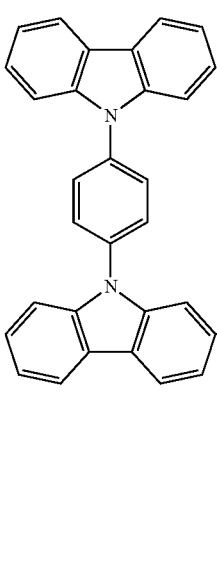

-continued
A-134
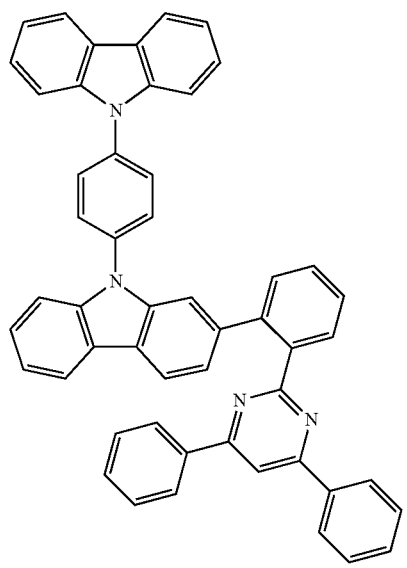
A-135
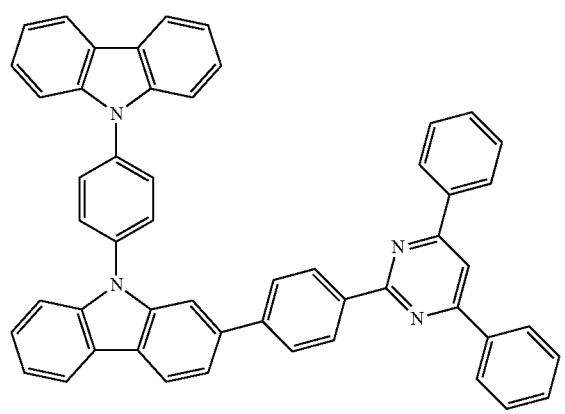
A-136
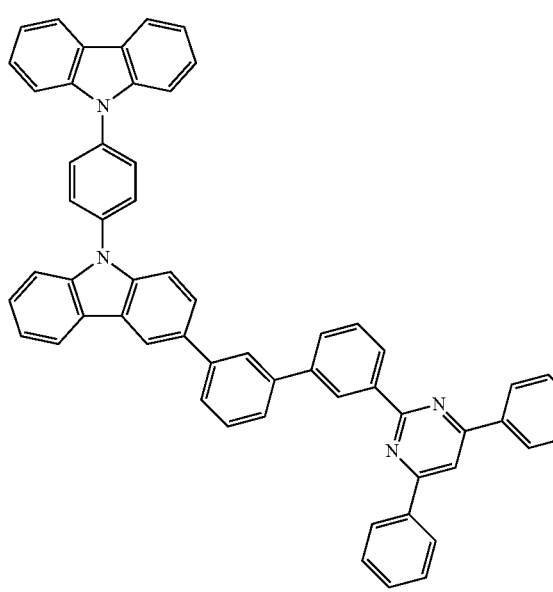
-continued
A-137
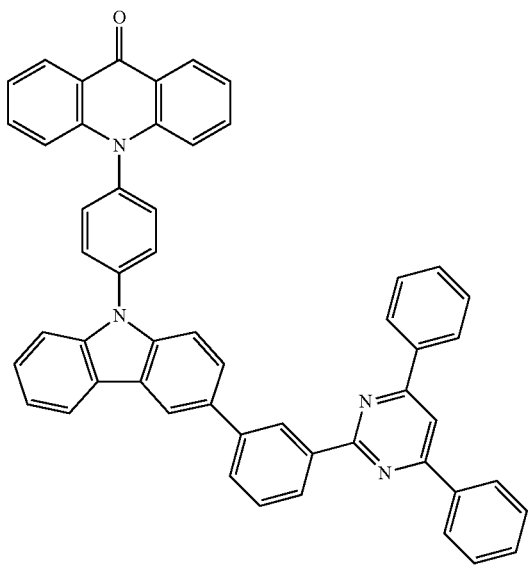
A-138
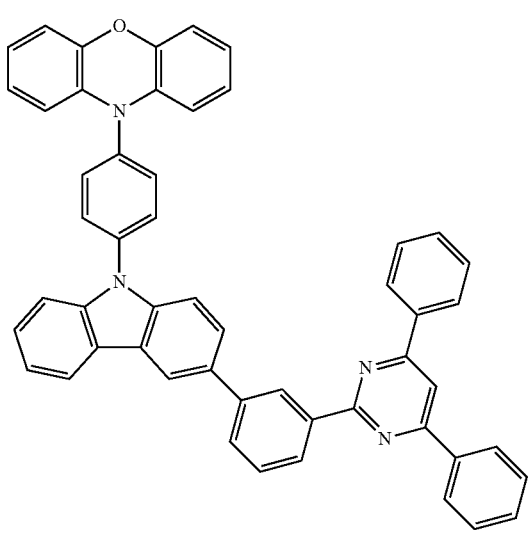
A-139
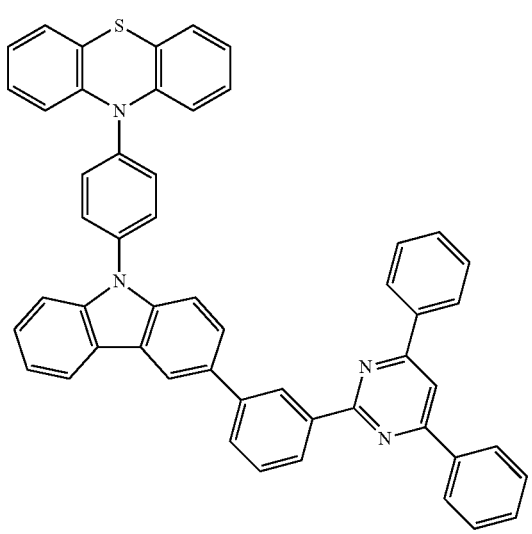

-continued

A-140

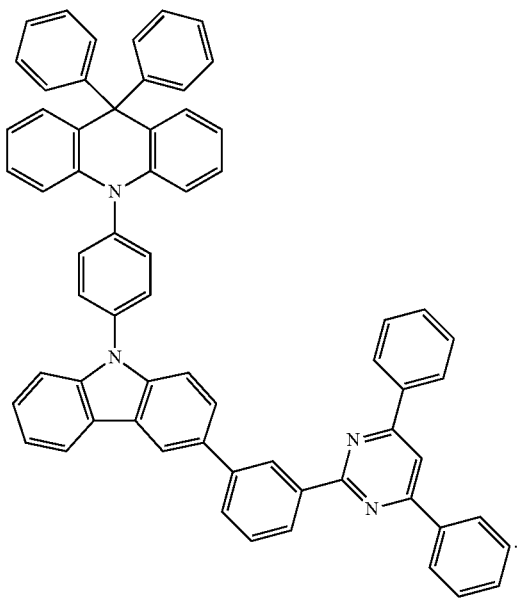

15. The compound for an organic optoelectronic device of claim 1, wherein the organic optoelectronic device is selected from an organic photoelectric device, an organic light emitting diode, an organic solar cell, an organic transistor, an organic photoconductor drum, and an organic memory device.

16. An organic light emitting diode comprising
an anode, a cathode, and at least one organic thin layer interposed between the anode and cathode,
wherein at least one organic thin layer comprises the compound of claim 1.

17. The organic light emitting diode of claim 16, wherein the organic thin layer is selected from an emission layer, a hole transport layer, a hole injection layer, an electron transport layer, an electron injection layer, a hole blocking layer, and a combination thereof.

18. The organic light emitting diode of claim 16, wherein the organic thin layer comprises an emission layer, and wherein the emission layer comprises the compound of claim 1.

19. A display device comprising the organic light emitting diode according to claim 16.

* * * * *